United States Patent
Park et al.

(10) Patent No.: US 11,552,253 B2
(45) Date of Patent: Jan. 10, 2023

(54) COMPOUND FOR ORGANIC ELECTRIC DEVICE, ORGANIC ELECTRIC DEVICE USING SAME, AND ELECTRONIC DEVICE

(71) Applicant: DUK SAN NEOLUX CO., LTD., Cheonan-si (KR)

(72) Inventors: Jong Gwang Park, Ulsan (KR); Yeon Hee Choi, Cheonan-si (KR); Yun Suk Lee, Seongnam-si (KR); Ki Ho So, Cheonan-si (KR); Hyung Keun Park, Chuncheon-si (KR); Yeon Seok Jeong, Gangwon-do (KR); Sun Pil Hwang, Ansan-si (KR); Sun Hee Lee, Hwaseong-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 166 days.

(21) Appl. No.: 15/780,672

(22) PCT Filed: Nov. 24, 2016

(86) PCT No.: PCT/KR2016/013626
§ 371 (c)(1),
(2) Date: Jun. 1, 2018

(87) PCT Pub. No.: WO2017/095075
PCT Pub. Date: Jun. 8, 2017

(65) Prior Publication Data
US 2018/0358563 A1 Dec. 13, 2018

(30) Foreign Application Priority Data
Dec. 1, 2015 (KR) .......................... 10-2015-0169758

(51) Int. Cl.
*H01L 51/00* (2006.01)
*C07D 333/76* (2006.01)
(Continued)

(52) U.S. Cl.
CPC ........ *H01L 51/0061* (2013.01); *C07D 209/82* (2013.01); *C07D 209/88* (2013.01);
(Continued)

(58) Field of Classification Search
CPC ..... H01L 51/0061; H01L 51/00; H01L 51/50; H01L 51/006; H01L 51/5278;
(Continued)

(56) References Cited

U.S. PATENT DOCUMENTS

2005/0100805 A1* 5/2005 Tanaka ................. G03G 5/0605
430/72
2007/0188089 A1* 8/2007 Choi ................... H01L 27/1229
313/506
(Continued)

FOREIGN PATENT DOCUMENTS

JP       2007065164 A  *  3/2007
KR    10-2009-0089332 A      8/2009
(Continued)

OTHER PUBLICATIONS

Q. Zhang, "Carbazole based hole transporting materials for electroluminescent devices" Synthetic Metals 137 (2003) 1111-1112 0379-6779/ (Year: 2003).*

*Primary Examiner* — Michael Y Sun
(74) *Attorney, Agent, or Firm* — Vorys, Sater, Seymour & Pease LLP; Mih Suhn Koh

(57) ABSTRACT

Provided is a novel compound capable of improving the luminous efficiency, stability and lifespan of a device, an organic electronic device using the same, and an electronic device.

15 Claims, 1 Drawing Sheet

(51) Int. Cl.
  *C07D 409/12* (2006.01)
  *C07D 307/91* (2006.01)
  *C07D 409/14* (2006.01)
  *C07D 209/82* (2006.01)
  *C09K 11/06* (2006.01)
  *C07D 407/12* (2006.01)
  *H01L 51/50* (2006.01)
  *H05B 33/14* (2006.01)
  *C07D 209/88* (2006.01)
  *C07D 405/12* (2006.01)
  *H01L 51/52* (2006.01)
  *H01L 51/56* (2006.01)

(52) U.S. Cl.
  CPC ......... *C07D 307/91* (2013.01); *C07D 333/76* (2013.01); *C07D 405/12* (2013.01); *C07D 407/12* (2013.01); *C07D 409/12* (2013.01); *C07D 409/14* (2013.01); *C09K 11/06* (2013.01); *H01L 51/00* (2013.01); *H01L 51/006* (2013.01); *H01L 51/50* (2013.01); *H01L 51/5278* (2013.01); *H05B 33/14* (2013.01); *H01L 51/001* (2013.01); *H01L 51/0072* (2013.01); *H01L 51/0073* (2013.01); *H01L 51/0074* (2013.01); *H01L 51/5004* (2013.01); *H01L 51/5016* (2013.01); *H01L 51/5056* (2013.01); *H01L 51/5072* (2013.01); *H01L 51/5092* (2013.01); *H01L 51/5096* (2013.01); *H01L 51/56* (2013.01); *H01L 2251/552* (2013.01); *H01L 2251/558* (2013.01)

(58) Field of Classification Search
  CPC ............... H01L 51/001; H01L 51/0072; H01L 51/0073; H01L 51/0074; H01L 51/5004; H01L 51/5016; H01L 51/5056; H01L 51/5072; H01L 51/5092; H01L 51/5096; H01L 51/56; H01L 2251/552; H01L 2251/558; C07D 409/14; C07D 209/82; C07D 407/12; C07D 209/88; C07D 405/12; C07D 333/76; C07D 409/12; C07D 307/91; C09K 11/06; H05B 33/14; Y02E 10/549; Y02P 70/50
  See application file for complete search history.

(56) References Cited

U.S. PATENT DOCUMENTS

| | | | | |
|---|---|---|---|---|
| 2010/0145067 | A1* | 6/2010 | Yokota | C07D 209/86 548/442 |
| 2014/0027734 | A1* | 1/2014 | Kwong | H01L 51/0071 257/40 |
| 2014/0319472 | A1* | 10/2014 | Cho | H01L 51/006 257/40 |
| 2015/0147964 | A1* | 5/2015 | Baek | H04W 4/80 455/41.2 |
| 2016/0005979 | A1* | 1/2016 | Kim | H01L 51/0072 257/40 |
| 2016/0322578 | A1* | 11/2016 | Hwang | H01L 51/0061 |

FOREIGN PATENT DOCUMENTS

| | | |
|---|---|---|
| KR | 10-0938524 B1 | 1/2010 |
| KR | 10-2010-0125004 A | 11/2010 |
| KR | 10-2011-0117678 A | 10/2011 |
| KR | 10-1493482 B1 | 2/2015 |

\* cited by examiner

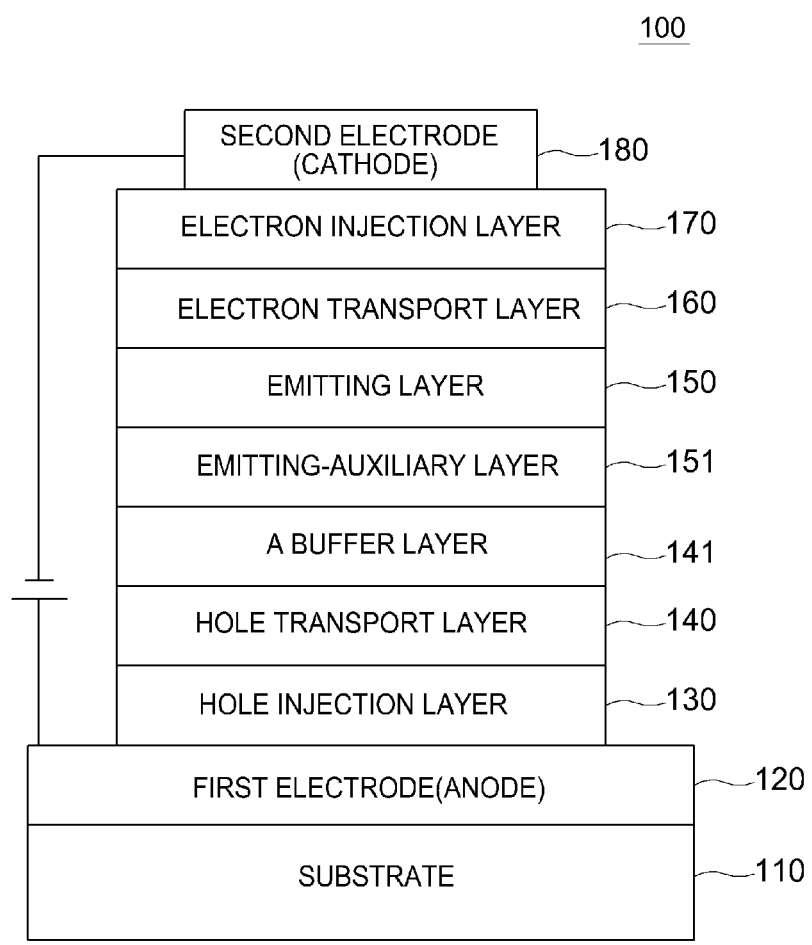

COMPOUND FOR ORGANIC ELECTRIC DEVICE, ORGANIC ELECTRIC DEVICE USING SAME, AND ELECTRONIC DEVICE

BACKGROUND

Technical Field

The present invention relates to compound for organic electric device, organic electric device using the same, and an electronic device thereof.

Background Art

In general, organic light emitting phenomenon refers to a phenomenon that converts electric energy into light energy by using an organic material. An organic electric element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electric element may be classified into a light emitting material and a charge transport material, such as a hole injection material, a hole transport material, an electron transport material, an electron injection material and the like depending on its function.

Currently, the portable display market is growing in size as a large-area display, which requires more power than the power consumption required by existing portable displays. Therefore, power consumption is a very important factor for portable displays, which have a limited power source, such as a battery, and efficiency and lifetime issues must be solved.

Efficiency, life span, driving voltage and the like are related to each other. As the efficiency is increased, the driving voltage is relatively decreased, and as the driving voltage drops, the crystallization of the organic material due to joule heating generated during driving is reduced, and as a result, the life span tends to increase. However, simply improving the organic material layer cannot maximize the efficiency. This is because, when the optimal combination of the energy level and T1 value between each organic material layer and the intrinsic properties (mobility, interface characteristics, etc.) of the material are achieved, long life and high efficiency can be achieved at the same time.

Further, recently, in organic electroluminescent devices, in order to solve the emission problem in the a hole transport layer, an emitting auxiliary layer must be present between the hole transport layer and an emitting layer, and it is necessary to develop different emitting auxiliary layers according to the respective emitting layers (R, G, B).

In general, electrons are transferred from the electron transport layer to the emitting layer, and holes are transferred from the hole transport layer to the emitting layer to generate excitons by recombination.

However, the material used for the hole transport layer has a low HOMO value and therefore has mostly low T1 value. As a result, the exciton generated in the emitting layer is transferred to the hole transport layer, resulting in charge unbalance in the emitting layer, and light is emitted at the interface of the hole transport layer.

When light is emitted from the interface of the hole transport layer, color purity and efficiency of the organic electronic device are lowered and the lifetime is shortened. Therefore, it is urgently required to develop an emitting auxiliary layer having a high T1 value and having a HOMO level between the HOMO energy level of the hole transport layer and the HOMO energy level of the emitting layer.

However, this cannot be achieved simply by the structural properties of the core of the emitting auxiliary layer material, and when the core and sub-substituent properties of the emitting auxiliary layer material, and a proper combination between the emitting auxiliary layer and the hole transport layer, and between the emitting auxiliary layer and the emitting layer are made, a device with high efficiency and long lifetime can be realized.

In addition, it is necessary to develop a hole injection/transport layer material that retards penetration/diffusion of metal oxides from an anode electrode (ITO) into an organic material layer, which is one cause for the shortened life span of an organic electric element, and has stability against Joule heating generated during the operation of an organic electric element, that is, a high glass transition temperature. Also, it has been reported that a low glass transition temperature of a hole transport layer material has a great effect on the life span of an organic electric element because the uniformity of a thin film surface collapses during the operation of the element.

In general, deposition is a main method of forming an OLED, and thus it is necessary to develop a material that is durable to such a deposition method, that is, a highly heat-resistant material.

That is, in order to sufficiently exhibit the excellent characteristics of the organic electric element, a material for forming an organic material layer in an element such as a hole injection material, a hole transport material, a light emitting material, an electron transport material, an electron injection material, an emitting auxiliary layer material should be supported by stable and efficient materials. However, such a stable and efficient organic material layer material for an organic electric element has not been sufficiently developed yet. Therefore, development of new materials is continuously required, and development of materials for the emitting auxiliary layer and the hole transport layer is urgently required.

(Patent Document 1) KR 10-1418146 B1.

DETAILED DESCRIPTION OF THE INVENTION

Summary

The present invention has been made to solve the above-mentioned problems occurring in the prior art, and it is an object of the present invention to provide a compound having efficient electron blocking ability and hole transporting ability, and a compound capable of improving the light emitting efficiency, the low driving voltage, the high heat resistance, the color purity and the lifetime of the device using such a compound, an organic electric device using the same, and an electronic device thereof.

Technical Solution

The present invention provides a compound represented by Formula (1).

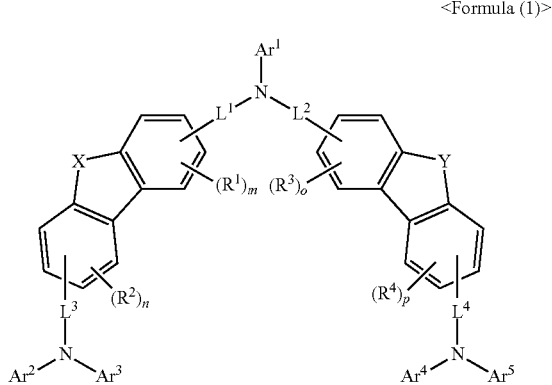

<Formula (1)>

Also, the present invention provides an organic electric element using the compound represented by Formula (1), and an electronic device thereof.

Effects of the Invention

According to the present invention, in the structure in which two heterocycles having hole properties are substituted with tertiary amines, by using a specific compound in which one amine each is introduced at the terminal of the heterocycle as a material of the organic electric device, the hole transfer ability and the thermal stability are improved, and a HOMO energy level, a high T1 value and a high refractive index, which are easy to balance charges in the emitting layer, can improve the luminous efficiency, heat resistance, life and the like of the organic electronic device and lower the driving voltage.

BRIEF DESCRIPTION OF THE DRAWINGS

The FIGURE illustrates an example of an organic electric element according to the present invention.
100: organic electric element,
110: substrate
120: the first electrode (anode),
130: the hole injection layer
140: the hole transport layer,
141: a buffer layer
150: the emitting layer,
151: the emitting auxiliary layer
160: the electron transport layer,
170: the electron injection layer
180: the second electrode (cathode)

DETAILED DESCRIPTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected", "coupled" or "connected" between each component.

As used in the specification and the accompanying claims, unless otherwise stated, the following is the meaning of the term as follows.

Unless otherwise stated, the term "halo" or "halogen", as used herein, comprises fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "haloalkyl" or "halogen alkyl", as used herein, comprises an alkyl group substituted with a halogen.

Unless otherwise stated, the term "heteroalkyl", as used herein, means alkyl substituted one or more of carbon atoms consisting of an alkyl with hetero atom.

Unless otherwise stated, the term "alkenyl" or "alkynyl", as used herein, has double or triple bonds of 2 to 60 carbon atoms, but is not limited thereto, and comprises a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "alkenoxyl group", "alkenoxy group", "alkenyloxy group" or "alkenyloxy group", as used herein, means an oxygen radical attached to an alkenyl group, but is not limited thereto, and has 2 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

Unless otherwise stated, the term "aryl group" or "arylene group", as used herein, has 6 to 60 carbon atoms, but is not limited thereto. Herein, the aryl group or arylene group means a monocyclic and polycyclic aromatic group, and includes an aromatic ring formed by neighboring substituents participating in a bond or a reaction. Examples of "aryl group" may comprise a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heteroalkyl", as used herein, means alkyl containing one or more of hetero atoms. Unless otherwise stated, the term "heteroaryl group" or "heteroarylene group", as used herein, means a C2 to C60 aryl containing one or more of hetero atoms or arylene group, but is not limited thereto, and comprises at least one of monocyclic and polycyclic rings, and may also be formed in conjunction with an adjacent group.

Unless otherwise stated, the term "heterocyclic group", as used herein, contains one or more heteroatoms, but is not limited thereto, has 2 to 60 carbon atoms, comprises any one of monocyclic and Polycyclic rings, and may comprise heteroaliphadic ring and/or heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may comprise a ring containing $SO_2$ instead of carbon consisting of cycle. For example, "heterocyclic group" comprises compound below.

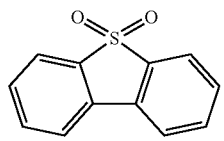

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and comprises a saturated or unsaturated ring.

Other hetero compounds or hetero radicals other than the above-mentioned hetero compounds contain, but are not limited thereto, one or more heteroatoms.

Unless otherwise stated, the term "carbonyl", as used herein, is represented by —COR', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "ether", as used herein, is represented by —R—O—R', wherein R or R' may be independently hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "substituted or unsubstituted", as used herein, means that substitution is substituted by at least one substituent selected from the group consisting of, but is not limited thereto, deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Unless otherwise expressly stated, the Formula used in the present invention, as used herein, is applied in the same manner as the substituent definition according to the definition of the exponent of the following Formula.

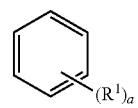

wherein, when a is an integer of zero, the substituent $R^1$ is absent, when a is an integer of 1, the sole substituent $R^1$ is linked to any one of the carbon constituting the benzene ring, when a is an integer of 2 or 3, each substituent $R^1$s may be the same and different, when a is an integer of 4 to 6, and is linked to the benzene ring in a similar manner, whereas the indication of hydrogen bound to the carbon forming the benzene ring is omitted.

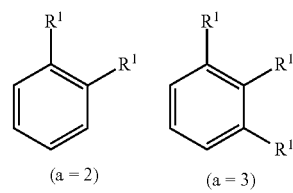

Hereinafter, a compound according to an aspect of the present invention and an organic electric element comprising the same will be described.

The present invention provides a compound represented Formula (1) below.

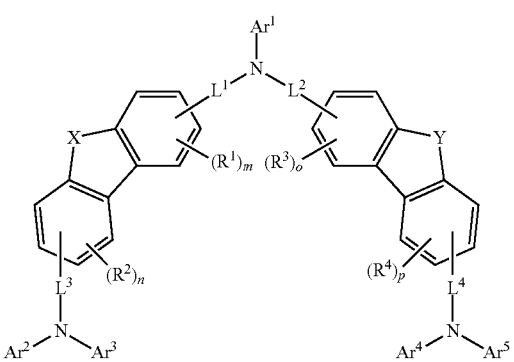

Formula (1)

{In Formula (1),

1) X and Y are each independently $NAr^6$, S or O, and except when X and Y are simultaneously $NAr^6$, 2) $Ar^1$, $Ar^2$, $Ar^3$, $Ar^4$, $Ar^4$, and $Ar^6$ are each independently selected from the group consisting of a $C_6$-$C_{60}$ aryl group; a $C_2$-$C_{60}$ heterocyclic group including at least one hetero atom of O, N, S, Si or P; a fluorenyl group; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group;

3) $R^1$, $R^2$, $R^3$, and $R^4$ are each independently selected from a hydrogen; a deuterium; tritium; a halogen; a cyano group; a nitro group; the group consisting of a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; when a plurality of $R^1$ to $R^4$ are present, at least one pair of adjacent $R^1$, $R^2$, $R^3$, and $R^4$ may bond independently to form a ring, and $R^1$ to $R^4$ which do not form a ring are the same as defined above, 4) m, n, o and p are each independently an integer of 0 to 3, and when each of these is an integer of 2 or more, $R^1$ to $R^4$ are the same or different from each other, and a plurality of $R^1$, $R^2$, $R^3$ and $R^4$ are the same or different from each other, 5) $L^1$, $L^2$, $L^3$, and $L^4$ are each independently selected from the group consisting of a single bond, a $C_6$-$C_{60}$ arylene group, and a fluorenylene group; a $C_2$-$C_{60}$ divalent heterocyclic group containing at least one heteroatom selected from O, N, S, Si or P; a divalent fused ring group of a $C_3$-$C_{60}$ aliphatic ring and a $C_6$-$C_{60}$ aromatic ring; and a divalent aliphatic hydrocarbon group, and when they are not a single bond, each may be substituted with one or more substituents selected from the group consisting of deuterium; halogen; a silane group; siloxane group; boron group; germanium group; cyano group; nitro group; a $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; -L'-N($R^a$)($R^b$); and $C_8$-$C_{20}$ arylalkenyl group, (wherein, the $R^a$ and $R^b$ are each independently selected from the group consisting of a $C_6$-$C_{60}$ aryl group; a fluorenyl group; a $C_2$-$C_{60}$ heterocyclic group including at least one hetero atom of O, N, S, Si or P), wherein, each of the aryl group, fluorenyl group, heterocyclic group, fused ring group, alkyl group, alkenyl group, alkynyl group, alkoxy group, and aryloxy group may be substituted with one or more substituents selected from the group consisting of deuterium; halogen; a silane group substituted or unsubstituted with $C_1$-$C_{20}$ alkyl group or $C_6$-$C_{20}$ aryl group; siloxane group; boron group; germanium group; cyano group; nitro group; a $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; a $C_2$-$C_{60}$ heterocyclic group including at least one hetero atom of O, N, S, Si or P; $C_3$-$C_{20}$ cycloalkyl group; $C_7$-$C_{20}$ arylalkyl group and $C_8$-$C_{20}$ arylalkenyl group, and when these substituents are adjacent to each other, they may be bonded to each other to form a ring.}

Specifically, a compound represented by Formula (1) is represented by any one of following Formula (2) to Formula (11)

Formula (2)

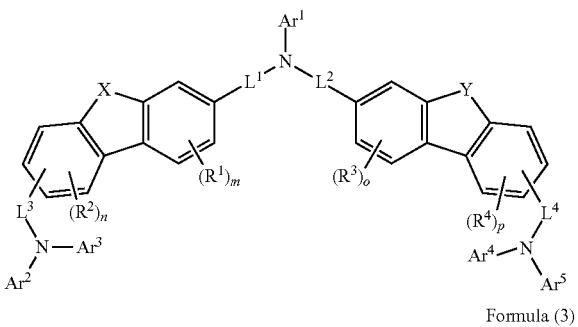

Formula (3)

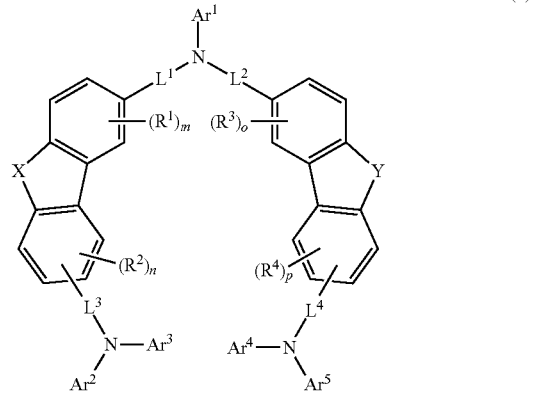

Formula (4)

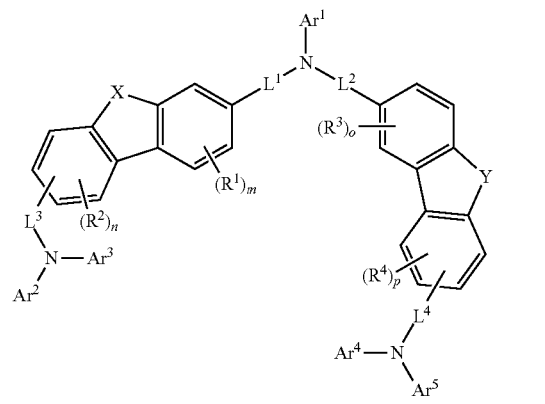

Formula (5)

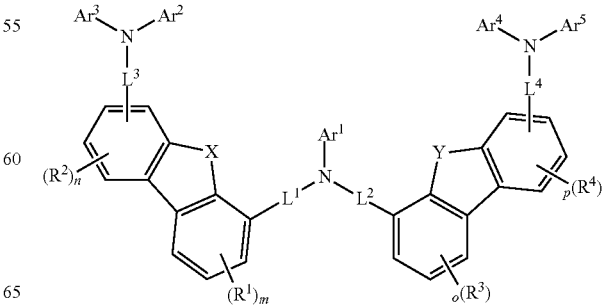

Formula (6)
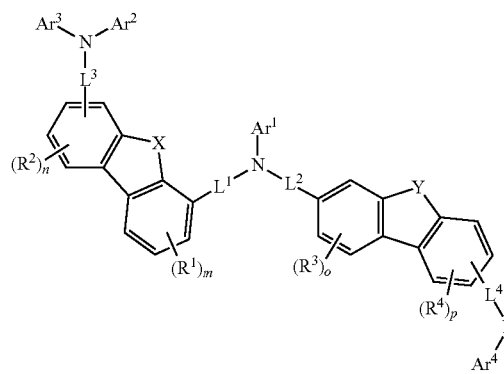
Formula (9)
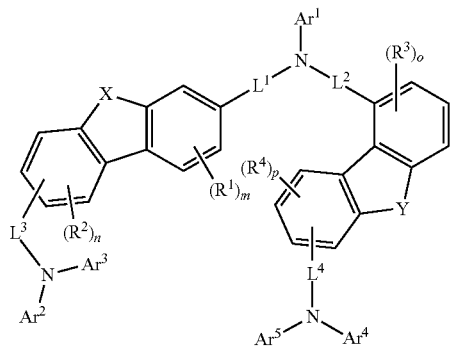
Formula (7)
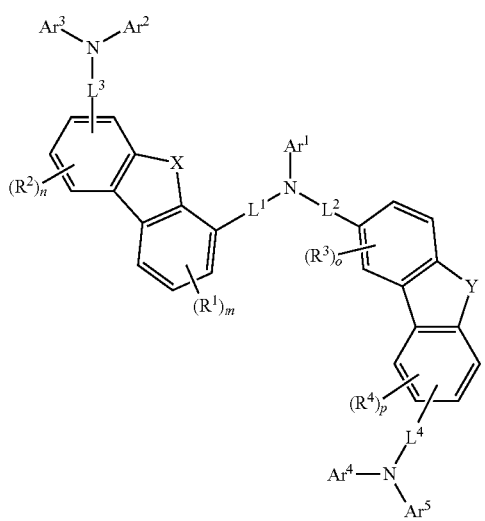
Formula (10)
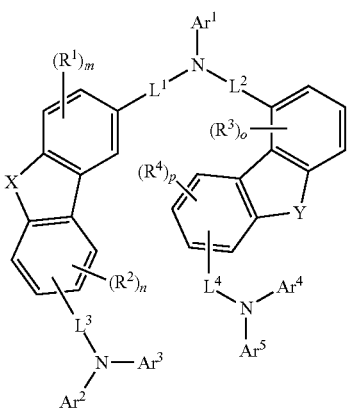
Formula (8)
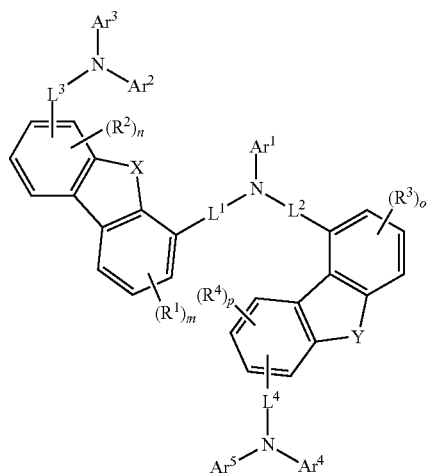
Formula (11)
(In Formula (2) to Formula (11),
X, Y, Ar$^1$, Ar$^2$, Ar$^3$, Ar$^4$, Ar$^5$, L$^1$, L$^2$, L$^3$, L$^4$, R$^1$, R$^2$, R$^3$, R$^4$, m, n, o, and p are the same as defined in Formula (1).)

Also, Formula (1) comprises a compound represented by any one of following Formula (12) to Formula (14)
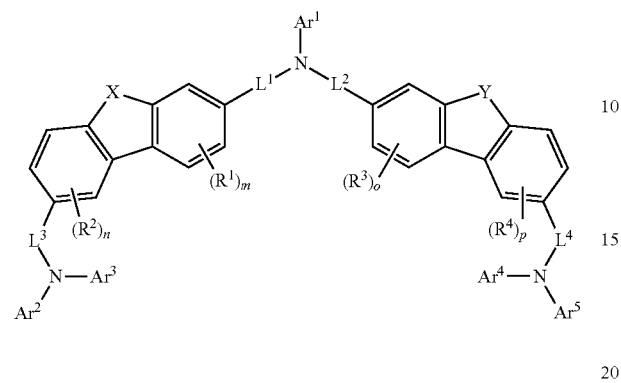
Formula (12)
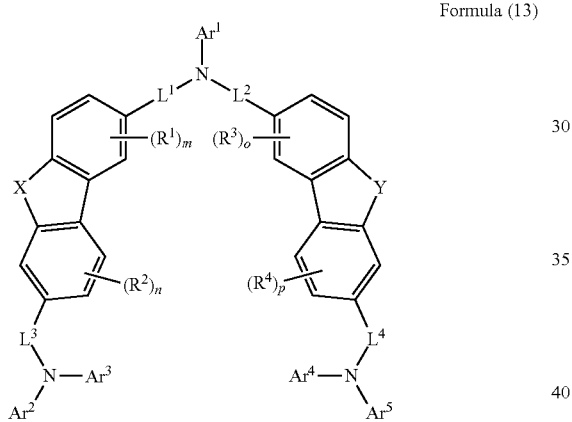
Formula (13)
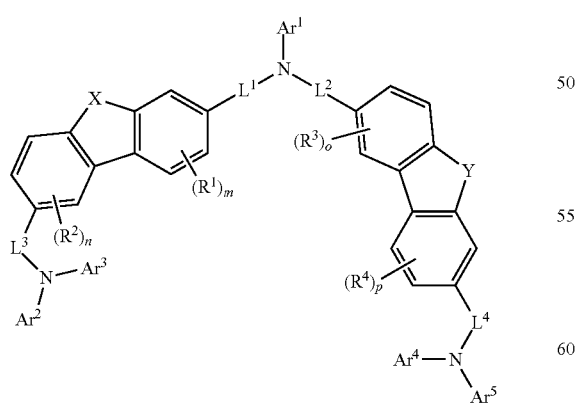
Formula (14)
(In Formula (12) to (14),
X, Y, $Ar^1$, $Ar^2$, $Ar^3$, $Ar^4$, $Ar^5$, $L^1$, $L^2$, $L^3$, $L^4$, $R^1$, $R^2$, $R^3$, $R^4$, m, n, o, and p are the same as defined in Formula (1).)
The compound represented by Formula (1) includes compounds represented by the following formulas.
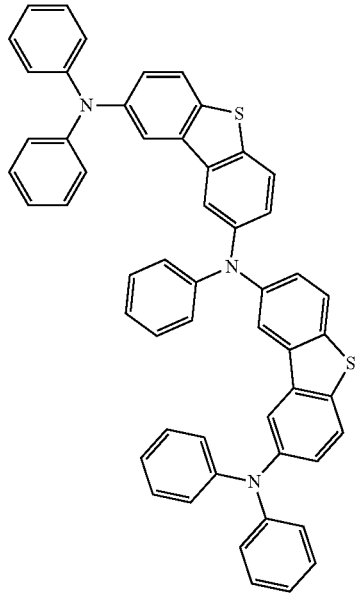
P 1-1
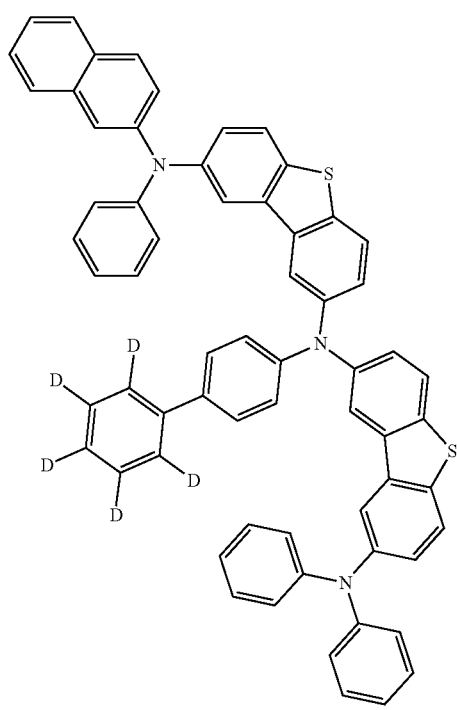
P 1-2

P 1-3
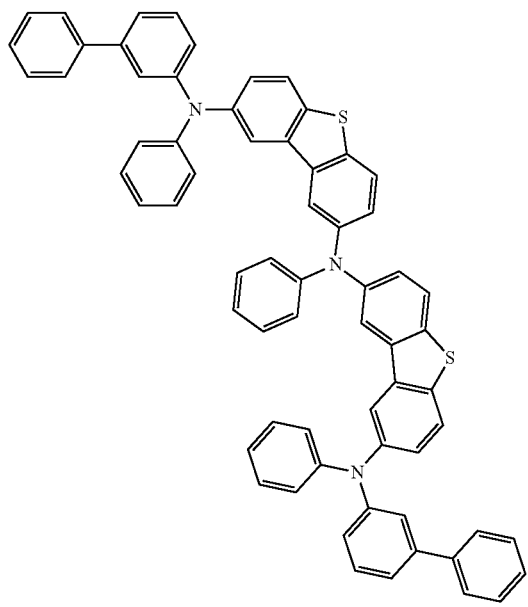
P 1-4
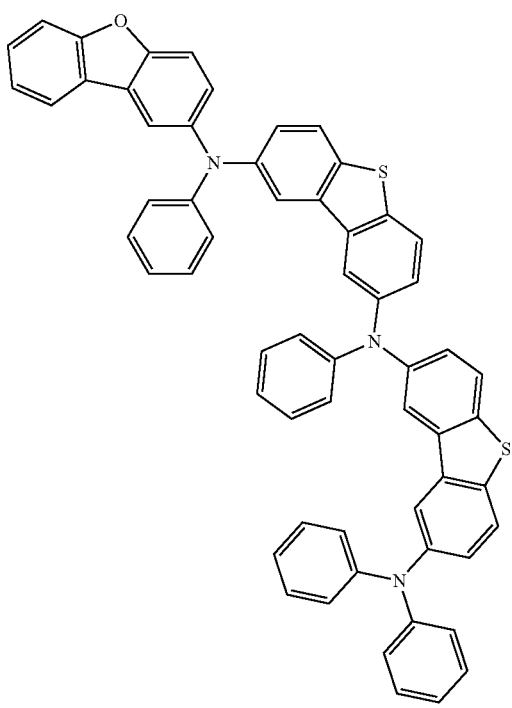
P 1-5
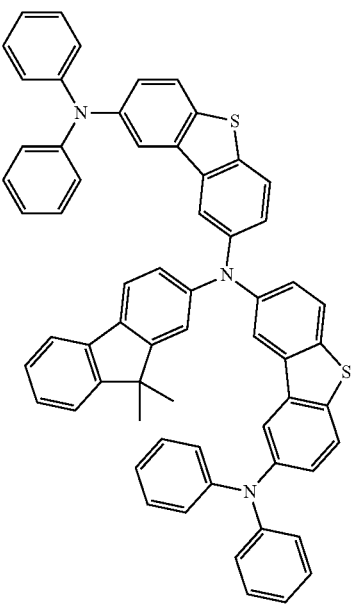
P 1-6
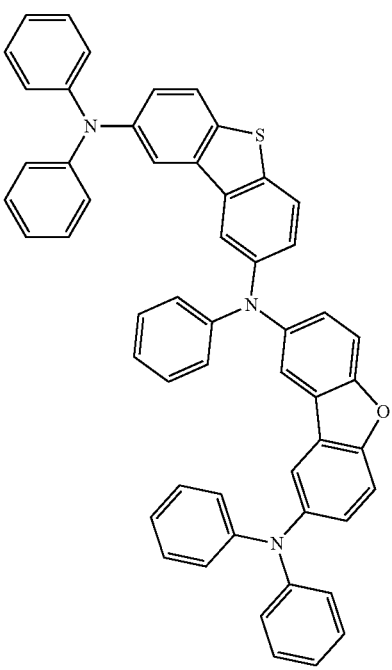

-continued
P 1-7
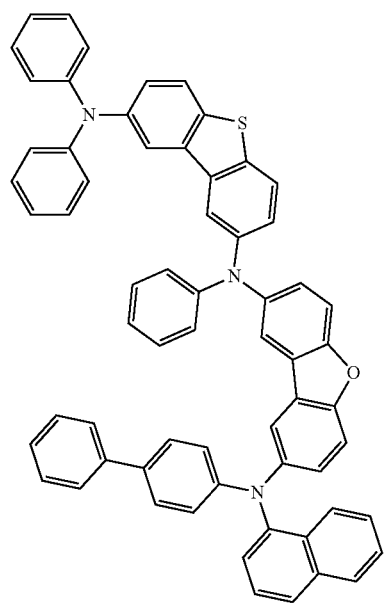
P 1-8
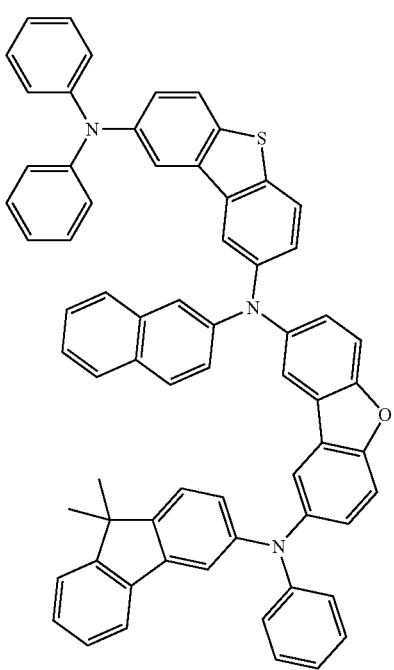
P 1-9
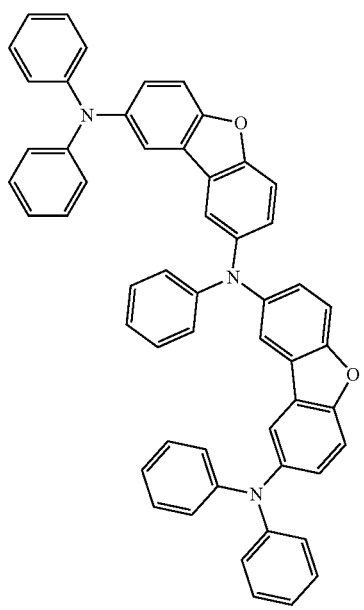
P 1-10
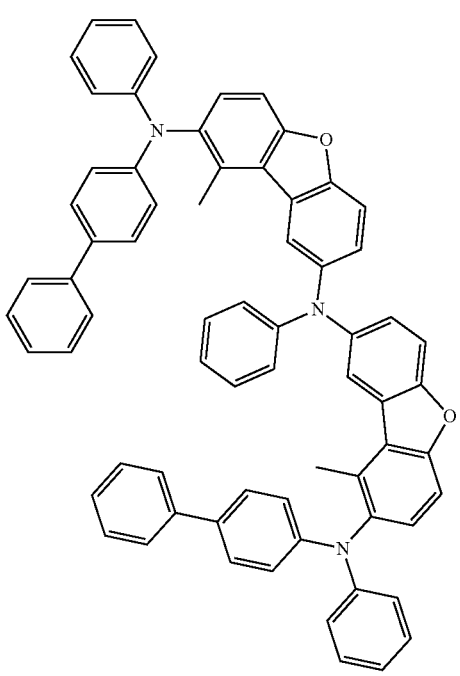

P 1-11
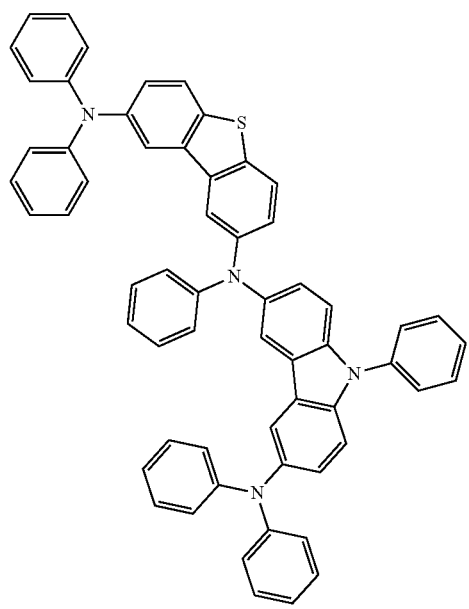
P 1-13
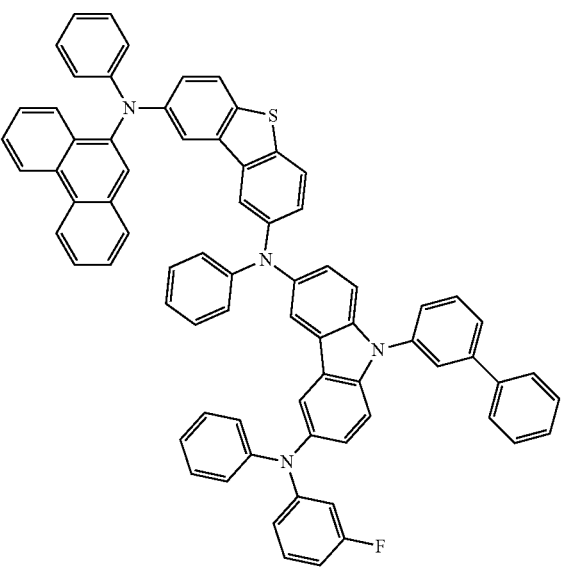
P 1-12
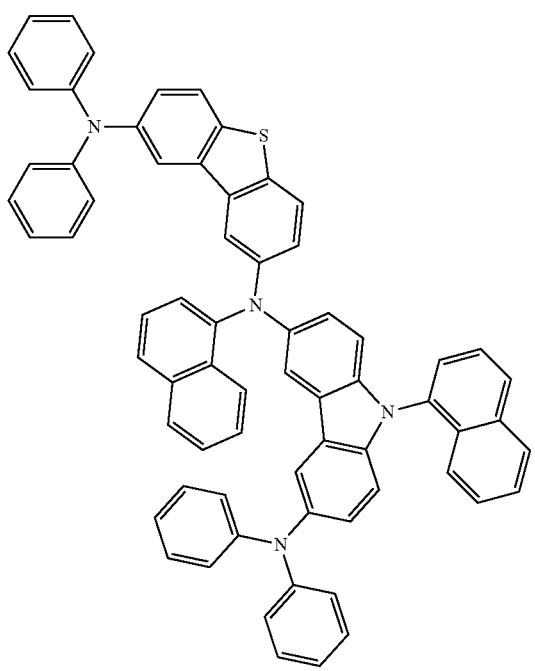
P 1-14
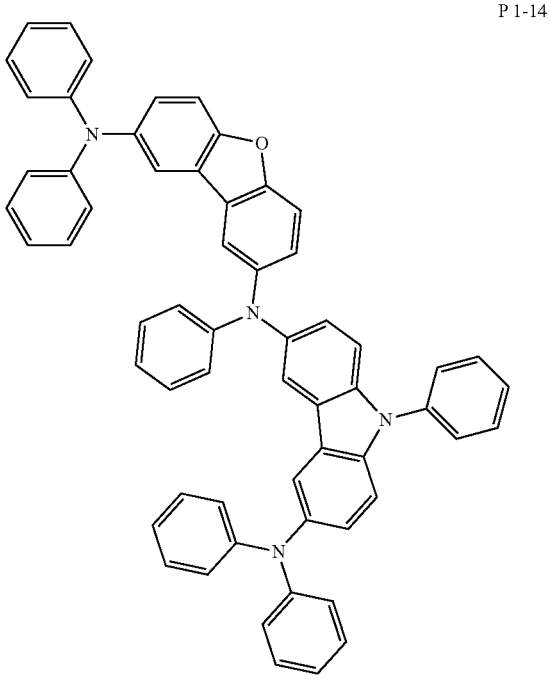

P 1-15
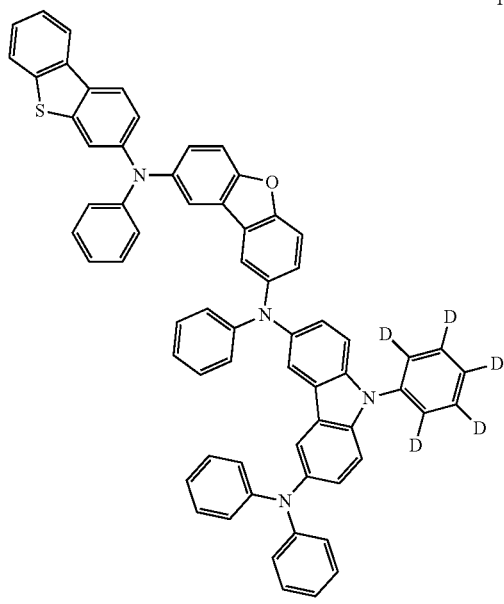
P 1-17
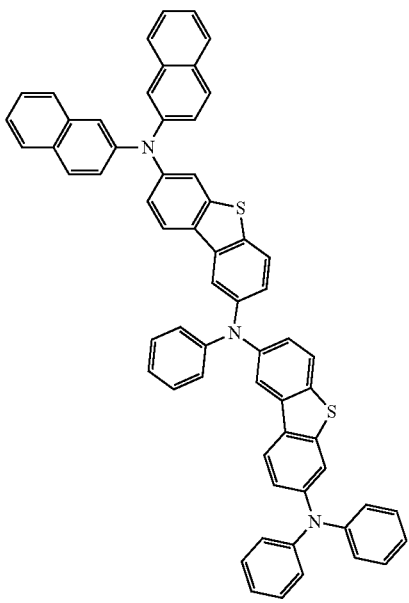
P 1-16
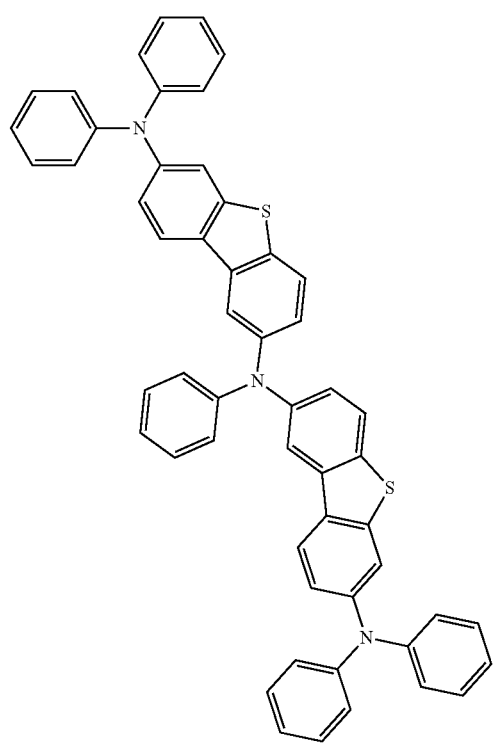
P 1-18
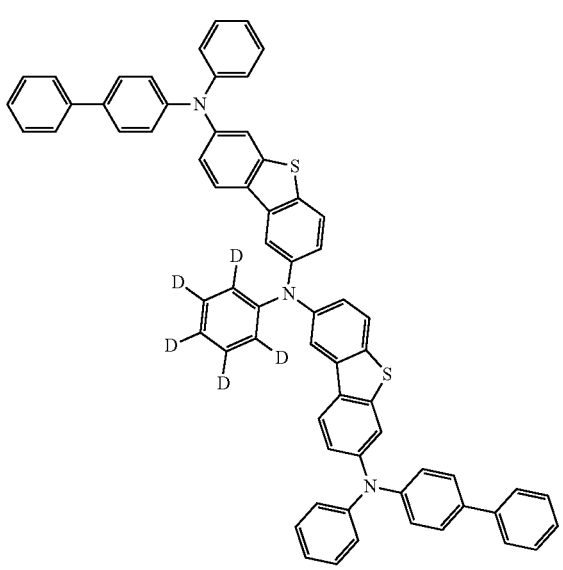

P 1-19
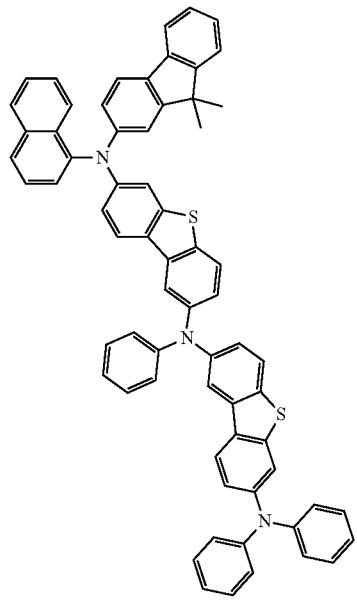
P 1-20
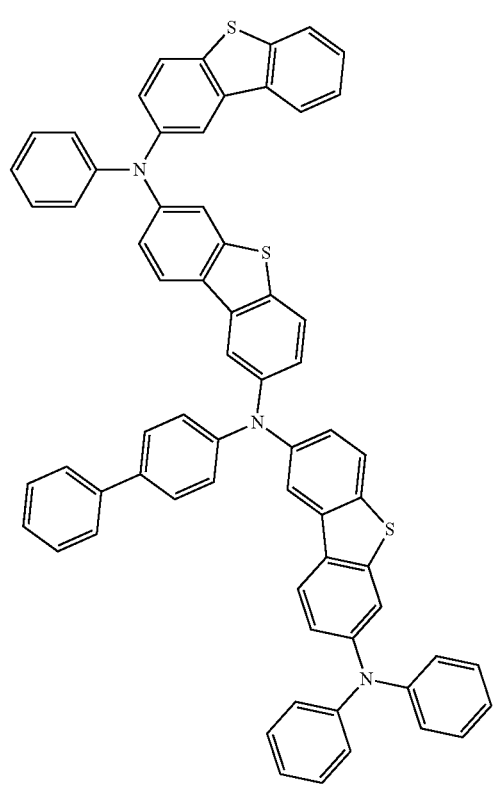
P 1-21
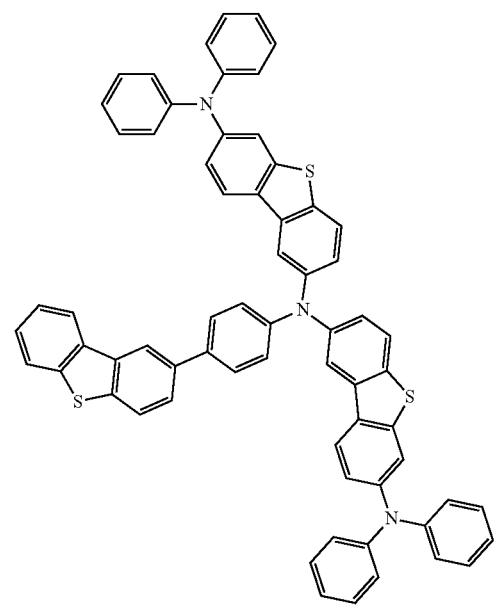
P 1-22
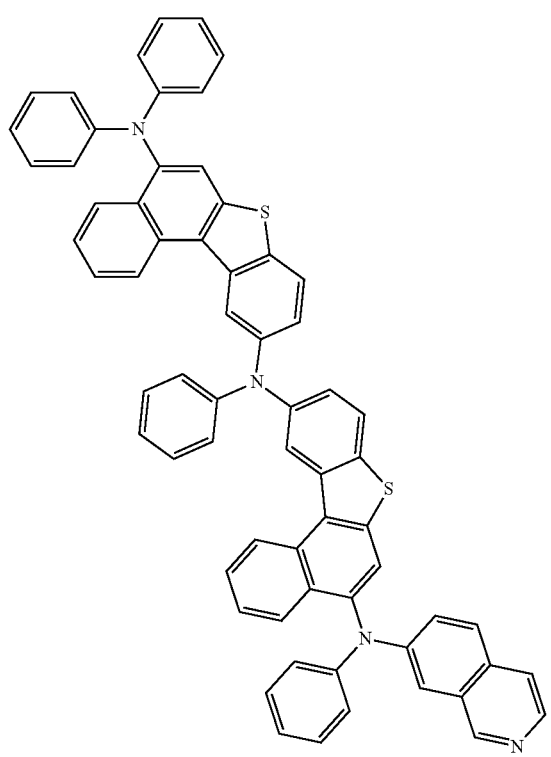

P 1-23
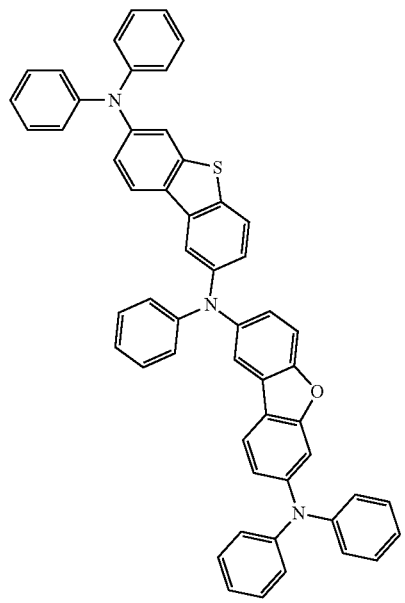
P 1-25
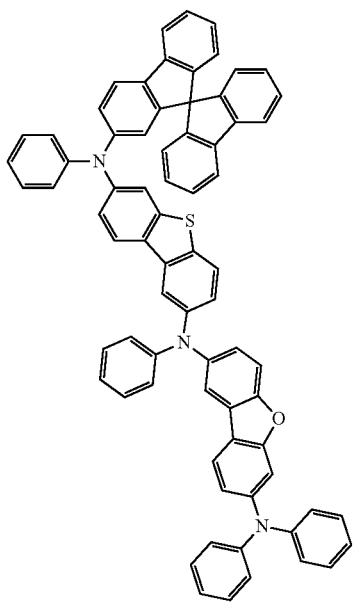
P 1-24
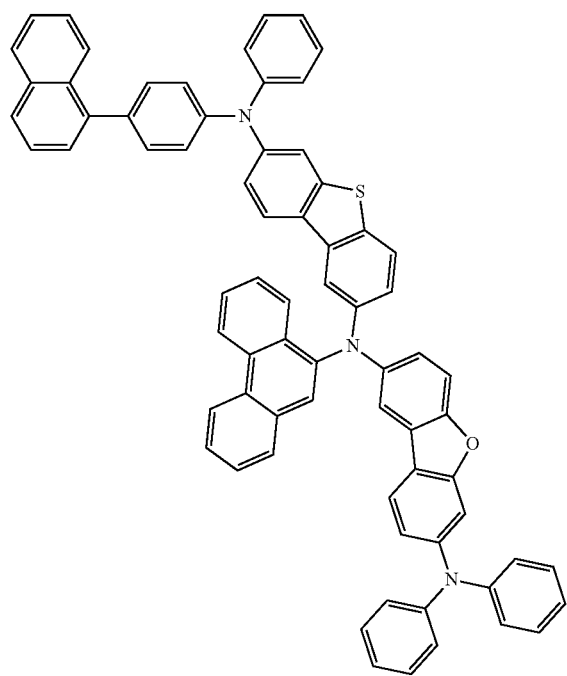
P 1-26
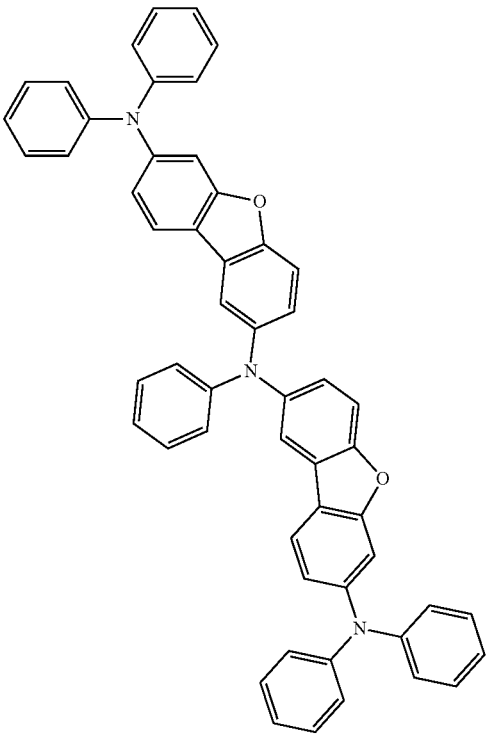

P 1-27
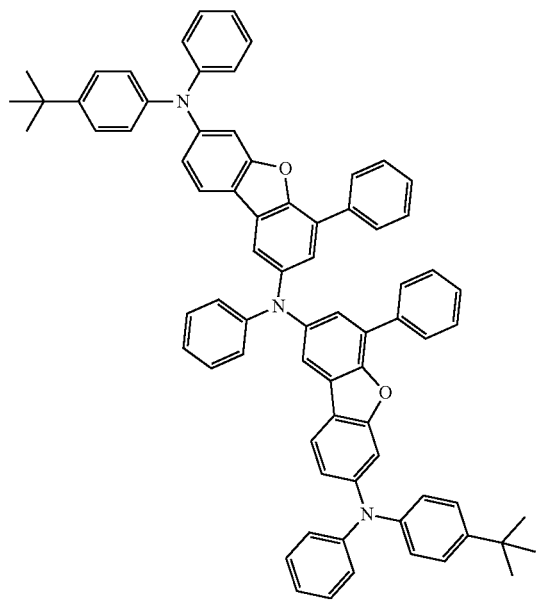
P 1-29
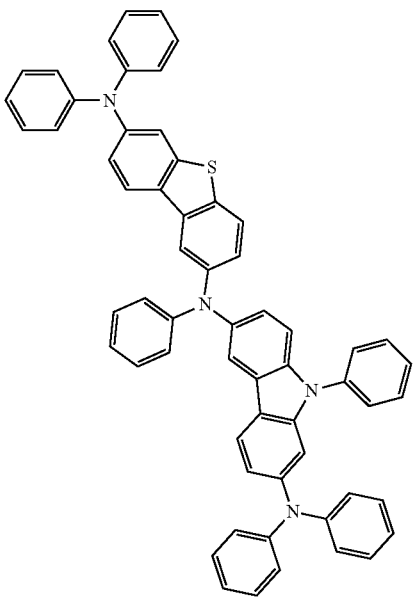
P 1-28
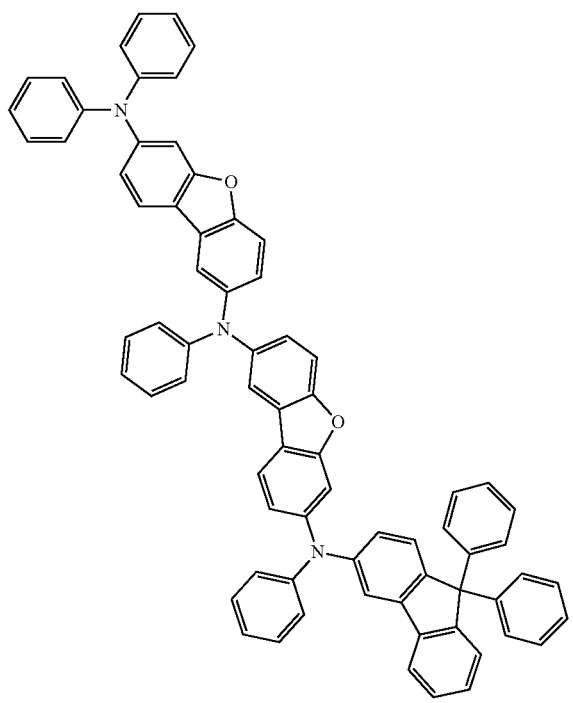
P 1-30
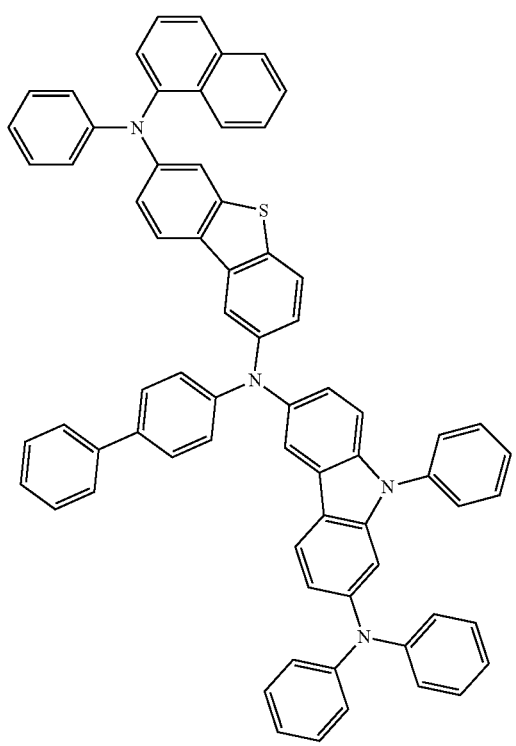

-continued
P 1-31
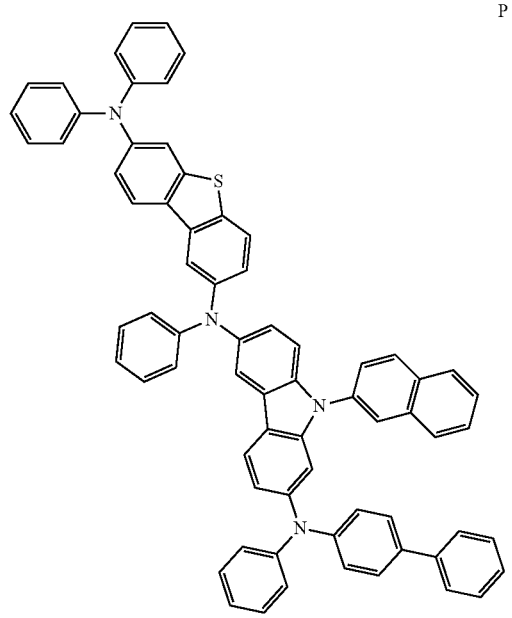
P 1-33
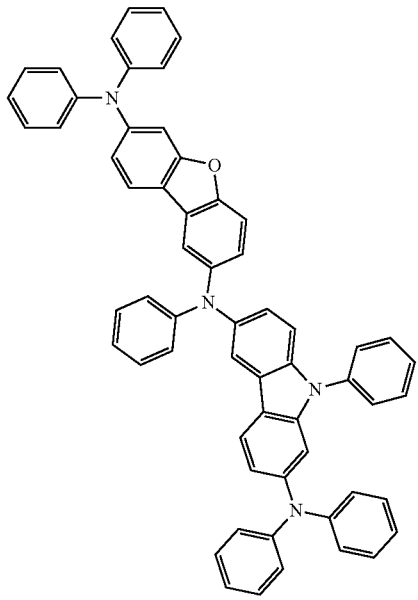
P 1-32
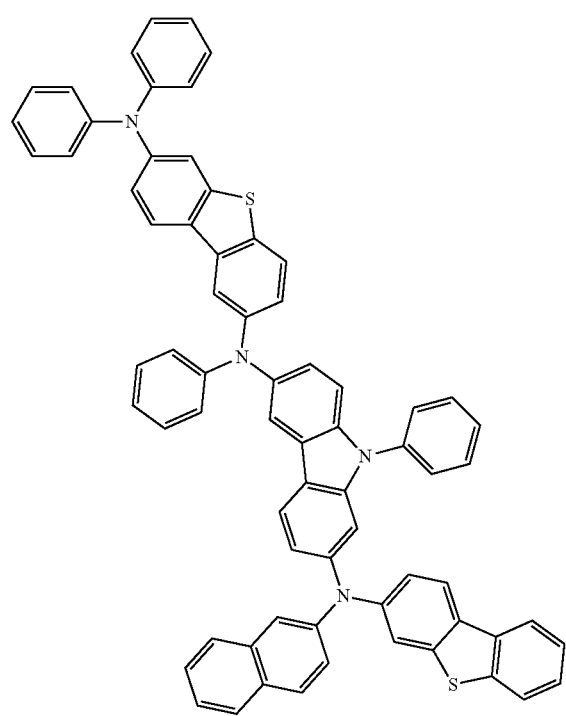
P 1-34
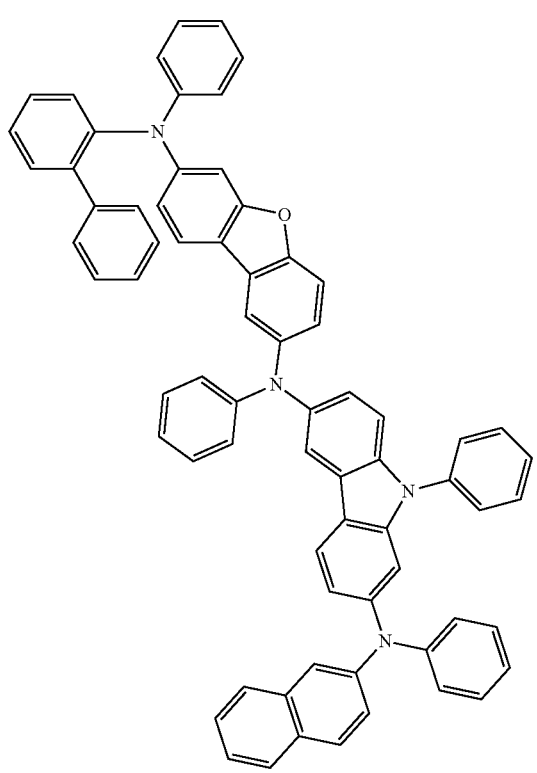

P 1-35
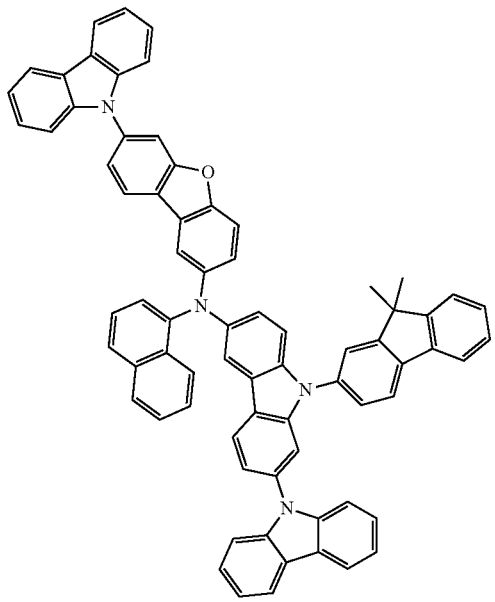
P 1-37
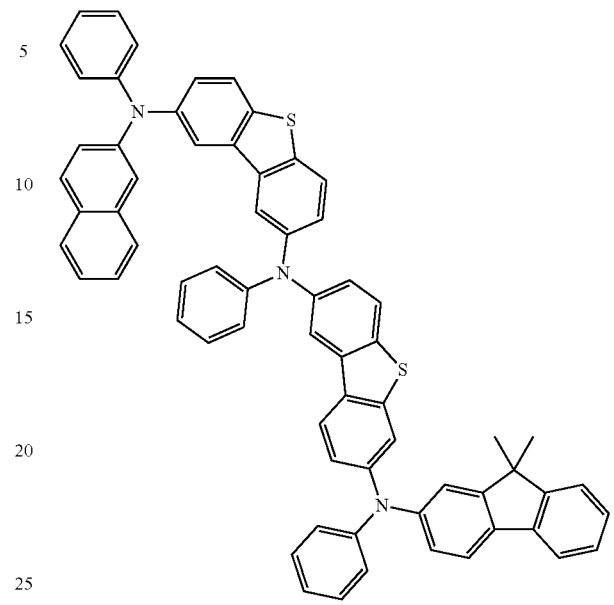
P 1-36
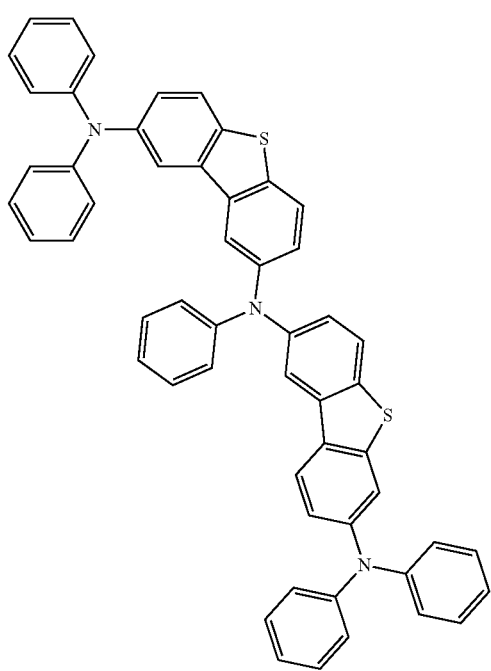
P 1-38
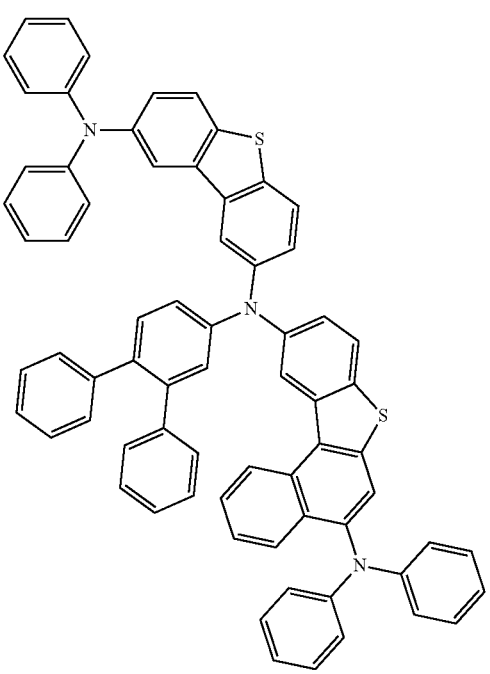

P 1-39
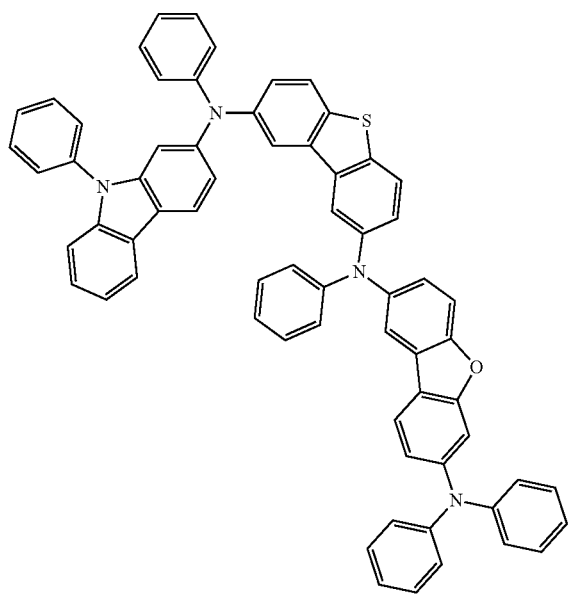
P 1-41
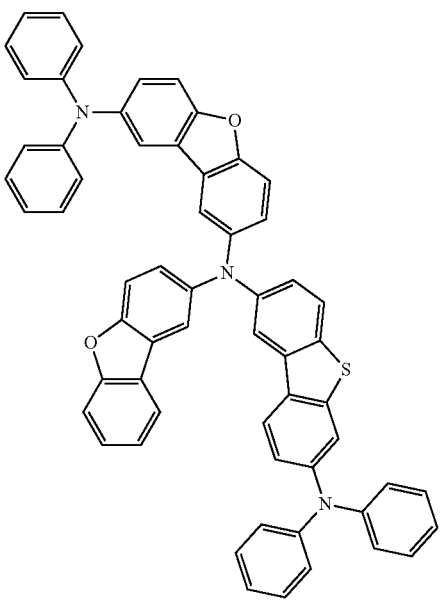
P 1-40
P 1-42
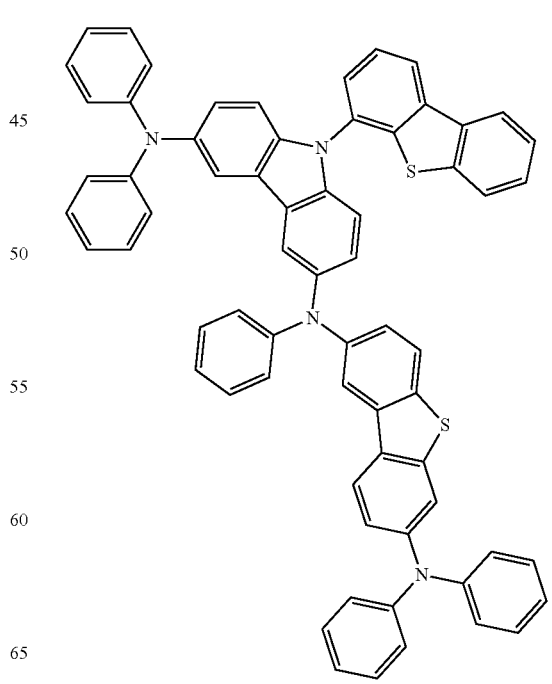

P 1-43
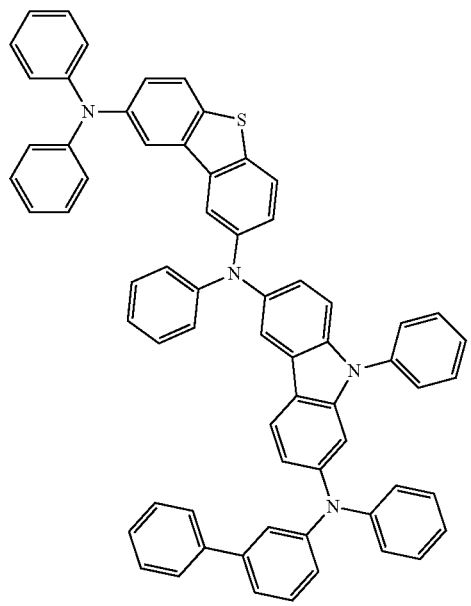
P 1-45
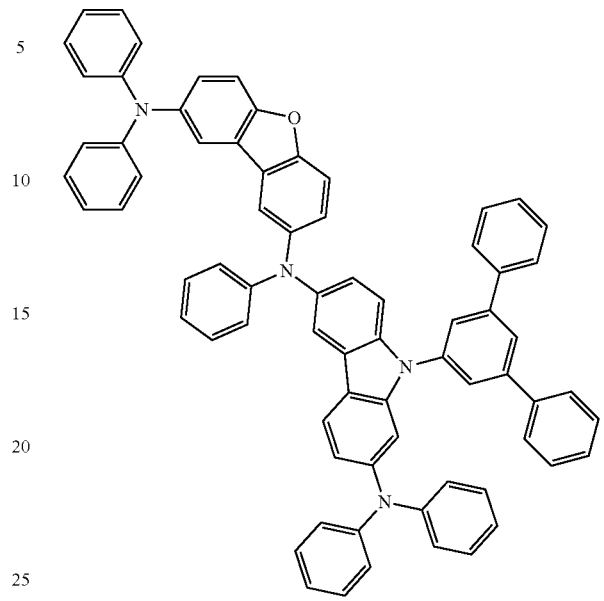
P 1-44
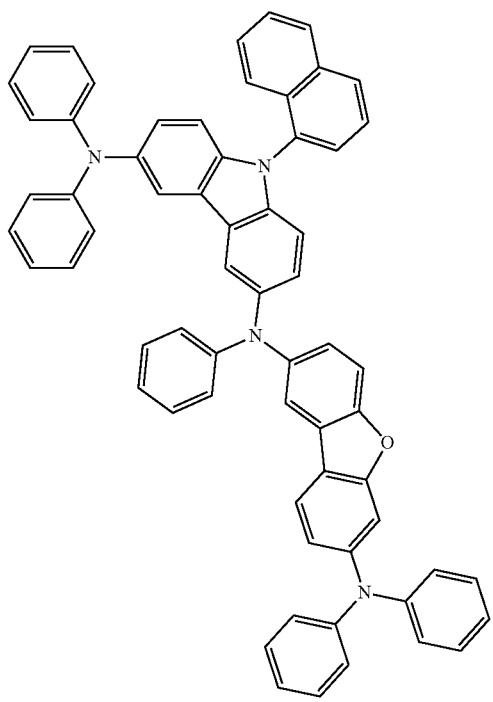
P 1-46
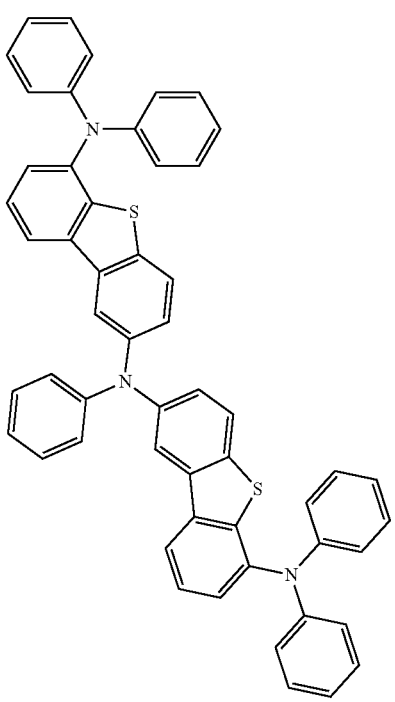

P 1-47
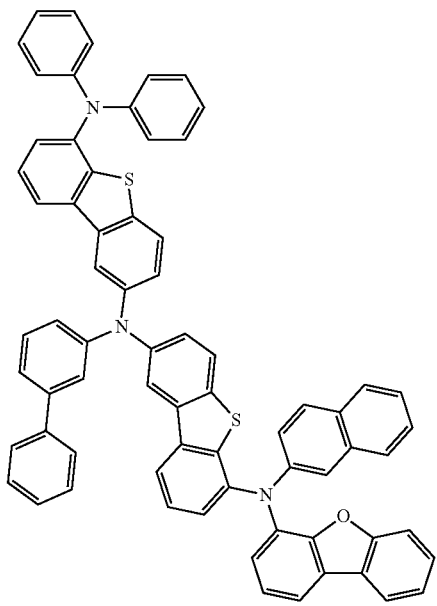
P 1-48
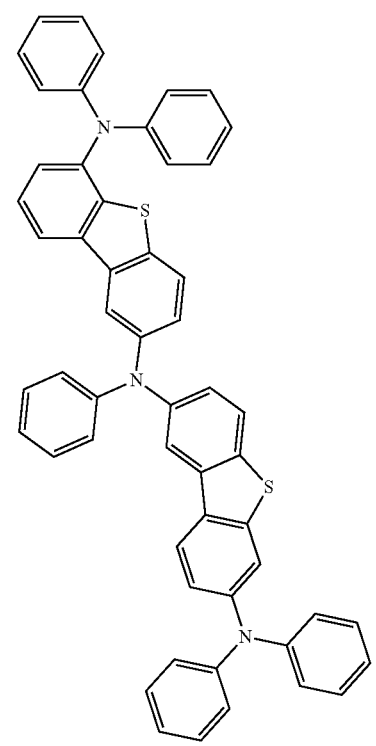
P 1-49
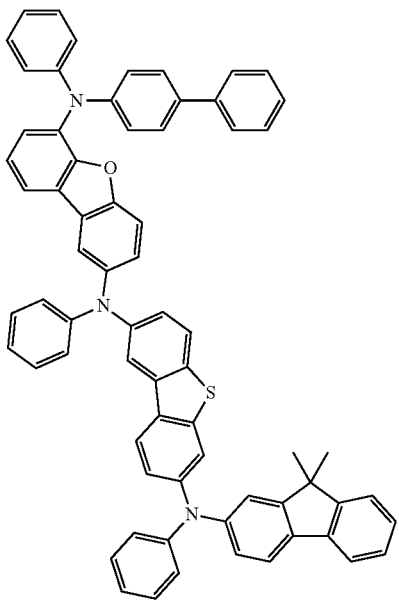
P 1-50
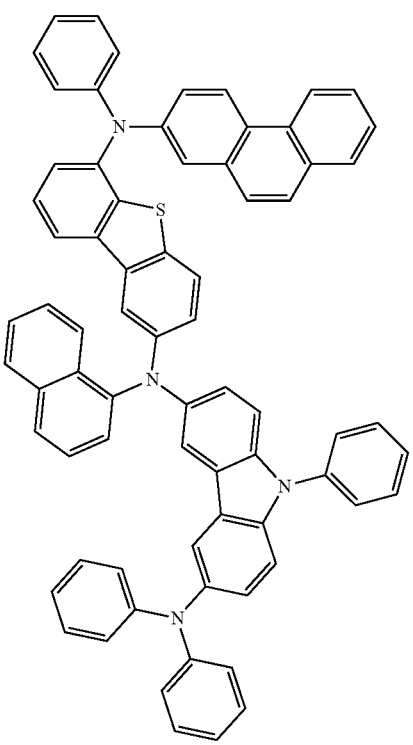

-continued
P 1-51
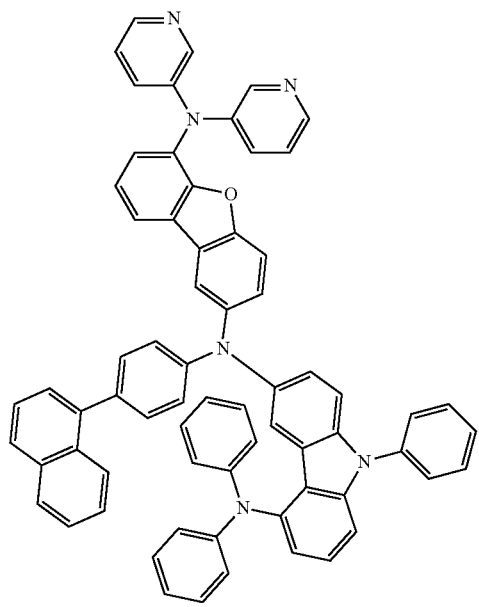
P 1-53
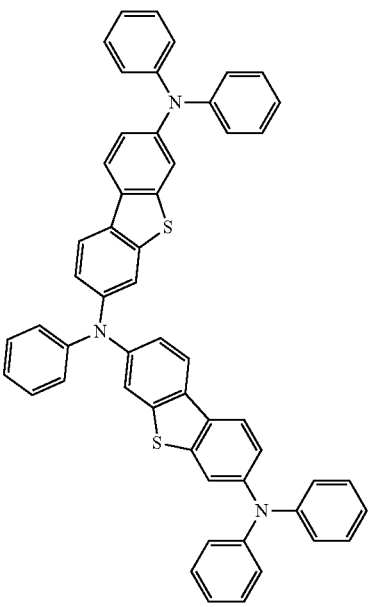
P 1-52
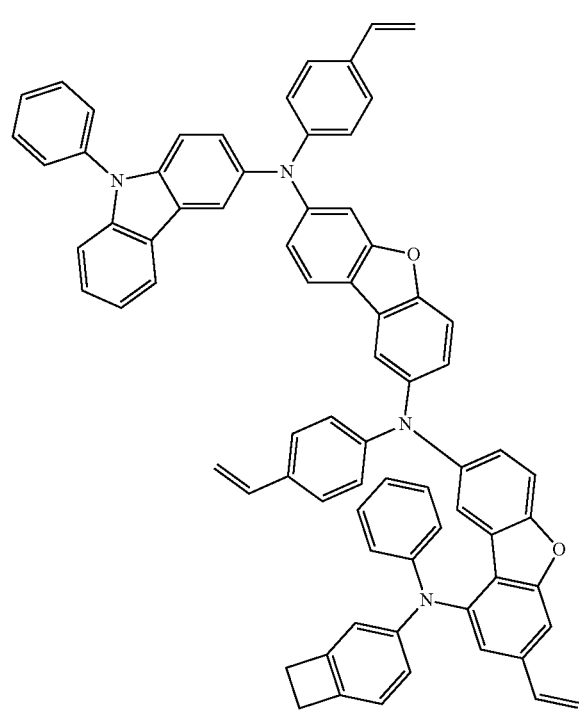
P 1-54
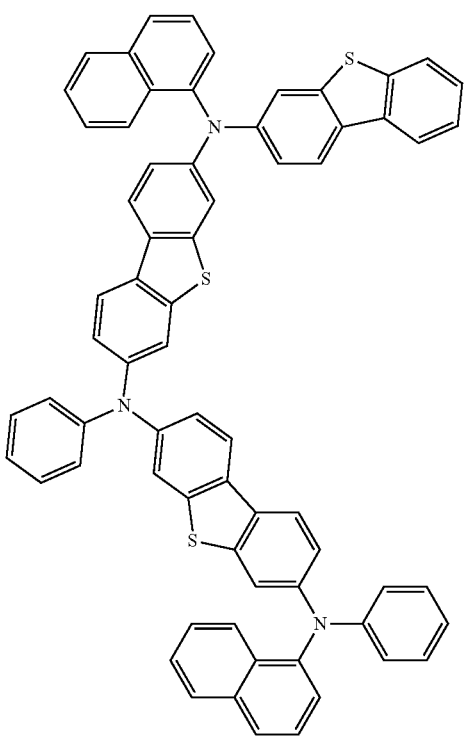

-continued
P 1-55
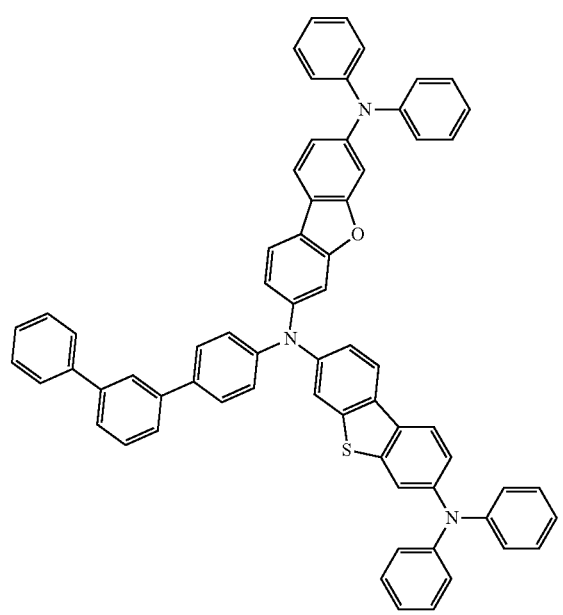
P 1-57
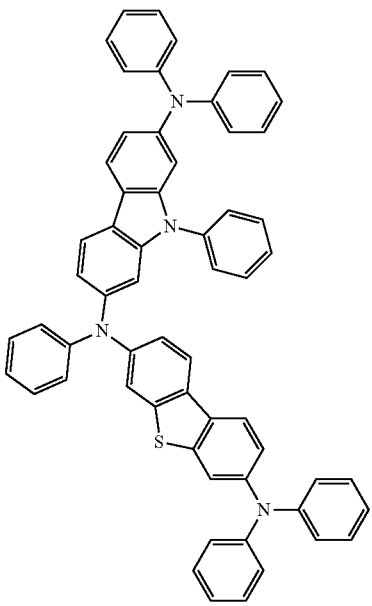
P 1-56
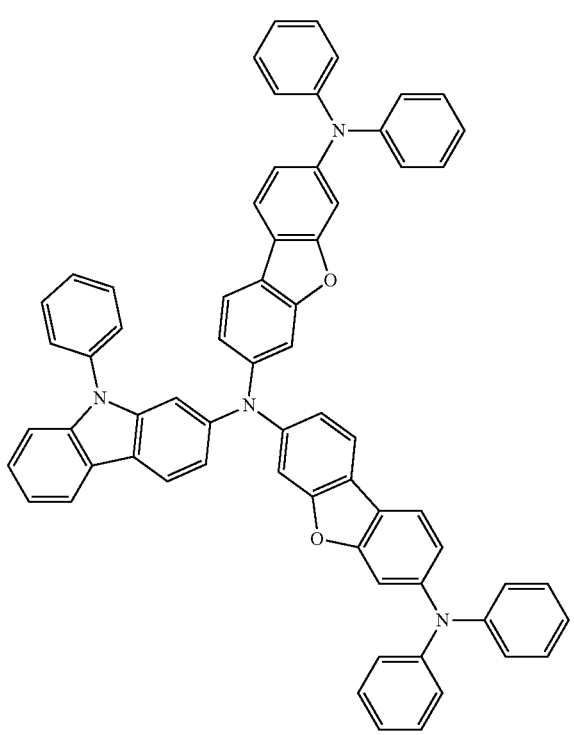
P 1-58
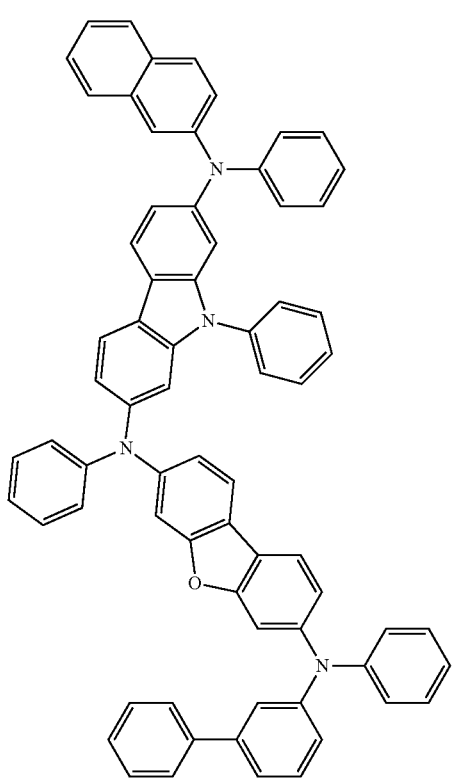

P 1-59
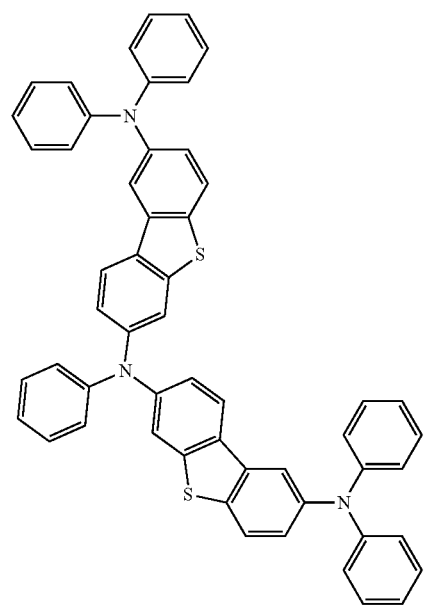
P 1-61
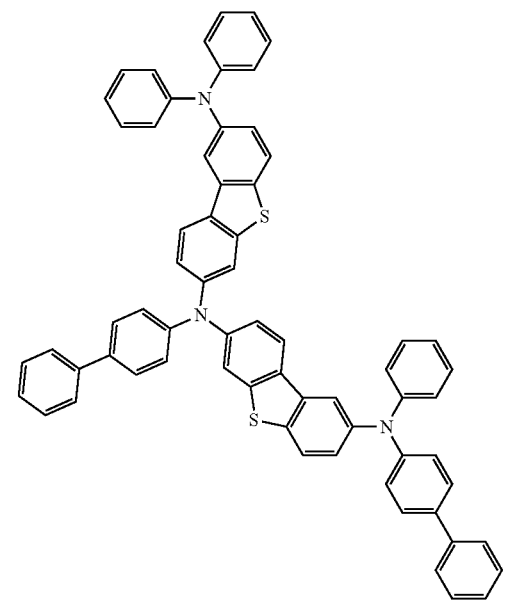
P 1-60
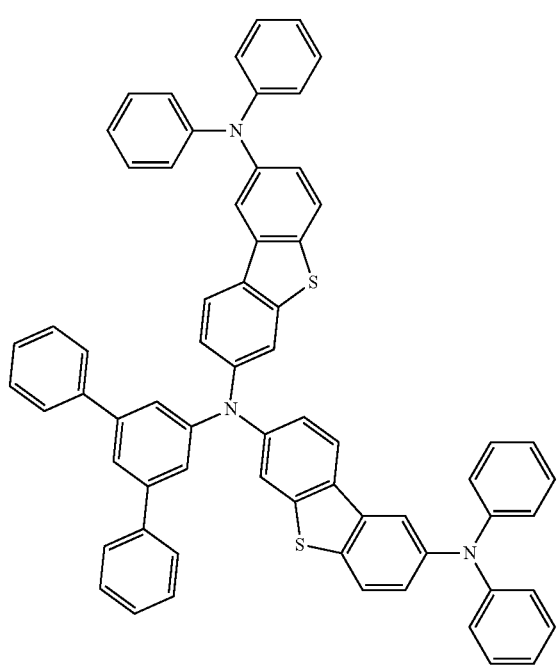
P 1-62
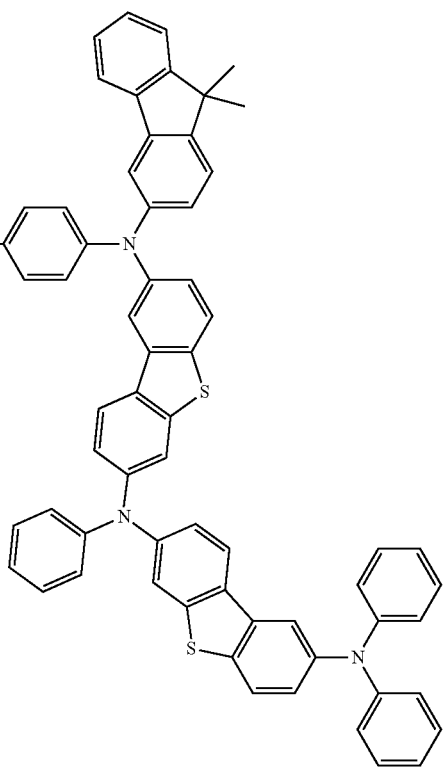

P 1-63
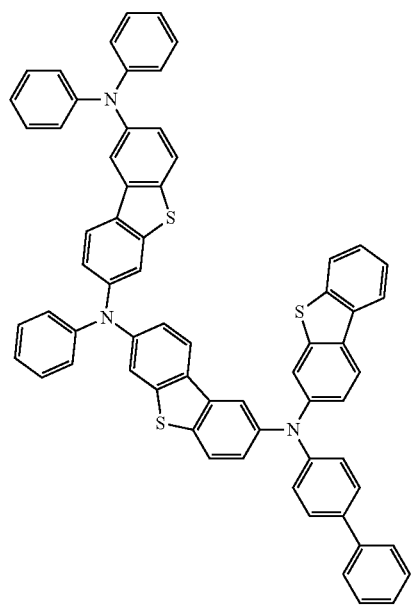
P 1-65
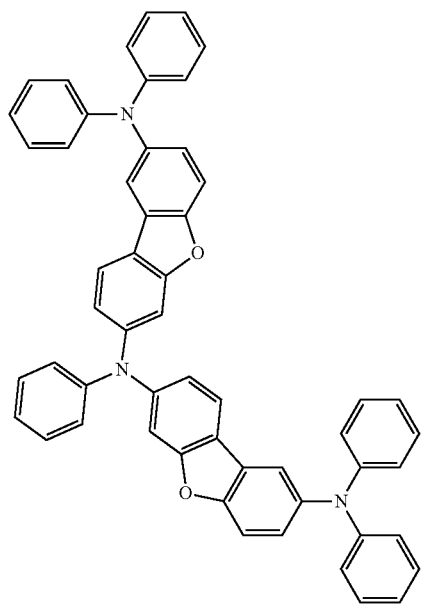
P 1-64
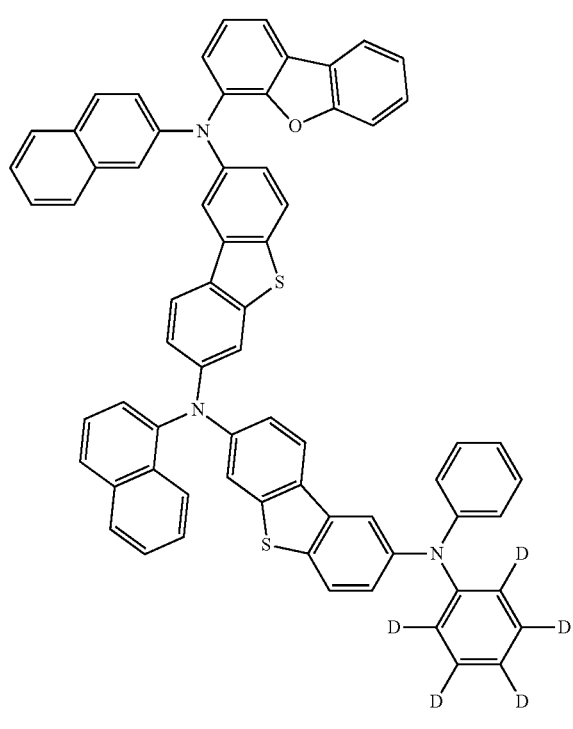
P 1-66
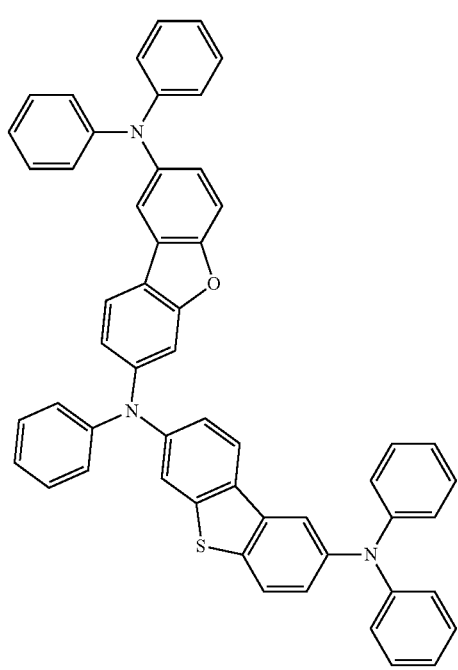

P 1-67
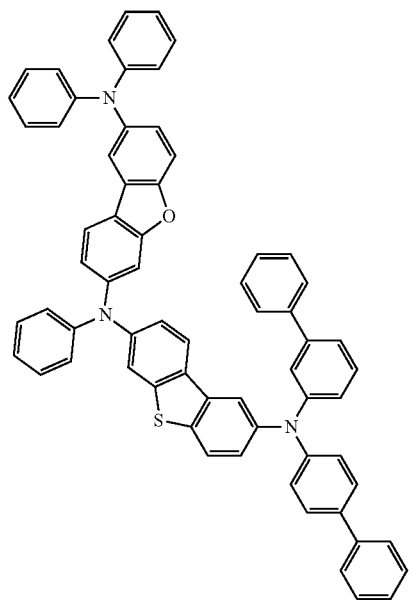
P 1-68
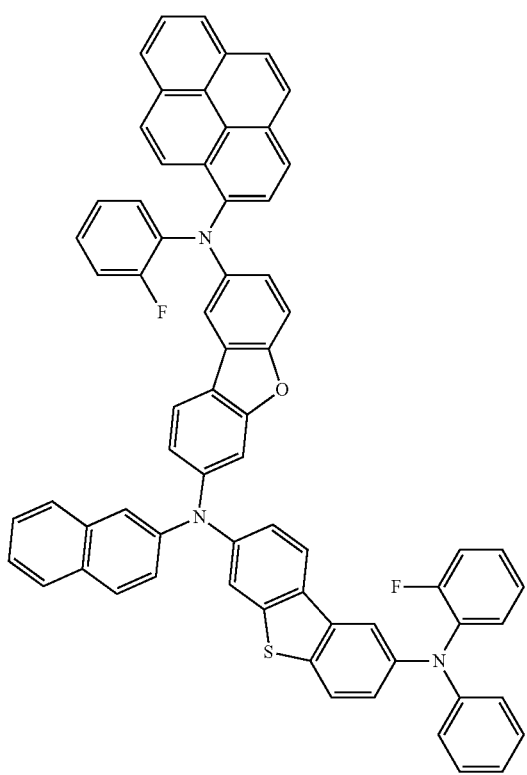
P 1-69
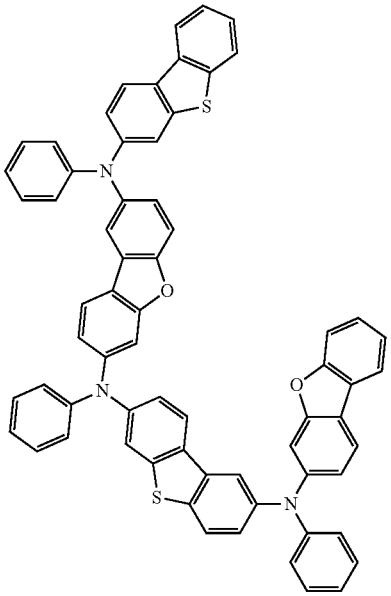
P 1-70
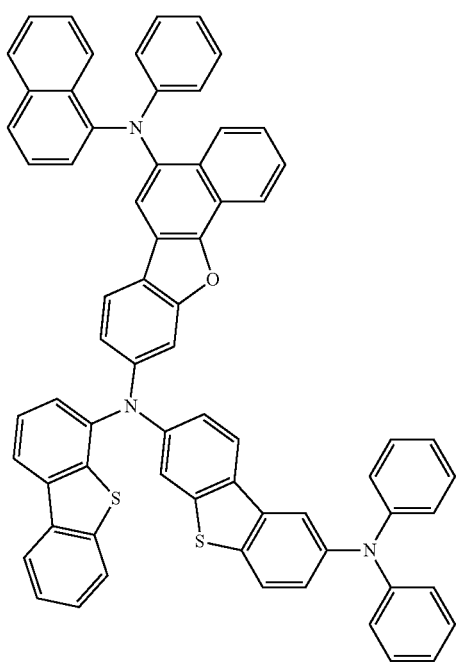

P 1-71
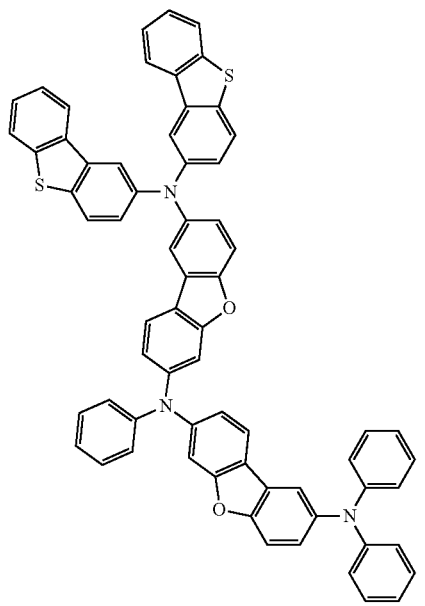
P 1-73
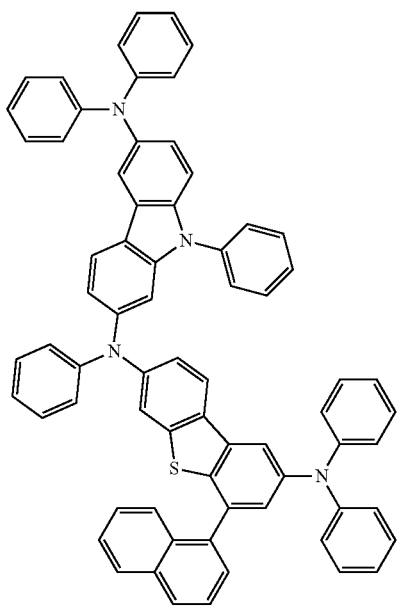
P 1-72
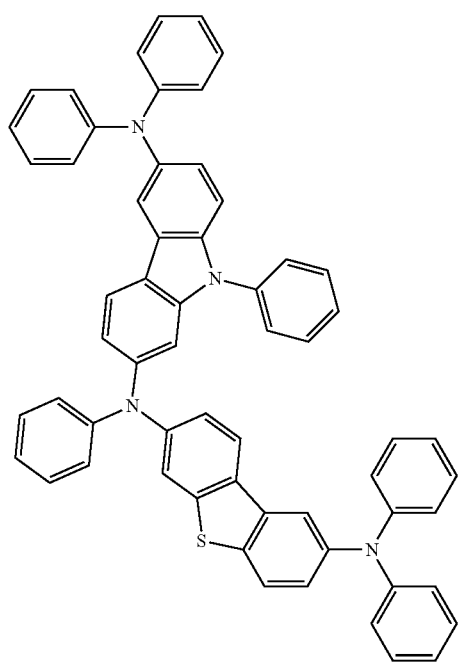
P 1-74
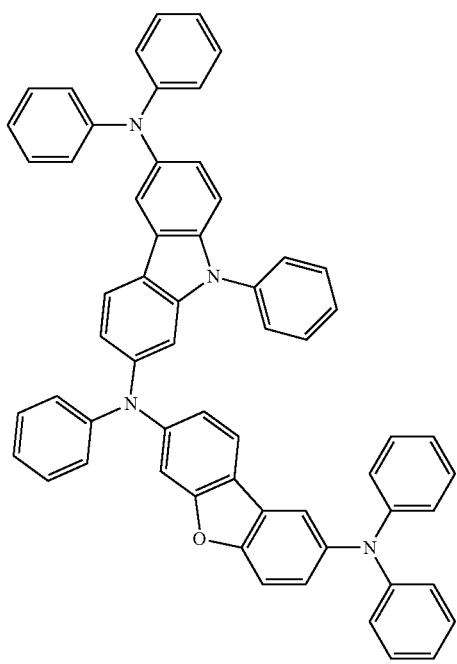

P 1-75
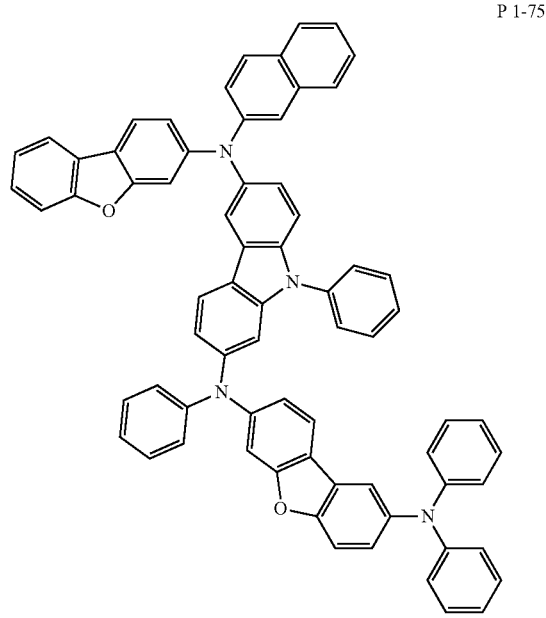
P 1-76
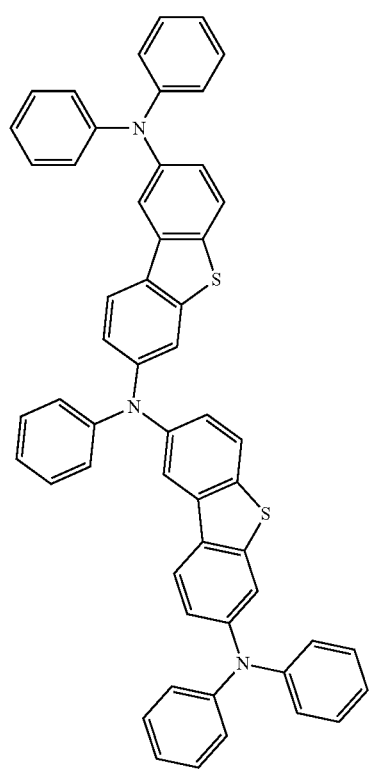
P 1-77
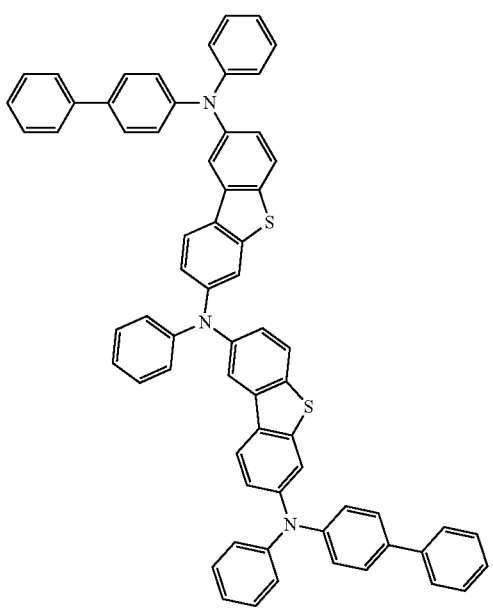
P 1-78
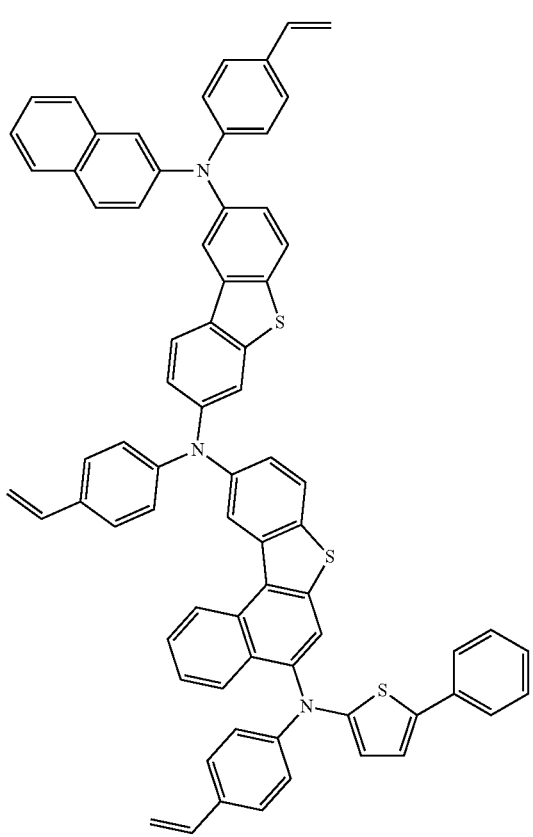

P 1-79
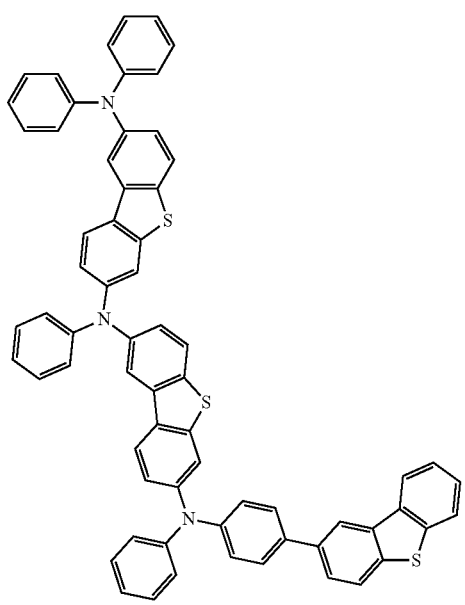
P 1-81
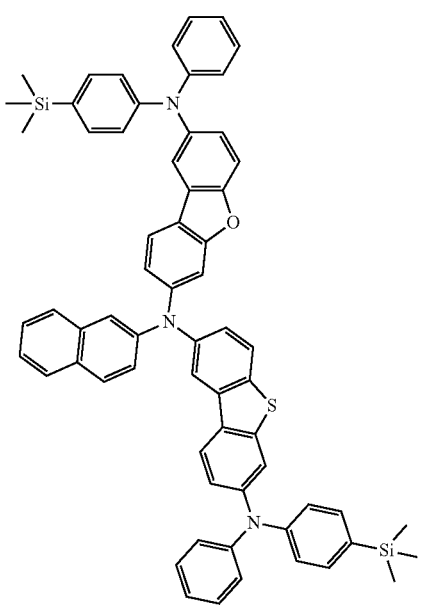
P 1-80
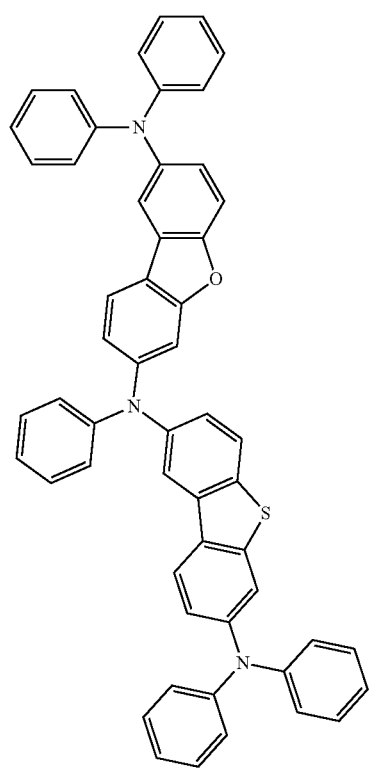
P 1-82
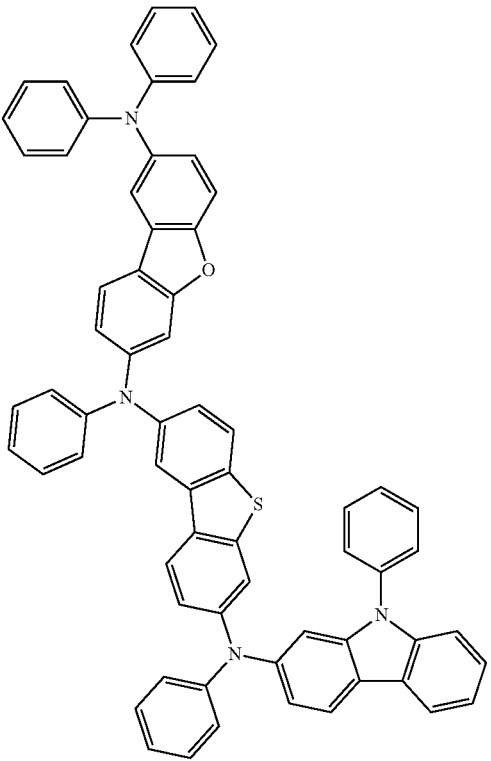

P 1-83
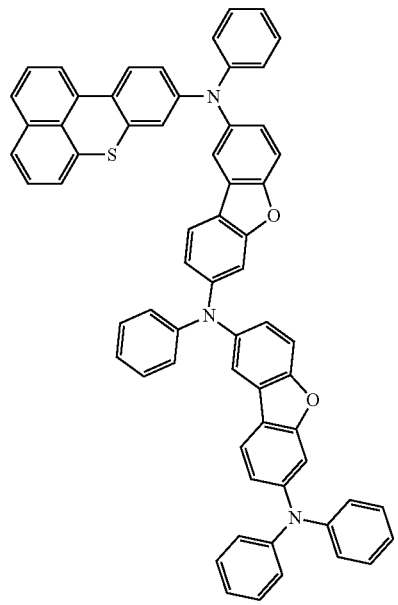
P 1-84
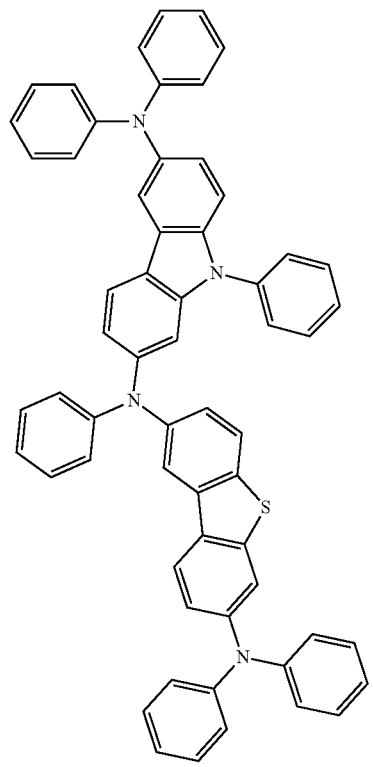
P 1-85
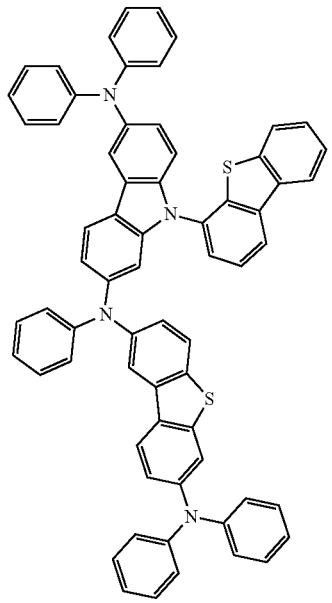
P 1-86
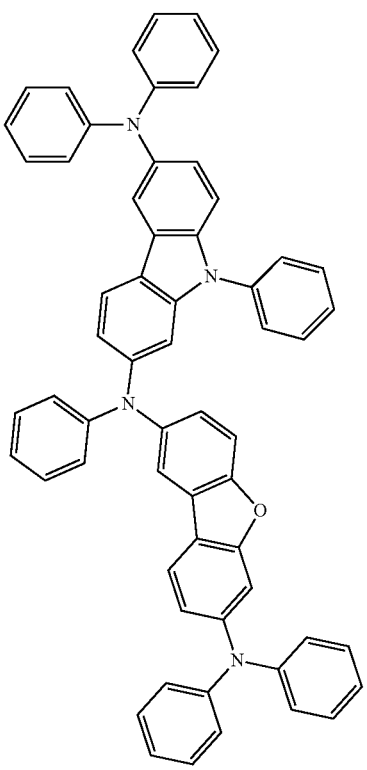

P 1-87
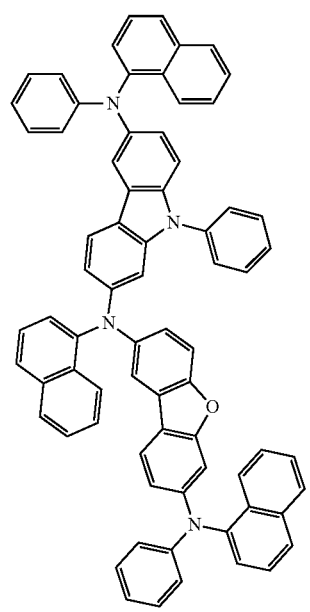
P 1-88
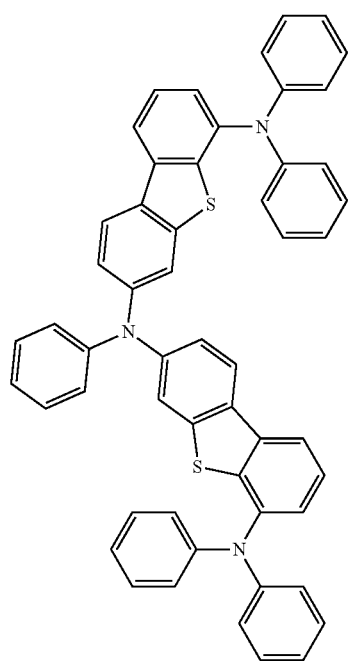
P 1-89
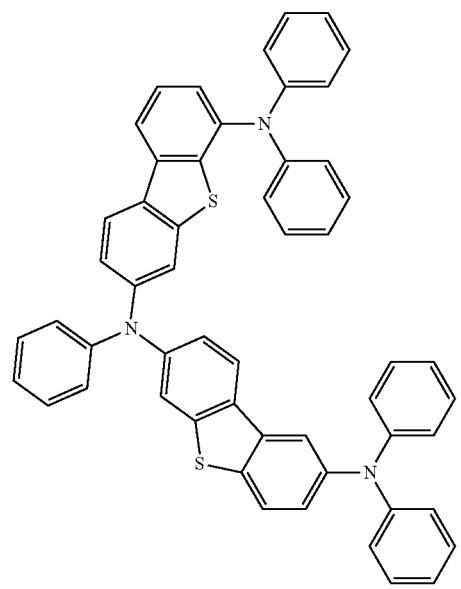
P 1-90
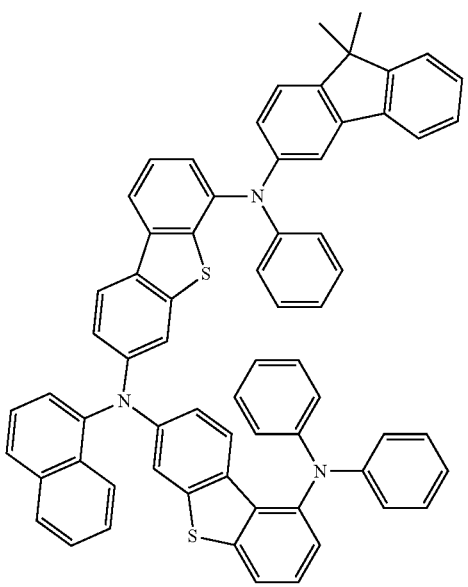

P 1-91
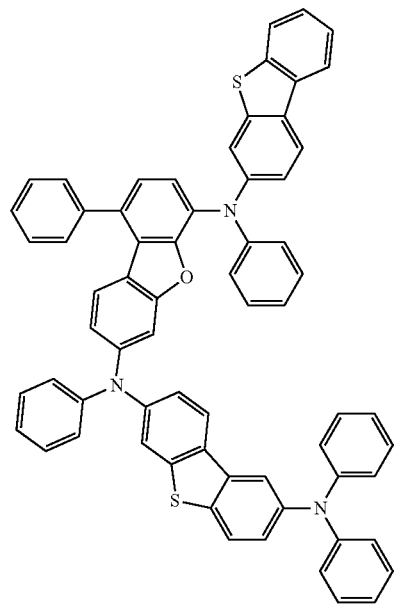
P 1-93
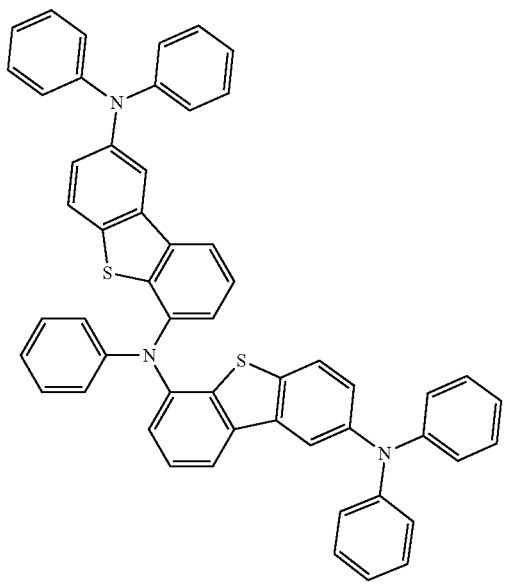
P 1-92
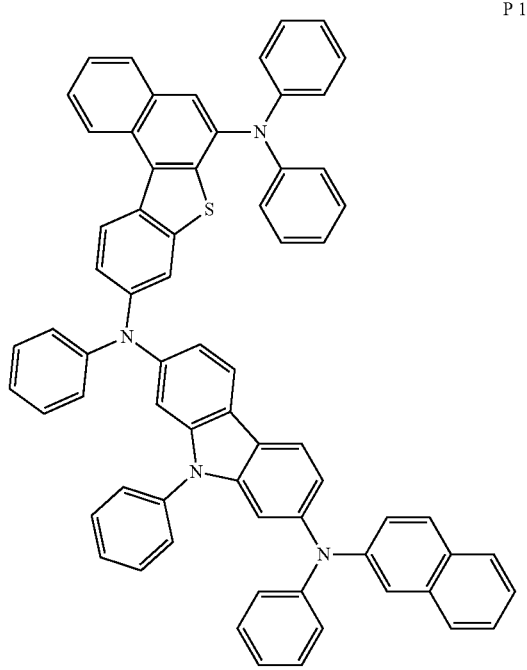
P 1-94
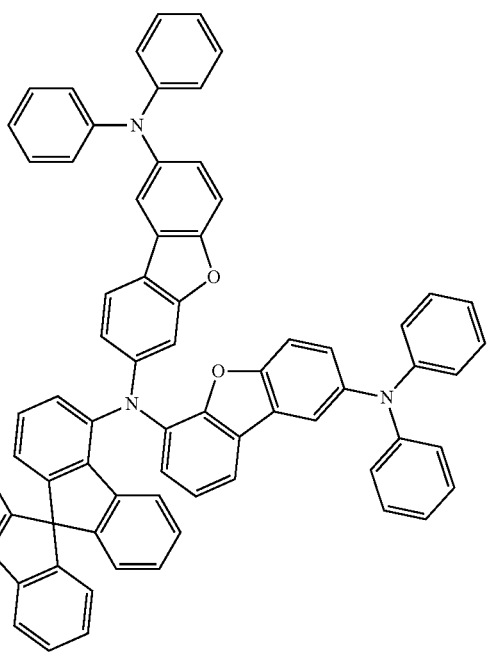

P 1-95
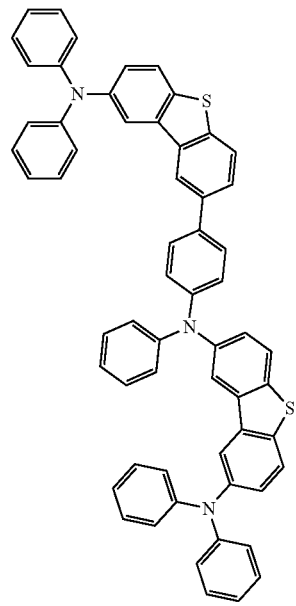
P 1-96
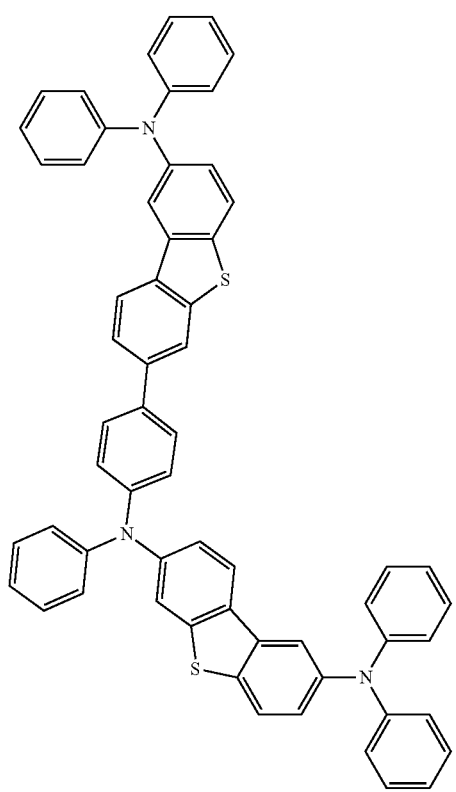
P 1-97
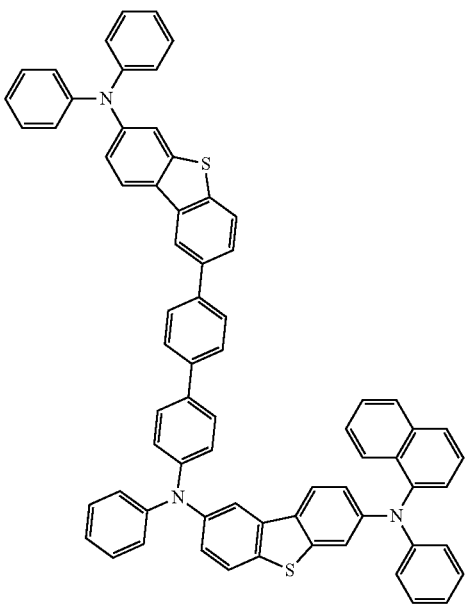
P 1-98
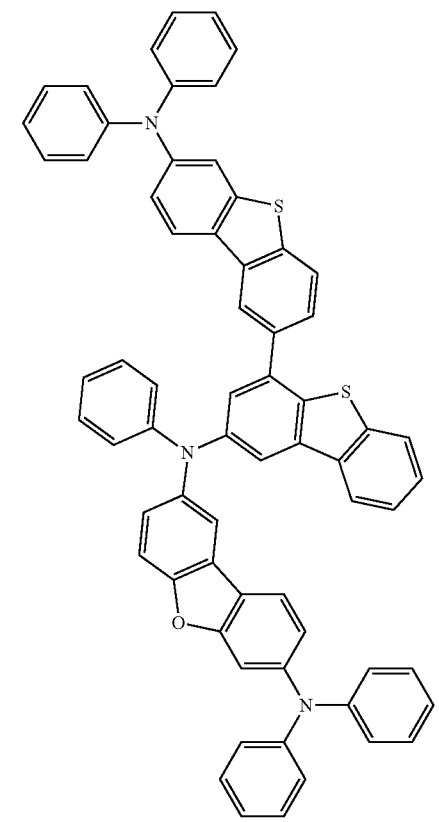

P 1-99
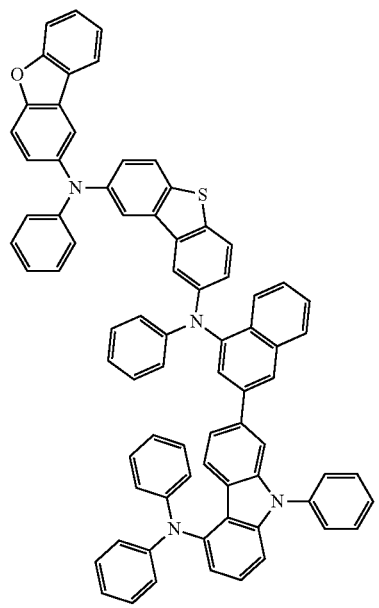
P 1-101
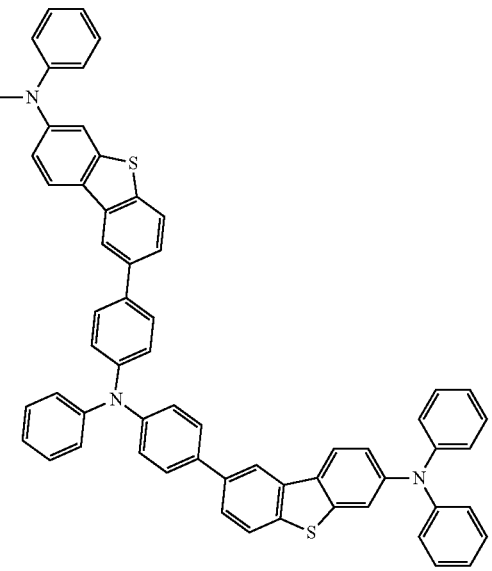
P 1-100
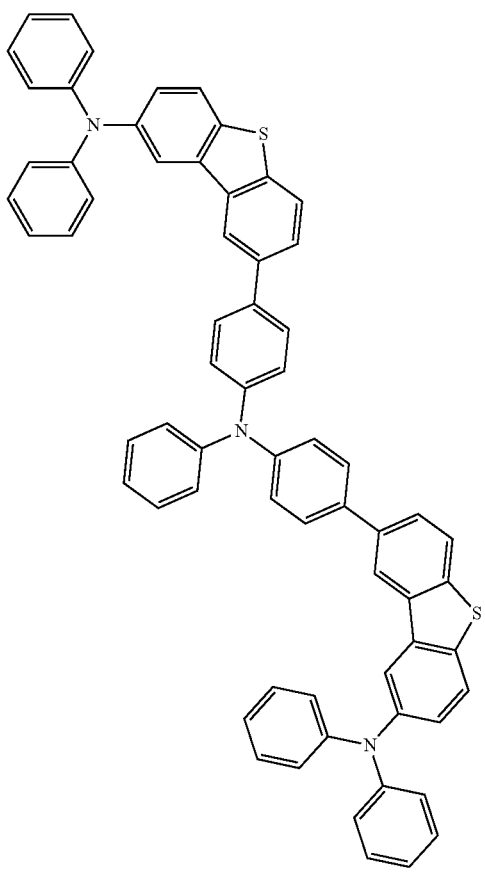
P 1-102
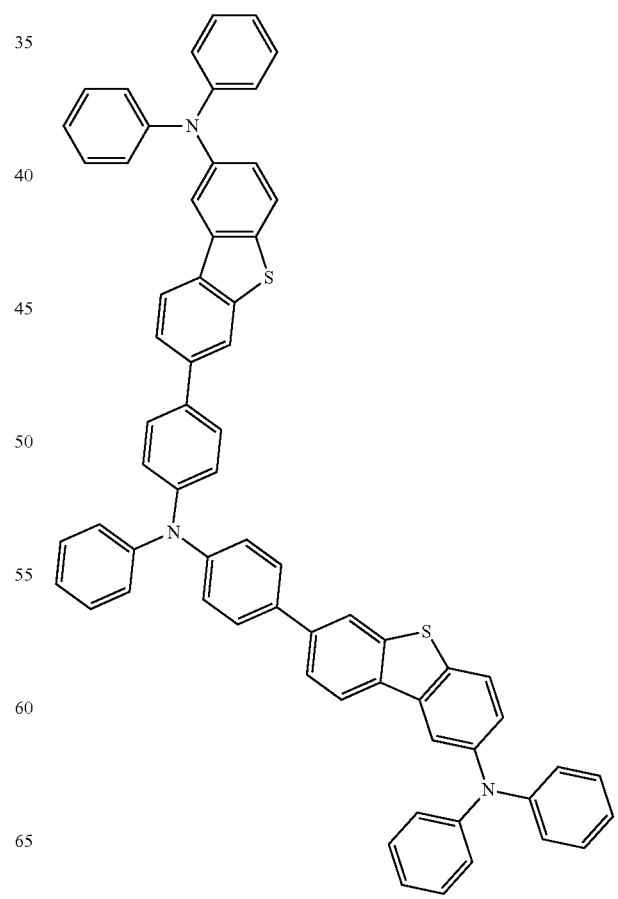

P 1-103
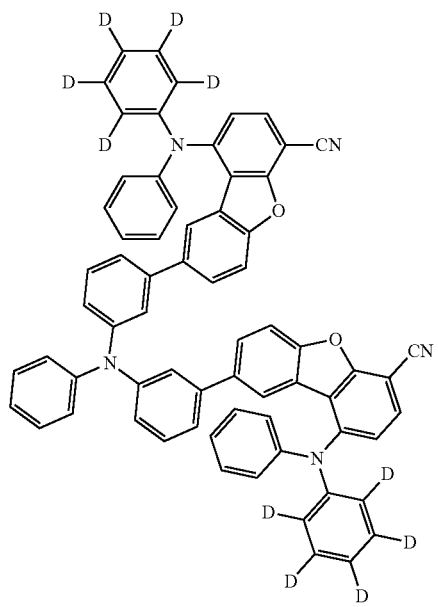
P 1-104
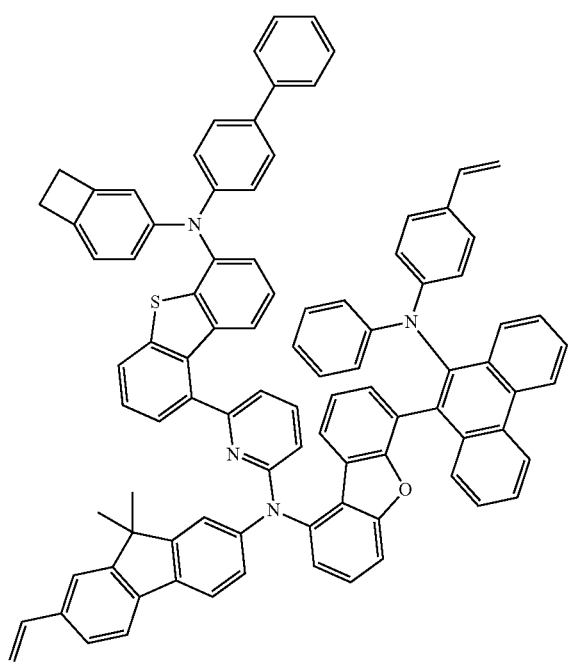
P 1-105
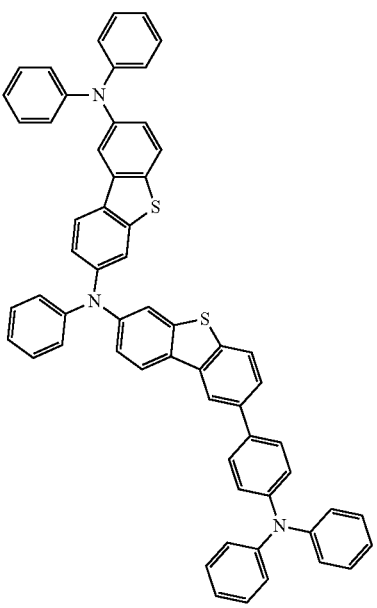
P 1-106
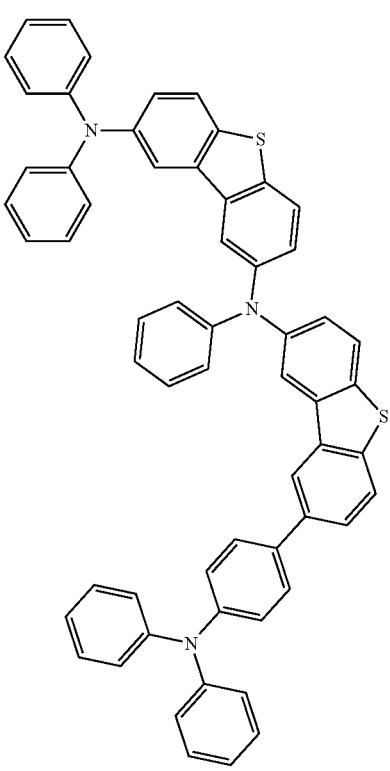

P 1-107
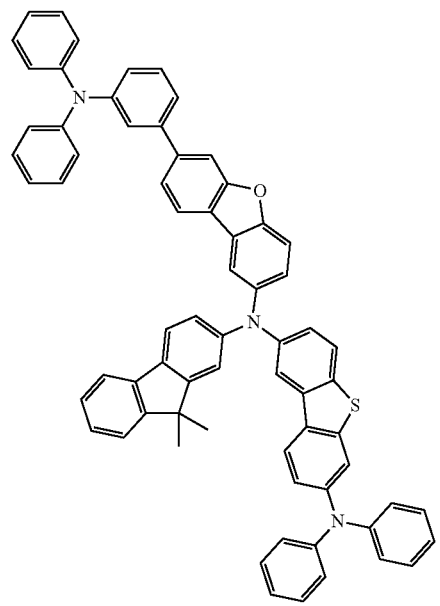
P 1-109
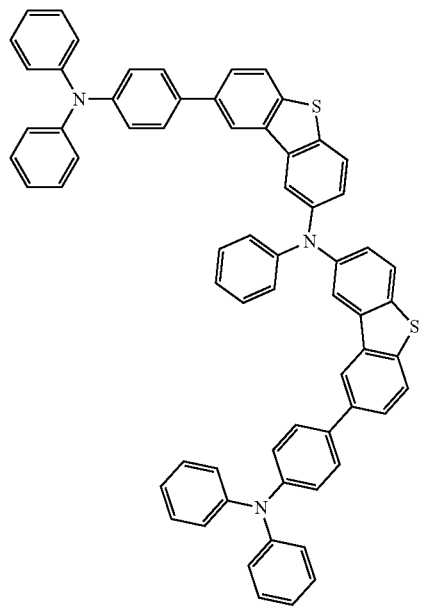
P 1-108
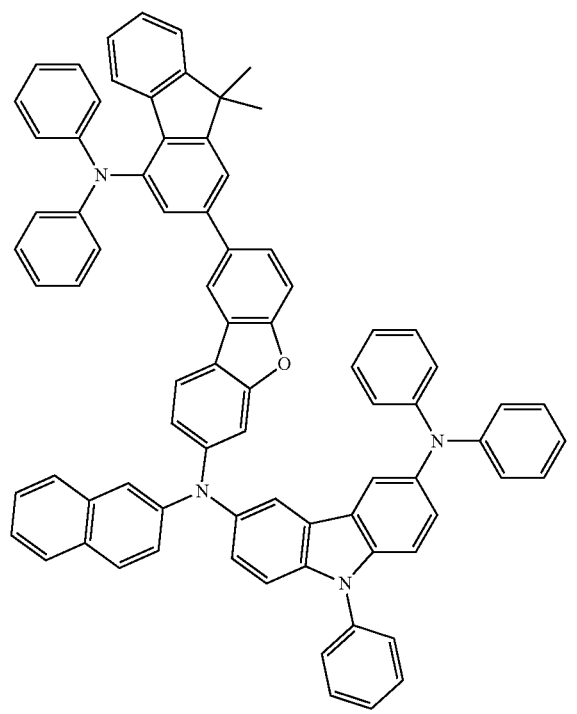
P 1-110
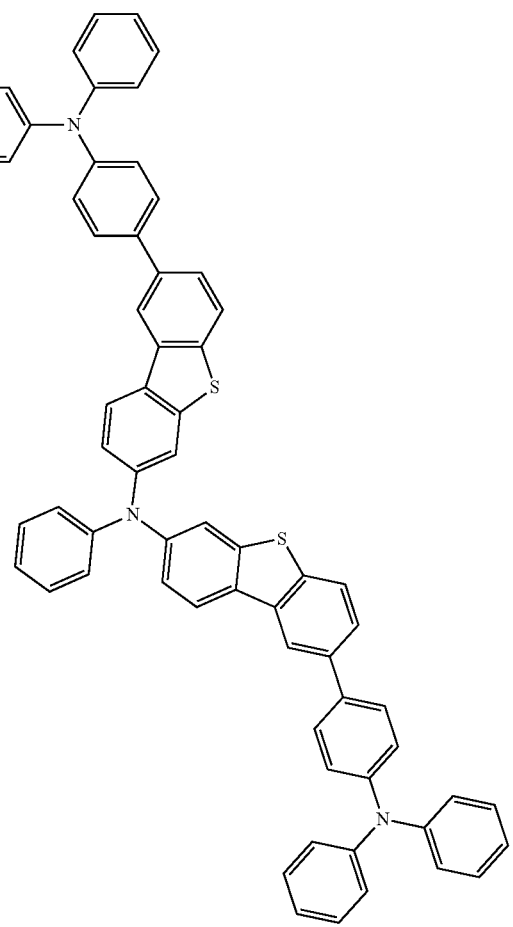

-continued

P 1-111

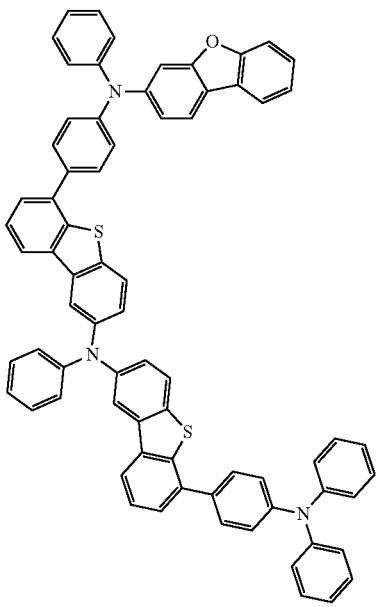

P 1-112

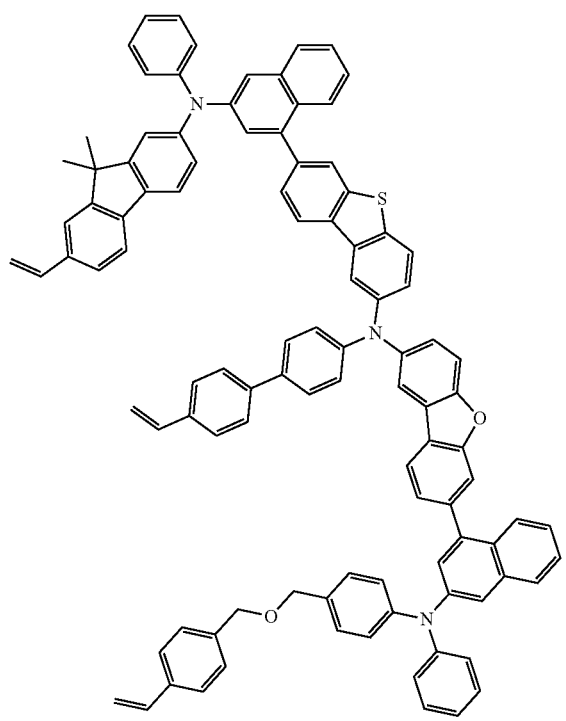

Referring to the FIGURE, the organic electric element (100) according to the present invention comprises a first electrode (120) formed on a substrate (110), a second electrode (180), and an organic material layer including the compound represented by Formula (1) between the first electrode (120) and the second electrode (180). Here, the first electrode (120) may be an anode (positive electrode), and the second electrode (180) may be a cathode (negative electrode). In the case of an inverted organic electric element, the first electrode may be a cathode, and the second electrode may be an anode.

The organic material layer may comprise a hole injection layer (130), a hole transport layer (140), an emitting layer (150), an emitting auxiliary layer (151), an electron transport layer (160), and an electron injection layer (170) formed in sequence on the first electrode (120).

Although not shown, the organic electric element according to the present invention may further comprise a protective layer formed on at least one surface of the first electrode and the second electrode opposite to the organic material layer.

Otherwise, even if the same core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels, T1 values and unique properties of materials (mobility, interfacial characteristics, etc.) of each organic material layer is achieved, a long life span and high efficiency can be achieved at the same time.

The organic electroluminescent device according to an embodiment of the present invention may be manufactured using a PVD (physical vapor deposition) method. For example, a metal or a metal oxide having conductivity or an alloy thereof is deposited on a substrate to form a cathode, and the organic material layer including the hole injection layer (130), the hole transport layer (140), the emitting layer (150), the emitting auxiliary layer (151), the electron transport layer (160), and the electron injection layer (170) is formed thereon, and then depositing a material usable as a cathode thereon can manufacture an organic electroluminescent device according to an embodiment of the present invention.

Accordingly, the present invention provides an organic electric element comprising a first electrode; a second electrode; and an organic material layer between the first electrode and the second electrode, wherein the organic material layer comprises a hole injection layer, a hole transport layer, an emitting auxiliary layer and an emitting layer, and wherein the organic material layer comprises a compound included in Formula (1).

In addition, the present invention provides an organic electric element, wherein the organic electric element comprises a compound according to Formula (1) in at least one of the hole injection layer, the hole transport layer, the emitting auxiliary layer and the emitting layer, and wherein the compound comprises a compound alone or a mixture of two or more compounds represented by Formula (1).

In addition, the present invention provides an organic electric element, wherein the organic electric element comprises the compound alone represented by Formula (1) or a mixture of two or more compounds having different structures, in the hole transport layer or the emitting auxiliary layer.

Further, as a specific example of the present invention, the emitting layer comprises a compound represented by Formula (16).

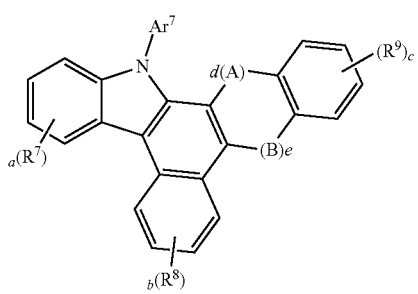

Formula (16)


Formula (17)


Formula (18)

{In Formula (16),

1) $Ar^7$ is each independently selected from the group consisting of a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; -L-N($R^a$)($R^b$); (where, L' may be selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic group, and the $R^a$ and $R^b$ may be each independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group containing at least one hetero atom of O, N, S, Si, or P)

2) a, b and c are integers of 0 to 4,

3) $R^7$, $R^8$ and $R^9$ are the same or different and are each independently selected from a deuterium; a halogen; the group consisting of a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$); and in case a, b and c are 2 or more, and are each in plural and are the same or different, or a plurality of $R^7$ or a plurality of $R^8$ or a plurality of $R^9$ may be bonded to each other to form an aromatic or a heteroaromatic ring, 4) A and B are single bond, and are S, O, NR' or CR'R", 5) R' and R" are a hydrogen; a $C_6$-$C_{60}$ aryl group; a fluorenyl group; a $C_3$-$C_{60}$ heterocyclic group; or a $C_1$-$C_{50}$ alkyl group; and R' and R" may be bonded to each other to form a spiro compound, 6) d and e are 0 or 1, and provided that d+e is not less than 1.}

In the present invention, the compound represented by Formula (16) is the following Formula (17) or (18), and an organic electric element includes the compound in the emitting layer.

(In Formula (17) and (18), $R^7$, $R^8$, $R^9$, A, b, c, $Ar^7$, A and B are the same as defined in Formula (16).)

The compound represented by Formula (16) comprises a compound represented by any one of following Formula (19) to Formula (34).

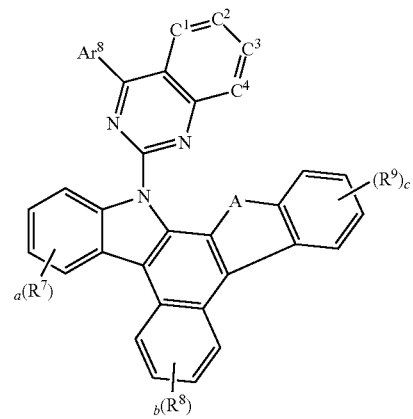

Formula (19)

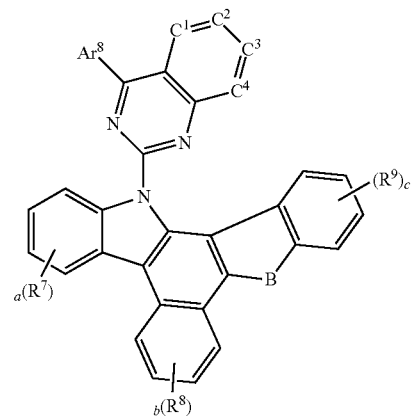

Formula (20)

Formula (21)
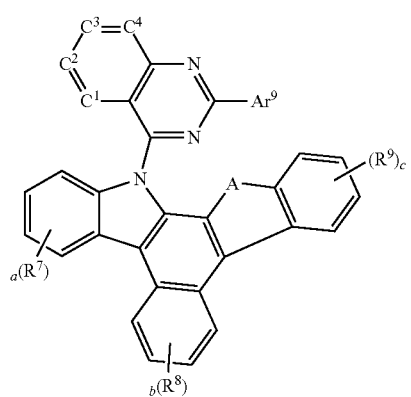
Formula (22)
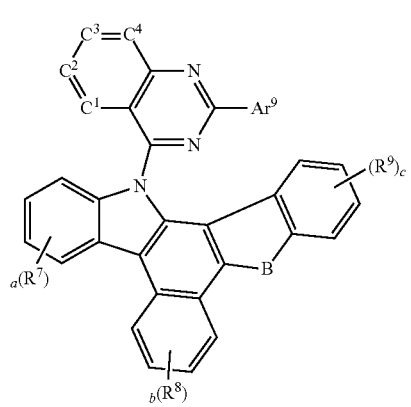
Formula (23)
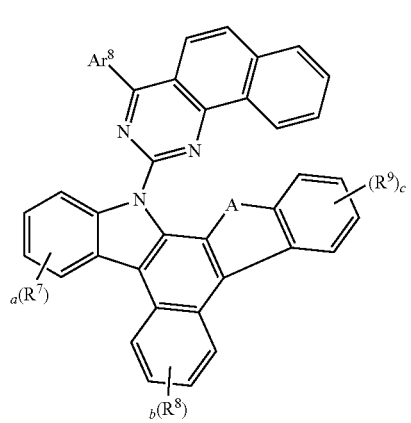
Formula (24)
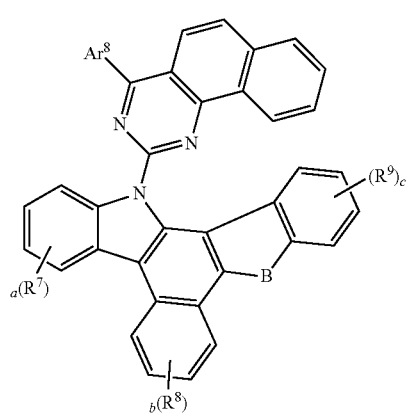
Formula (25)
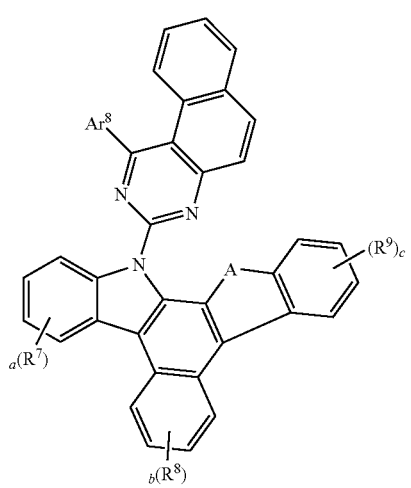
Formula (26)
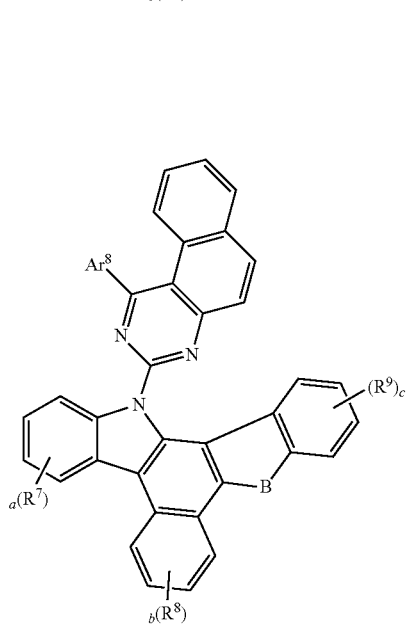
Formula (27)
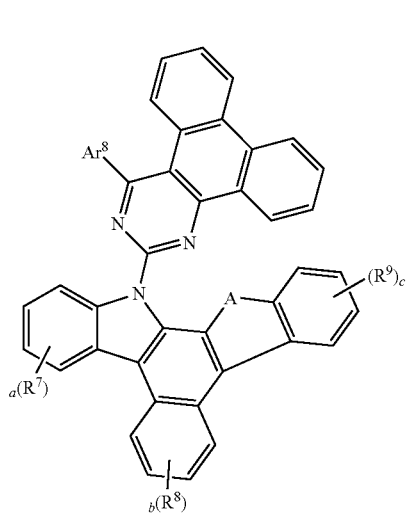

Formula (28)
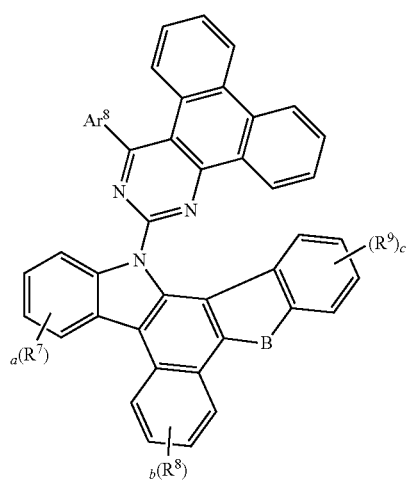
Formula (29)
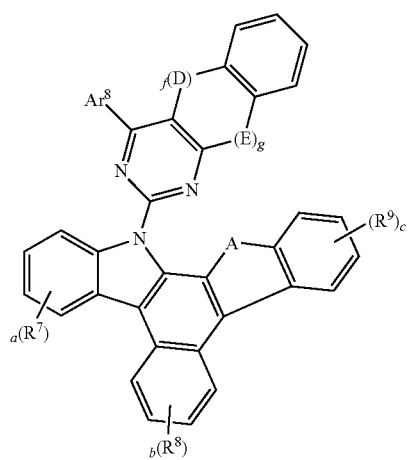
Formula (30)
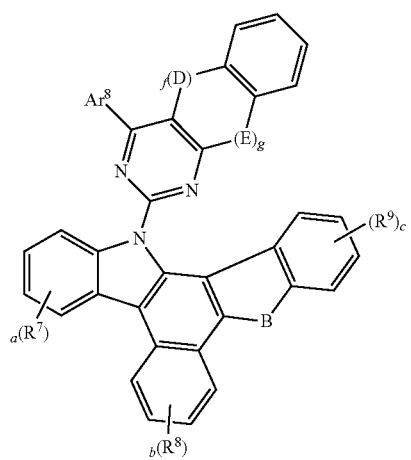
Formula (31)
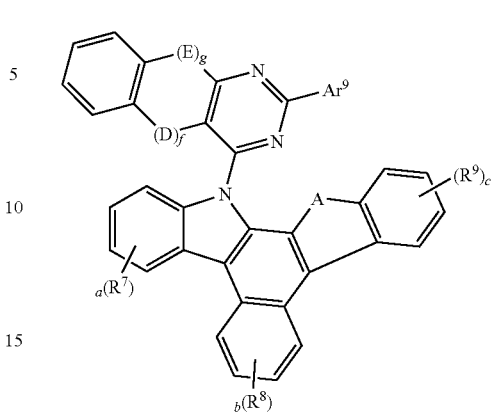
Formula (32)
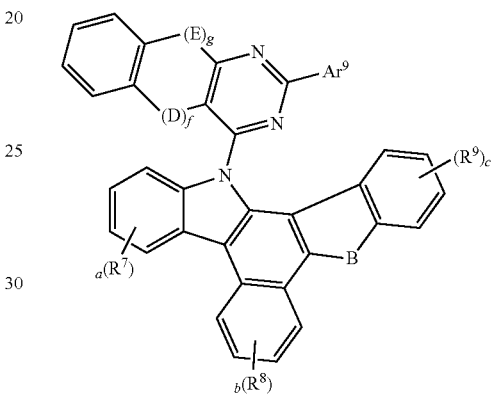
Formula (33)
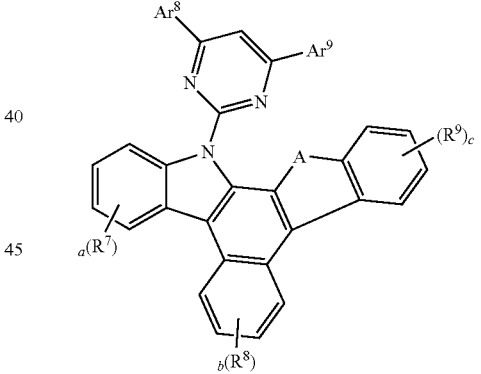
Formula (34)
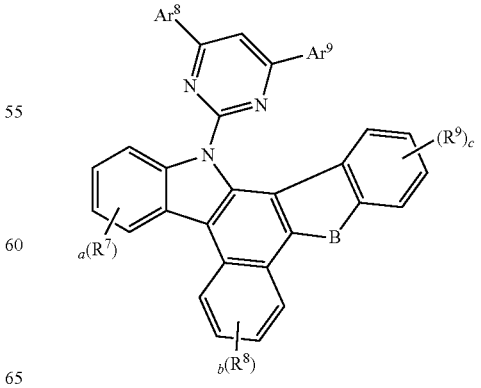

{In Formula (19) to Formula (34),

1) $R^7$, $R^8$, $R^9$, a, b, c, A and B are the same as defined above.

2) $Ar^8$ and $Ar^9$ are each independently selected from the group consisting of a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring;

3) $C^1$, $C^2$, $C^3$ and $C^4$ are each independently selected from the group consisting of CH, N, 4) D and E are single bond, S, O, NR', CR'R", and R' and R" are a hydrogen; a $C_6$-$C_{60}$ aryl group; a fluorenyl group; a $C_3$-$C_{60}$ heterocyclic group; or a $C_1$-$C_{50}$ alkyl group;

5) R' and R" may be bonded to each other to form a spiro compound, 6) f and g are 0 or 1, and provided that f+g is not less than 1.}

More specifically, the present invention provides an organic electric element wherein the compound represented by Formula (16) is any one of the following Formulas (P16-1) to (P16-33) in the emitting layer.

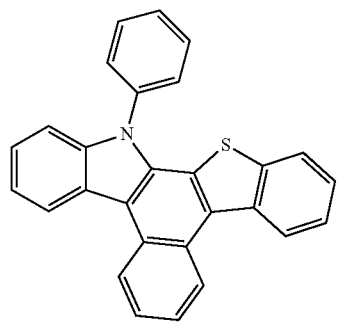

P16-1

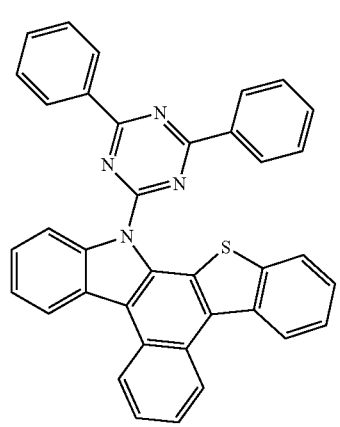

P16-2

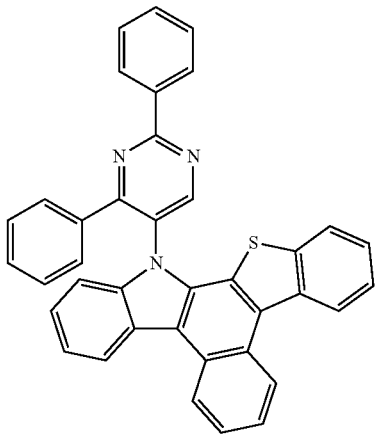

P16-3

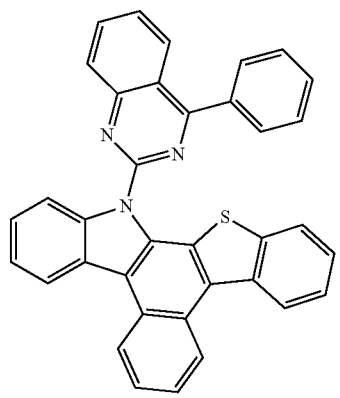

P16-4

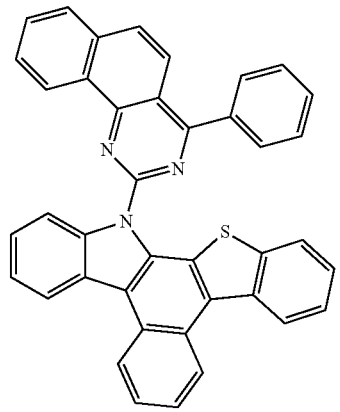

P16-5

-continued
P16-6
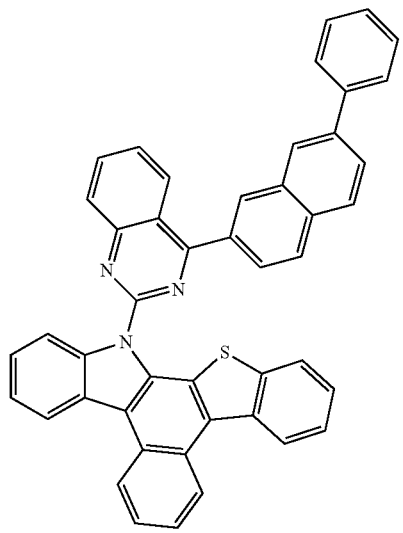
P16-7
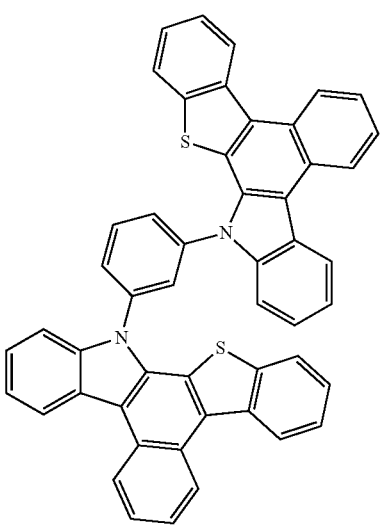
P16-8
-continued
P16-9
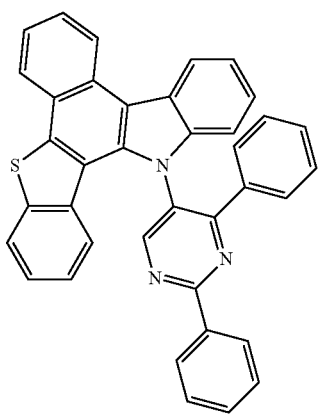
P16-10
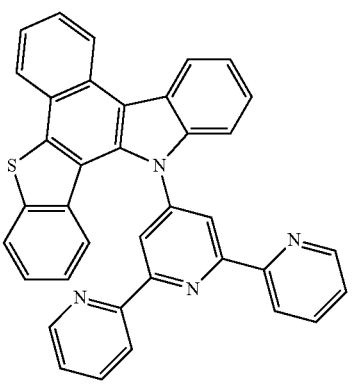
P16-11
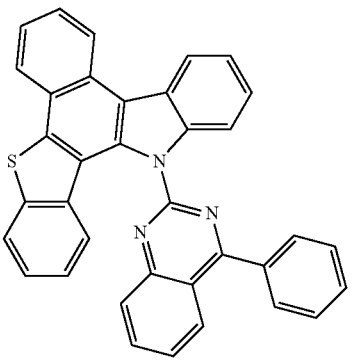
P16-12
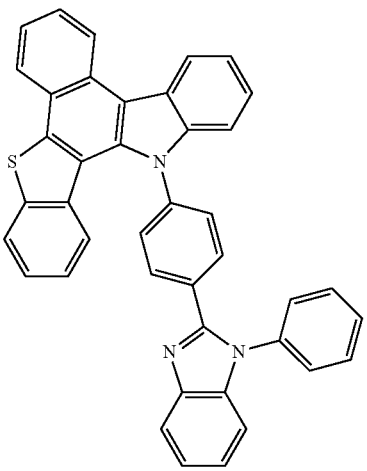

P16-13
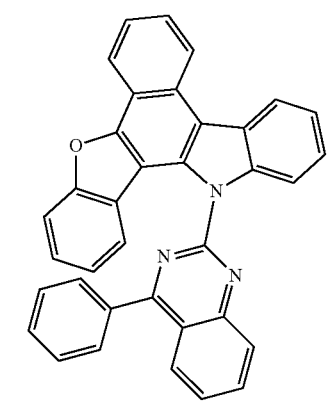
P16-14
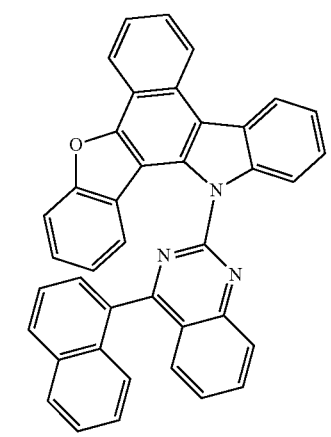
P16-15
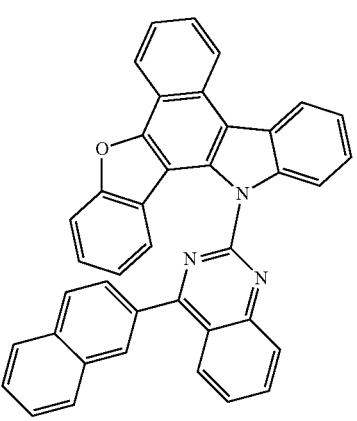
P16-16
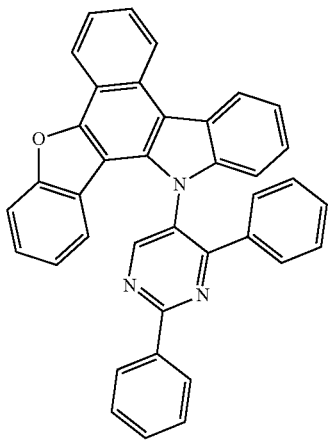
P16-17
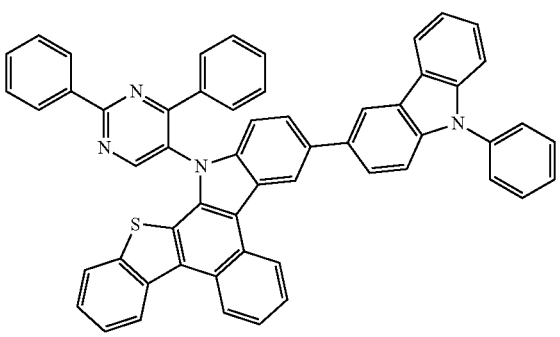
P16-18
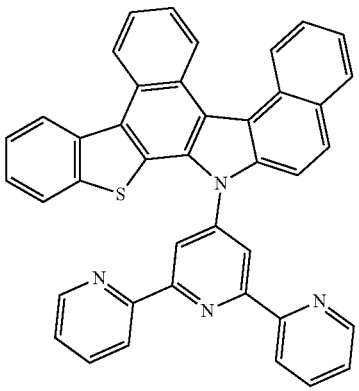
P16-19
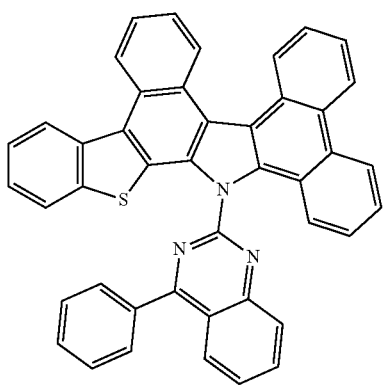

P16-20
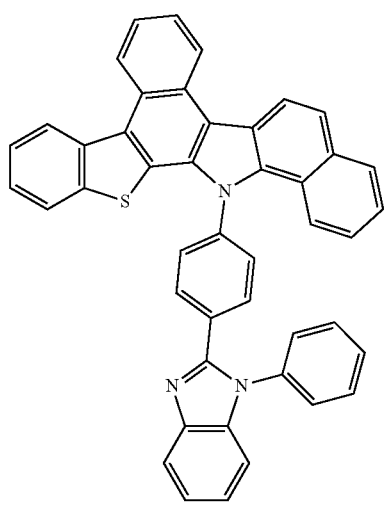
P16-21
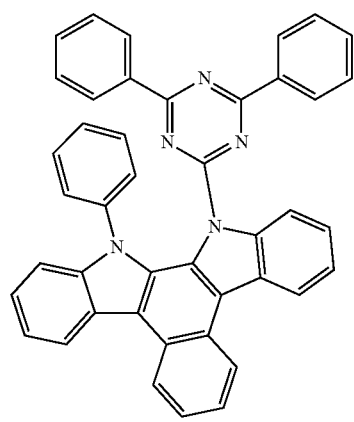
P16-22
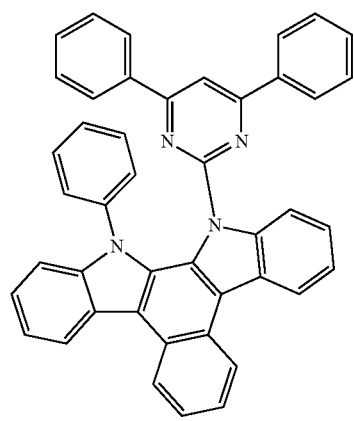
P16-23
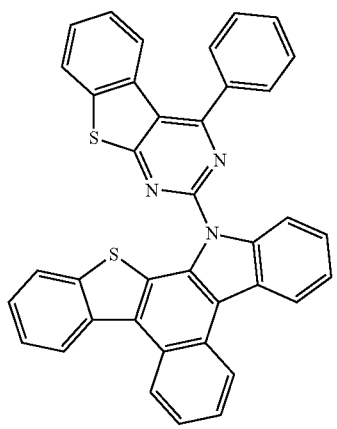
P16-24
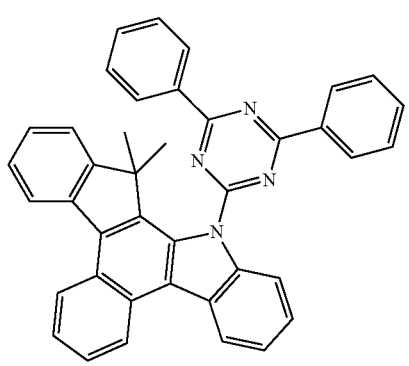
P16-25
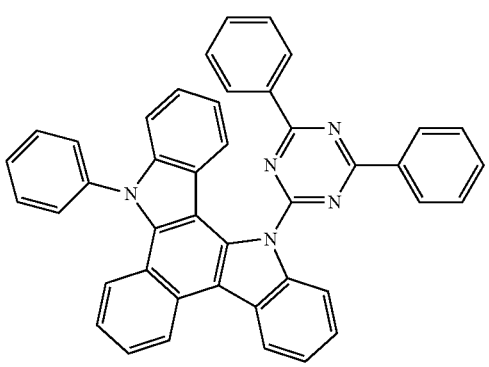
P16-26
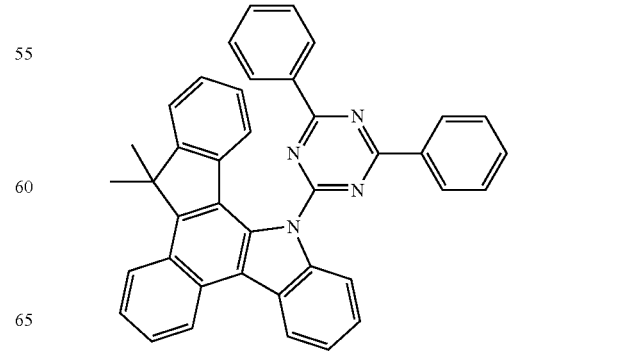

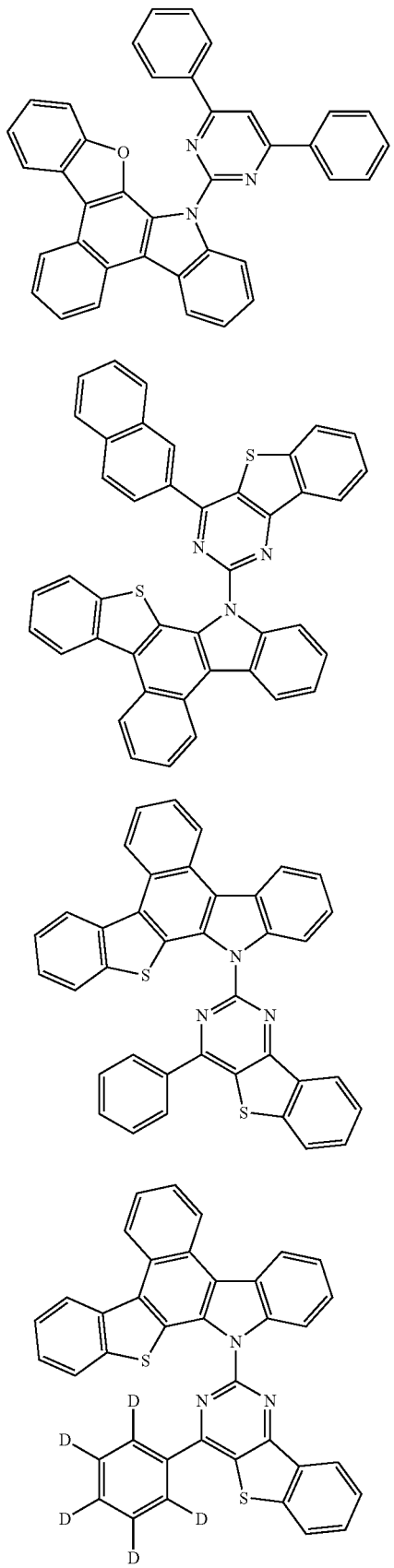
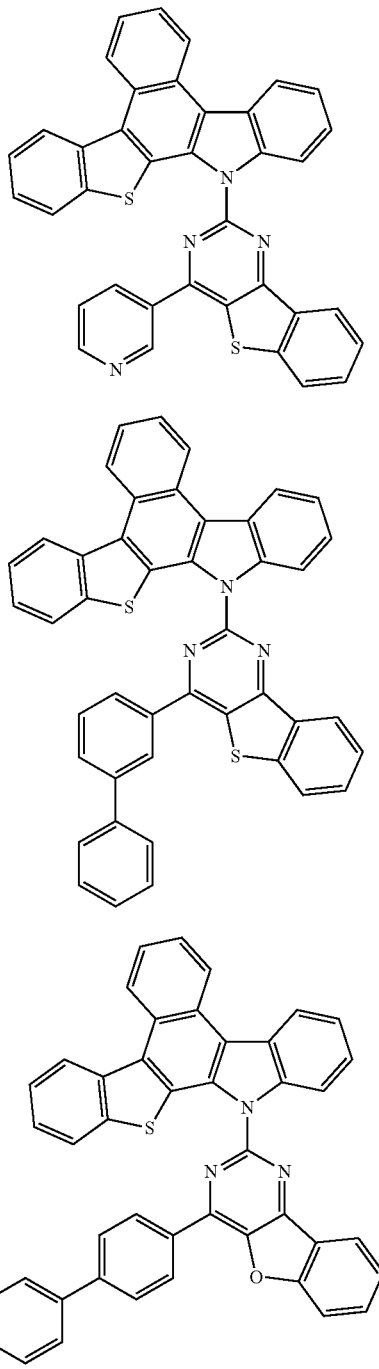

The present invention provides a compound further comprising a light efficiency enhancing layer formed on at least one of the opposite side to the organic material layer among one side of the first electrode, or one of the opposite side to the organic material layer among one side of the second electrode.

Also, the present invention provides the organic electric element wherein the organic material layer is formed by one of a spin coating process, a nozzle printing process, an inkjet printing process, a slot coating process, a dip coating process or a roll-to-roll process, and since the organic material layer according to the present invention can be formed by various methods, the scope of the present invention is not limited by the method of forming the organic material layer.

The present invention also provides an electronic device comprising a display device including the organic electric element; and a control unit for driving the display device.

According to another aspect, the present invention provides an electronic device characterized in that the organic electric element is at least one of an OLED, an organic solar cell, an organic photo conductor, an organic transistor and an element for monochromic or white illumination. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, synthesis examples of the compound represented by Formula (1) according to the present invention and preparation examples of the organic electric element will be described in detail by way of example, but are not limited to the following examples of the invention.

Synthesis Example

The final products 1 represented by Formula (1) of the present invention can be synthesized by reaction between Sub 1 and Sub 2 as illustrated in the following Reaction Scheme 1, but is not limited thereto.

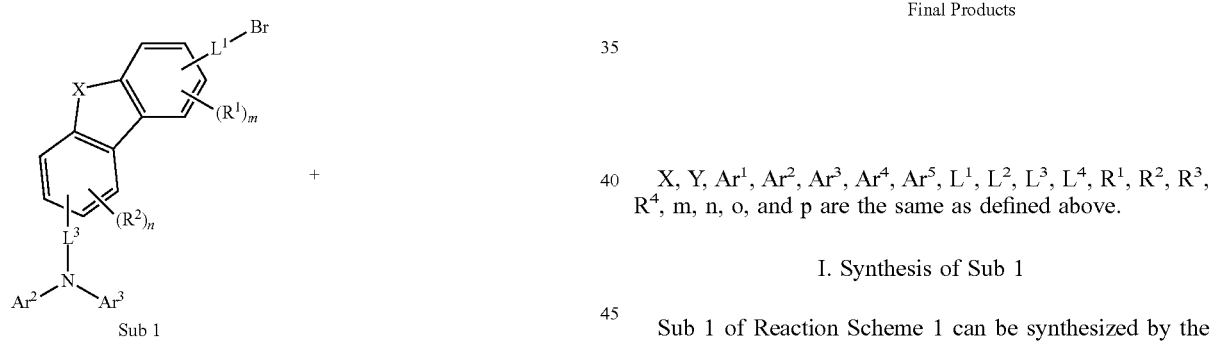

X, Y, Ar$^1$, Ar$^2$, Ar$^3$, Ar$^4$, Ar$^5$, L$^1$, L$^2$, L$^3$, L$^4$, R$^1$, R$^2$, R$^3$, R$^4$, m, n, o, and p are the same as defined above.

I. Synthesis of Sub 1

Sub 1 of Reaction Scheme 1 can be synthesized by the reaction path of the following Reaction Scheme 2 and Reaction Scheme 3, but is not limited thereto.

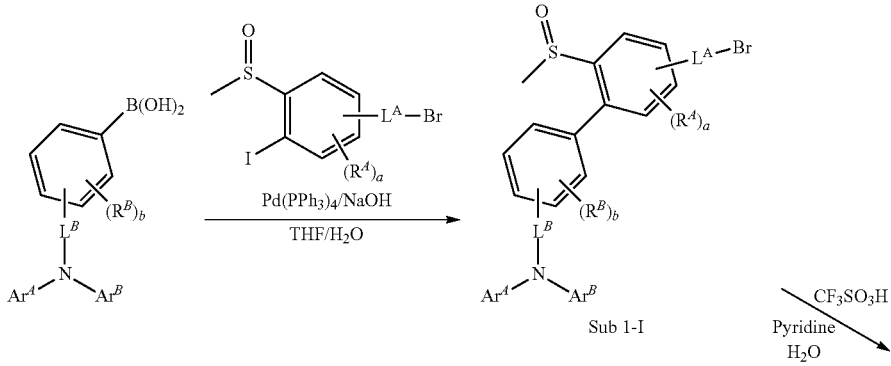

-continued
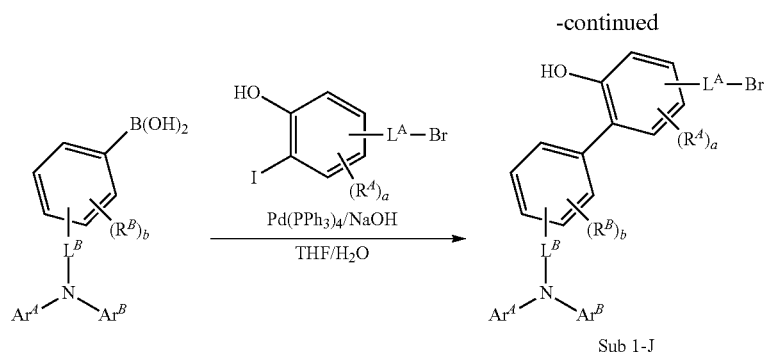
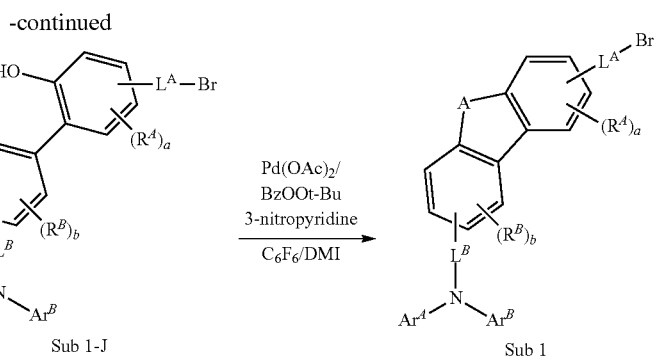
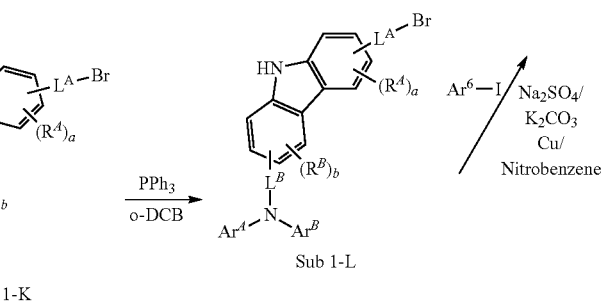
<Reaction Scheme 3>
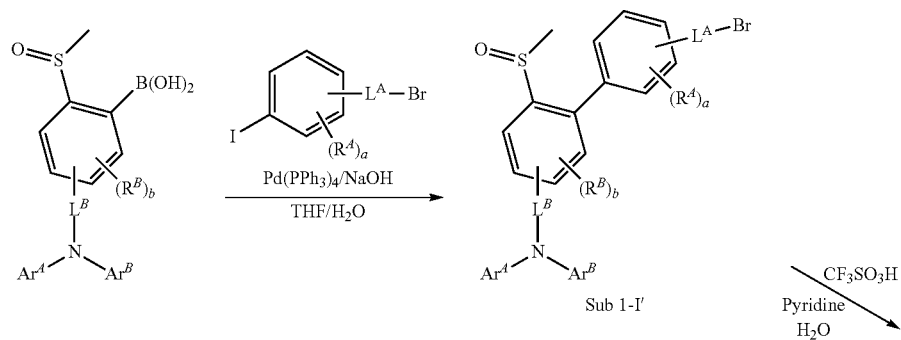
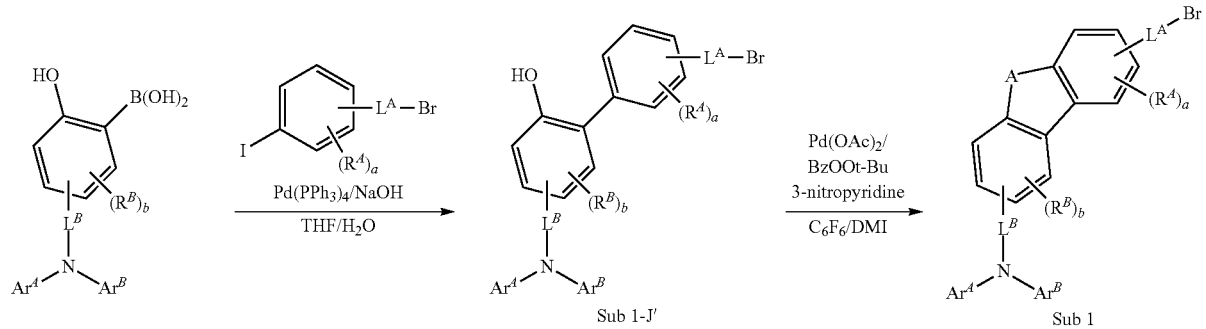

-continued

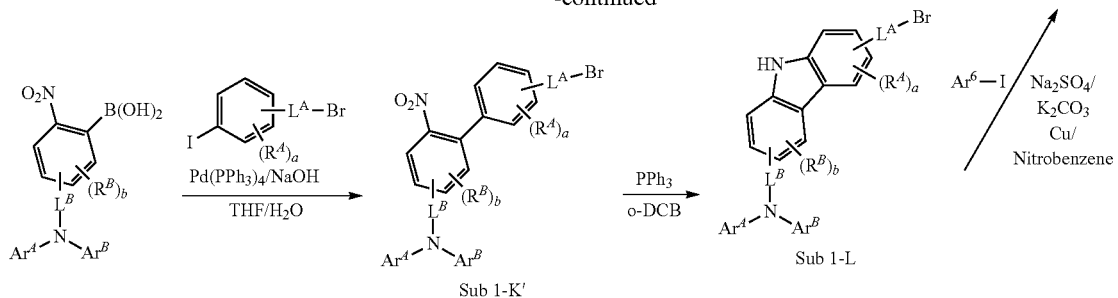

Sub 1-K'    Sub 1-L

A is X or Y; and $Ar^A$ is $Ar^2$ or $Ar^3$; and $Ar^B$ is $Ar^4$ or $Ar^5$; and $L^A$ is $L^1$ or $L^2$; and $L^B$ is $L^3$ or $L^4$; and $(R^A)_a$ is $(R^1)_m$ or $(R^2)_n$; and $(R^B)_b$ is $(R^3)_o$ or $(R^4)_p$.

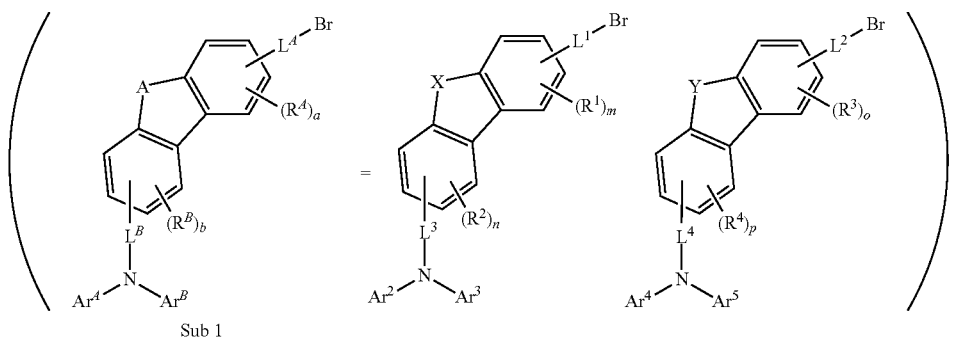

Sub 1

The synthesis examples of specific compounds belonging to Sub 1 are as follows.

1. Synthesis Example of Sub 1-8

<Reaction Scheme 4>

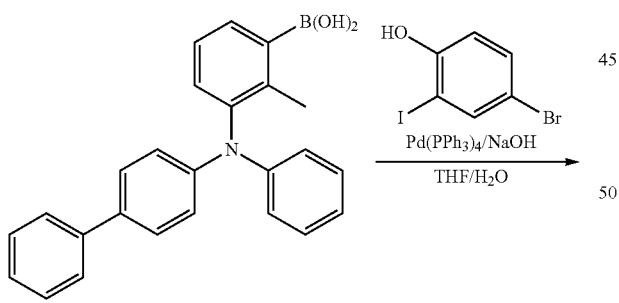

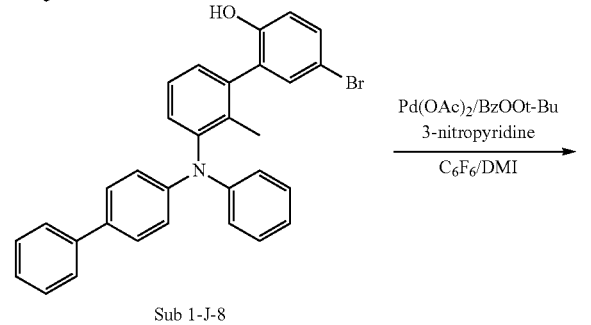

Sub 1-J-8

-continued

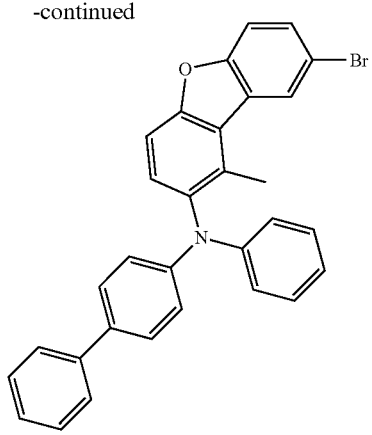

Sub 1-8

(1) Synthesis of Sub 1-J-8

Starting material (3-([1,1'-biphenyl]-4-yl(phenyl)amino)-2-methylphenyl)boronic acid (39.42 g, 103.94 mmol) was dissolved in THF 360 ml in a round bottom flask, and 4-bromo-2-iodophenol (34.17 g, 114.33 mmol), Pd(PPh$_3$)$_4$ (4.80 g, 4.16 mmol), NaOH (12.47 g, 311.81 mmol), and water (180 ml) were added and stirred at 80° C. After the reaction was completed, the reaction mixture was extracted with CH$_2$Cl$_2$ and water. The organic layer was dried over MgSO$_4$ and concentrated. The resulting compound was separated by silicagel column chromatography and recrystallized to obtain 41.06 g of the product. (yield: 78%)

(2) Synthesis of Sub 1-8

Sub 1-J-8 (41.06 g, 81.08 mmol) was placed in a round bottom flask together with Pd(OAc)$_2$ (1.82 g, 8.11 mmol), 3-nitropyridine (1.01 g, 8.11 mmol), and after dissolving in C$_6$F$_6$ (120 ml), DMI (80 ml), tert-butyl peroxybenzoate (31.49 g, 162.15 mmol) was added and stirred at 90° C. After the reaction was completed, the reaction mixture was extracted with CH$_2$Cl$_2$ and water. The organic layer was dried over MgSO$_4$ and concentrated. The resulting compound was separated by silicagel column chromatography and recrystallized to obtain 16.36 g of the product. (yield: 40%)

2. Synthesis Example of Sub 1-16

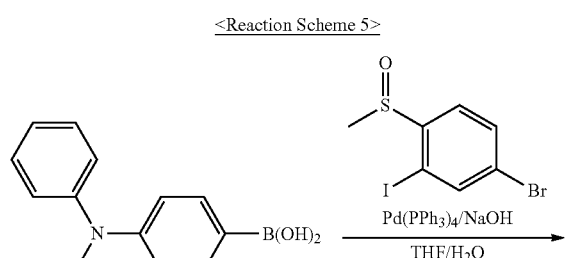

<Reaction Scheme 5>

Sub 1-I-16

Sub 1-16

(1) Synthesis of Sub 1-I-16

To the starting material, (4-(diphenylamino)phenyl)boronic acid (29.40 g, 101.68 mmol), 4-bromo-2-iodo-1-(methylsulfinyl)benzene (38.59 g, 111.85 mmol), Pd(PPh$_3$)$_4$ (4.70 g, 4.07 mmol), NaOH (12.20 g, 305.04 mmol), THF (360 ml), and water (180 ml) were added and 34.32 g was obtained using the above synthetic method Sub1-J-8. (yield: 73%)

(2) Synthesis of Sub 1-16

Sub 1-I-16 (34.32 g, 74.22 mmol) was placed in a round bottom flask with triflic acid (98.5 ml, 1113.30 mmol), stirred at room temperature for 24 hours, and the pyridine aqueous solution (1300 ml, pyridine:H$_2$O=1:5) was slowly added dropwise and refluxed for 30 minutes. After the reaction was completed, the reaction mixture was extracted with CH$_2$Cl$_2$ and water. The organic layer was dried over MgSO$_4$ and concentrated. The resulting compound was separated by silicagel column chromatography and recrystallized to obtain 16.61 g of the product. (yield: 52%)

3. Synthesis Example of Sub 1-26

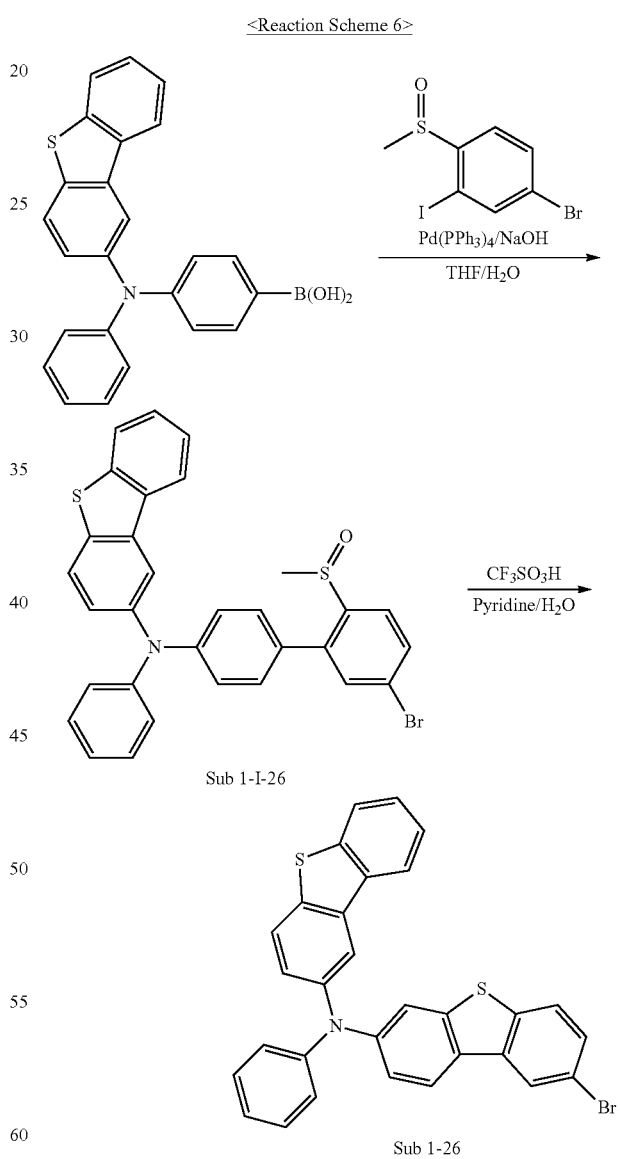

<Reaction Scheme 6>

Sub 1-I-26

Sub 1-26

(1) Synthesis of Sub 1-I-26

To the starting material, (4-(dibenzo[b,d]thiophen-2-yl(phenyl)amino)phenyl)boronic acid (19.35 g, 48.95 mmol), 4-bromo-2-iodo-1-(methylsulfinyl)benzene (18.58 g, 53.85 mmol), Pd(PPh₃)₄ (2.26 g, 1.96 mmol), NaOH (5.87 g, 146.86 mmol), THF (170 ml), and water (85 ml) were added and 19.48 g was obtained using the above synthetic method Sub 1-J-8. (yield: 70%)

(2) Synthesis of Sub 1-26

To Sub 1-I-26 (19.48 g, 34.26 mmol), triflic acid (45.5 ml, 513.94 mmol), pyridine aqueous solution (600 ml, pyridine:H₂O=1:5) were added and 9.01 g was obtained using the above synthetic method Sub 1-16. (yield: 49%)

4. Synthesis Example of Sub 1-56 mmol), THF (130 ml), and water (65 ml) were added and 14.64 g was obtained using the above synthetic method Sub 1-J-8. (yield: 81%)

(2) Synthesis of Sub 1-56

To Sub 1-J'-56 (14.64 g, 29.73 mmol), Pd(OAc)₂ (0.67 g, 2.97 mmol), 3-nitropyridine (0.37 g, 2.97 mmol), tert-butyl peroxybenzoate (11.55 g, 59.46 mmol), C₆F₆ (45 ml), and DMI (30 ml) were added and 6.27 g was obtained using the above synthetic method Sub 1-8. (yield: 43%)

5. Synthesis Example of Sub 1-58

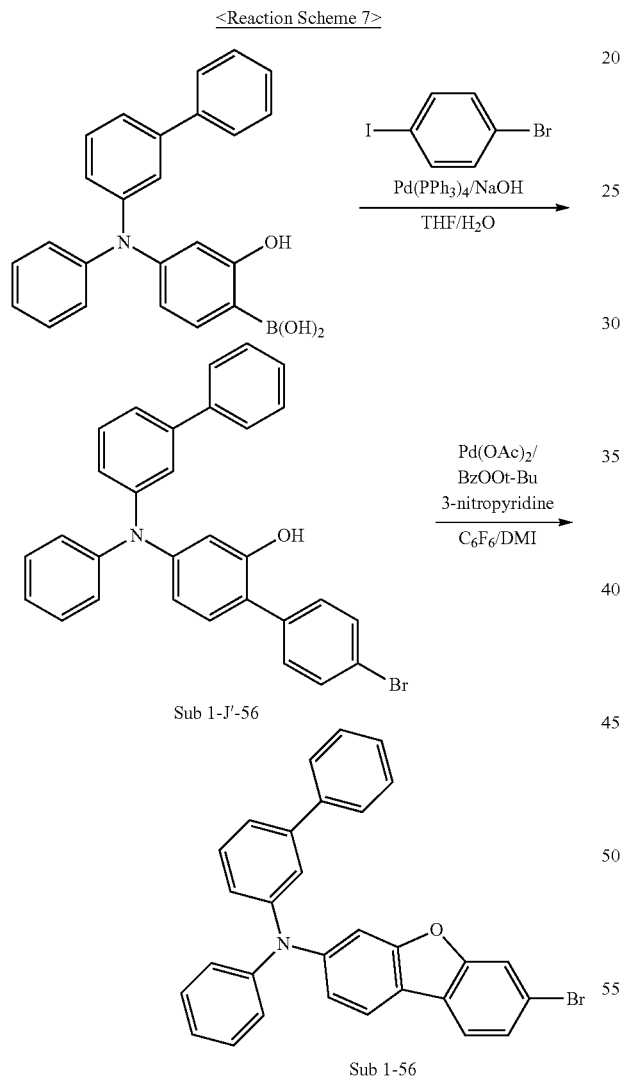

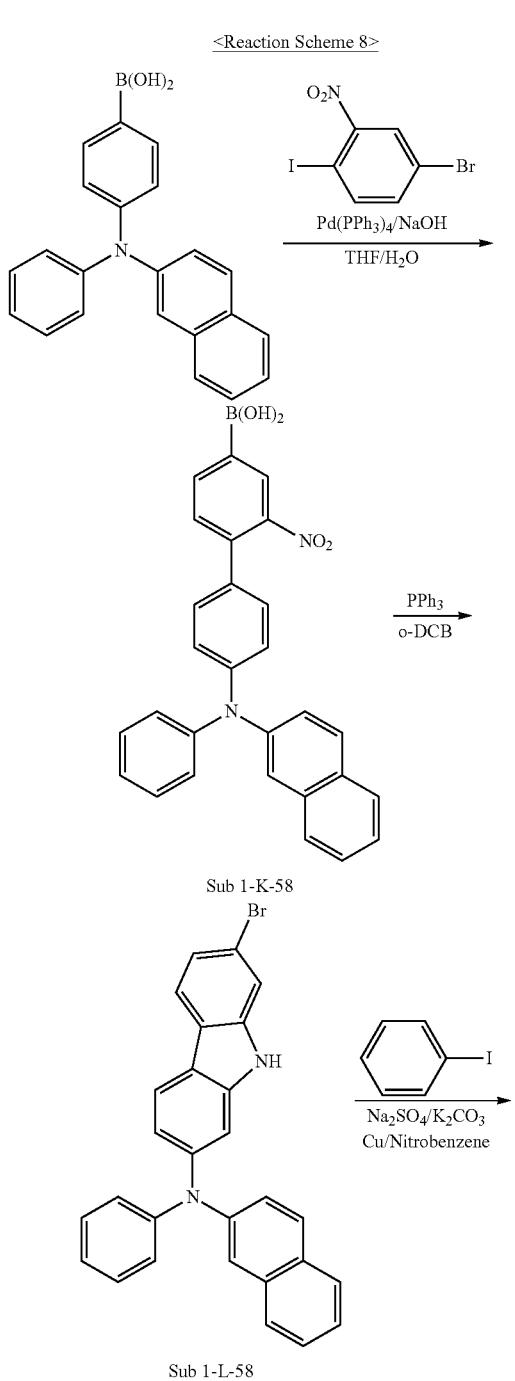

(1) Synthesis of Sub 1-J'-56

To the starting material, (4-([1,1'-biphenyl]-3-yl(phenyl)amino)-2-hydroxyphenyl)boronic acid (13.99 g, 36.70 mmol), 1-bromo-4-iodobenzene (11.42 g, 40.37 mmol), Pd(PPh₃)₄ (1.70 g, 1.47 mmol), NaOH (4.40 g, 110.09

6. Synthesis Example of Sub 1-59

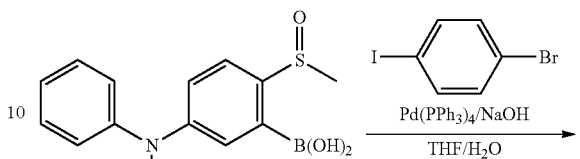

<Reaction Scheme 9>

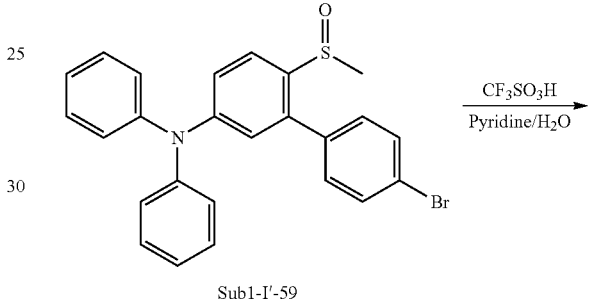

Sub1-I'-59

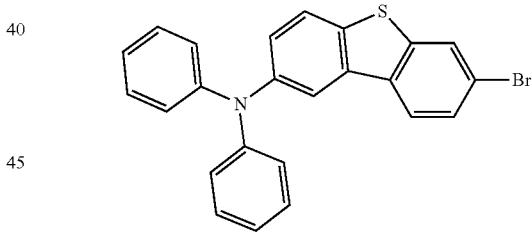

Sub 1-59

(1) Synthesis of Sub 1-I'-59

To the starting material, (5-(diphenylamino)-2-(methylsulfinyl)phenyl)boronic acid (51.77 g, 147.40 mmol), 1-bromo-4-iodobenzene (45.87 g, 162.14 mmol), Pd(PPh$_3$)$_4$ (6.81 g, 5.90 mmol), NaOH (17.69 g, 442.19 mmol), THF (520 ml), and water (260 ml) were added and 53.84 g was obtained using the above synthetic method Sub 1-J-8. (yield: 79%)

(2) Synthesis of Sub 1-59

To Sub 1-I'-59 (53.84 g, 116.43 mmol), triflic acid (154.5 ml, 1746.50 mmol), pyridine aqueous solution (2040 ml, pyridine:H$_2$O=1:5) were added, and 27.06 g was obtained using the above synthetic method Sub 1-16. (yield: 54%)

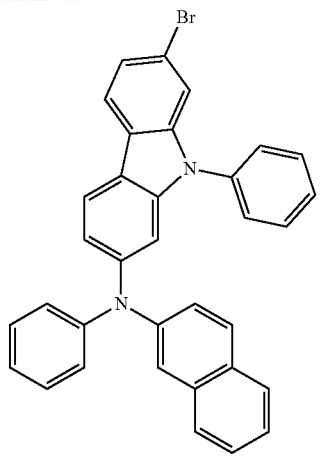

Sub 1-58

(1) Synthesis of Sub 1-K-58

To the starting material, (4-(naphthalen-2-yl(phenyl)amino)phenyl)boronic acid (25.01 g, 73.73 mmol), 4-bromo-1-iodo-2-nitrobenzene (26.59 g, 81.11 mmol), Pd(PPh$_3$)$_4$ (3.41 g, 2.95 mmol), NaOH (8.85 g, 221.20 mmol), THF (260 ml), and water (130 ml) were added, and 31.05 g was obtained using the above synthetic method Sub 1-J-8. (yield: 85%)

(2) Synthesis of Sub 1-L-58

Sub 1-K-58 (31.05 g, 62.68 mmol) was dissolved in o-dichlorobenzene (550 ml) in a round bottom flask, and triphenylphosphine (41.10 g, 156.70 mmol) was added and stirred at 200° C. When the reaction is complete, o-dichlorobenzene is removed by distillation, and was extracted with CH$_2$Cl$_2$ and water. The organic layer was dried over MgSO$_4$ and concentrated. The resulting compound was separated by silicagel column chromatography and recrystallized to obtain 21.49 g of the product. (yield: 74%)

(3) Synthesis of Sub 1-58

Sub 1-L-58 (21.49 g, 46.38 mmol) was dissolved in nitrobenzene (290 ml) in a round bottom flask, and iodobenzene (14.19 g, 69.56 mmol), Na$_2$SO$_4$ (6.59 g, 46.38 mmol), K$_2$CO$_3$ (6.41 g, 46.38 mmol), Cu (0.88 g, 13.91 mmol) were added and stirred at 200° C. When the reaction is complete, nitrobenzene is removed by distillation, and was extracted with CH$_2$Cl$_2$ and water. The organic layer was dried over MgSO$_4$ and concentrated. The resulting compound was separated by silicagel column chromatography and recrystallized to obtain 17.01 g of the product. (yield: 68%)

7. Synthesis Example of Sub 1-76

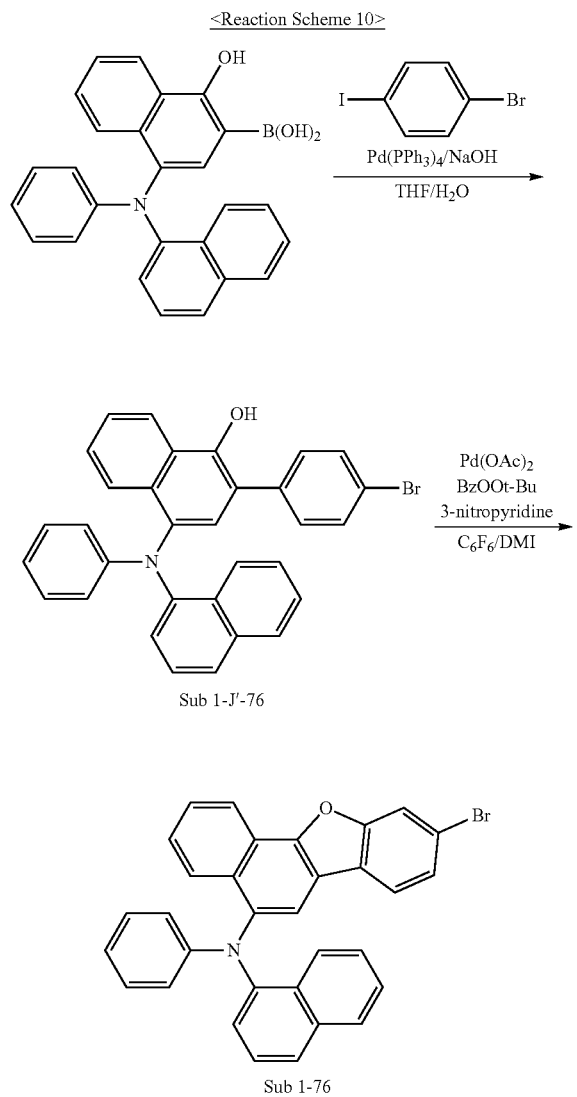

8. Synthesis Example of Sub 1-83

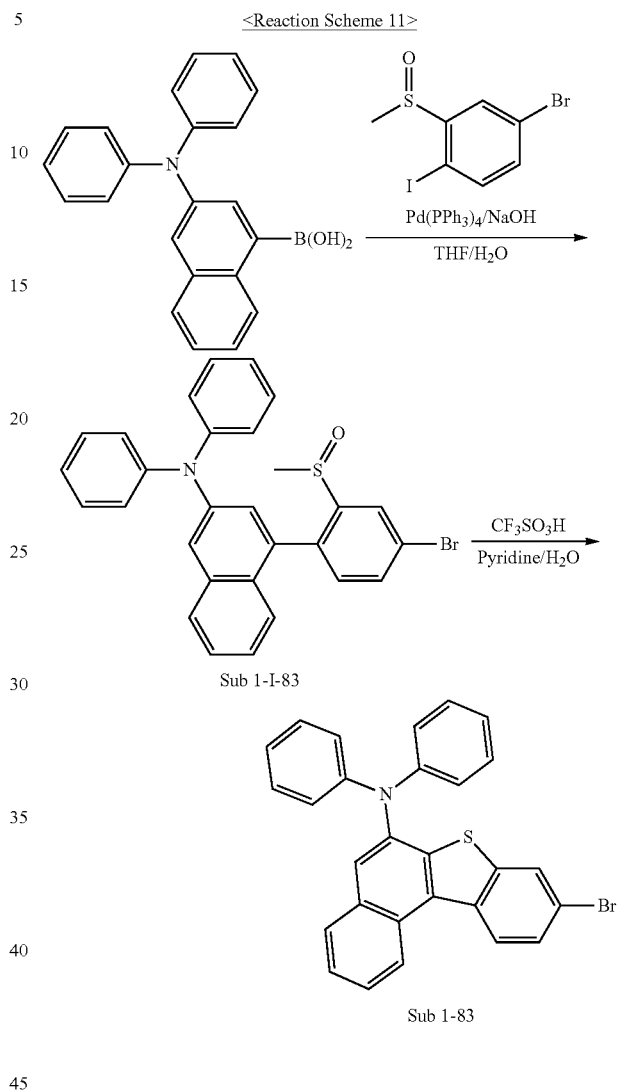

(1) Synthesis of Sub 1-J'-76

To the starting material, (1-hydroxy-4-(naphthalen-1-yl (phenyl)amino)naphthalen-2-yl)boronic acid (25.55 g, 63.05 mmol), 1-bromo-4-iodobenzene (19.62 g, 69.35 mmol), Pd(PPh$_3$)$_4$ (2.91 g, 2.52 mmol), NaOH (7.57 g, 189.14 mmol), THF (220 ml), and water (110 ml) were added and 22.79 g was obtained using the above synthetic method Sub 1-J-8. (yield: 70%)

(2) Synthesis of Sub 1-76

To Sub 1-J'-76 (22.79 g, 44.13 mmol), Pd(OAc)$_2$ (0.99 g, 4.41 mmol), 3-nitropyridine (0.55 g, 4.41 mmol), tert-butyl peroxybenzoate (17.14 g, 88.26 mmol), C$_6$F$_6$ (66 ml), and DMI (44 ml) were added and 8.85 g was obtained using the above synthetic method Sub 1-8. (yield: 39%)

(1) Synthesis of Sub 1-I-83

To the starting material, (3-(diphenylamino)naphthalen-1-yl)boronic acid (15.49 g, 45.67 mmol), 4-bromo-1-iodo-2-(methylsulfinyl)benzene (17.33 g, 50.23 mmol), Pd(PPh$_3$)$_4$ (2.11 g, 1.83 mmol), NaOH (5.48 g, 137.00 mmol), THF (160 ml), and water (80 ml) were added and 15.21 g was obtained using the above synthetic method Sub 1-J-8. (yield: 65%)

(2) Synthesis of Sub 1-83

To Sub 1-I-83 (15.21 g, 29.68 mmol), triflic acid (39.4 ml, 445.20 mmol), pyridine aqueous solution (520 ml, pyridine: H$_2$O=1:5) were added and 6.70 g was obtained using the above synthetic method Sub 1-16. (yield: 47%)

9. Synthesis Example of Sub 1-95

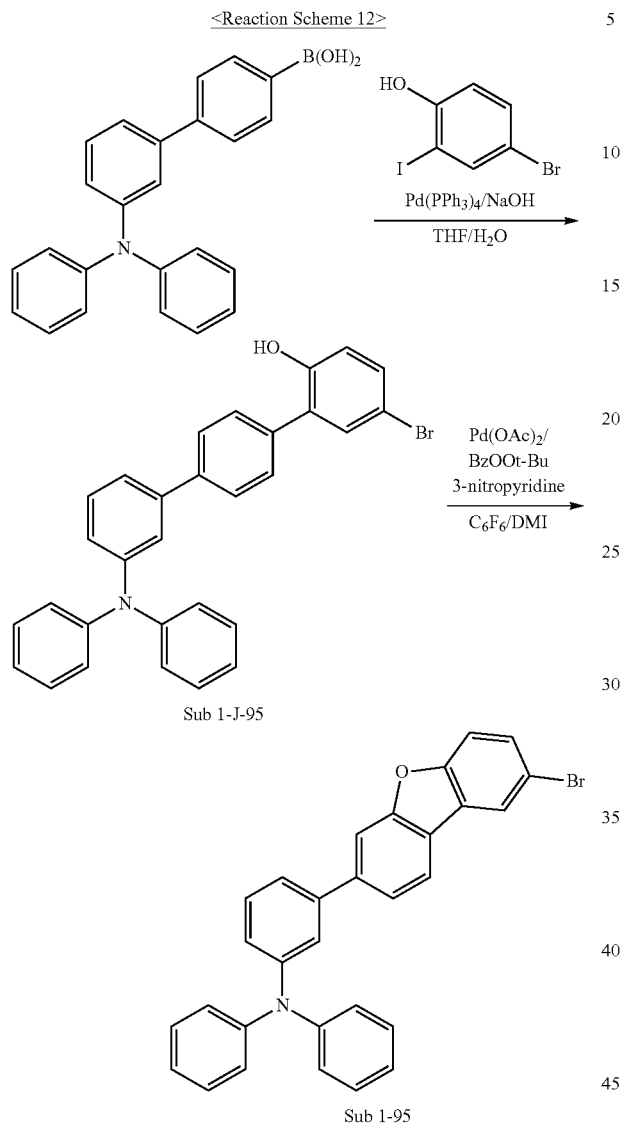

Sub 1-95

(1) Synthesis of Sub 1-J-95

To the starting material, (3'-(diphenylamino)-[1,1'-biphenyl]-4-yl)boronic acid (27.56 g, 75.46 mmol), 4-bromo-2-iodophenol (24.81 g, 83.00 mmol), Pd(PPh$_3$)$_4$ (3.49 g, 3.02 mmol), NaOH (9.05 g, 226.37 mmol), THF (260 ml), and water (130 ml) were added and 29.73 g was obtained using the above synthetic method Sub 1-J-8. (yield: 80%)

(2) Synthesis of Sub 1-95

To Sub 1-J-95 (29.73 g, 60.38 mmol), Pd(OAc)$_2$ (1.36 g, 6.04 mmol), 3-nitropyridine (0.75 g, 6.04 mmol), tert-butyl peroxybenzoate (23.45 g, 120.75 mmol), C$_6$F$_6$ (90 ml), and DMI (60 ml) were added and 12.14 g was obtained using the above synthetic method Sub 1-8. (yield: 41%)

10. Synthesis Example of Sub 1-101

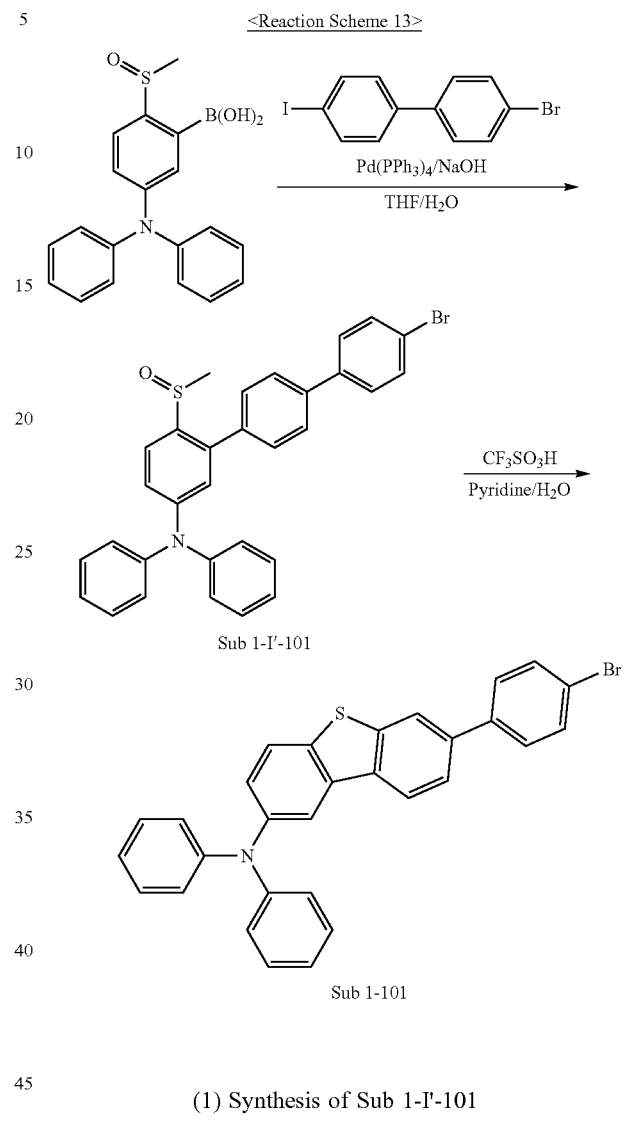

Sub 1-101

(1) Synthesis of Sub 1-I'-101

To the starting material, (5-(diphenylamino)-2-(methylsulfinyl)phenyl)boronic acid (42.04 g, 119.69 mmol), 4-bromo-4'-iodo-1,1'-biphenyl (47.27 g, 131.66 mmol), Pd(PPh$_3$)$_4$ (5.53 g, 4.79 mmol), NaOH (14.36 g, 359.08 mmol), THF (420 ml), and water (210 ml) were added and 49.63 g was obtained using the above synthetic method Sub 1-J-8. (yield: 77%)

(2) Synthesis of Sub 1-101

To Sub 1-I'-101 (49.63 g, 92.16 mmol), triflic acid (122.3 ml, 1382.45 mmol), pyridine aqueous solution (1615 ml, pyridine:H$_2$O=1:5) were added and 23.34 g was obtained using the above synthetic method Sub 1-16. (yield: 50%)

The compound belonging to Sub 1 may be, but not limited to, the following compounds, and Table 1 shows FD-MS (Field Desorption-Mass Spectrometry) values of some compounds belonging to Sub 1.

Sub 1-1
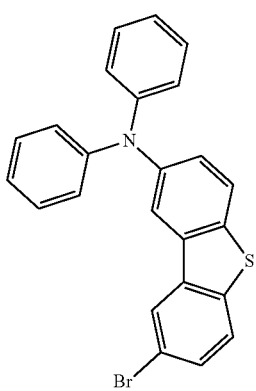
Sub 1-2
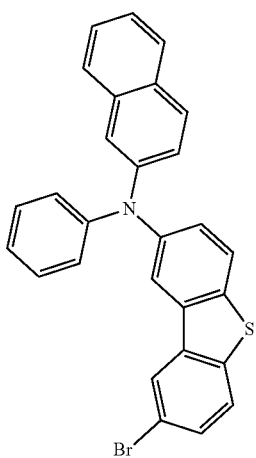
Sub 1-3
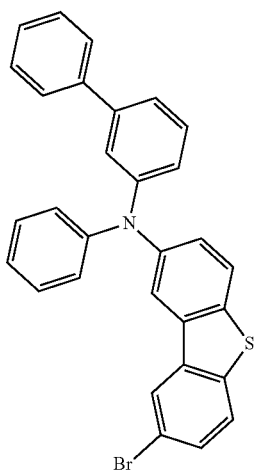
Sub 1-4
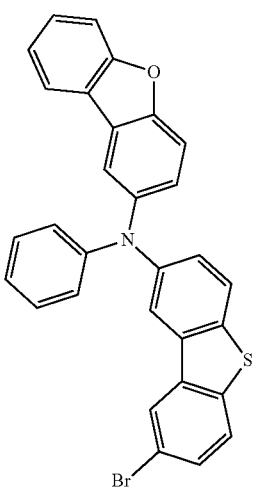
Sub 1-5
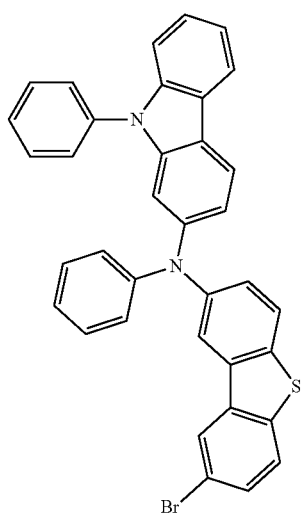
Sub 1-6
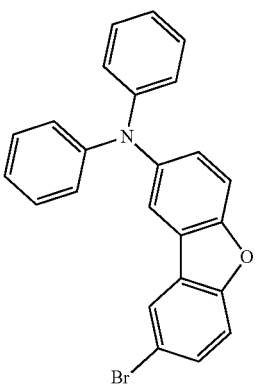

Sub 1-7
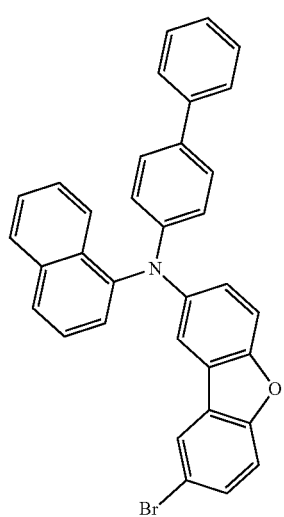
Sub 1-8
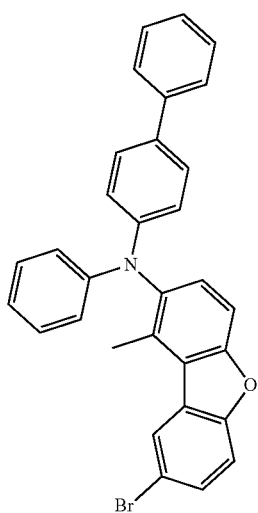
Sub 1-9
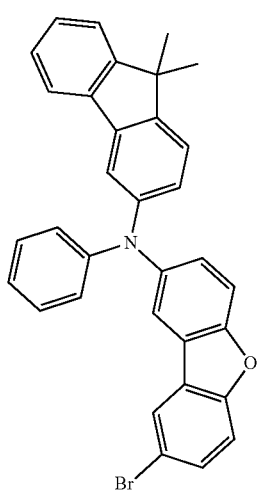
Sub 1-10
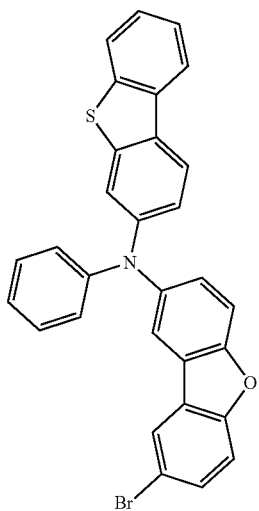
Sub 1-11
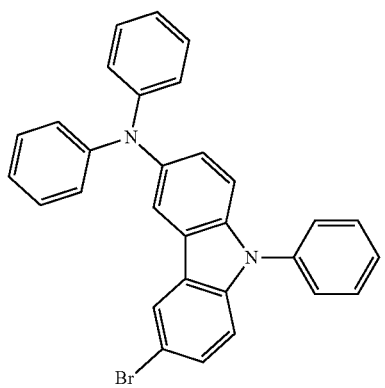
Sub 1-12
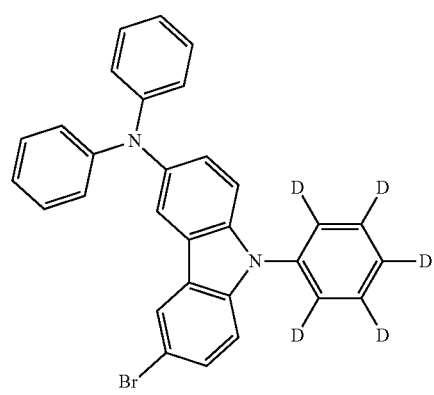

Sub 1-13
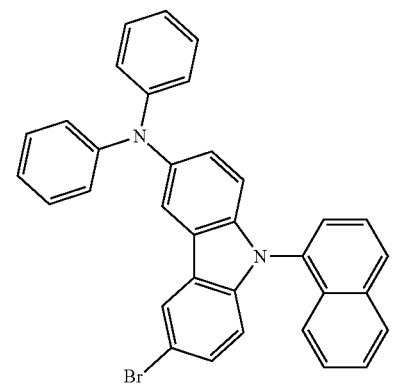
Sub 1-14
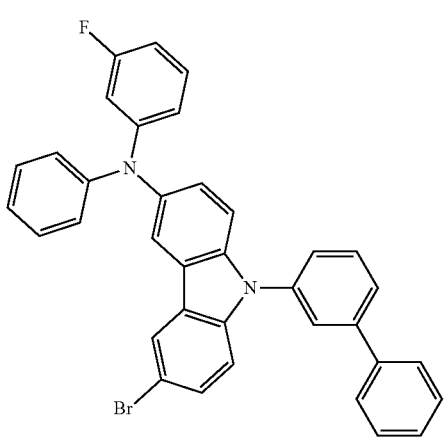
Sub 1-15
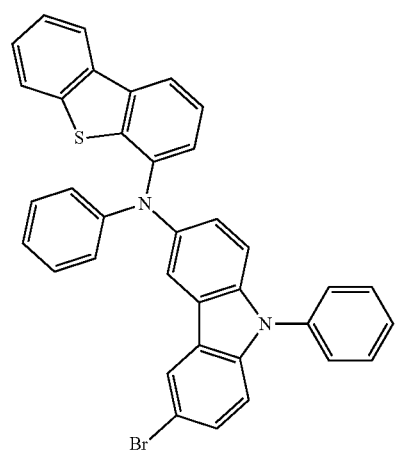
Sub 1-16
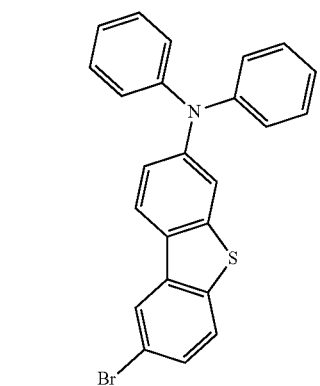
Sub 1-17
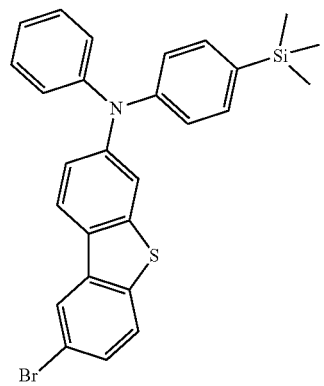
Sub 1-18
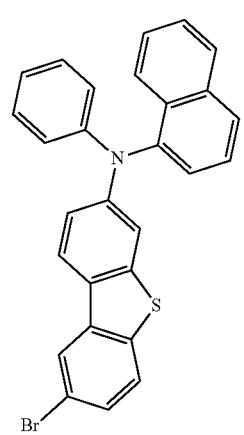
Sub 1-19
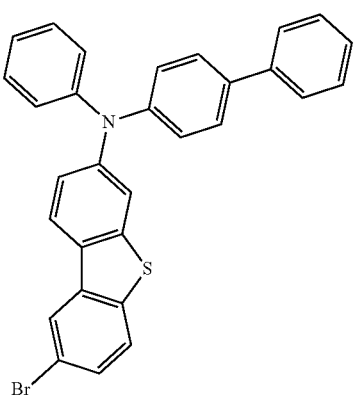

Sub 1-20
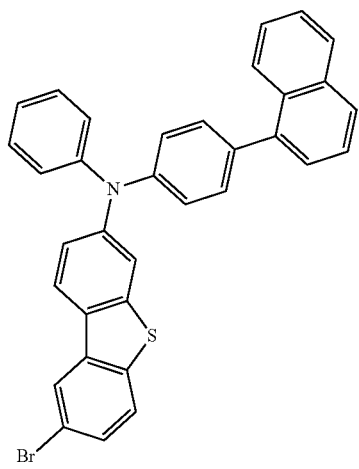
Sub 1-21
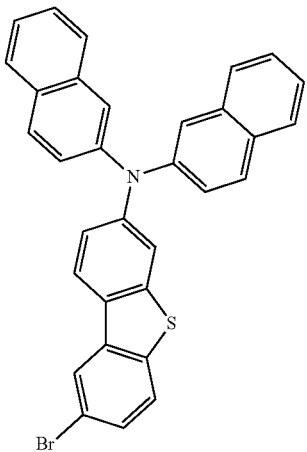
Sub 1-22
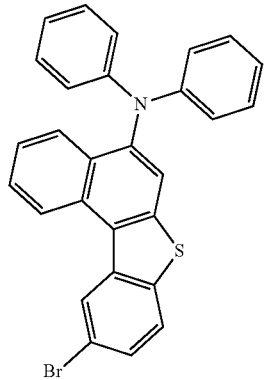
Sub 1-23
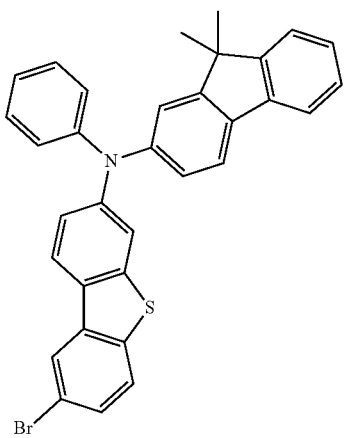
Sub 1-24
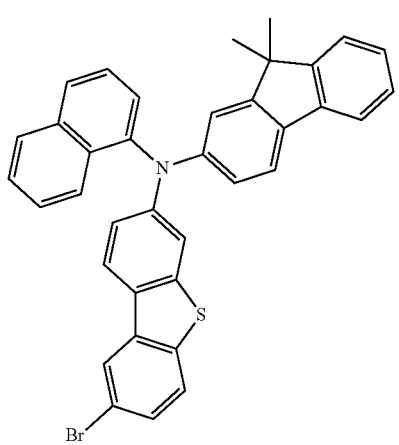
Sub 1-25
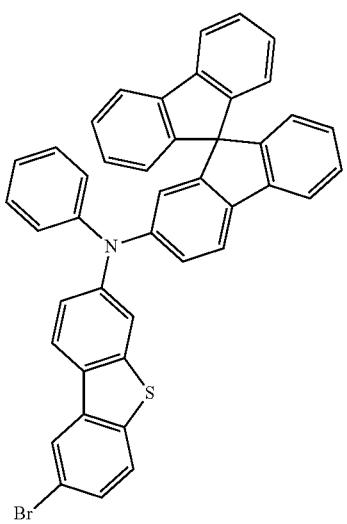

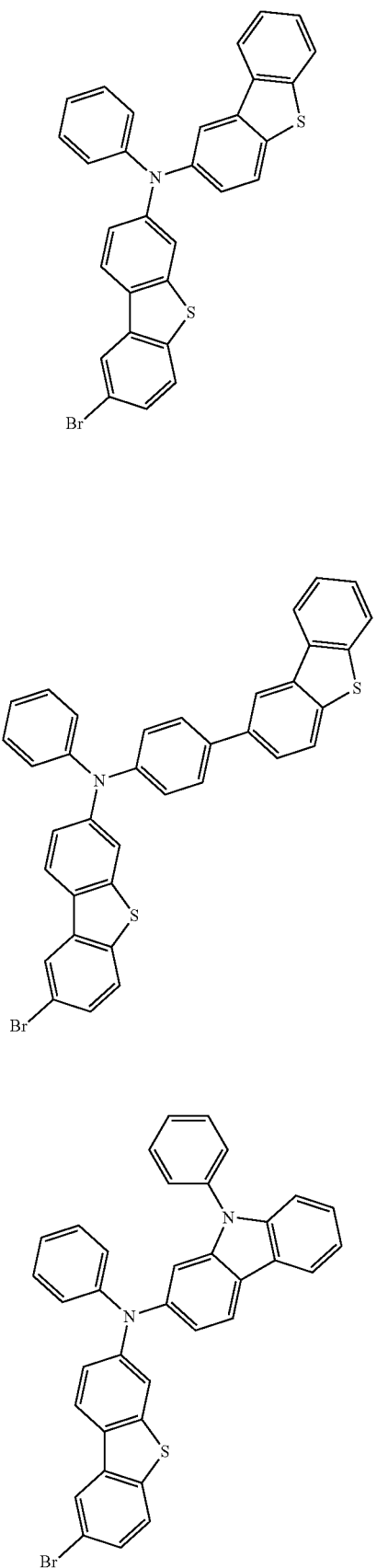
Sub 1-26
Sub 1-27
Sub 1-28
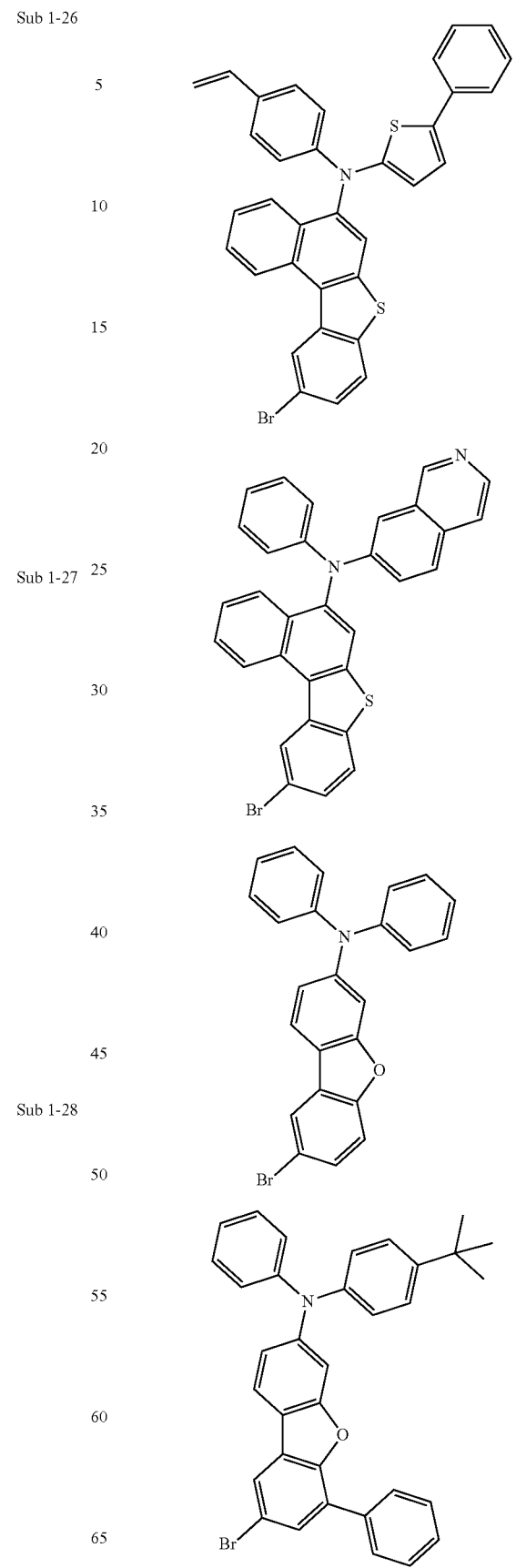
Sub 1-29
Sub 1-30
Sub 1-31
Sub 1-32

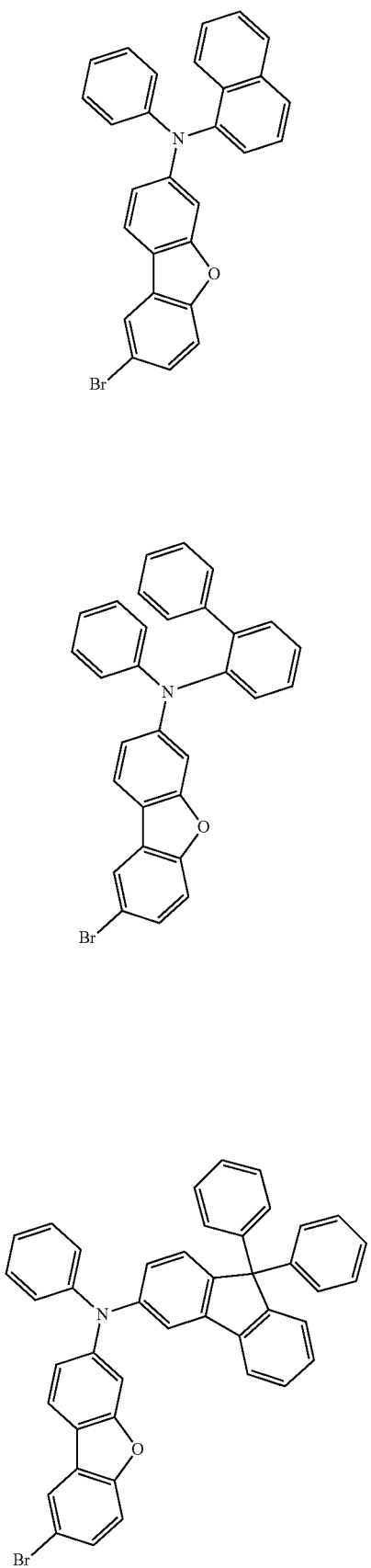
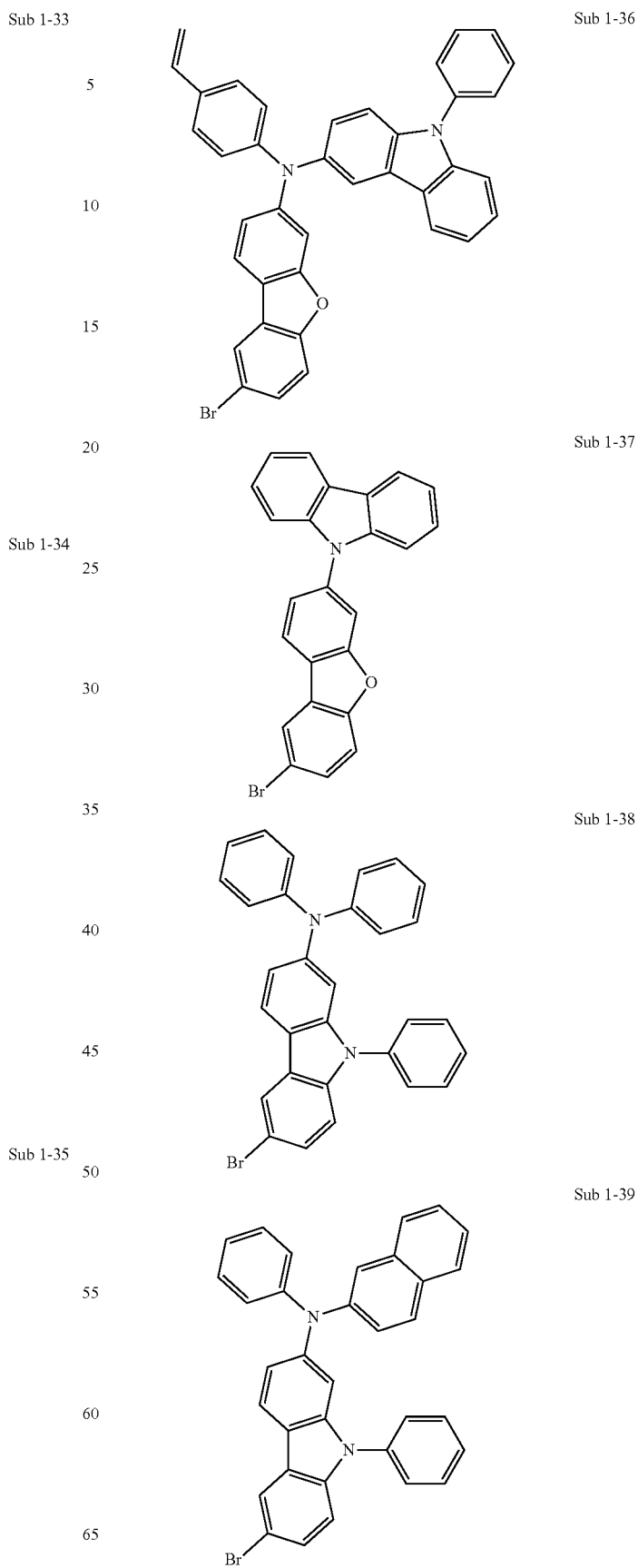

Sub 1-40
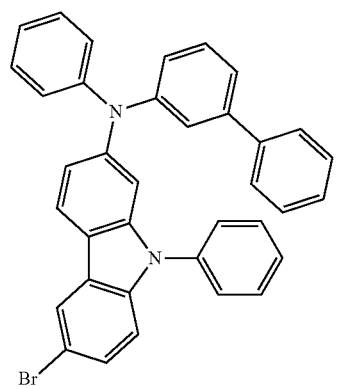
Sub 1-41
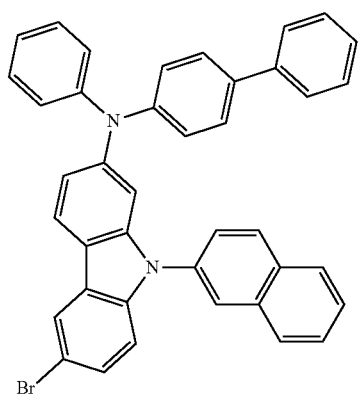
Sub 1-42
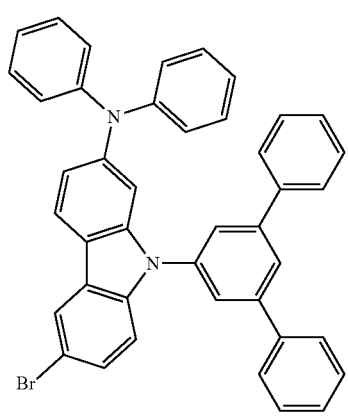
Sub 1-43
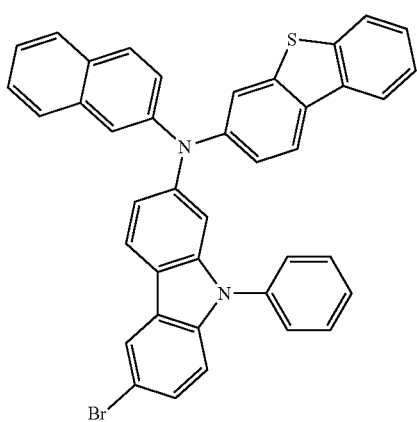
Sub 1-44
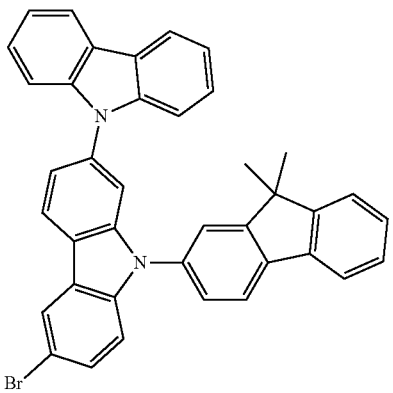
Sub 1-45
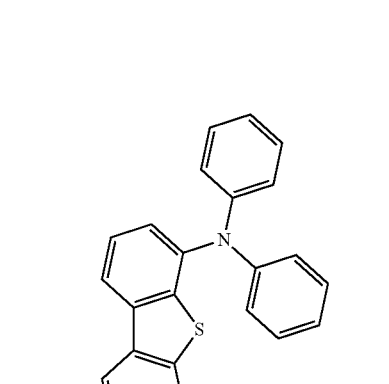
Sub 1-46
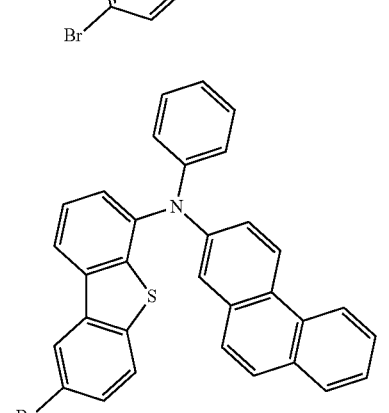
Sub 1-47
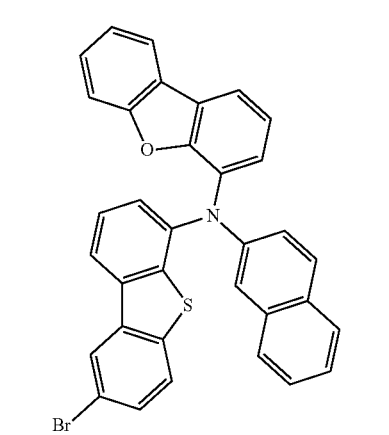

Sub 1-48
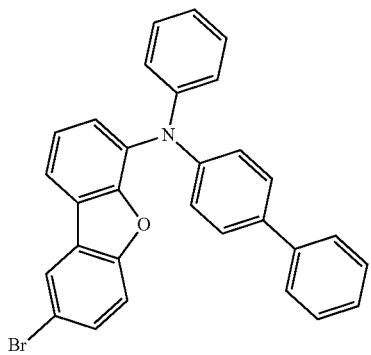
Sub 1-49
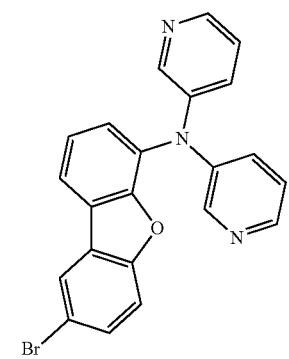
Sub 1-50
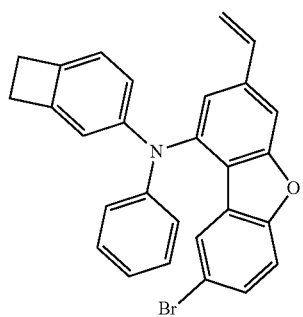
Sub 1-51
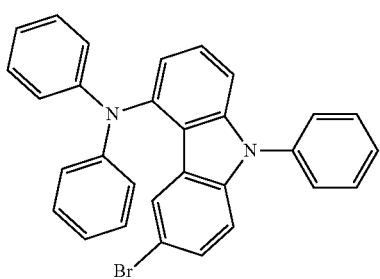
Sub 1-52
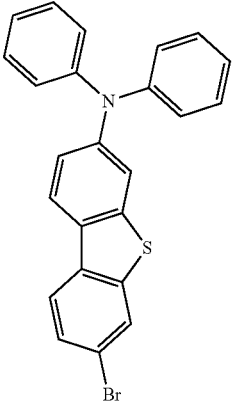
Sub 1-53
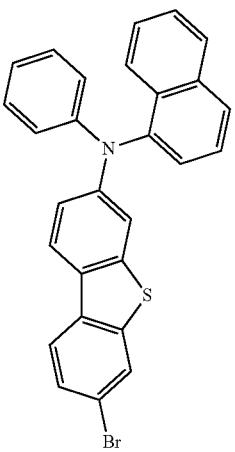
Sub 1-54
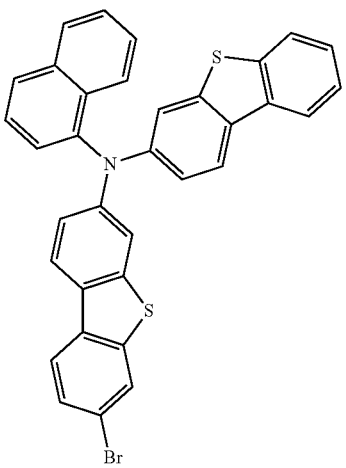

Sub 1-55
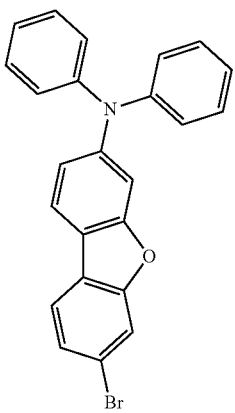
Sub 1-56
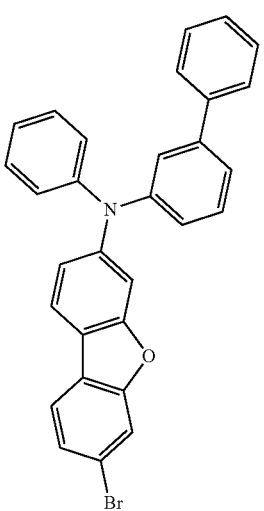
Sub 1-57
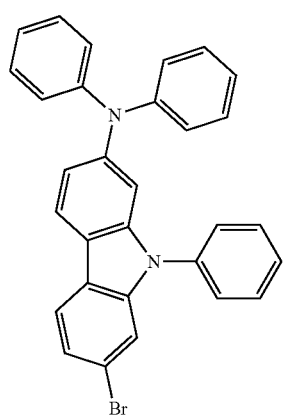
Sub 1-58
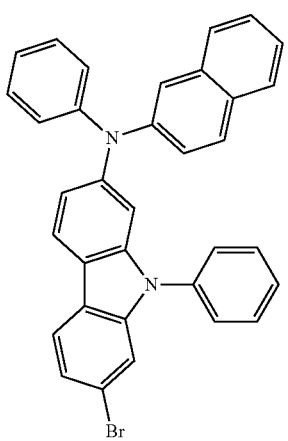
Sub 1-59
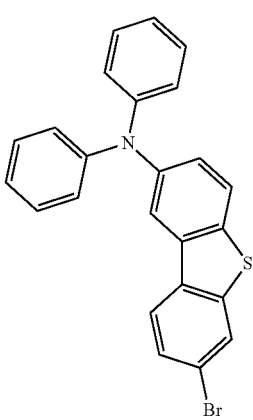
Sub 1-60
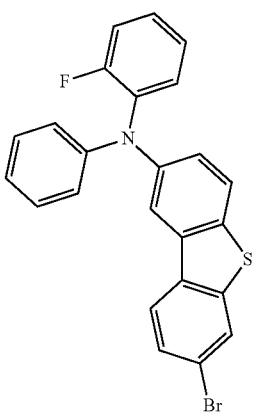

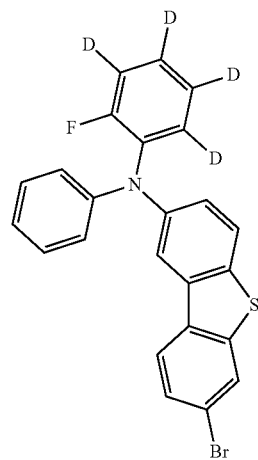
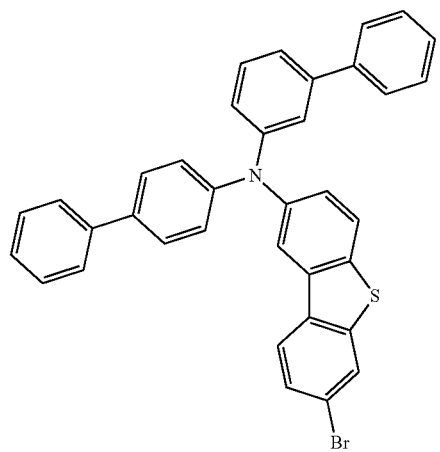
Sub 1-61
Sub 1-64
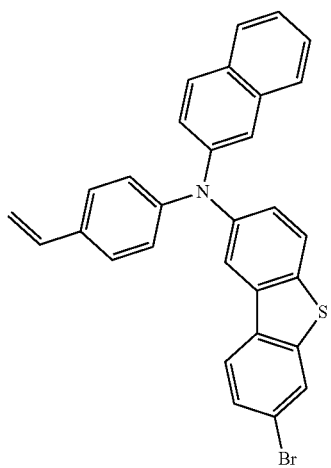
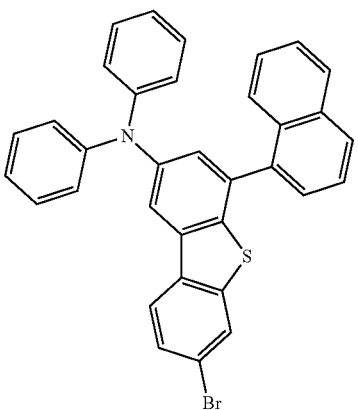
Sub 1-62
Sub 1-65
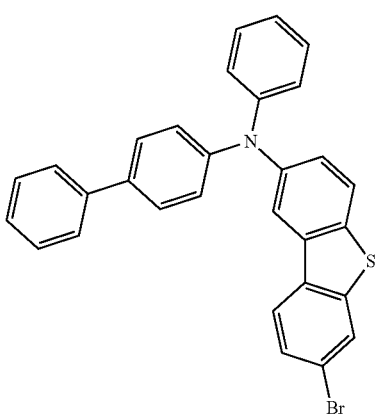
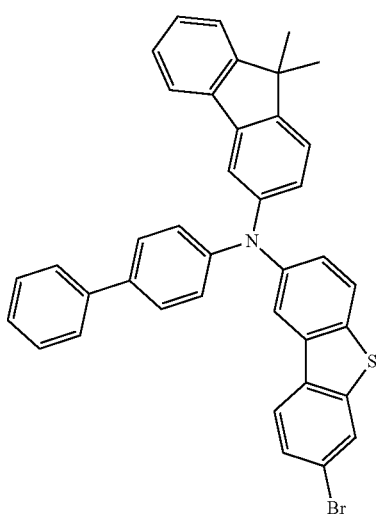
Sub 1-63
Sub 1-66

-continued
Sub 1-67
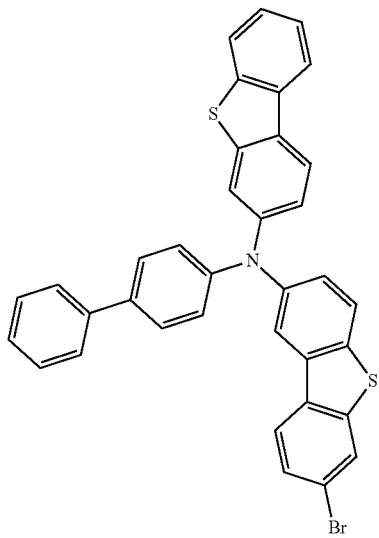
Sub 1-68
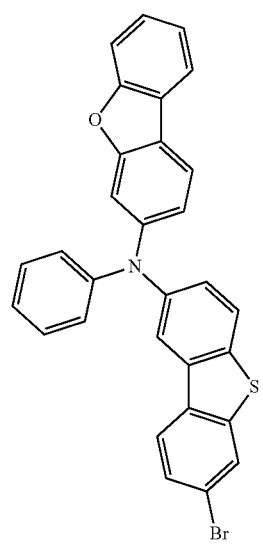
Sub 1-69
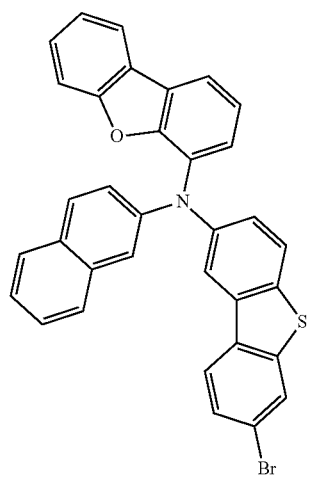
-continued
Sub 1-70
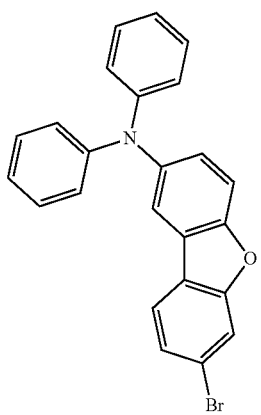
Sub 1-71
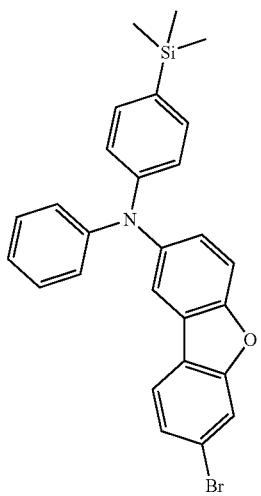
Sub 1-72
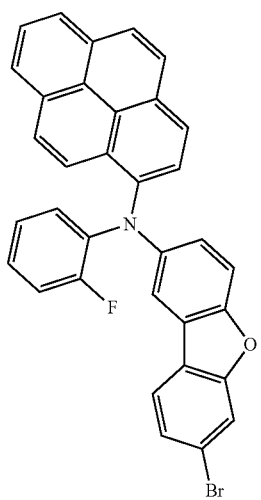

Sub 1-73
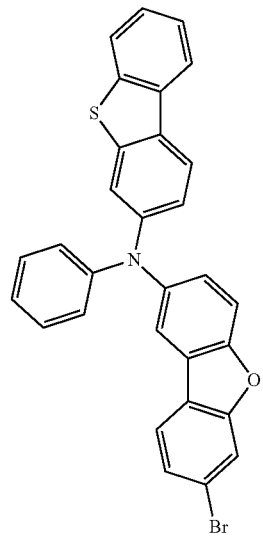
Sub 1-74
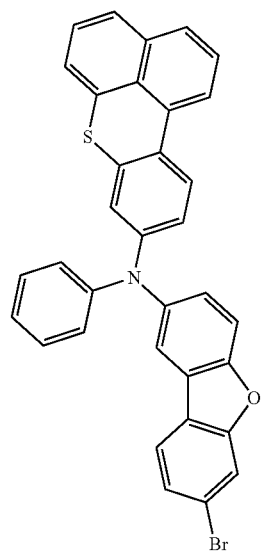
Sub 1-75
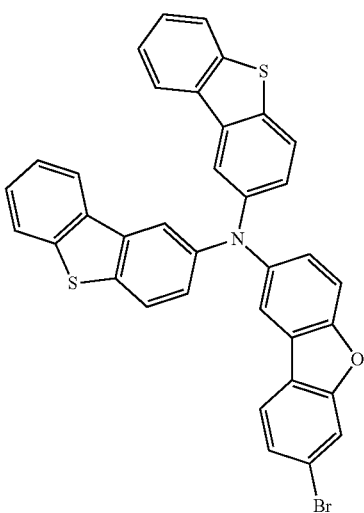
Sub 1-76
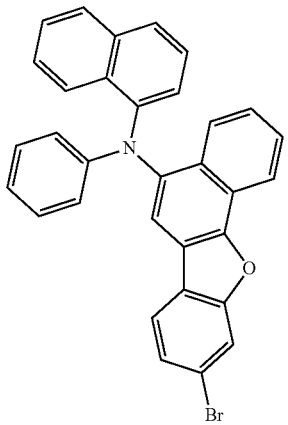
Sub 1-77
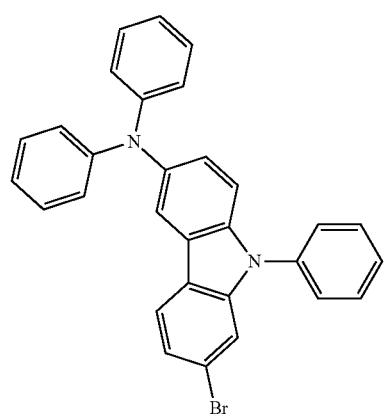
Sub 1-78
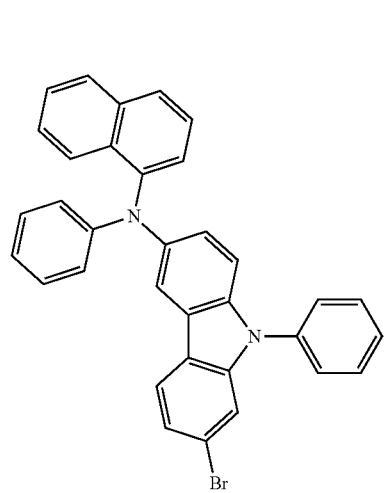

Sub 1-79
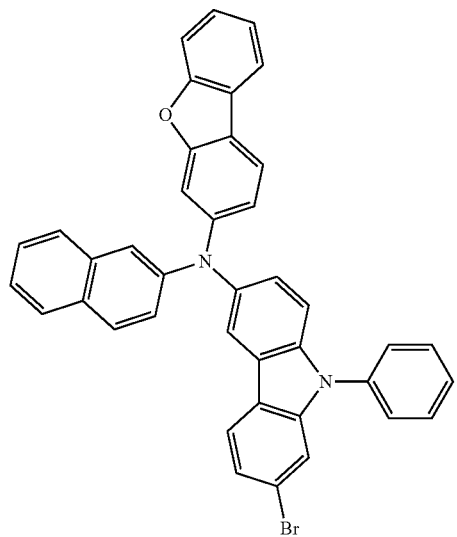
Sub 1-80
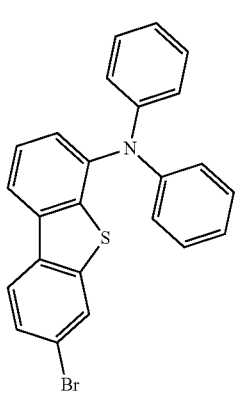
Sub 1-81
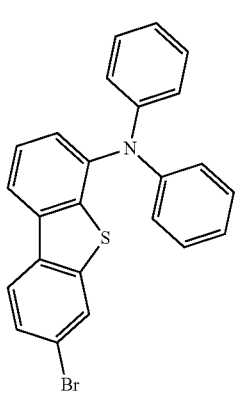
Sub 1-82
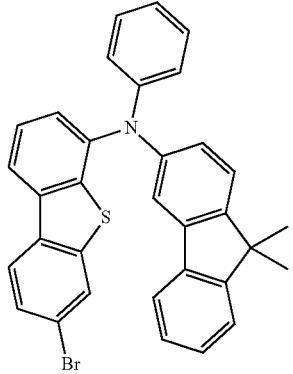
Sub 1-83
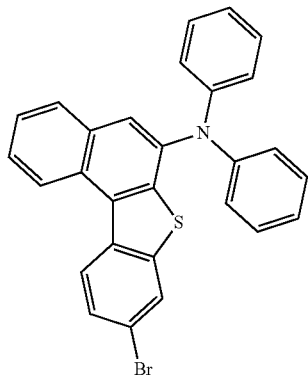
Sub 1-84
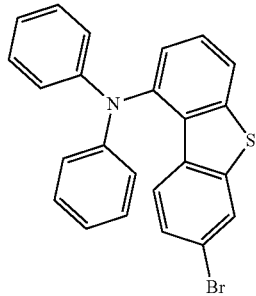
Sub 1-85
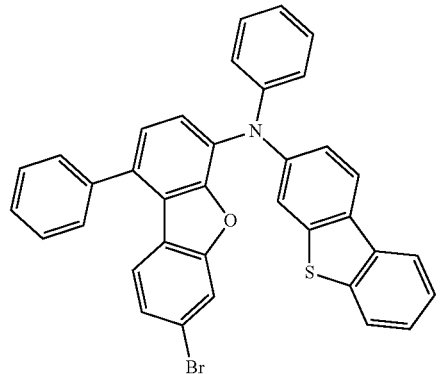

Sub 1-86
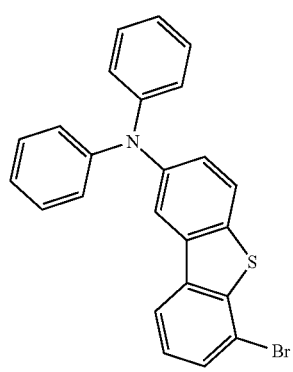
Sub 1-89
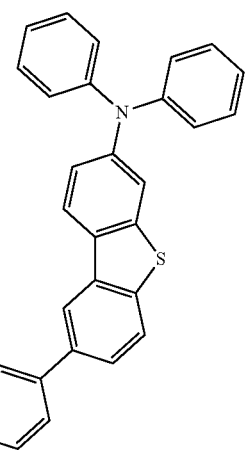
Sub 1-87
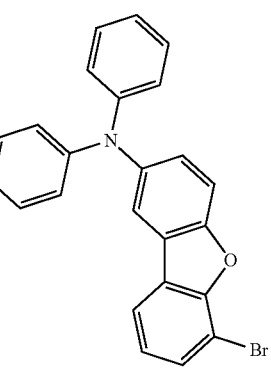
Sub 1-90
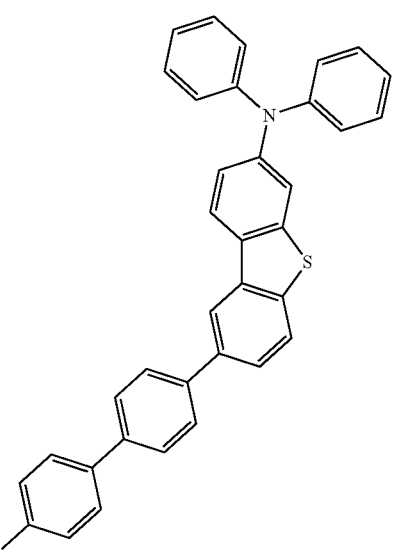
Sub 1-88
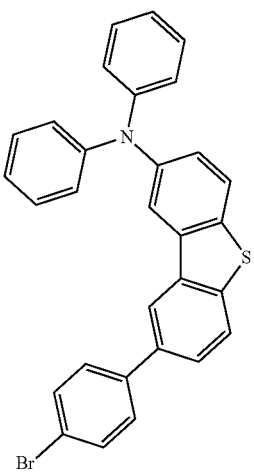
Sub 1-91
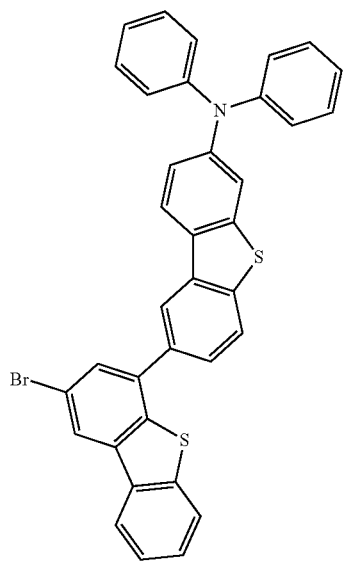

Sub 1-92
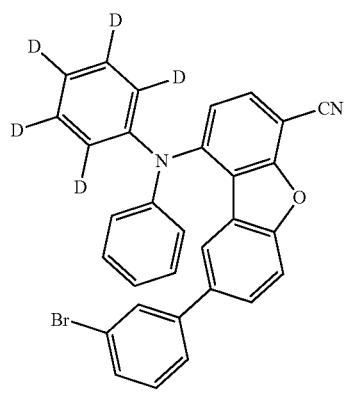
Sub 1-93
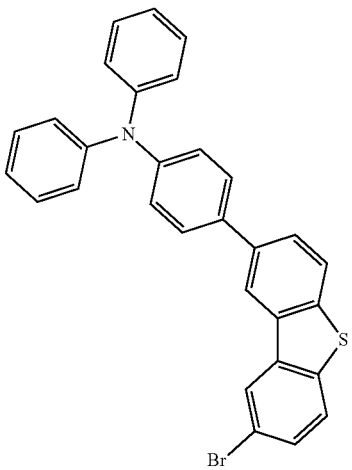
Sub 1-94
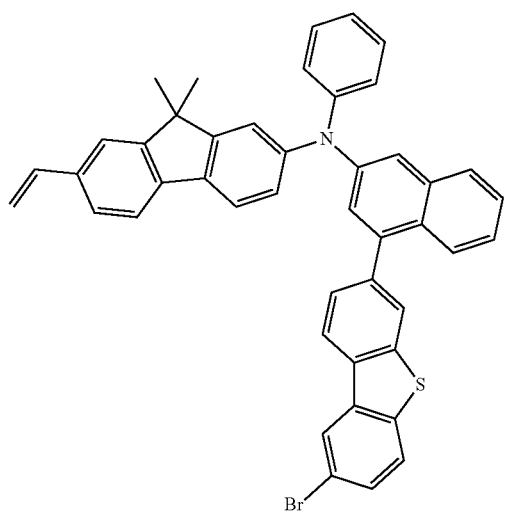
Sub 1-95
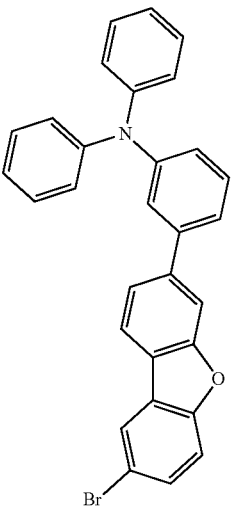
Sub 1-96
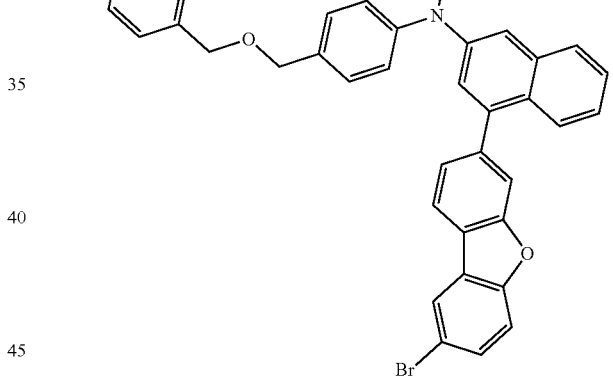
Sub 1-97
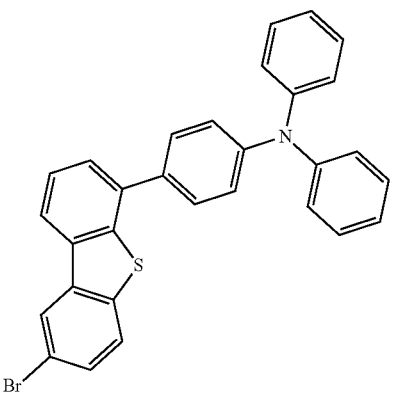

-continued
Sub 1-98
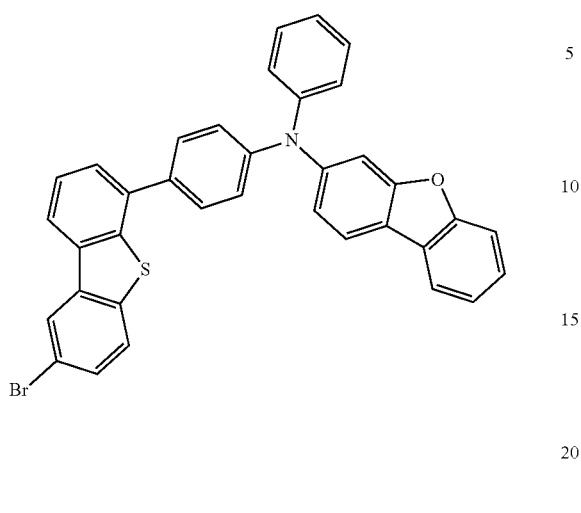
Sub 1-99
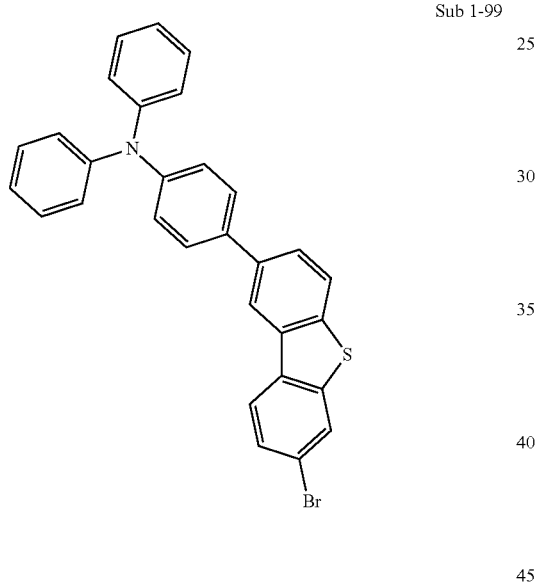
Sub 1-100
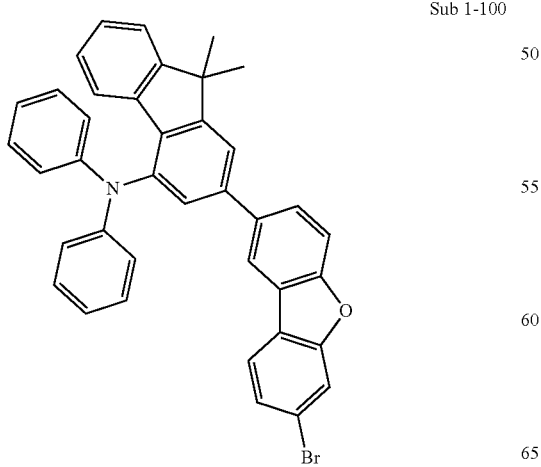
-continued
Sub 1-101
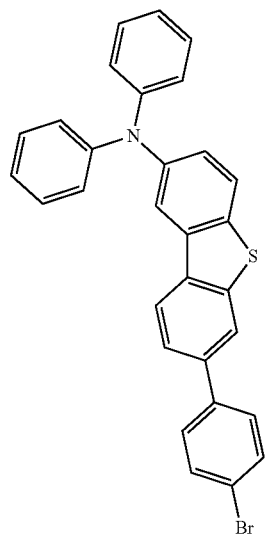
Sub 1-102
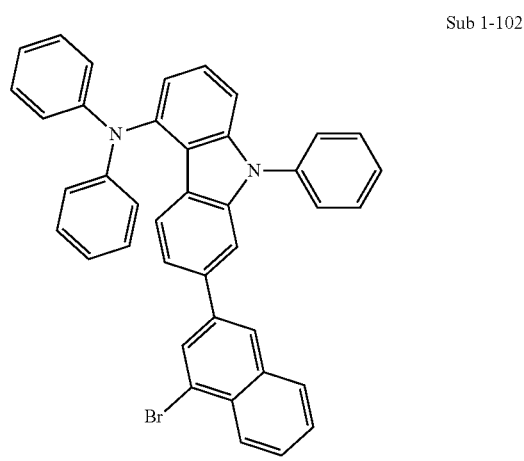
Sub 1-103
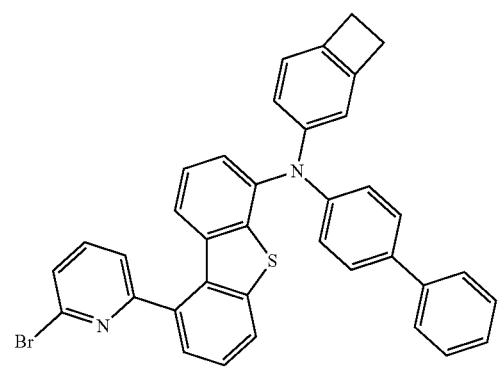

Sub 1-104

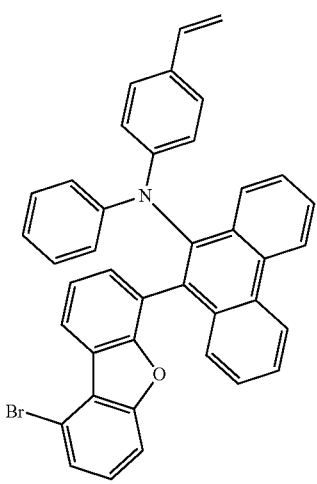

1. Synthesis Example of Sub 2-11

<Reaction Scheme 15>

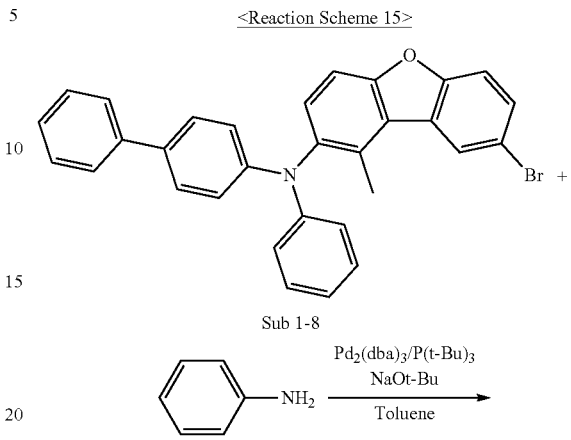

TABLE 1

| compound | FD-MS | compound | FD-MS |
|---|---|---|---|
| Sub 1-8 | m/z = 503.09($C_{31}H_{22}BrNO$ = 504.43) | Sub 1-16 | m/z = 429.02($C_{24}H_{16}BrNS$ = 430.36) |
| Sub 1-26 | m/z = 535.01($C_{30}H_{18}BrNS_2$ = 536.51) | Sub 1-56 | m/z = 489.07($C_{30}H_{20}BrNO$ = 490.40) |
| Sub 1-58 | m/z = 538.10($C_{34}H_{23}BrN_2$ = 539.48) | Sub 1-59 | m/z = 429.02($C_{24}H_{16}BrNS$ = 430.36) |
| Sub 1-76 | m/z = 513.07($C_{32}H_{20}BrNO$ = 514.42) | Sub 1-83 | m/z = 479.03($C_{28}H_{18}BrNS$ = 480.42) |
| Sub 1-95 | m/z = 489.07($C_{30}H_{20}BrNO$ = 490.40) | Sub 1-101 | m/z = 505.05($C_{30}H_{20}BrNS$ = 506.46) |

II. Synthesis of Sub 2

Sub 2 of Reaction Scheme 1 can be synthesized by the reaction path of the following Reaction Scheme 14, but is not limited thereto.

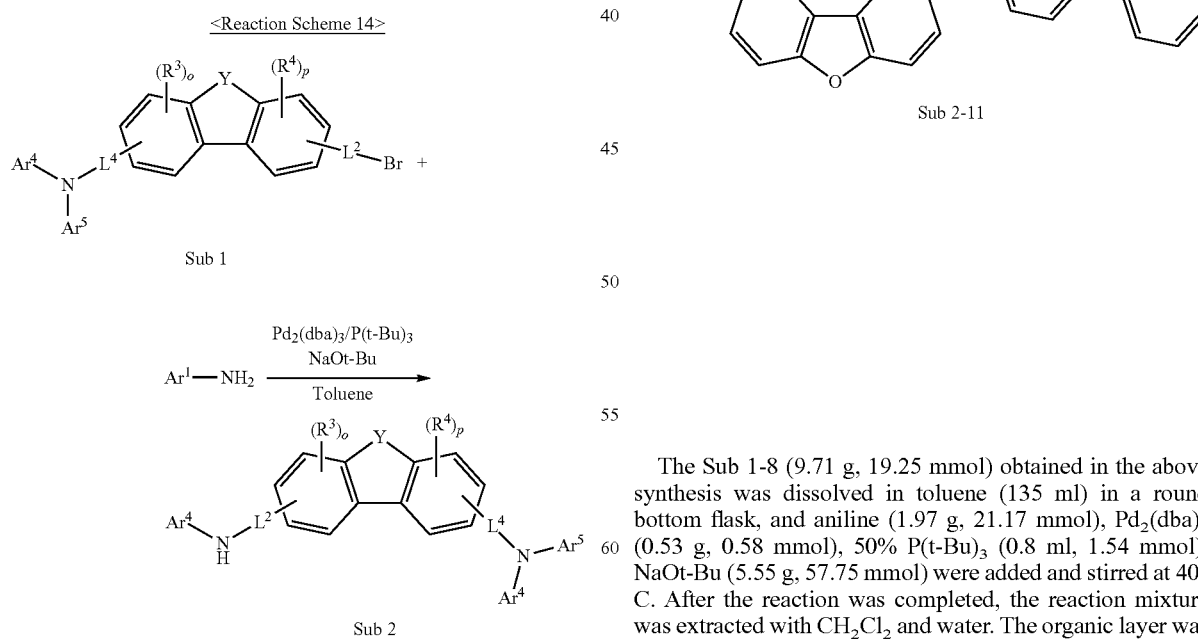

Examples of the synthesis of specific compounds belonging to Sub 2 are as follows.

The Sub 1-8 (9.71 g, 19.25 mmol) obtained in the above synthesis was dissolved in toluene (135 ml) in a round bottom flask, and aniline (1.97 g, 21.17 mmol), $Pd_2(dba)_3$ (0.53 g, 0.58 mmol), 50% P(t-Bu)$_3$ (0.8 ml, 1.54 mmol), NaOt-Bu (5.55 g, 57.75 mmol) were added and stirred at 40° C. After the reaction was completed, the reaction mixture was extracted with $CH_2Cl_2$ and water. The organic layer was dried over $MgSO_4$ and concentrated. The resulting compound was separated by silicagel column chromatography and recrystallized to obtain 7.16 g of the product. (yield: 72%)

2. Synthesis Example of Sub 2-21

<Reaction Scheme 16>

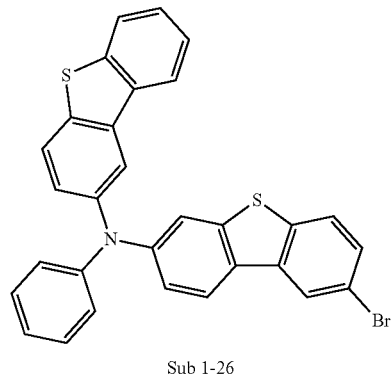

Sub 1-26

+

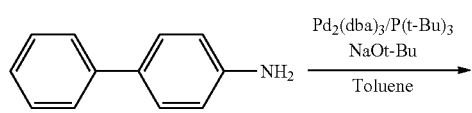

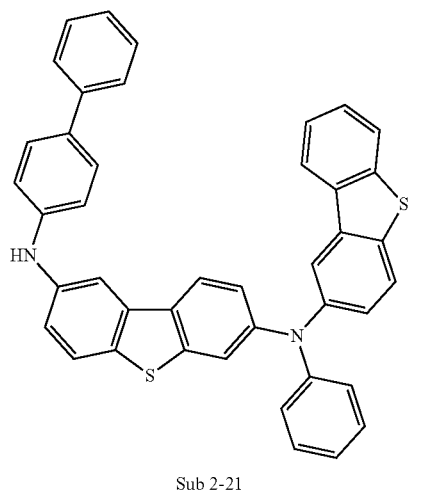

Sub 2-21

The Sub 1-26 (8.45 g, 15.75 mmol), [1,1'-biphenyl]-4-amine (2.93 g, 17.32 mmol), Pd$_2$(dba)$_3$ (0.43 g, 0.47 mmol), 50% P(t-Bu)$_3$ (0.6 ml, 1.26 mmol), NaOt-Bu (4.54 g, 47.25 mmol), toluene (110 ml) were added and 7.58 g was obtained using the above synthetic method Sub 2-11. (yield: 77%)

3. Synthesis Example of Sub 2-38

<Reaction Scheme 17>

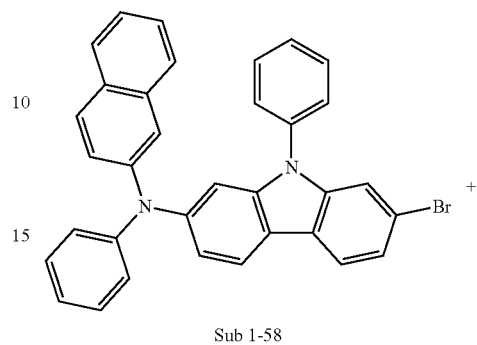

Sub 1-58

+

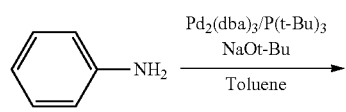

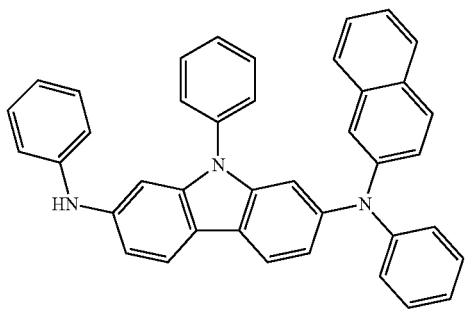

Sub 2-38

To Sub 1-58 (15.80 g, 29.29 mmol), aniline (3.00 g, 32.22 mmol), Pd$_2$(dba)$_3$ (0.80 g, 0.88 mmol), 50% P(t-Bu)$_3$ (1.1 ml, 2.34 mmol), NaOt-Bu (8.44 g, 87.86 mmol), toluene (205 ml) were added and 13.09 g was obtained using the above synthetic method Sub 2-11. (yield: 81%)

4. Synthesis Example of Sub 2-39

<Reaction Scheme 18>

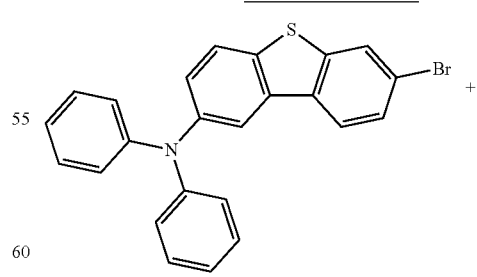

Sub 1-59

+

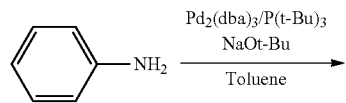

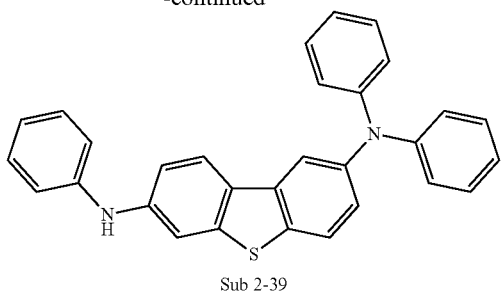

Sub 2-39

To Sub 1-59 (12.46 g, 28.95 mmol), aniline (2.97 g, 31.85 mmol), Pd$_2$(dba)$_3$ (0.80 g, 0.87 mmol), 50% P(t-Bu)$_3$ (1.1 ml, 2.32 mmol), NaOt-Bu (8.35 g, 86.86 mmol), toluene (205 ml) were added and 10.89 g was obtained using the above synthetic method Sub 2-11. (yield: 85%)

5. Synthesis Example of Sub 2-50

<Reaction Scheme 19>

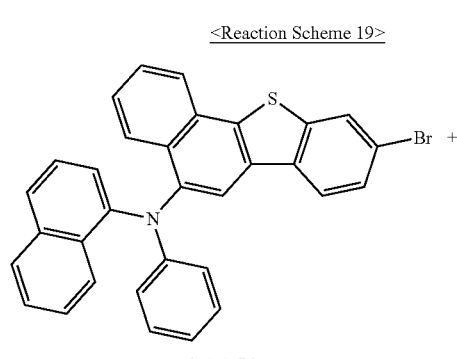

Sub 1-76

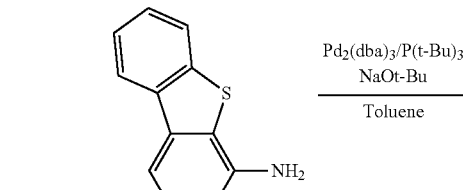

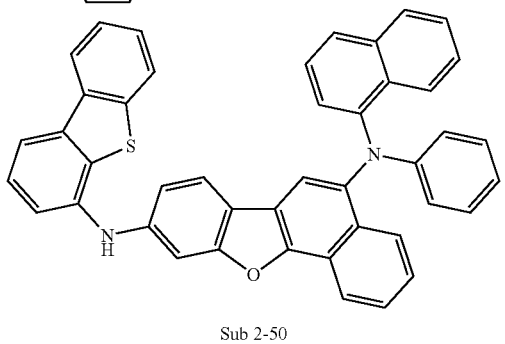

Sub 2-50

To Sub 1-76 (8.39 g, 16.31 mmol), dibenzo[b,d]thiophen-4-amine (3.58 g, 17.94 mmol), Pd$_2$(dba)$_3$ (0.45 g, 0.49 mmol), 50% P(t-Bu)$_3$ (0.6 ml, 1.30 mmol), NaOt-Bu (4.70 g, 48.93 mmol), toluene (115 ml) were added and 7.02 g was obtained using the above synthetic method Sub 2-11. (yield: 68%)

6. Synthesis Example of Sub 2-59

<Reaction Scheme 20>

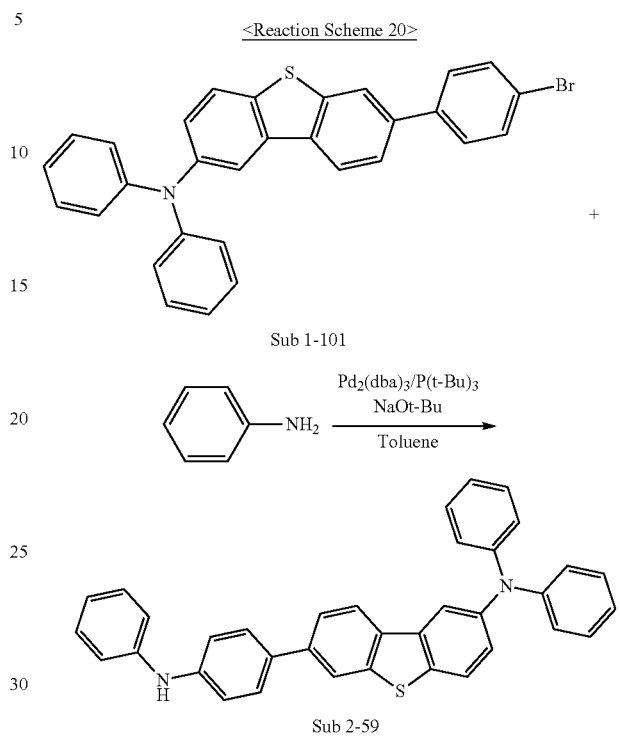

Sub 2-59

To Sub 1-101 (16.47 g, 32.52 mmol), aniline (3.33 g, 35.77 mmol), Pd$_2$(dba)$_3$ (0.89 g, 0.98 mmol), 50% P(t-Bu)$_3$ (1.3 ml, 2.60 mmol), NaOt-Bu (9.38 g, 97.56 mmol), toluene (230 ml) were added and 13.33 g was obtained using the above synthetic method Sub 2-11. (yield: 79%)

7. Synthesis Example of Sub 2-63

<Reaction Scheme 21>

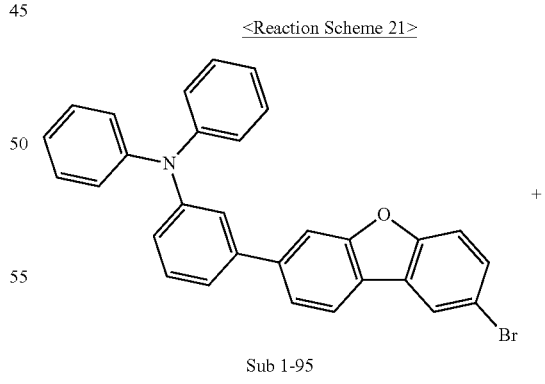

Sub 1-95

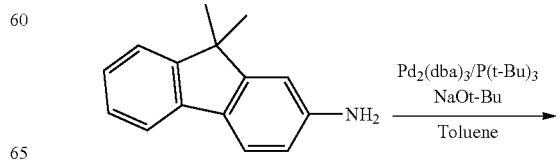

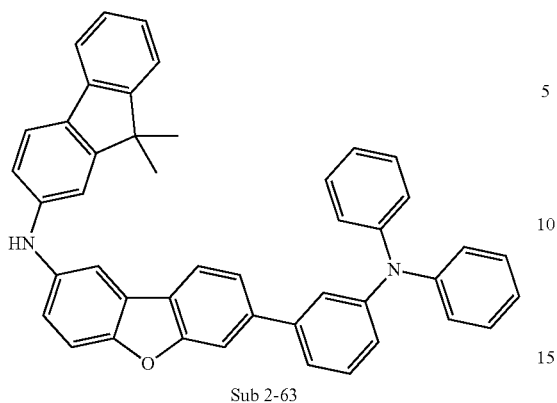

Sub 2-63

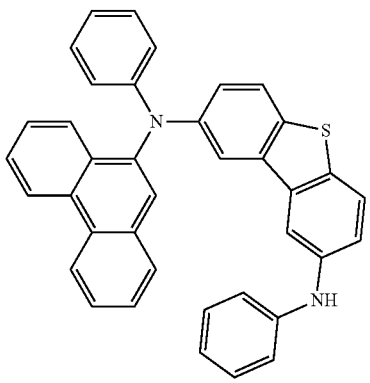

Sub 2-3

To Sub 1-95 (10.54 g, 21.49 mmol), 9,9-dimethyl-9H-fluoren-2-amine (4.95 g, 23.64 mmol), Pd$_2$(dba)$_3$ (0.59 g, 0.64 mmol), 50% P(t-Bu)$_3$ (0.8 ml, 1.72 mmol), NaOt-Bu (6.20 g, 64.48 mmol), toluene (150 ml) were added and 9.97 g was obtained using the above synthetic method Sub 2-11. (yield: 75%)

The compounds belonging to Sub 2 may be, but not limited to, the following compounds, and Table 2 shows FD-MS (Field Desorption-Mass Spectrometry) values of some compounds belonging to Sub 2.

Sub 2-1

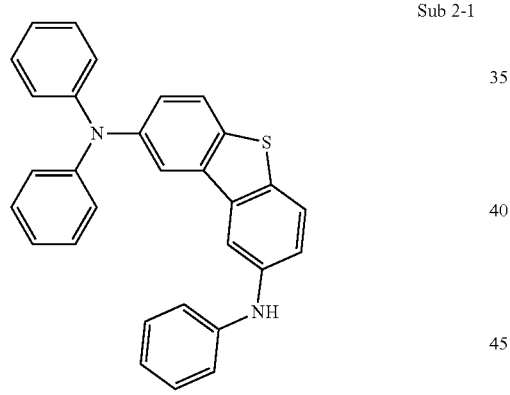

Sub 2-4

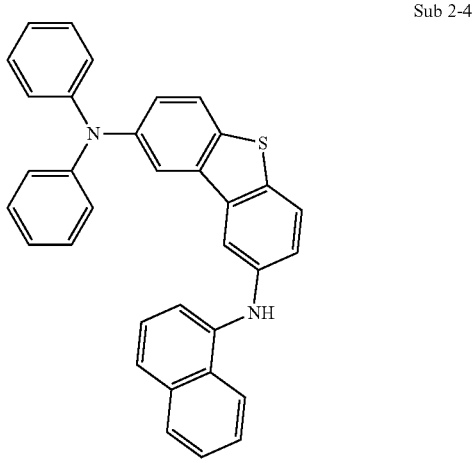

Sub 2-2

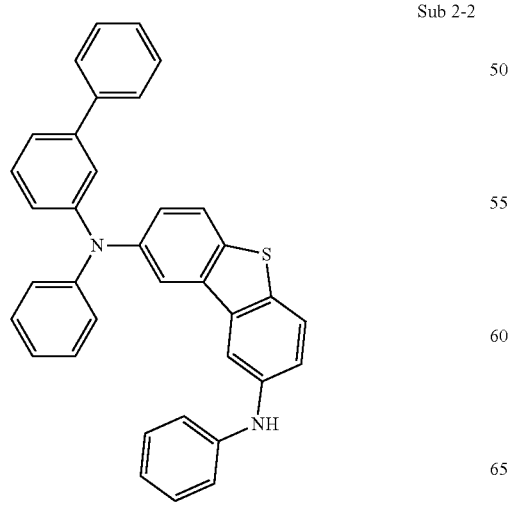

Sub 2-5

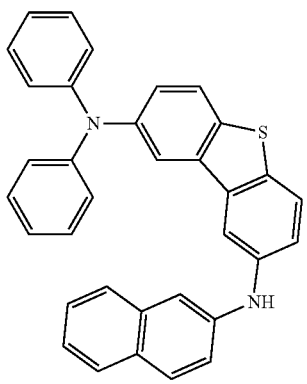

Sub 2-6
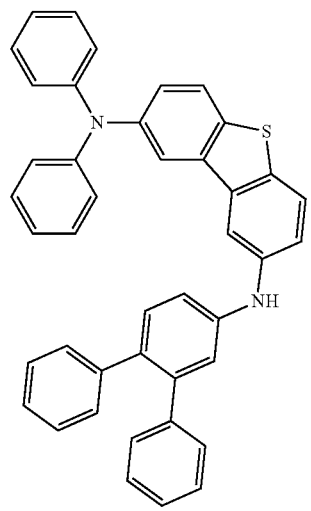
Sub 2-9
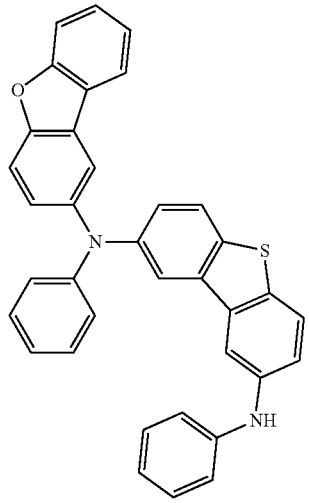
Sub 2-7
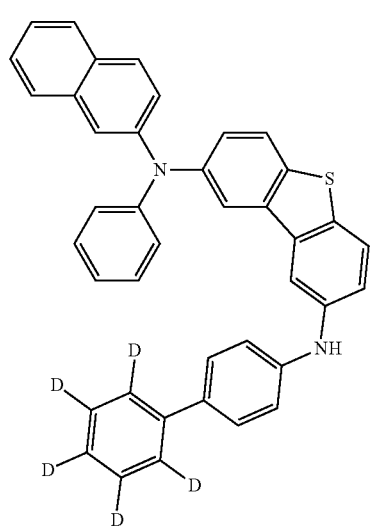
Sub 2-10
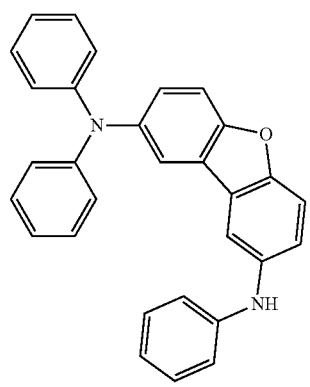
Sub 2-8
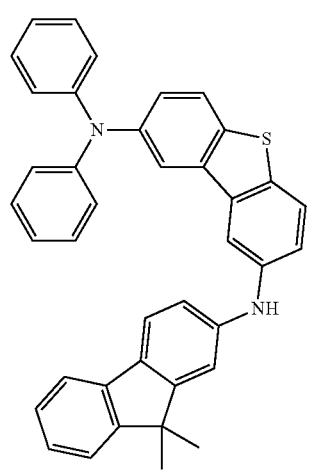
Sub 2-11
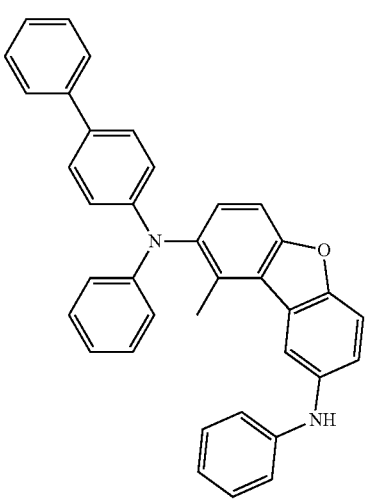

Sub 2-12
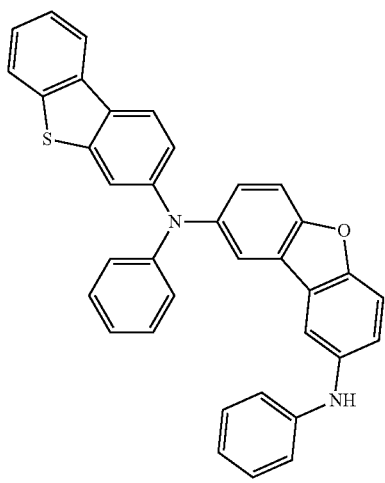
Sub 2-15
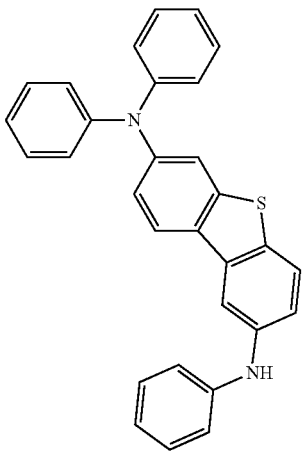
Sub 2-13
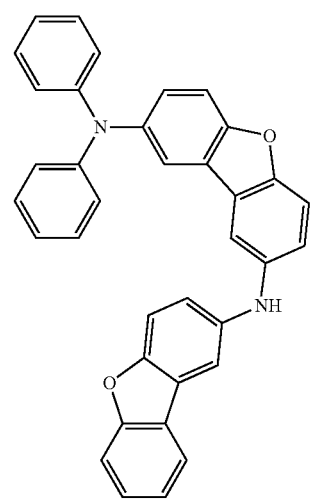
Sub 2-15
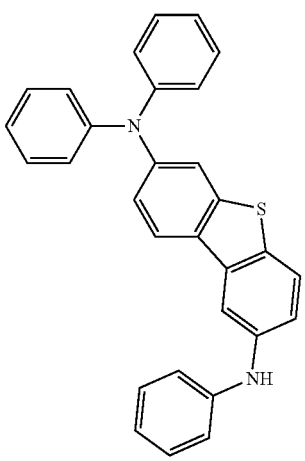
Sub 2-14
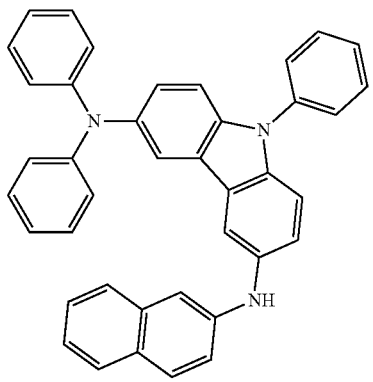
Sub 2-16
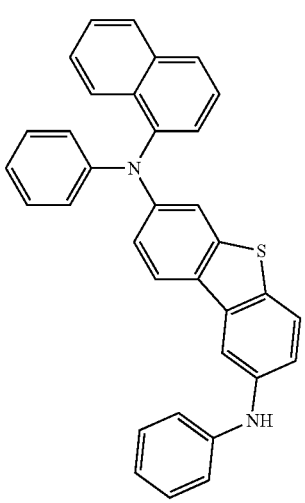

Sub 2-17
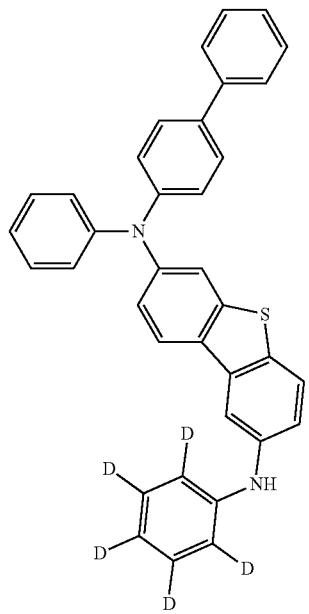
Sub 2-19
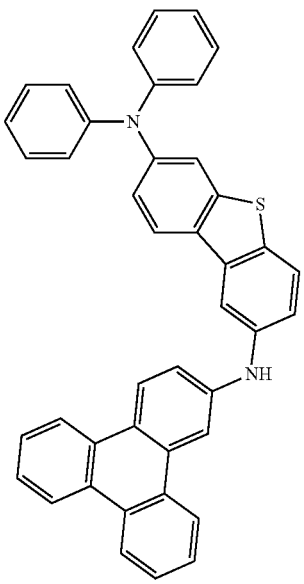
Sub 2-18
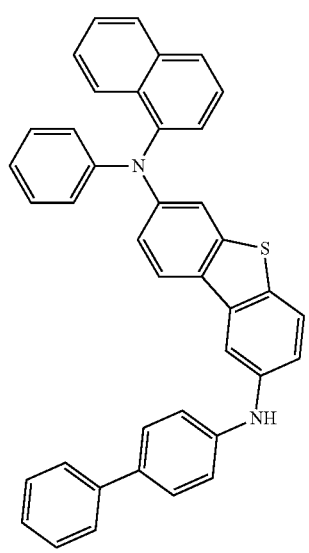
Sub 2-20
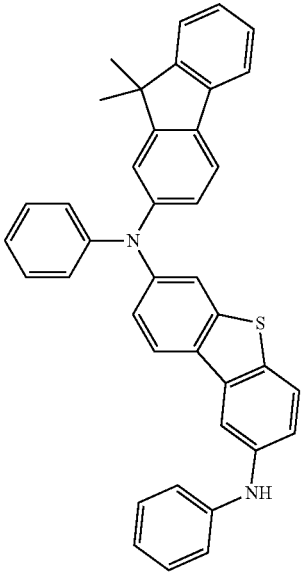

Sub 2-21
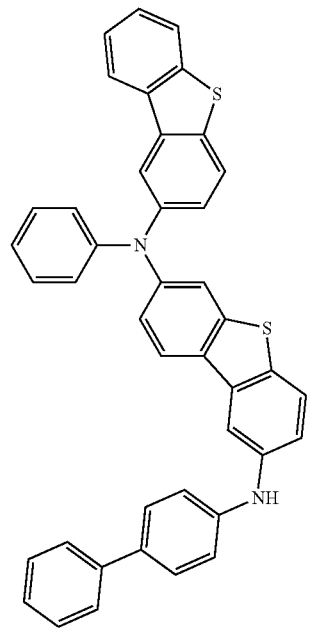
Sub 2-22
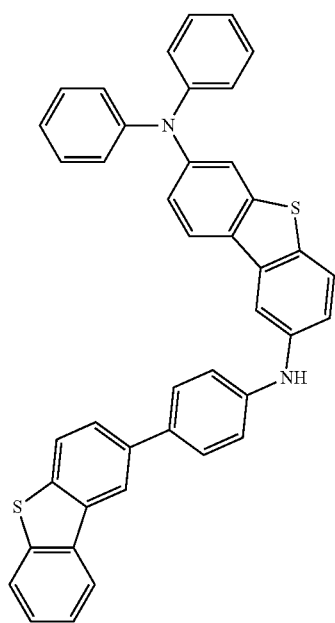
Sub 2-23
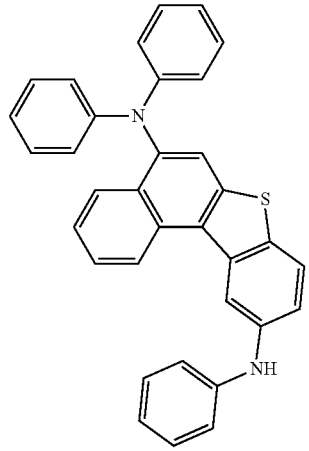
Sub 2-24
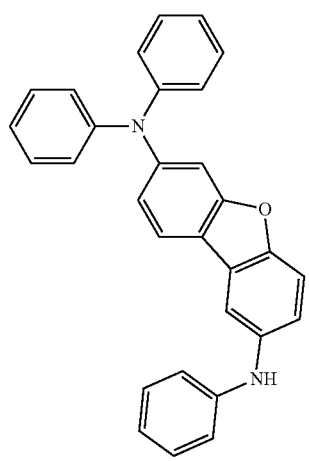
Sub 2-25
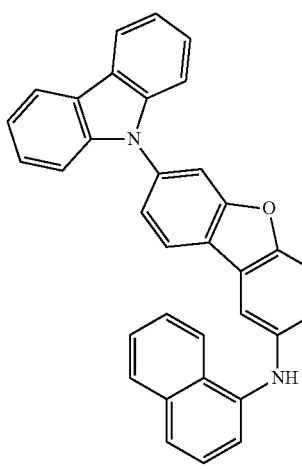

-continued
Sub 2-26
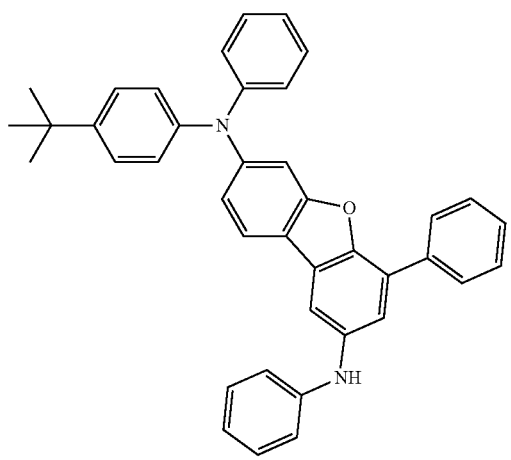
Sub 2-27
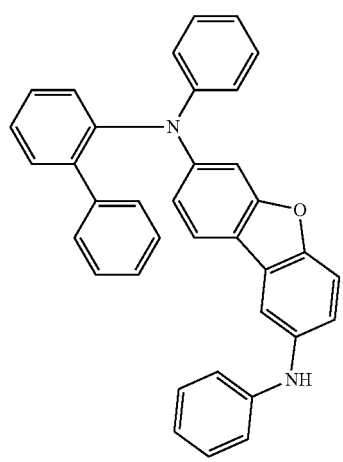
Sub 2-28
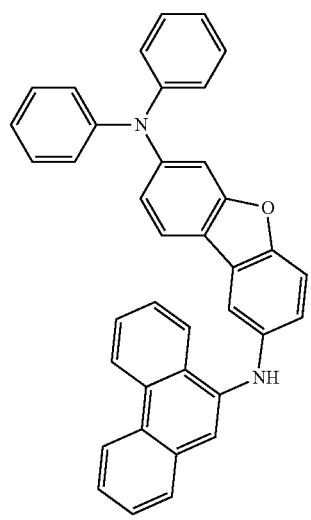
-continued
Sub 2-29
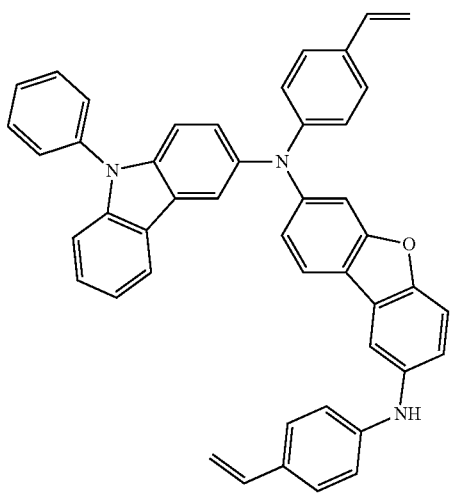
Sub 2-30
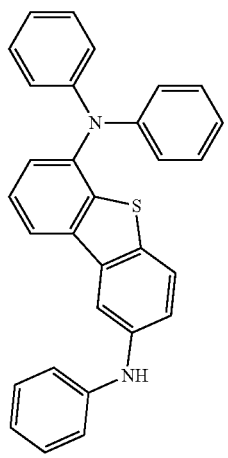
Sub 2-31
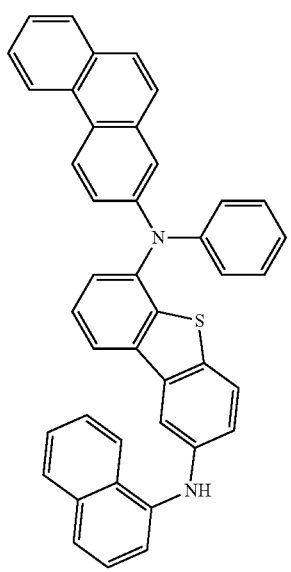

Sub 2-32
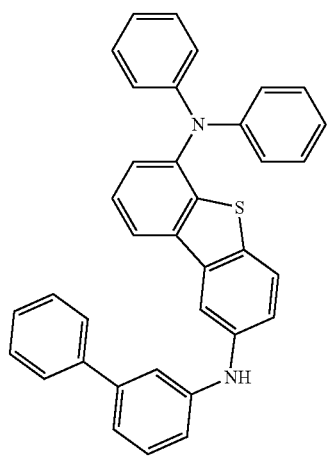
Sub 2-35
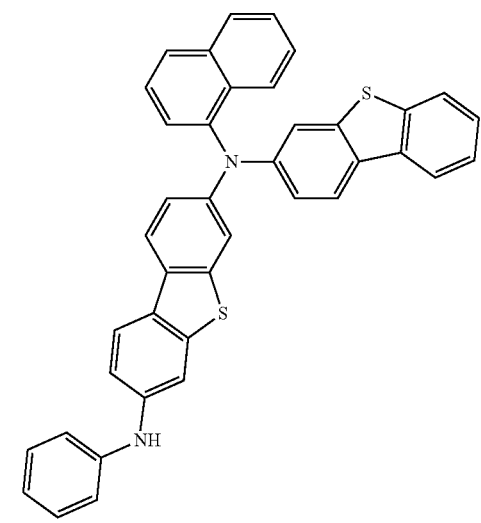
Sub 2-33
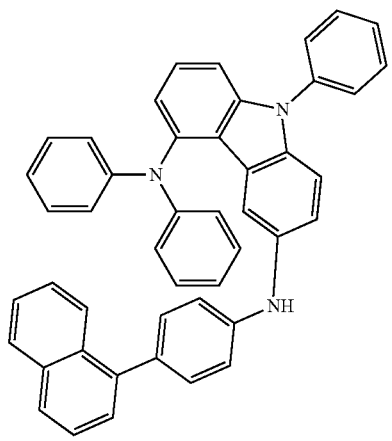
Sub 2-36
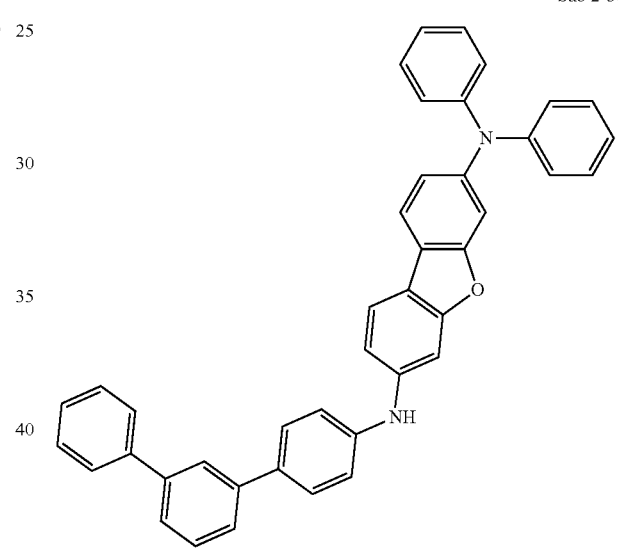
Sub 2-34
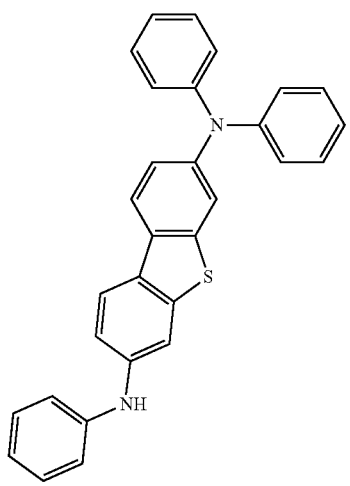
Sub 2-37
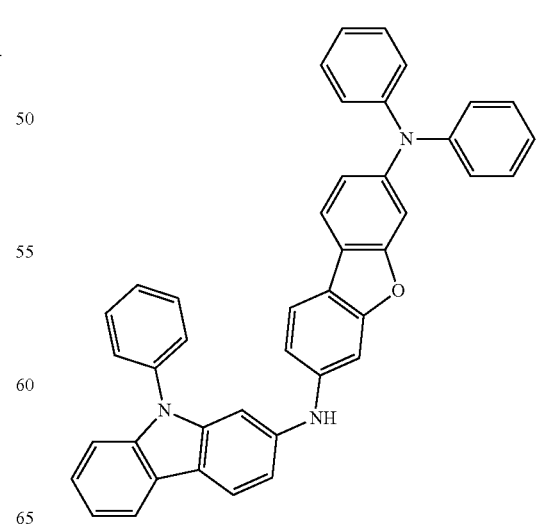

-continued
Sub 2-38
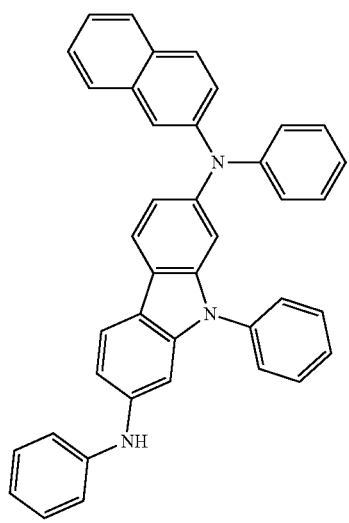
Sub 2-39
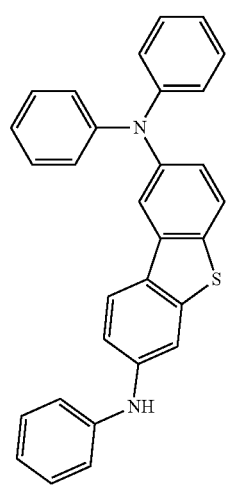
Sub 2-40
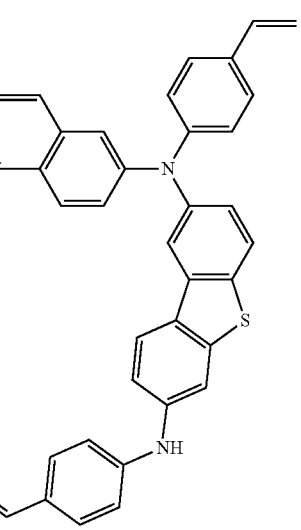
-continued
Sub 2-41
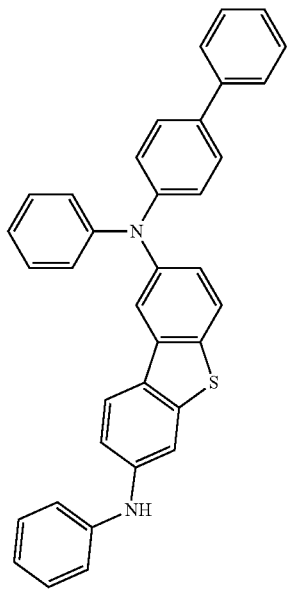
Sub 2-42
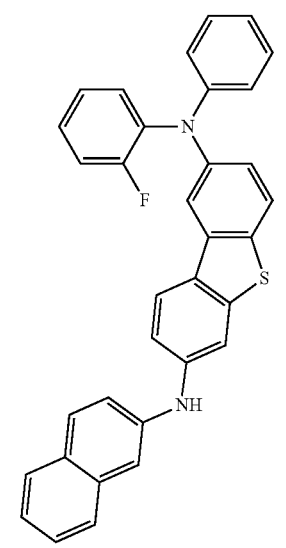
Sub 2-43
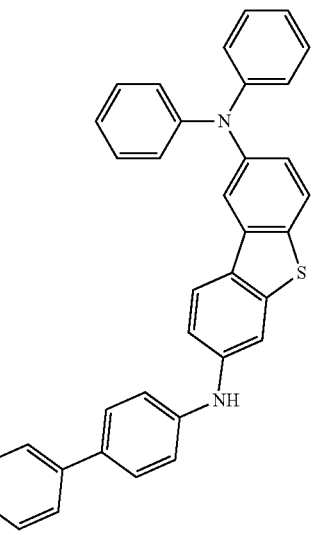

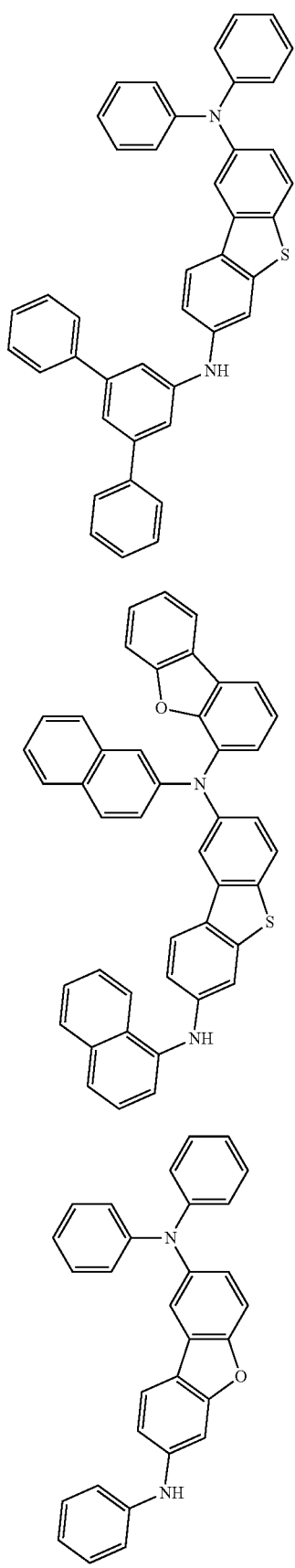
Sub 2-44
Sub 2-45
Sub 2-46
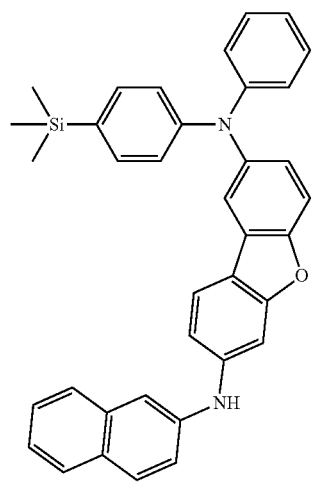
Sub 2-47
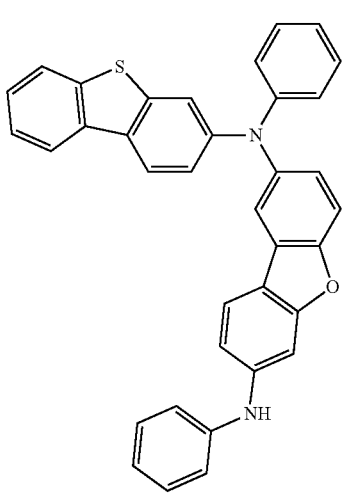
Sub 2-48
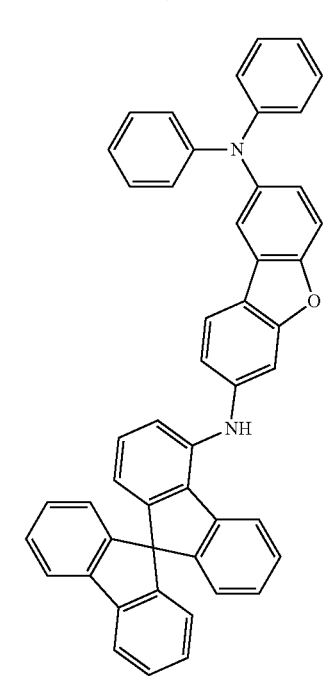
Sub 2-49

Sub 2-50
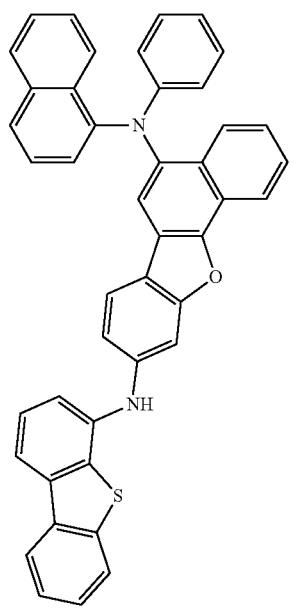
Sub 2-51
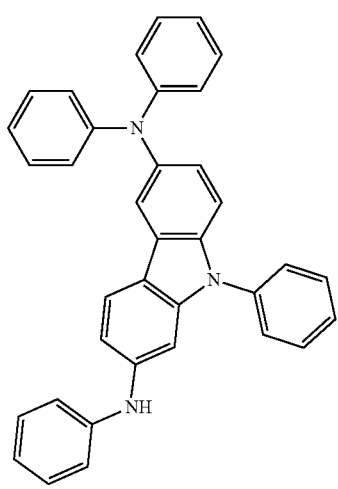
Sub 2-52
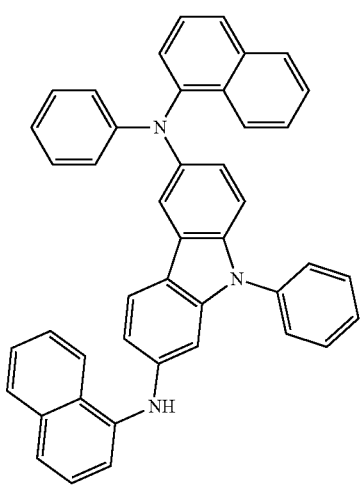
Sub 2-53
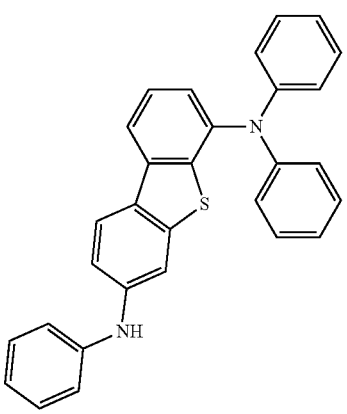
Sub 2-54
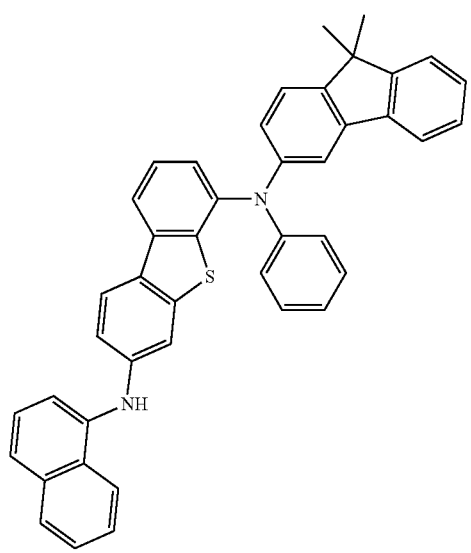
Sub 2-55
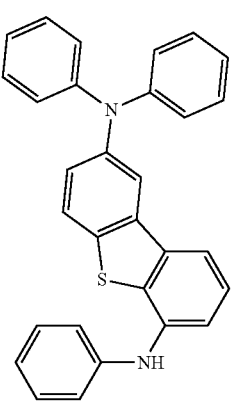

Sub 2-56
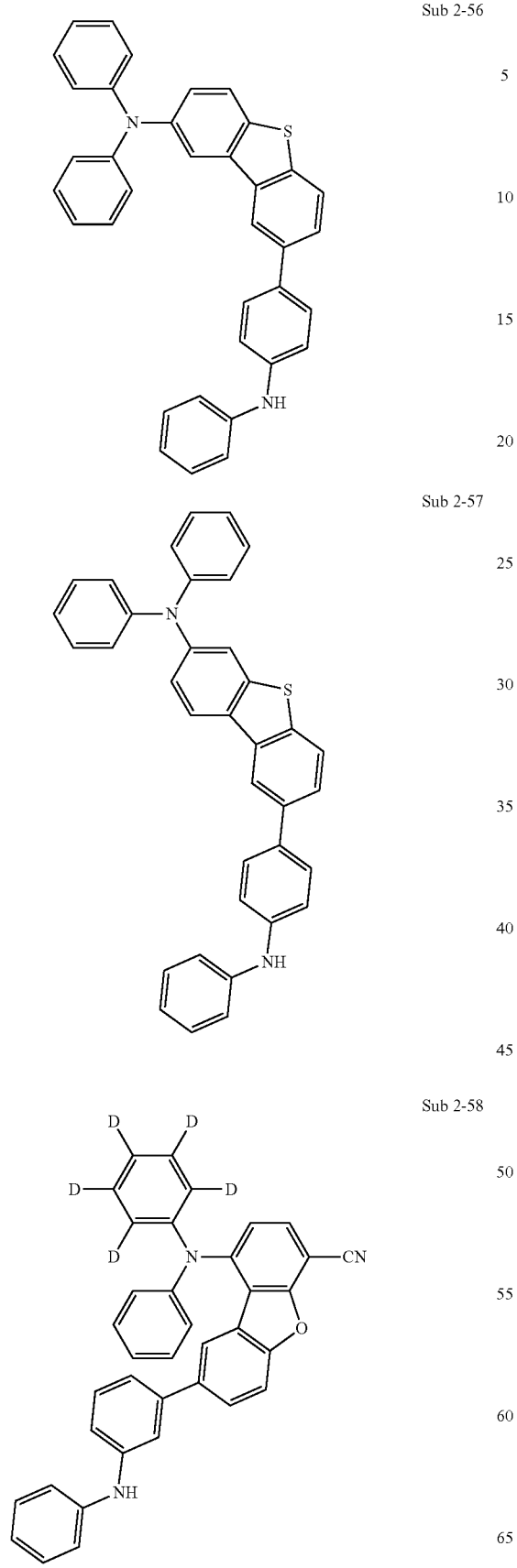
Sub 2-57
Sub 2-58
Sub 2-59
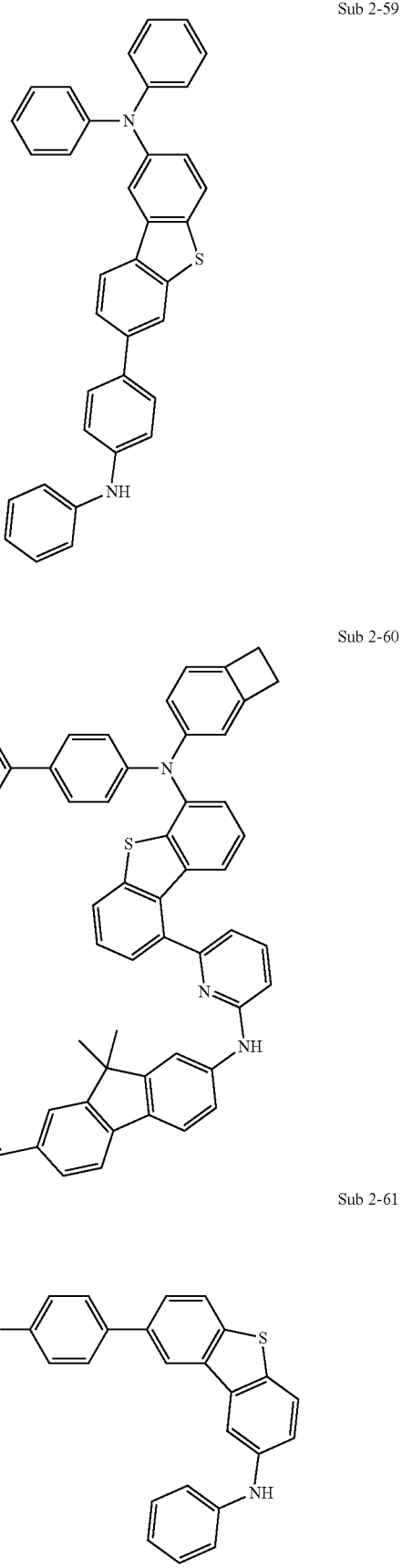
Sub 2-60
Sub 2-61

Sub 2-62
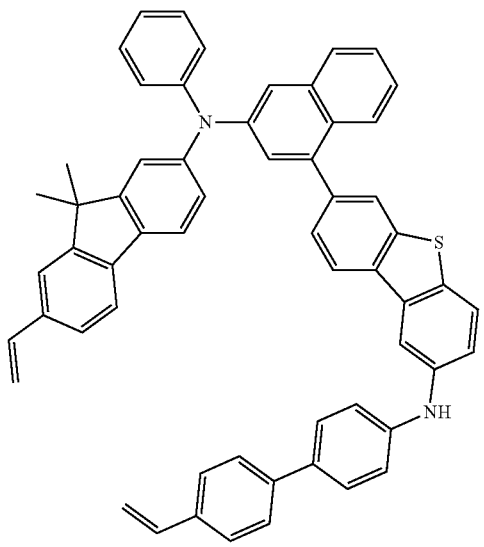
Sub 2-64
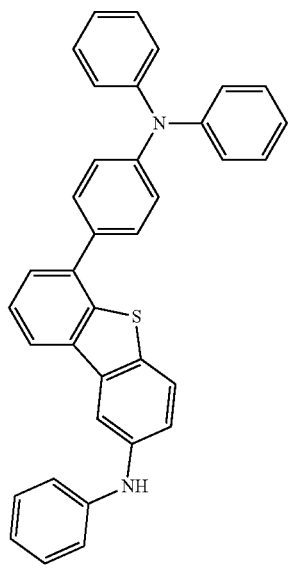
Sub 2-63
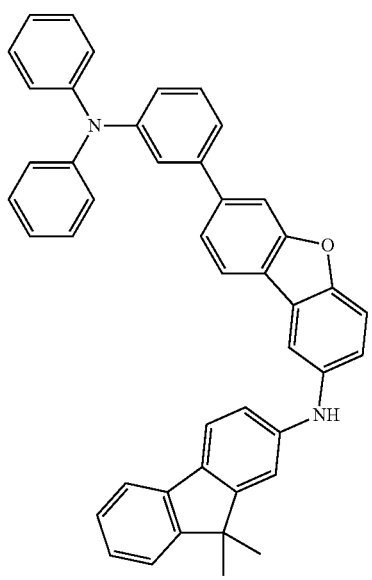
Sub 2-65
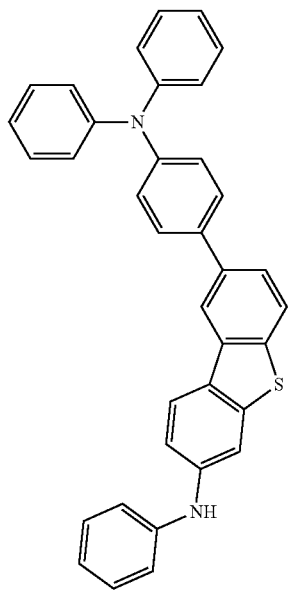
TABLE 2
| compound | FD-MS | compound | FD-MS |
|---|---|---|---|
| Sub 2-11 | m/z = 516.22($C_{37}H_{28}N_2O$ = 516.64) | Sub 2-21 | m/z = 624.17($C_{42}H_{28}N_2S_2$ = 624.82) |
| Sub 2-38 | m/z = 551.24($C_{40}H_{29}N_3$ = 551.69) | Sub 2-39 | m/z = 442.15($C_{30}H_{22}N_2S$ = 442.58) |
| Sub 2-50 | m/z = 632.19($C_{44}H_{28}N_2OS$ = 632.78) | Sub 2-59 | m/z = 518.18($C_{36}H_{26}N_2S$ = 518.68) |
| Sub 2-63 | m/z = 618.27($C_{45}H_{34}N_2O$ = 618.78) | | |

III. Product Synthesis

Sub 1 (1 eq.) was dissolved in toluene in a round bottom flask, and Sub2 (1 eq.), Pd$_2$(dba)$_3$ (0.03 eq.), (t-Bu) 3P (0.06 eq.) and NaOt-Bu (3 eq.) were stirred at 100° C. After the reaction was completed, the reaction mixture was extracted with CH$_2$Cl$_2$ and water. The organic layer was dried over MgSO$_4$ and concentrated. The resulting compound was separated by silicagel column chromatography and recrystallized to obtain final product.

1. Synthesis Example of P1-10

Sub 1-8 (6.07 g, 12.03 mmol) was dissolved in toluene (120 ml) in a round bottom flask, Sub 2-11 (6.22 g, 12.03 mmol), Pd$_2$(dba)$_3$ (0.33 g, 0.36 mmol), 50% P(t-Bu)$_3$ (0.4 ml, 0.72 mmol), NaOt-Bu (3.47 g, 36.10 mmol) were added and stirred at 100° C. After the reaction was completed, the reaction mixture was extracted with CH$_2$Cl$_2$ and water. The organic layer was dried over MgSO$_4$ and concentrated. The resulting compound was separated by silicagel column chromatography and recrystallized to obtain 7.01 g of the product. (yield: 62%)

2. Synthesis Example of P1-20

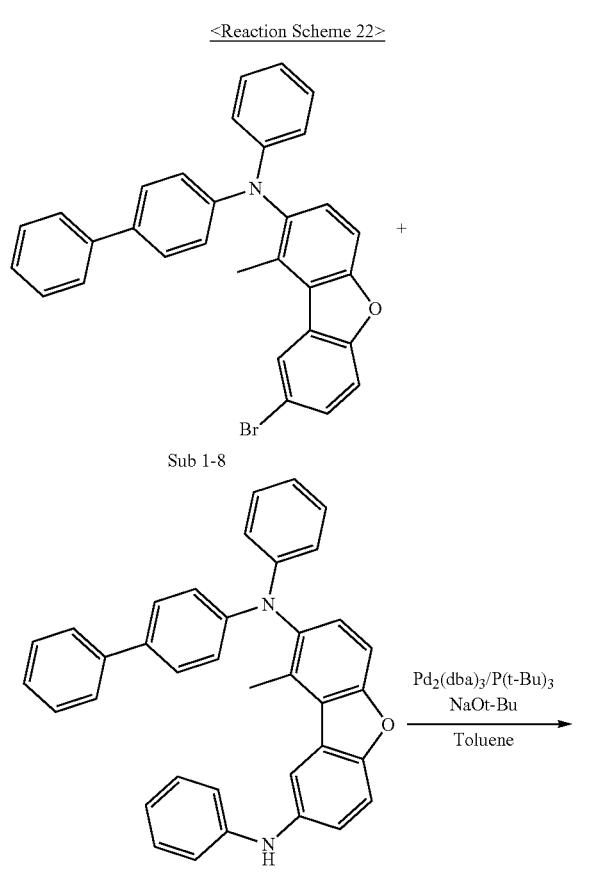

<Reaction Scheme 22>

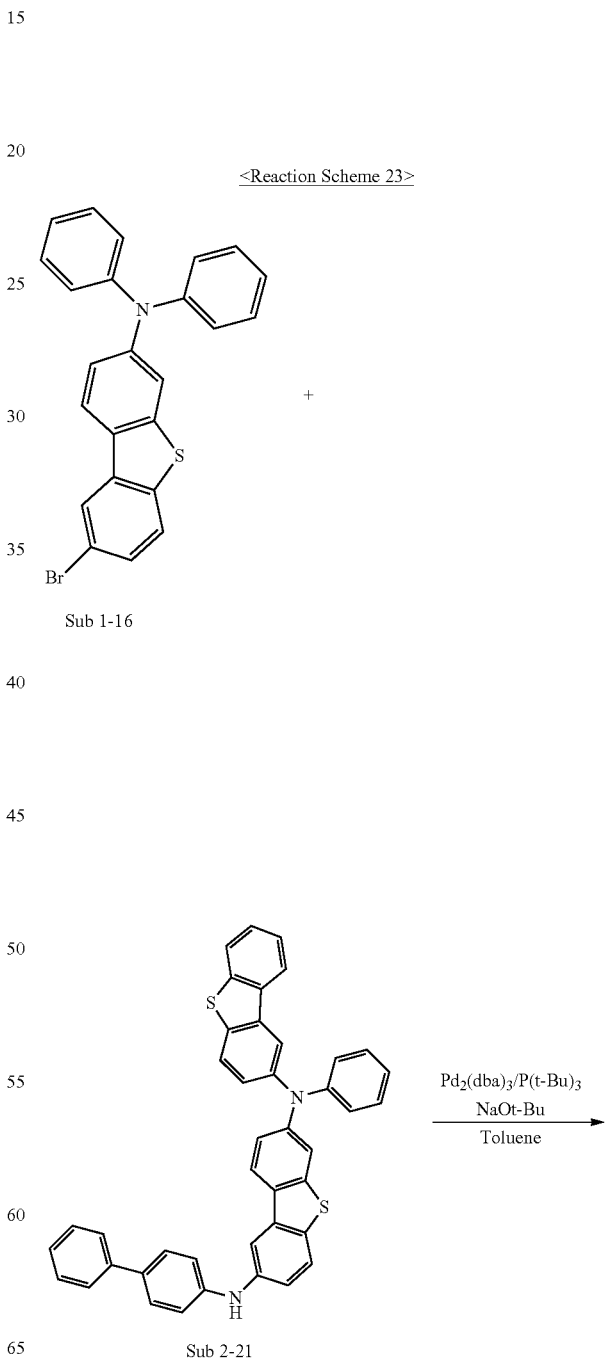

<Reaction Scheme 23>

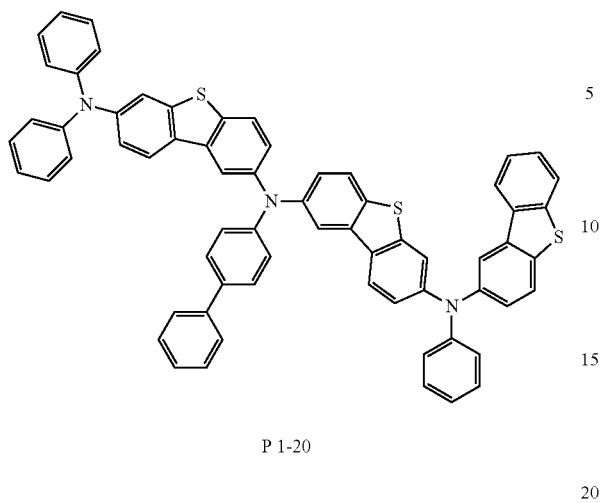
P 1-20
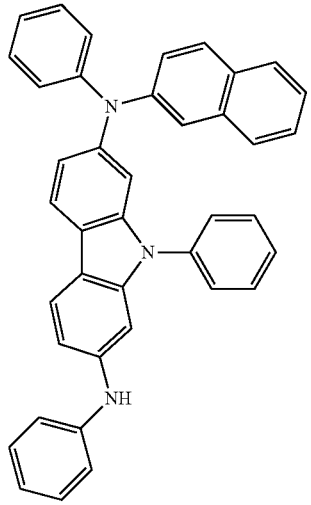
Sub 2-38
To Sub 1-16 (4.33 g, 10.06 mmol), Sub 2-21 (6.29 g, 10.06 mmol), Pd$_2$(dba)$_3$ (0.28 g, 0.30 mmol), 50% P(t-Bu)$_3$ (0.3 ml, 0.60 mmol), NaOt-Bu (2.90 g, 30.18 mmol), toluene (100 ml) were added and 7.74 g was obtained using the above synthetic method P 1-10. (yield: 79%)
3. Synthesis Example of P1-58
<Reaction Scheme 24>
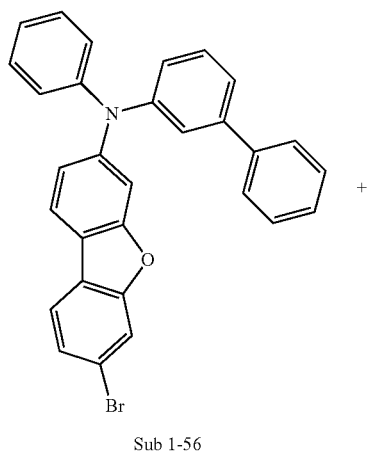
Sub 1-56
+
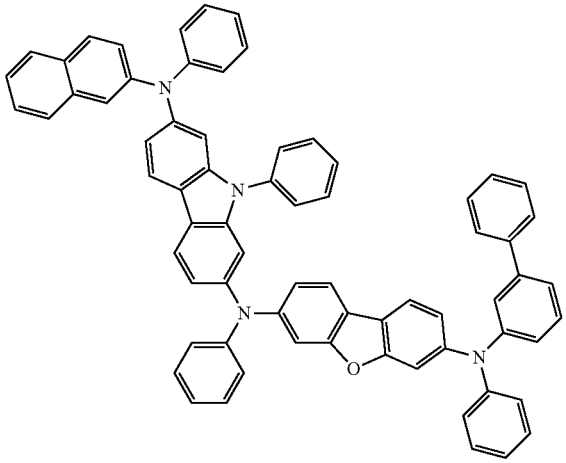
P 1-58
To Sub 1-56 (4.42 g, 9.01 mmol), Sub 2-38 (4.97 g, 9.01 mmol), Pd$_2$(dba)$_3$ (0.25 g, 0.27 mmol), 50% P(t-Bu)$_3$ (0.3 ml, 0.54 mmol), NaOt-Bu (2.60 g, 27.04 mmol), toluene (90 ml) were added and 6.67 g was obtained using the above synthetic method P 1-10. (yield: 77%)

4. Synthesis Example of P1-59
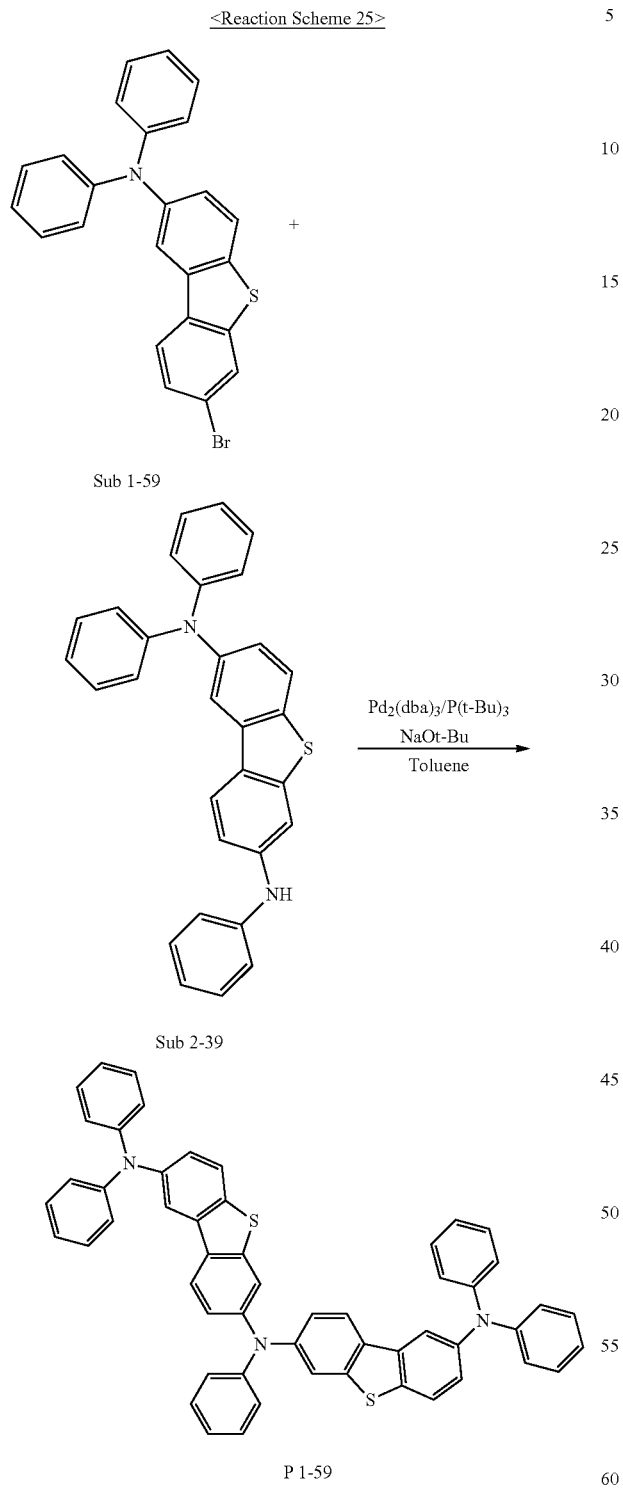
To Sub 1-59 (5.15 g, 11.97 mmol), Sub 2-39 (5.30 g, 11.97 mmol), Pd$_2$(dba)$_3$ (0.33 g, 0.36 mmol), 50% P(t-Bu)$_3$ (0.4 ml, 0.72 mmol), NaOt-Bu (3.45 g, 35.90 mmol), toluene (120 ml) were added and 7.96 g was obtained using the above synthetic method P 1-10. (yield: 84%).
5. Synthesis Example of P1-70
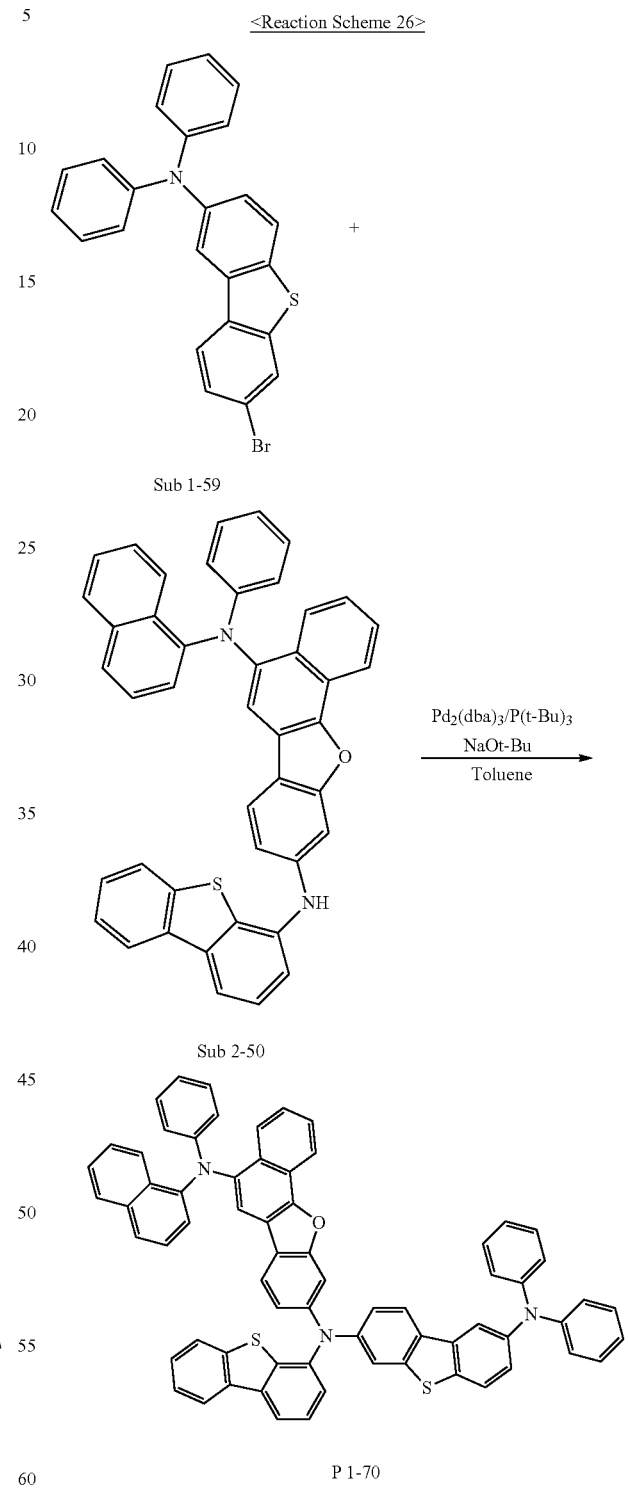
To Sub 1-59 (4.31 g, 10.01 mmol), Sub 2-50 (6.34 g, 10.01 mmol), Pd$_2$(dba)$_3$ (0.28 g, 0.30 mmol), 50% P(t-Bu)$_3$ (0.3 ml, 0.60 mmol), NaOt-Bu (2.89 g, 30.04 mmol), toluene (100 ml) were added and 7.18 g was obtained using the above synthetic method P 1-10. (yield: 73%).

6. Synthesis Example of P1-76
7. Synthesis Example of P1-92
To Sub 1-16 (4.94 g, 11.48 mmol), Sub 2-39 (5.08 g, 11.48 mmol), $Pd_2(dba)_3$ (0.32 g, 0.34 mmol), 50% $P(t\text{-}Bu)_3$ (0.3 ml, 0.69 mmol), NaOt-Bu (3.31 g, 34.44 mmol), toluene (115 ml) were added and 7.73 g was obtained using the above synthetic method P 1-10. (yield: 85%).
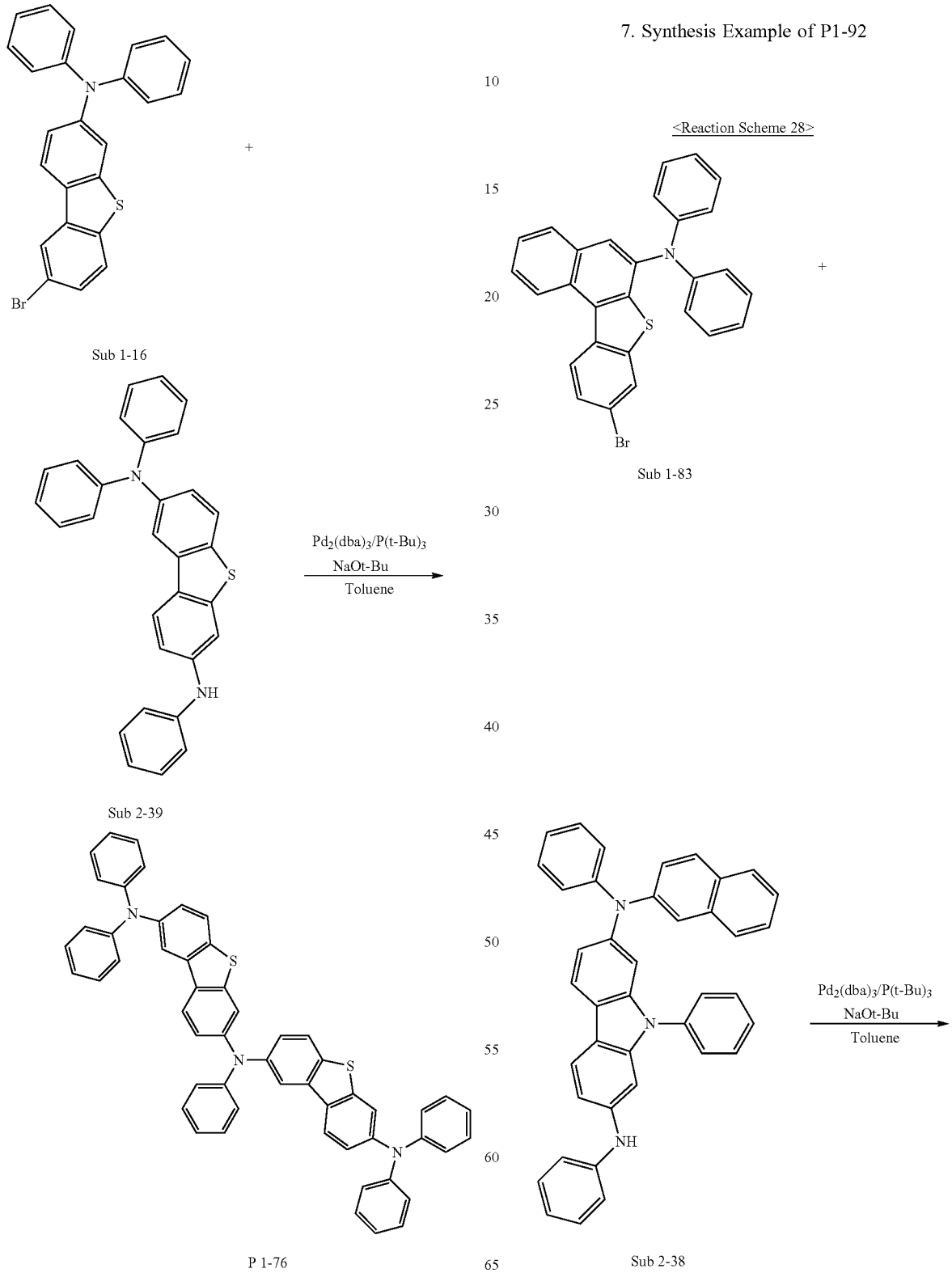

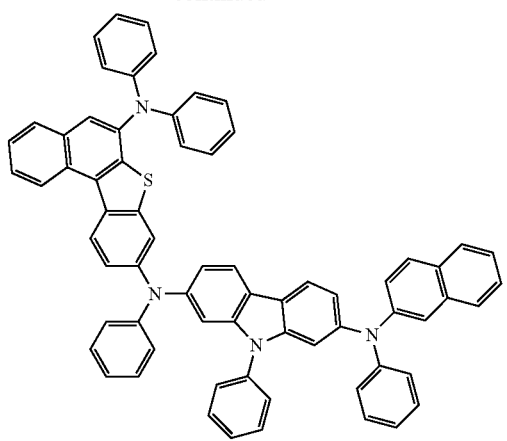
P 1-92
To Sub 1-83 (5.14 g, 10.70 mmol), Sub 2-38 (5.90 g, 10.70 mmol), Pd$_2$(dba)$_3$ (0.29 g, 0.32 mmol), 50% P(t-Bu)$_3$ (0.3 ml, 0.64 mmol), NaOt-Bu (3.08 g, 32.10 mmol), toluene (105 ml) were added and 7.73 g was obtained using the above synthetic method P 1-10. (yield: 76%).
8. Synthesis Example of P1-96
<Reaction Scheme 29>
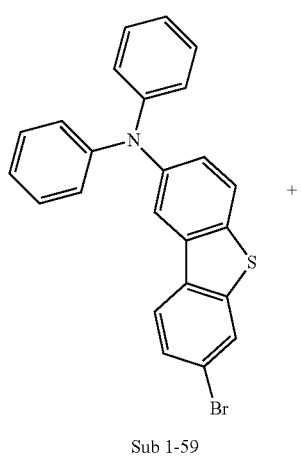
Sub 1-59
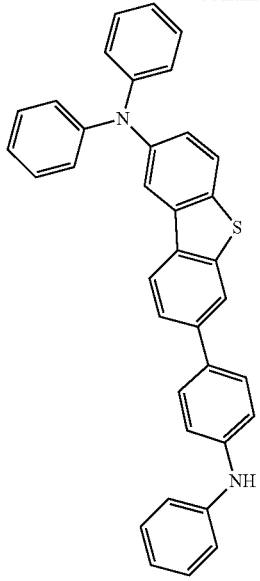
Sub 2-59
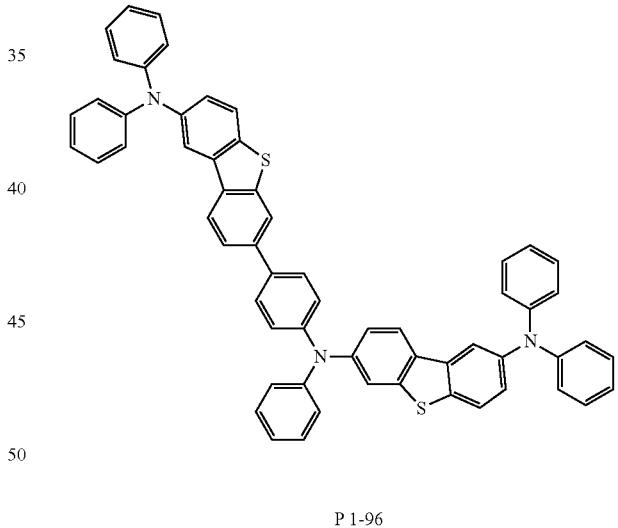
P 1-96
To Sub 1-59 (4.95 g, 11.04 mmol), Sub 2-38 (5.90 g, 10.70 mmol), Sub 2-59 (5.72 g, 11.04 mmol), Pd$_2$(dba)$_3$ (0.30 g, 0.33 mmol), 50% P(t-Bu)$_3$ (0.3 ml, 0.66 mmol), NaOt-Bu (3.18 g, 33.11 mmol), toluene (110 ml) were added and 6.52 g was obtained using the above synthetic method P 1-10. (yield: 68%).

9. Synthesis Example of P1-102
<Reaction Scheme 30>
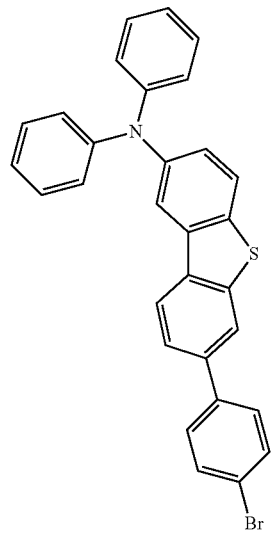
Sub 1-101
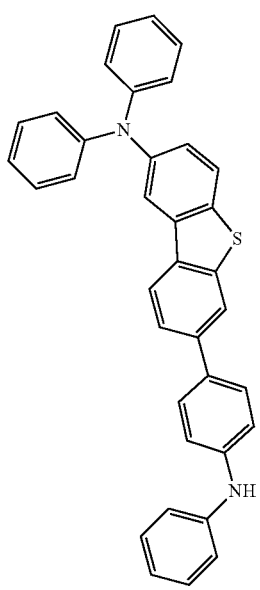
Sub 2-59
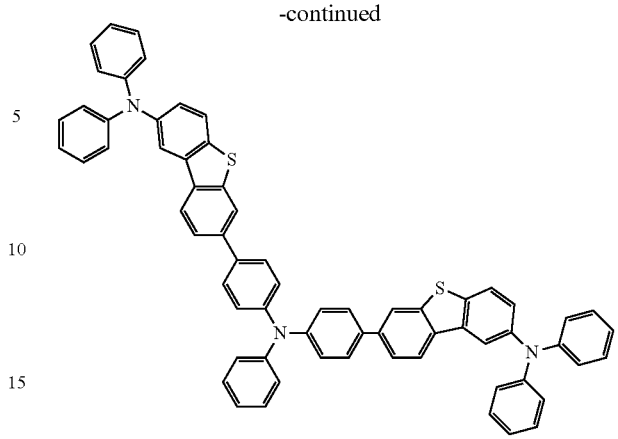
P 1-102
To Sub 1-101 (6.16 g, 12.16 mmol), Sub 2-59 (6.31 g, 12.16 mmol), Pd$_2$(dba)$_3$ (0.33 g, 0.36 mmol), 50% P(t-Bu)$_3$ (0.4 ml, 0.73 mmol), NaOt-Bu (3.51 g, 36.49 mmol), toluene (120 ml) were added and 6.89 g was obtained using the above synthetic method P 1-10. (yield: 60%).

10. Synthesis Example of P1-107

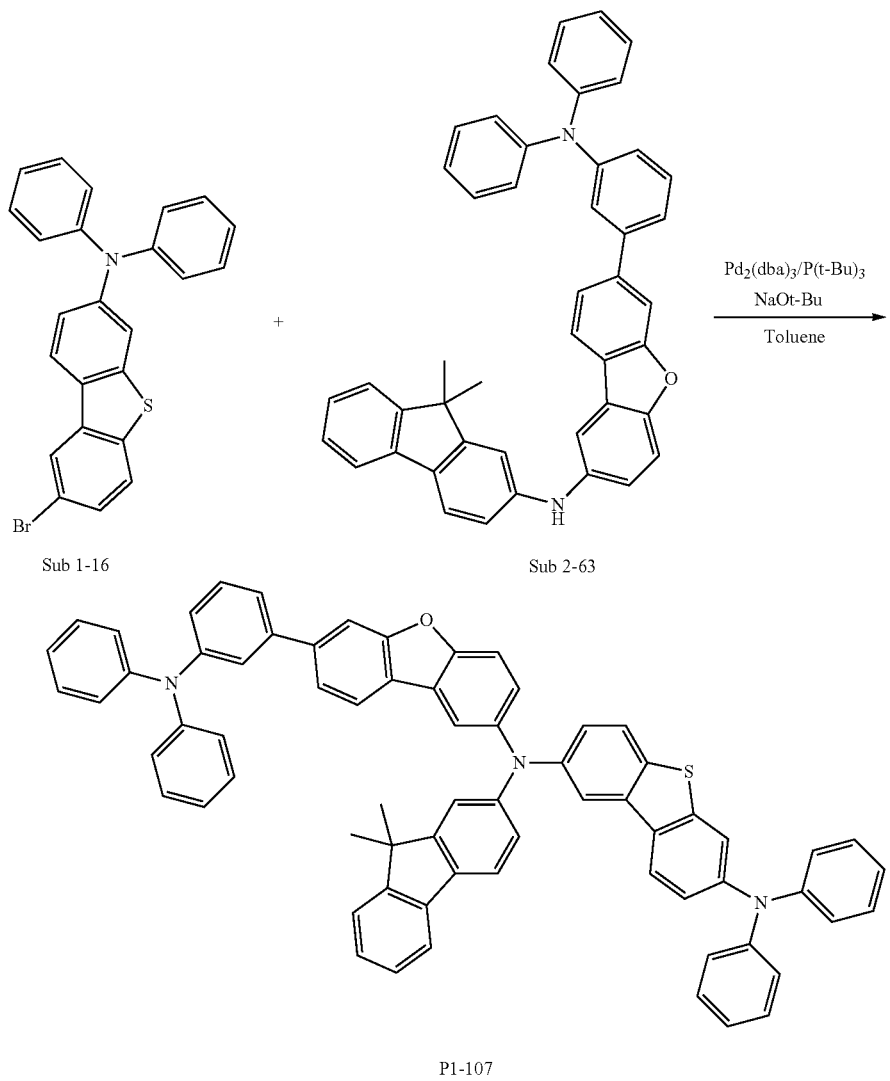

<Reaction Scheme 31>

To Sub 1-16 (5.99 g, 13.92 mmol), Sub 2-63 (8.61 g, 13.92 mmol), Pd$_2$(dba)$_3$ (0.38 g, 0.42 mmol), 50% P(t-Bu)$_3$ (0.4 ml, 0.84 mmol), NaOt-Bu (4.01 g, 41.76 mmol), toluene (140 ml) were added and 7.68 g was obtained using the above synthetic method P 1-10. (yield: 57%).

The FD-MS values of some compounds of the present invention prepared according to the above Synthesis Examples are shown in Table 3 below.

TABLE 3

| compound | FD-MS | compound | FD-MS |
|---|---|---|---|
| P 1-10 | m/z = 939.38(C$_{68}$H$_{49}$N$_3$O$_2$ = 940.16) | P 1-20 | m/z = 973.26(C$_{66}$H$_{43}$N$_3$S$_3$ = 974.27) |
| P 1-58 | m/z = 960.38(C$_{70}$H$_{48}$N$_4$O = 961.18) | P 1-59 | m/z = 791.24(C$_{54}$H$_{37}$N$_3$S$_2$ = 792.03) |
| P 1-70 | m/z = 981.28(C$_{68}$H$_{43}$N$_3$OS$_2$ = 982.23) | P 1-76 | m/z = 791.24(C$_{54}$H$_{37}$N$_3$S$_2$ = 792.03) |
| P 1-92 | m/z = 950.34(C$_{68}$H$_{46}$N$_4$S = 951.20) | P 1-96 | m/z = 867.27(C$_{60}$H$_{41}$N$_3$S$_2$ = 868.13) |
| P 1-102 | m/z = 943.31(C$_{66}$H$_{45}$N$_3$S$_2$ = 944.23) | P 1-107 | m/z = 967.36(C$_{66}$H$_{49}$N$_3$OS = 968.23) |

Otherwise, although the exemplary synthesis example of the present invention represented by Formula (1) has been described above, they are all based on the Buchwald-Hartwig cross coupling reaction, Suzuki cross-coupling reaction, Intramolecular acid-induced cyclization reaction (*J. mater. Chem.* 1999, 9, 2095.), Pd(II)-catalyzed oxidative cyclization reaction (*Org. Lett.* 2011, 13, 5504), PPh$_3$-mediated reductive cyclization reaction (*J. Org. Chem.* 2005, 70, 5014.), Ullmann reaction, etc., and those skilled in the art can easily understand that the above reaction proceeds even when other substituents (X, Y, Ar$^1$ to Ar$^6$, L$^1$ to L$^4$, R$^1$ to R$^4$, etc. substituents) defined in Formula (1) are bonded in addition to the substituents specified in the specific Synthesis Examples. For example, Sub 1 and Sub-→Final Product reaction in Reaction Scheme 1, and Sub 1→Sub 2 in Reaction scheme 14 are based on Buchwald-Hartwig cross coupling reaction, and starting material→Sub 1-I reaction, starting material→Sub 1-J reaction, starting material→Sub 1-K reaction, starting material→Sub 1-I' reaction, starting material→Sub 1-J' reaction, and starting material→Sub 1-K' reaction in Reaction scheme 2 and Reaction scheme 3 are all based on Suzuki cross-coupling reaction, and Sub 1-I→Sub 1, and Sub 1-I'→Sub 1 in Reaction scheme 2 and 3 are all based on Intramolecular acid-induced cyclization reaction (*J. mater. Chem.* 1999, 9, 2095.) Next, Sub 1-J→Sub 1 reaction, and Sub 1-J'→Sub 1 reaction in Reaction scheme 2 and 3 are based on Pd(II)-catalyzed oxidative cyclization reaction (*Org. Lett.* 2011, 13, 5504), and Sub 1-K→Sub 1-L reaction, and Sub 1-K'→Sub 1-L reaction in Reaction scheme 2 and 3, are based on PPh$_3$-mediated reductive cyclization reaction (*J. Org. Chem.* 2005, 70, 5014.), and Sub 1-L→Sub 1 reaction is based on Ullmann reaction. The above reactions will proceed even if a substituent not specifically mentioned is attached.

Manufacture and Evaluation of Organic Electric Element

Example 1) Green Organic Electroluminescent Light Emitting Diode (Hole Transport Layer)

An organic electroluminescent device was fabricated according to a conventional method using the compound of the present invention as a hole transport layer material. First, on an ITO layer (anode) formed on a glass substrate, 4,4',4''-Tris[2-naphthyl(phenyl)amino]triphenylamine (hereinafter will be abbreviated as 2-TNATA) was vacuum-deposited to a thickness of 60 nm to form a hole injection layer, and subsequently, the compound P 1-11 of the present invention was vacuum deposited on the hole injection layer to a thickness of 60 nm to form a hole transport layer. On the hole transport layer, 4,4'-N,N'-dicarbazole-biphenyl(hereinafter will be abbreviated as CBP) were used as a host material, and tris(2-phenylpyridine)-iridium (hereinafter will be abbreviated as Ir(ppy)$_3$) were used as a dopant material, an emitting layer with a thickness of 30 nm was vacuum deposited by doping with a weight of 95:10. Subsequently, on the emitting layer, (1,1'-bisphenyl)-4-olato)bis(2-methyl-8-quinolinolato)aluminum (hereinafter will be abbreviated as BAlq) was vacuum-deposited to a thickness of 10 nm to form a hole blocking layer, and on the hole blocking layer, tris(8-quinolinol)aluminum (hereinafter will be abbreviated as Alq$_3$) was deposited to a thickness of 40 nm to form an electron transport layer. After that, an alkali metal halide, LiF was vacuum deposited as an electron injection layer to a thickness of 0.2 nm, and Al was deposited to a thickness of 150 nm to form a cathode to manufacture an OLED.

[Example 2] to [Example 16] Green Organic Electroluminescent Light Emitting Diode (Hole Transport Layer)

An organic electroluminescence device was fabricated in the same manner as in Example 1, except that the compounds P 1-14 to P-108 of the present invention were respectively used instead of the compound P 1-11 of the present invention as the hole transport layer material.

[Comparative Example 1] to [Comparative Example 5]

An organic electroluminescence device was fabricated in the same manner as in Example 1, except that the following Comparative Compounds 1 to 6 described in Table 4 below were used instead of the compound P 1-11 of the present invention as the hole transport layer material.

<Comparative Compounds 1>

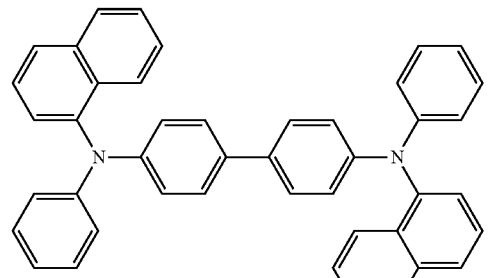

<Comparative Compound 2>

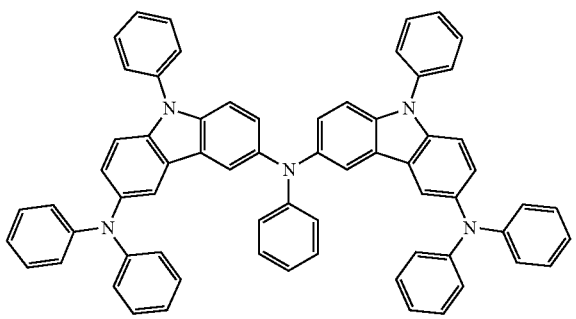

<Comparative Compound 3>

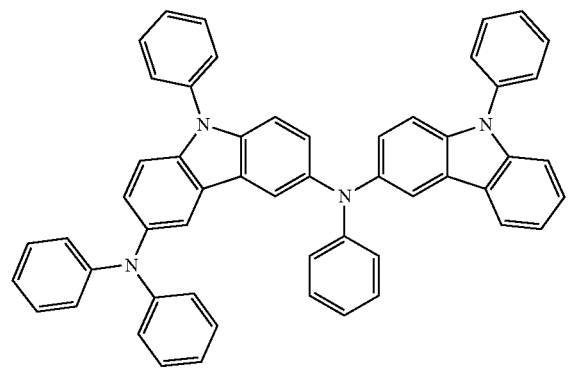

-continued

<Comparative Compound 4>

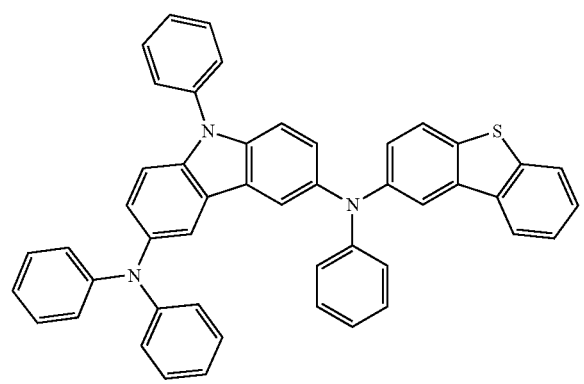

<Comparative Compound 5>

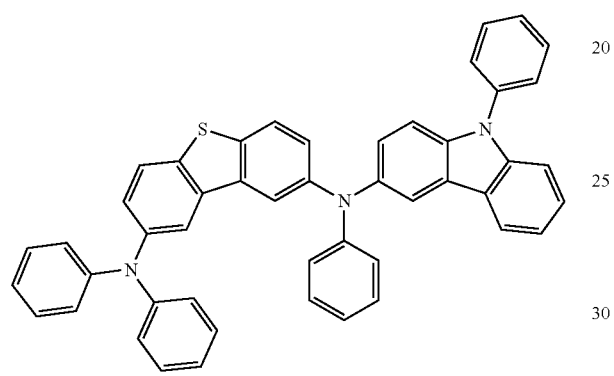

-continued

<Comparative Compound 6>

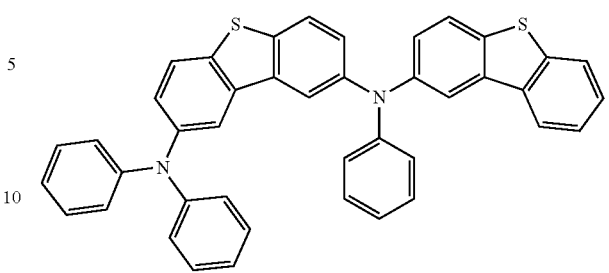

To the organic electroluminescence devices manufactured according to Examples 1 to 16 and Comparative Examples 1 to 6 of the present invention, a forward bias direct current voltage was applied, and electroluminescent (EL) properties were measured using PR-650 of Photoresearch Co., and T95 life was measured using a life measuring apparatus manufactured by McScience Inc. with a reference luminance of 5000 cd/m², and the measurement results are shown in Table 4 below.

TABLE 4

|   | compound | Voltage (V) | Current Density (mA/cm2) | Brightness (cd/m2) | Efficiency (cd/A) | Lifetime T(95) | CIE x | CIE y |
|---|---|---|---|---|---|---|---|---|
| comparative example (1) | comparative compound1 | 6.0 | 21.5 | 5000 | 23.3 | 57.2 | 0.33 | 0.61 |
| comparative example (2) | comparative compound2 | 5.9 | 18.7 | 5000 | 26.8 | 70.3 | 0.33 | 0.61 |
| comparative example (3) | comparative compound3 | 5.9 | 20.2 | 5000 | 24.8 | 66.8 | 0.33 | 0.62 |
| comparative example (4) | comparative compound4 | 5.8 | 17.6 | 5000 | 28.4 | 88.8 | 0.33 | 0.61 |
| comparative example (5) | comparative compound5 | 5.8 | 17.3 | 5000 | 28.8 | 90.1 | 0.33 | 0.62 |
| comparative example (6) | comparative compound6 | 5.8 | 18.3 | 5000 | 27.3 | 82.8 | 0.33 | 0.61 |
| example (1) | Compound (P 1-11) | 5.6 | 14.3 | 5000 | 35.0 | 128.0 | 0.33 | 0.62 |
| example (2) | Compound (P 1-14) | 5.6 | 14.6 | 5000 | 34.4 | 127.3 | 0.33 | 0.62 |
| example (3) | Compound (P 1-29) | 5.5 | 12.6 | 5000 | 39.8 | 139.3 | 0.33 | 0.61 |
| example (4) | Compound (P 1-30) | 5.5 | 12.8 | 5000 | 39.1 | 134.8 | 0.33 | 0.61 |
| example (5) | Compound (P 1-31) | 5.6 | 12.8 | 5000 | 39.2 | 134.4 | 0.33 | 0.61 |
| example (6) | Compound (P 1-32) | 5.6 | 12.8 | 5000 | 38.9 | 135.9 | 0.33 | 0.61 |
| example (7) | Compound (P 1-33) | 5.6 | 13.0 | 5000 | 38.5 | 132.0 | 0.33 | 0.61 |

TABLE 4-continued

| compound | Voltage (V) | Current Density (mA/cm2) | Brightness (cd/m2) | Efficiency (cd/A) | Lifetime T(95) | CIE x | CIE y |
|---|---|---|---|---|---|---|---|
| example (8) Compound (P 1-34) | 5.6 | 13.3 | 5000 | 37.6 | 130.6 | 0.33 | 0.61 |
| example (9) Compound (P 1-50) | 5.6 | 14.5 | 5000 | 34.6 | 124.2 | 0.33 | 0.61 |
| example (10) Compound (P 1-72) | 5.5 | 11.7 | 5000 | 42.9 | 153.8 | 0.33 | 0.62 |
| example (11) Compound (P 1-73) | 5.5 | 11.9 | 5000 | 42.0 | 148.9 | 0.33 | 0.62 |
| example (12) compound (P 1-74) | 5.5 | 12.2 | 5000 | 41.0 | 145.6 | 0.33 | 0.61 |
| example (13) compound (P 1-75) | 5.5 | 12.5 | 5000 | 40.2 | 141.3 | 0.33 | 0.62 |
| example (14) compound (P 1-84) | 5.6 | 13.1 | 5000 | 38.2 | 132.0 | 0.33 | 0.61 |
| example (15) compound (P 1-92) | 5.6 | 14.5 | 5000 | 34.6 | 124.1 | 0.33 | 0.61 |
| example (16) compound (P 1-108) | 5.7 | 15.2 | 5000 | 33.0 | 120.1 | 0.33 | 0.62 |

As it is apparent from the results of Table 4, the organic electroluminescent device using the compound of the present invention as a hole transport layer material has a relatively low driving voltage and improved luminous efficiency as well as an improved lifetime and the like as compared with an organic electroluminescent device using Comparative Compounds 1 to 6 as a hole transport layer material.

In particular, by comparing the compound of the present invention with the Comparative Compound 2, it can be confirmed that even the structure having the same skeleton (in the structure in which the tertiary amine is substituted with two heterocycles, one amine is introduced at the terminal of the heterocycle) shows different results depending on the kind of the heterocycle.

Compounds of the present invention in which at least one is substituted by dibenzofuran/dibenzothiophene instead of carbazole shows remarkably improved luminous efficiency and lifetime than Comparative Compound 2 in which all of the tertiary amine-substituted heterocycle is composed of carbazole.

This is because it has a deep HOMO energy level and a high refractive index, as dibenzofuran/dibenzothiophene is substituted for tertiary amine instead of carbazole, and as a result, when a device is manufactured, the luminous efficiency is increased by providing a high light transmittance, and as a result, the charge balance of holes and electrons in the emitting layer is increased as a result of facilitating the movement of holes through the deep HOMO energy level, thereby maximizing the luminous efficiency and lifetime.

Further, it is also confirmed by comparing Comparative Compounds 3 to 6 that different results are obtained by changing the type of the heterocycle on the same skeleton, and Comparative Compound 6 has a deeper HOMO energy level than Comparative Compounds 3 to 5, and as a result, it can be confirmed that the introduction of a heterocycle having the same form as that of Comparative Compound 6 (two substitutions of dibenzofuran/dibenzothiophene in the tertiary amine) is more suitable as the emitting auxiliary layer material.

Finally, it can be confirmed that, in the structure in which two heteroaryls are substituted in the tertiary amine, different results are obtained depending on the number of amines introduced into the heteroaryl terminal.

The compound of the present invention having a structure in which one amine is bonded to each of the two heterocycles terminal exhibits better device performance (higher luminous efficiency and longer lifetime) than Comparative Compound 4 and Comparative Compound 5 having a structure in which one amine is bonded to only one heterocycle terminal of two heterocycles. This is because the compound of the present invention introduces an amine within an appropriate range without excessively increasing the number of introduced amines at the heterocycle end than Comparative Compounds 4 to 5, the HOMO energy level of the hole transport layer is controlled and the hole transport layer has the most appropriate HOMO energy level difference with the emitting layer, so that the charge balance improves and the light emission in the emitting layer becomes better.

In terms of the above-described characteristics (high refractive index, deep HOMO energy level), it shows that the band gap, electrical characteristics, and interface characteristics are largely changed depending on the kind of the heteroaryl substituted for the tertiary amine and the number of the amine introduced at the heteroaryl terminal, and it can be confirmed that this is a major factor in improving the performance of the device.

Further, in the case of the hole transport layer, the correlation with the emitting layer (host) must be grasped, and even if similar cores are used, it is very difficult for those skilled in the art to deduce the characteristics of the hole transport layer in which the compound according to the present invention is used.

[Example 17] Red Organic Light Emitting Diode (Emitting Auxiliary Layer)

An organic electroluminescent device was fabricated according to a conventional method using the compound of the present invention as an emitting auxiliary layer material. First, on an ITO layer (anode) formed on a glass substrate, 2-TNATA was vacuum-deposited to a thickness of 60 nm to form a hole injection layer, and NPB was vacuum deposited on the hole injection layer to a thickness of 60 nm to form a hole transport layer. Subsequently, the compound P 1-1 of the present invention was vacuum-deposited on the hole transport layer to a thickness of 20 nm to form an emitting auxiliary layer, and CBP was used as a host in the upper of the emitting auxiliary layer, and bis-(1-phenylisoquinolyl) iridium(III)acetylacetonate (hereinafter will be abbreviated as (piq)$_2$Ir(acac).) was used as a dopant material, doped at a weight ratio of 95:5, and vacuum deposited at a thickness of 30 nm to form an emitting layer. Subsequently, BAlq was vacuum deposited on the emitting layer to a thickness of 10 nm to form a hole blocking layer, and Alq3 was vacuum deposited on the hole blocking layer to a thickness of 40 nm to form an electron transport layer. Thereafter, an alkali metal halide, LiF was deposited to a thickness of 0.2 nm to form an electron injection layer, and Al was deposited to a thickness of 150 nm to form a cathode to manufacture an OLED.

[Example 18] to [Example 45] Red Organic Light Emitting Diode (Emitting Auxiliary Layer)

An organic electroluminescence device was fabricated in the same manner as in Example 33, except that the compounds P 1-5 to P 1-105 of the present invention described in the following Table 5 are used instead of the compound P 1-1 of the present invention as the emitting auxiliary layer material.

Comparative Example 7

An organic electroluminescent device was fabricated in the same manner as in Example 33, except that the emitting auxiliary layer was not formed.

[Comparative Example 8] to [Comparative Example 12]

An organic electroluminescent device was fabricated in the same manner as in Example 17 except that Comparative Compounds 2 to 6 described in the following Table 5 were used instead of the compound P 1-1 of the present invention as the luminescent auxiliary layer material.

To the organic electroluminescent devices prepared according to Examples 17 to 45 and Comparative Examples 7 and 12 of the present invention, a forward bias direct current voltage was applied, and electroluminescent (EL) properties were measured using PR-650 of Photoresearch Co., and T95 life was measured using a life measuring apparatus manufactured by McScience Inc. with a reference luminance of 2500 cd/m$^2$. The measurement results are shown in Table 5 below.

TABLE 5

|  | compound | Voltage (V) | Current Density (mA/cm2) | Brightness (cd/m2) | Efficiency (cd/A) | Lifetime T(95) | CIE x | CIE y |
|---|---|---|---|---|---|---|---|---|
| comparative example (7) | — | 6.5 | 34.2 | 2500 | 7.3 | 63.8 | 0.66 | 0.32 |
| comparative example (8) | comparative compound2 | 7.1 | 29.8 | 2500 | 8.4 | 83.5 | 0.66 | 0.33 |
| comparative example (9) | comparative compound3 | 7.2 | 31.6 | 2500 | 7.9 | 75.2 | 0.66 | 0.33 |
| comparative example (10) | comparative compound4 | 7.1 | 28.7 | 2500 | 8.7 | 91.7 | 0.66 | 0.32 |
| comparative example (11) | comparative compound5 | 7.0 | 27.8 | 2500 | 9.0 | 95.0 | 0.66 | 0.33 |
| comparative example (12) | comparative compound6 | 6.9 | 26.0 | 2500 | 9.6 | 108.3 | 0.66 | 0.32 |
| example (17) | compound (P 1-1) | 6.7 | 18.2 | 2500 | 13.7 | 143.8 | 0.66 | 0.33 |
| example (18) | compound (P 1-5) | 6.8 | 18.6 | 2500 | 13.4 | 138.7 | 0.66 | 0.32 |
| example (19) | compound (P 1-6) | 6.7 | 19.1 | 2500 | 13.1 | 139.5 | 0.66 | 0.32 |
| example (20) | compound (P 1-9) | 6.8 | 19.7 | 2500 | 12.7 | 127.6 | 0.66 | 0.32 |
| example (21) | compound (P 1-16) | 6.6 | 15.5 | 2500 | 16.1 | 167.7 | 0.66 | 0.33 |
| example (22) | compound (P 1-17) | 6.7 | 15.8 | 2500 | 15.8 | 163.3 | 0.66 | 0.32 |
| example (23) | compound (P 1-20) | 6.6 | 16.0 | 2500 | 15.6 | 161.2 | 0.66 | 0.32 |
| example (24) | compound (P 1-23) | 6.6 | 16.2 | 2500 | 15.4 | 165.9 | 0.66 | 0.33 |
| example (25) | compound (P 1-26) | 6.7 | 17.7 | 2500 | 14.1 | 149.1 | 0.66 | 0.33 |
| example (26) | compound (P 1-36) | 6.8 | 18.0 | 2500 | 13.9 | 142.3 | 0.66 | 0.32 |
| example (27) | compound (P 1-46) | 6.7 | 18.3 | 2500 | 13.7 | 143.1 | 0.66 | 0.32 |
| example (28) | compound (P 1-53) | 6.8 | 18.2 | 2500 | 13.8 | 141.8 | 0.66 | 0.32 |
| example (29) | compound (P 1-59) | 6.6 | 14.5 | 2500 | 17.2 | 185.0 | 0.66 | 0.33 |

TABLE 5-continued

| | compound | Voltage (V) | Current Density (mA/cm2) | Brightness (cd/m2) | Efficiency (cd/A) | Lifetime T(95) | CIE x | CIE y |
|---|---|---|---|---|---|---|---|---|
| example (30) | compound (P 1-60) | 6.6 | 14.8 | 2500 | 16.9 | 178.0 | 0.66 | 0.32 |
| example (31) | compound (P 1-61) | 6.6 | 14.7 | 2500 | 17.0 | 180.6 | 0.66 | 0.33 |
| example (32) | compound (P 1-62) | 6.6 | 15.1 | 2500 | 16.5 | 175.7 | 0.66 | 0.33 |
| example (33) | compound (P 1-63) | 6.6 | 15.0 | 2500 | 16.7 | 176.0 | 0.66 | 0.32 |
| example (34) | compound (P 1-64) | 6.6 | 15.1 | 2500 | 16.5 | 177.0 | 0.66 | 0.33 |
| example (35) | compound (P 1-65) | 6.6 | 16.1 | 2500 | 15.5 | 163.3 | 0.66 | 0.32 |
| example (36) | compound (P 1-66) | 6.6 | 15.3 | 2500 | 16.4 | 173.2 | 0.66 | 0.33 |
| example (37) | compound (P 1-69) | 6.6 | 15.6 | 2500 | 16.1 | 167.4 | 0.66 | 0.33 |
| example (38) | compound (P 1-76) | 6.7 | 15.8 | 2500 | 15.8 | 165.6 | 0.66 | 0.32 |
| example (39) | compound (P 1-80) | 6.7 | 16.2 | 2500 | 15.5 | 166.4 | 0.66 | 0.33 |
| example (40) | compound (P 1-82) | 6.7 | 16.4 | 2500 | 15.3 | 160.1 | 0.66 | 0.32 |
| example (41) | compound (P 1-88) | 6.7 | 18.3 | 2500 | 13.7 | 143.1 | 0.66 | 0.32 |
| example (42) | compound (P 1-93) | 6.7 | 18.3 | 2500 | 13.6 | 142.9 | 0.66 | 0.32 |
| example (43) | compound (P 1-96) | 6.8 | 19.7 | 2500 | 12.7 | 123.6 | 0.66 | 0.33 |
| example (44) | compound (P 1-102) | 6.8 | 20.2 | 2500 | 12.4 | 121.7 | 0.66 | 0.33 |
| example (45) | compound (P 1-105) | 6.8 | 20.0 | 2500 | 12.5 | 124.7 | 0.66 | 0.33 |

As can be seen from the results of Table 5, the organic electroluminescent device using the compound of the present invention as the emitting auxiliary layer material has improved luminous efficiency and significantly improved lifetime as compared with the organic electroluminescent devices of Comparative Examples 7 to 12.

Particularly, devices using Comparative Compounds 2 to 6 and the compound of the present invention as an emitting auxiliary layer were improved in luminous efficiency and lifetime compared to devices not using the emitting auxiliary layer, and most of all, it can be confirmed that the compound of the present invention is remarkably high in light emitting efficiency and life span. This is because heteroaryl species substituted with tertiary amine and amine introduction of heteroaryl terminal serve as main factors for improving the performance of the device not only in the hole transport layer but also in the emitting auxiliary layer (red phosphorescence), and a high refractive index, a high T1 value, and a deep HOMO energy level capable of efficiently transporting holes in the hole transport layer, thereby facilitate the charge balance in the emitting layer.

A high refractive index, a high T1 value, and a deep HOMO energy level capable of efficiently transporting holes in the hole transport layer, thereby facilitating charge balance within the light emitting layer In addition, in the evaluation results of the device fabrication described above, the device characteristics of applying the compound of the present invention to only one layer of the hole transport layer and the emitting auxiliary layer have been described, but the compound of the present invention can be used by applying both the hole transport layer and the emitting auxiliary layer.

Synthesis Example 2

The final product 2 represented by the formula (16) according to the present invention is prepared by reacting Sub 3 and Sub 4 as shown in the following Reaction Scheme (33).

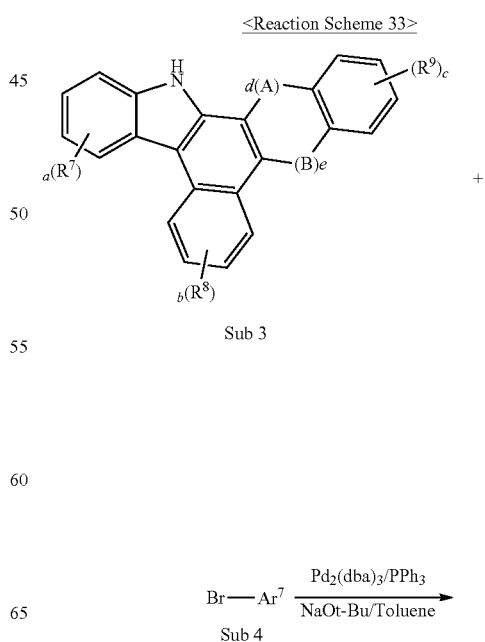

-continued
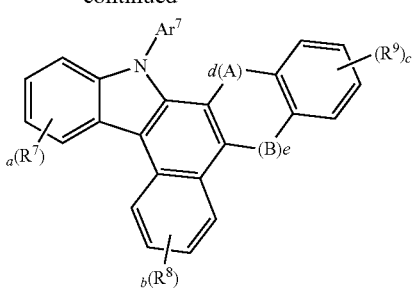
Final products 2
Synthesis Example of Sub 3
Sub 3 of Reaction Scheme 33 can be synthesized by the reaction path of Reaction Scheme 34 below, but is not limited thereto.
<Reaction Scheme 34>
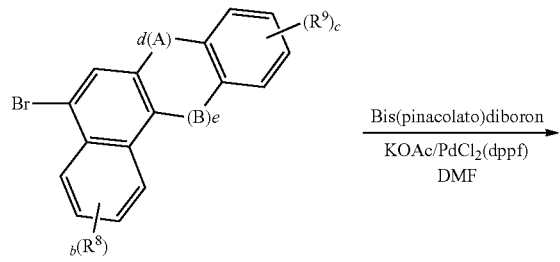
-continued
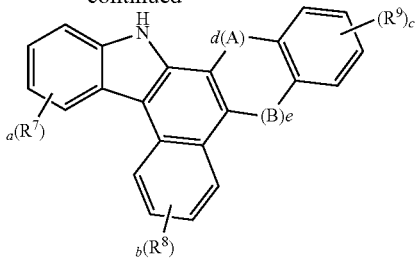
Sub 3
Synthesis Example of Sub 3(1)
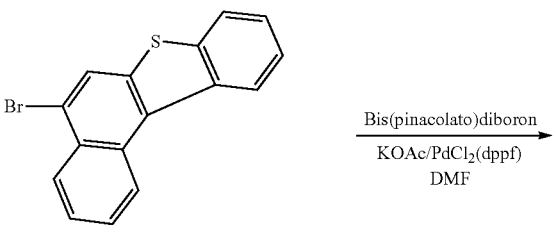
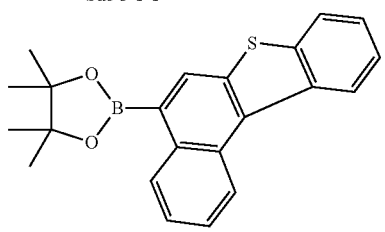
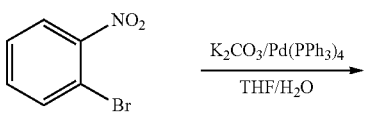
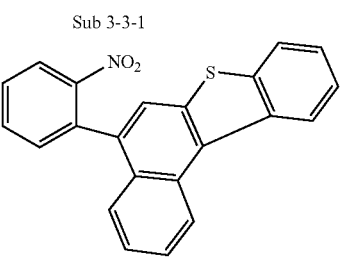
Sub 3-4-1
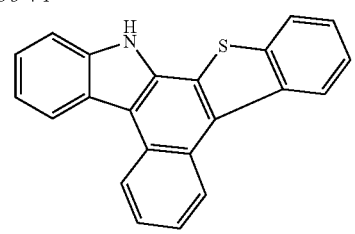
Sub 3(1)

Synthesis of Sub 3-2-1

5-bromobenzo[b]naphtha[1,2-d]thiophene (50 g, 0.16 mol), bis(pinacolato)diboron (48.65 g, 0.19 mol), KOAc (47 g, 0.48 mol), PdCl$_2$(dppf) (5.21 g, 4 mol %) was dissolved in DMF solvent and refluxed at 120° C. for 12 hours. When the reaction was completed, the temperature of the reaction mixture was cooled to room temperature, extracted with CH$_2$Cl$_2$ and wiped with water.

The organic layer was dried over MgSO$_4$ and concentrated. The resulting organic material was recrystallized from CH$_2$Cl$_2$ and methanol to obtain the desired Sub 3-2-1 (46 g, 80%).

Synthesis of Sub 3-4-1

Sub 3-2-1 (40 g, 0.11 mol), bromo-2-nitrobenzene (26.91 g, 0.13 mol), K$_2$CO$_3$ (46.03 g, 0.33 mol), Pd(PPh$_3$)$_4$ (5.13 g, 4 mol %) was dissolved in anhydrous THF and a small amount of water, and then refluxed at 80° C. for 12 hours. When the reaction was completed, the temperature of the reaction mixture was cooled to room temperature, extracted with CH$_2$Cl$_2$ and wiped with water. The organic layer was dried over MgSO$_4$ and concentrated. The resulting organics were separated by silicagel column to obtain desired Sub 3-4-1 (27.62 g, 70%).

Synthesis of Sub 3(1)

Sub 3-4-1 (20 g, 0.05 mol) and triphenylphosphine (44.28 g, 0.17 mol) were dissolved in o-dichlorobenzene and refluxed for 24 hours. After the reaction was completed, the solvent was removed by distillation under reduced pressure, and the concentrated product was purified by silicagel column and recrystallization to obtain the desired Sub 3(1) (26.68 g, 75%).

Synthesis Example of Sub 3(2)

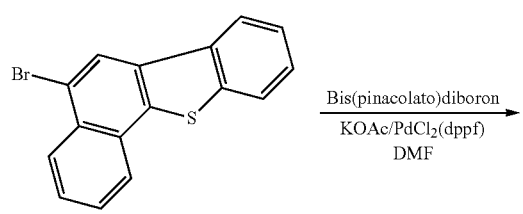

Sub 3-1-2

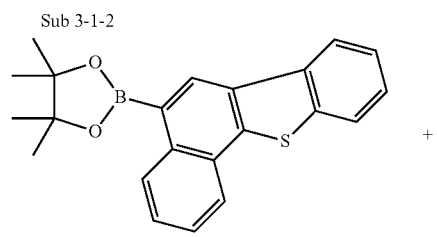

Sub 3-2-2

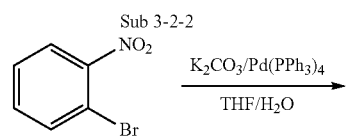

Sub 3-3

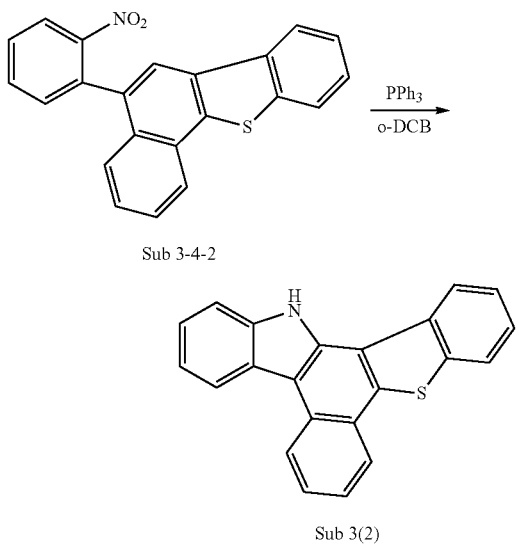

Sub 3-4-2

Sub 3(2)

Synthesis of Sub 3-2-2

5-bromobenzo[b]naphtho[2,1-d]thiophene (50 g, 0.16 mol), bis(pinacolato)diboron (48.65 g, 0.19 mol), KOAc (47 g, 0.48 mol), PdCl$_2$(dppf) (5.21 g, 4 mol %) was dissolved in DMF solvent and refluxed at 120° C. for 12 hours. When the reaction was completed, the temperature of the reaction mixture+was cooled to room temperature, extracted with CH$_2$Cl$_2$ and wiped with water.

The organic layer was dried over MgSO$_4$ and concentrated. The resulting organic material was recrystallized from CH$_2$Cl$_2$ and methanol to obtain the desired Sub 3-2-2 (45 g, 78%).

Synthesis of Sub 3-4-2

Sub 3-2-2 (40 g, 0.11 mol), bromo-2-nitrobenzene (26.91 g, 0.13 mol), K$_2$CO$_3$ (46.03 g, 0.33 mol), Pd(PPh$_3$)$_4$ (5.13 g, 4 mol %) was dissolved in anhydrous THF and a small amount of water, and then refluxed at 80° C. for 12 hours. When the reaction was completed, the temperature of the reaction mixture was cooled to room temperature, extracted with CH$_2$Cl$_2$ and wiped with water. The organic layer was dried over MgSO$_4$ and concentrated. The resulting organics were separated by silicagel column to obtain desired Sub 3-4-2 (25.4 g, 65%).

Synthesis of Sub 3(2)

Sub 3-4-2 (20 g, 0.05 mol) and triphenylphosphine (44.28 g, 0.17 mol) were dissolved in o-dichlorobenzene and refluxed for 24 hours. After the reaction was completed, the solvent was removed by distillation under reduced pressure, and the concentrated product was purified by silicagel column and recrystallization to obtain the desired Sub 3(2) (23.48 g, 66%).

Examples of Sub 3 include, but are not limited to, the following.

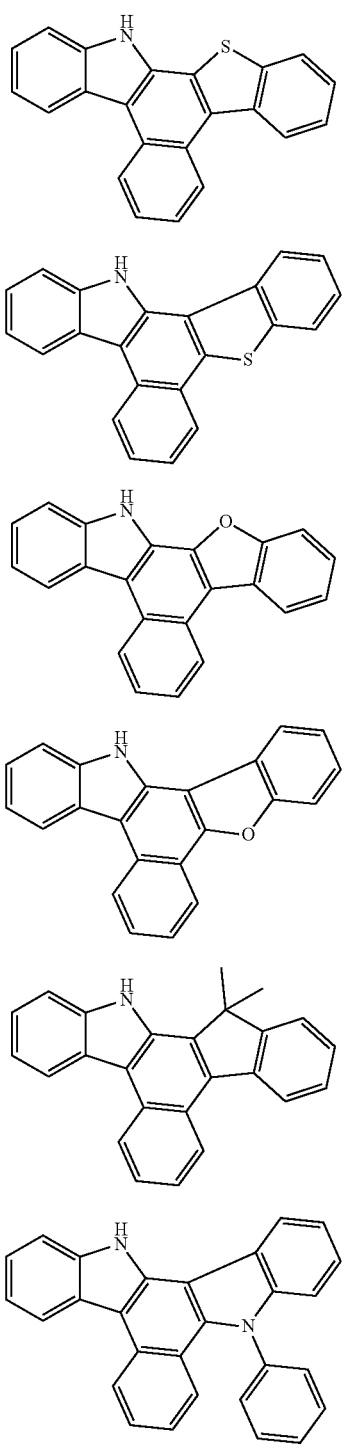
Sub 3(1)
Sub 3(2)
Sub 3(3)
Sub 3(4)
Sub 3(5)
Sub 3(6)
Examples of Sub 4
Examples of Sub 4 include, but are not limited to, the following.
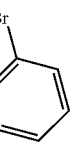
Sub 4-1
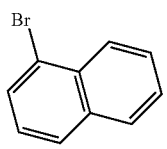
Sub 4-2
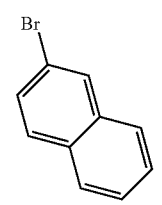
Sub 4-3
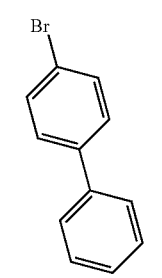
Sub 4-4
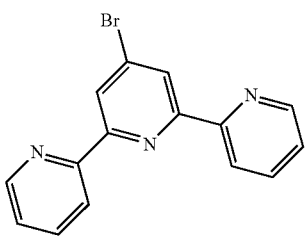
Sub 4-5
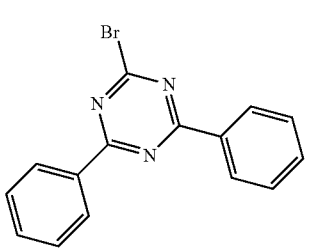
Sub 4-6
TABLE 6
| compound | FD-MS | compound | FD-MS |
|---|---|---|---|
| Sub 3(1) | m/z = 323.08($C_{22}H_{13}NS$ = 323.41) | Sub 3(2) | m/z = 323.08($C_{22}H_{13}NS$ = 323.41) |
| Sub 3(3) | m/z = 307.10($C_{22}H_{13}NO$ = 307.34) | Sub 3(4) | m/z = 307.10($C_{22}H_{13}NO$ = 307.34) |
| Sub 3(5) | m/z = 333.15($C_{25}H_{19}N$ = 333.43) | Sub 3(6) | m/z = 382.15($C_{28}H_{18}N_2$ = 382.46) |

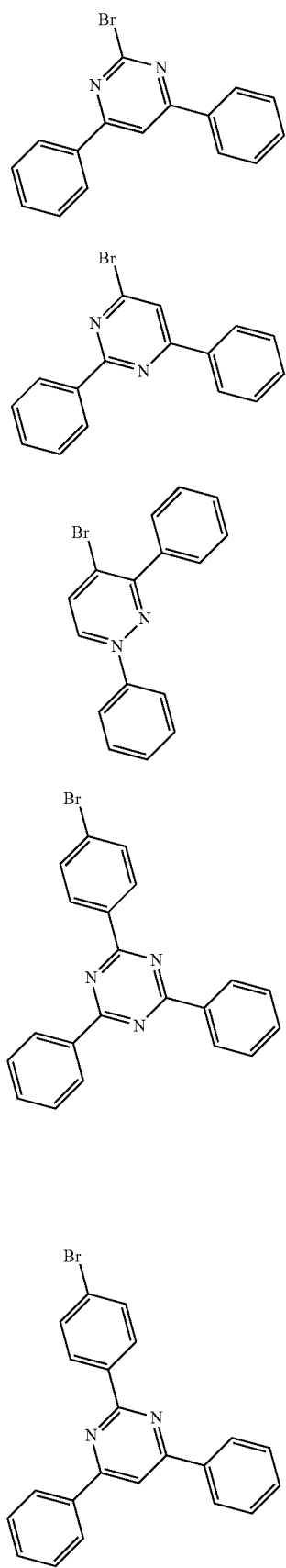
Sub 4-7
Sub 4-8
Sub 4-9
Sub 4-10
Sub 4-11
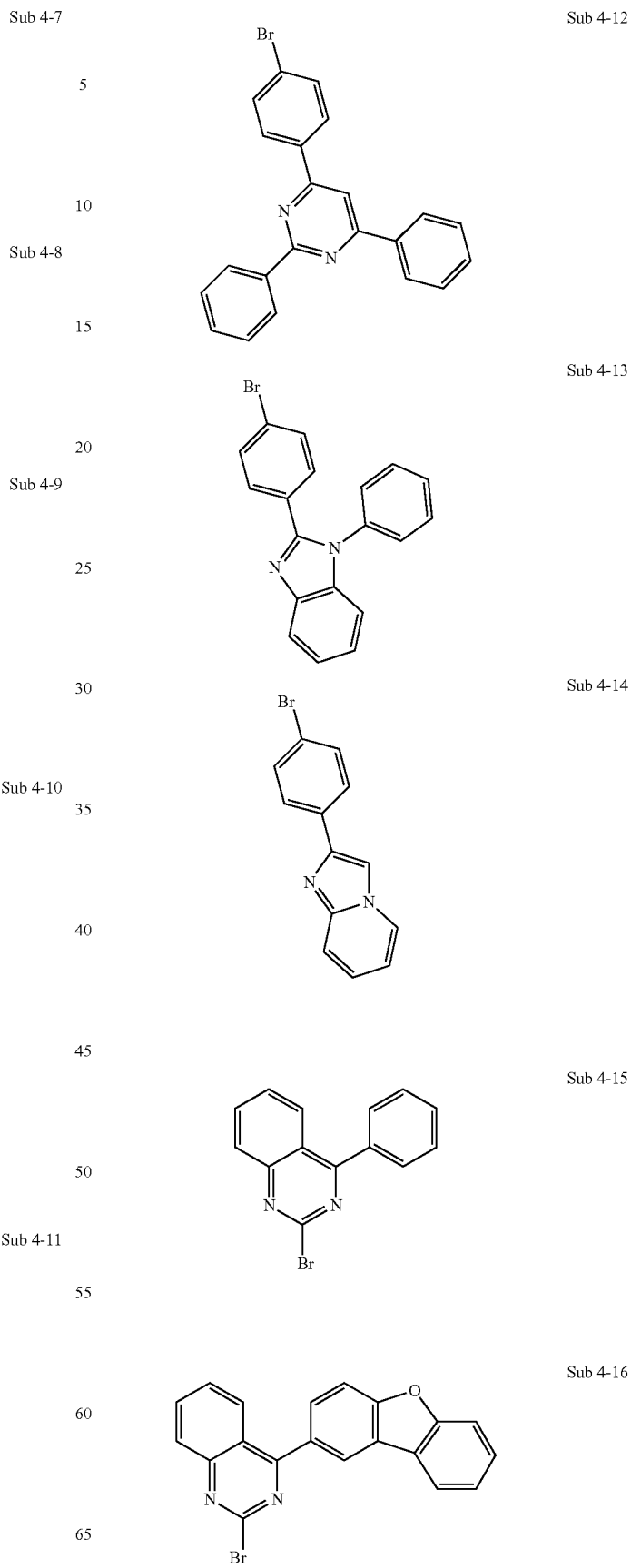
Sub 4-12
Sub 4-13
Sub 4-14
Sub 4-15
Sub 4-16

Sub 4-17
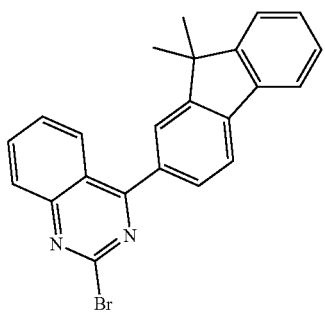
Sub 4-18
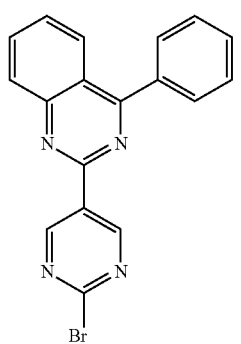
Sub 4-19
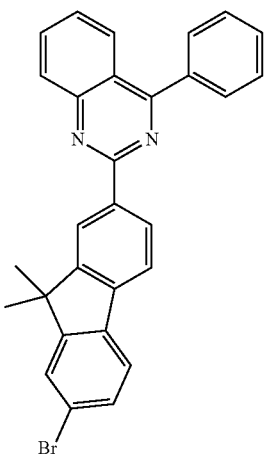
Sub 4-20
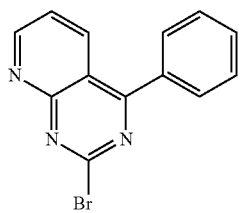
Sub 4-21
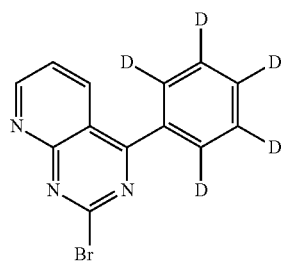
Sub 4-22
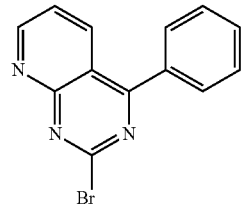
Sub 4-23
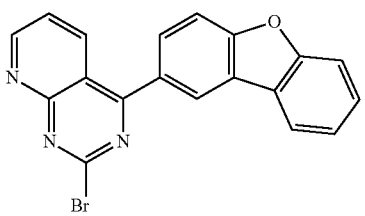
Sub 4-24
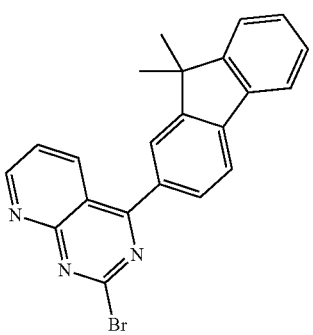
Sub 4-25
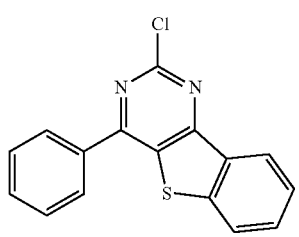
Sub 4-26
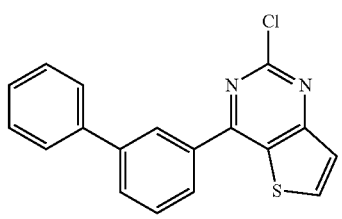
Sub 4-27
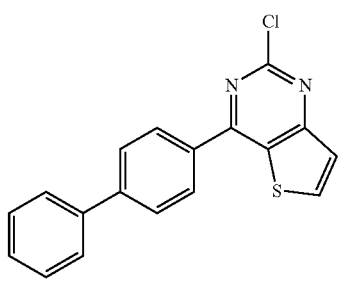

Sub 4-28
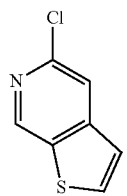
Sub 4-29
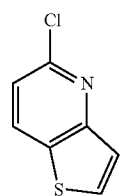
Sub 4-30
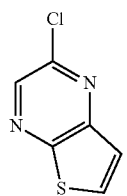
Sub 4-31
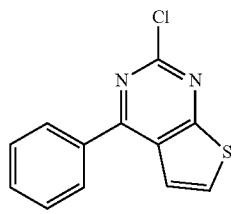
Sub 4-32
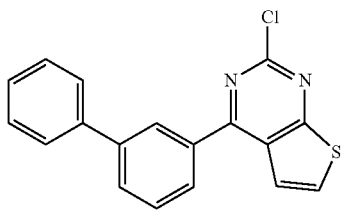
Sub 4-33
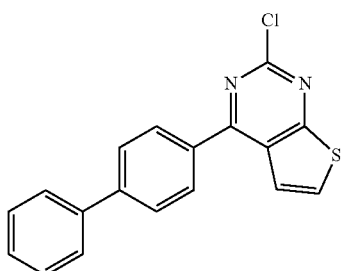
Sub 4-34
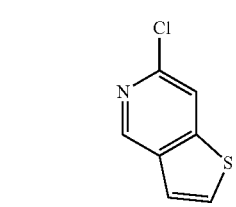
Sub 4-35
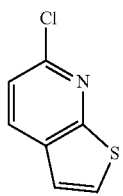
Sub 4-36
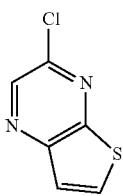
Sub 4-25
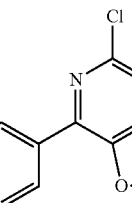
Sub 4-26
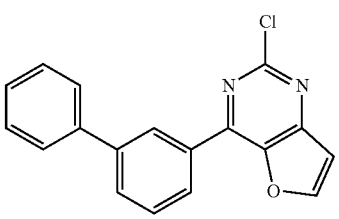
Sub 4-27
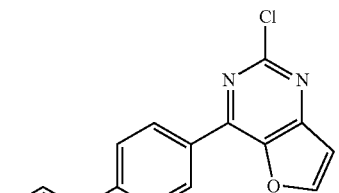
Sub 4-28
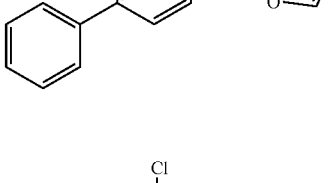
Sub 4-29
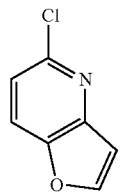

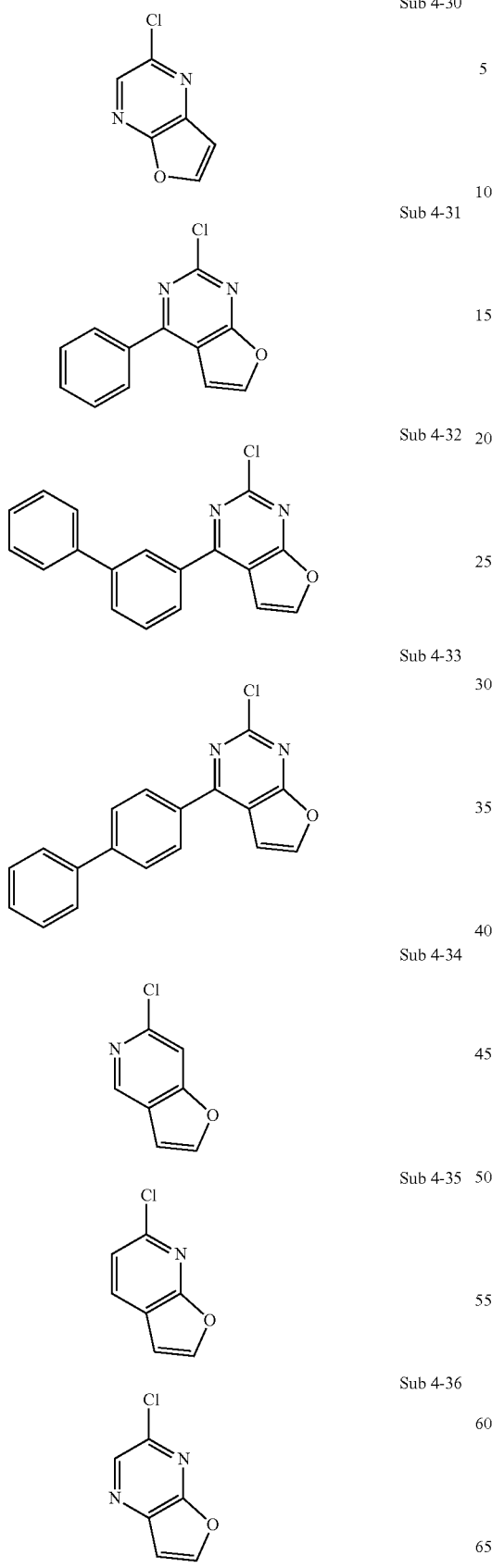
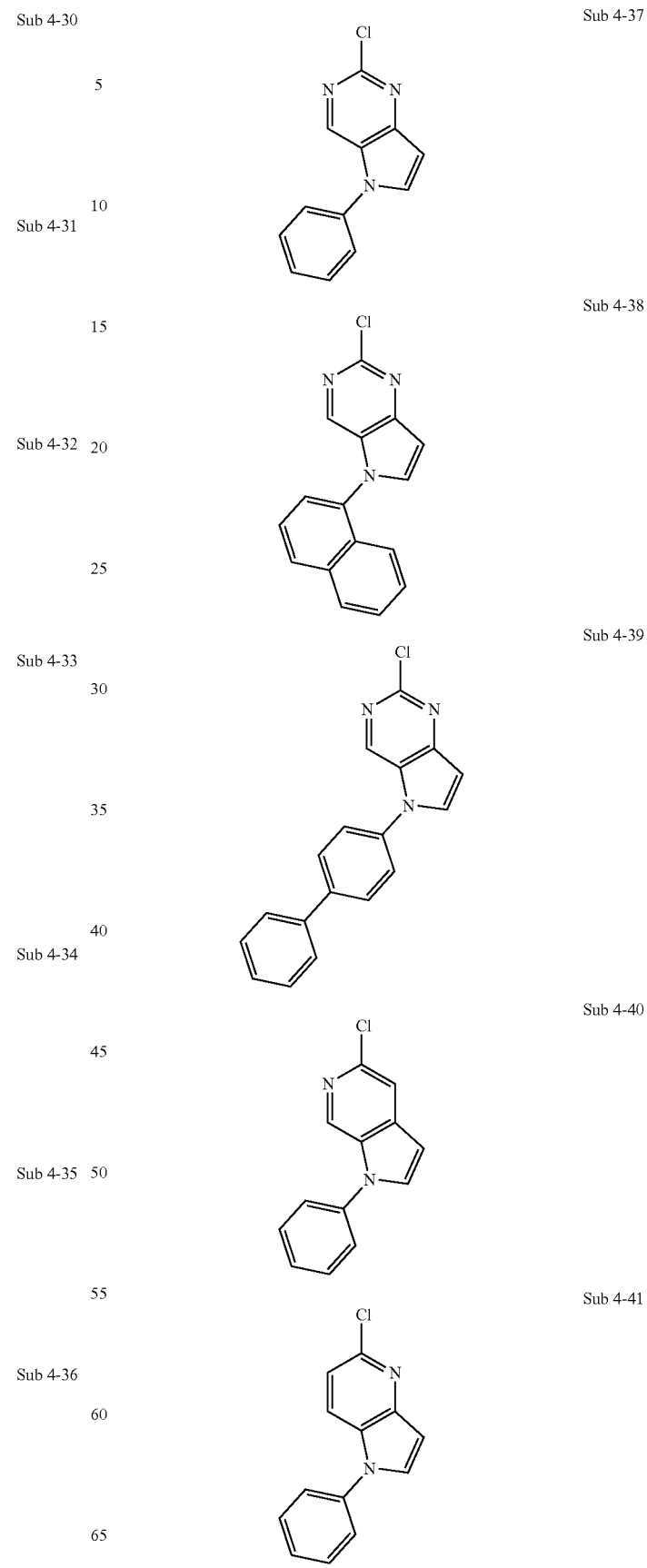

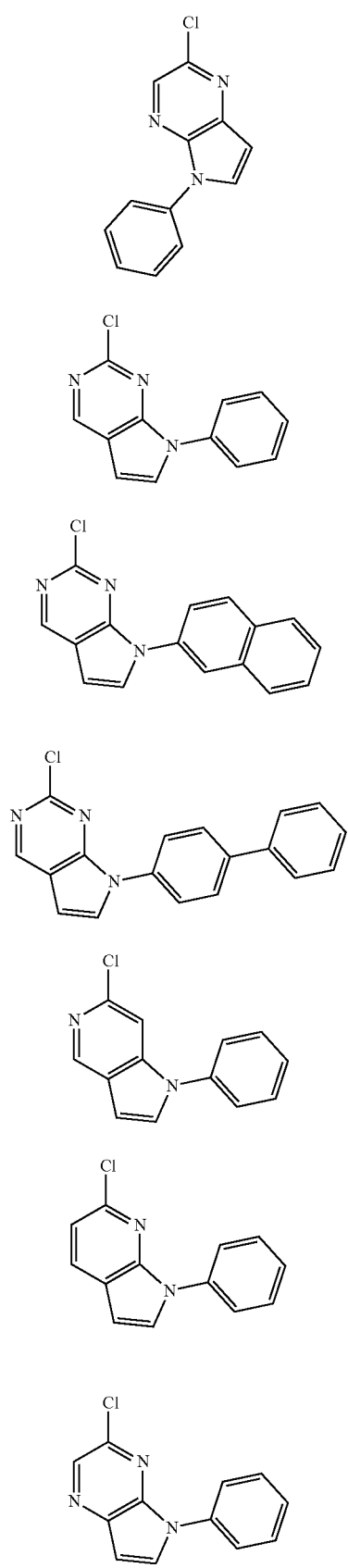
Sub 4-42
Sub 4-43
Sub 4-44
Sub 4-45
Sub 4-46
Sub 4-47
Sub 4-48
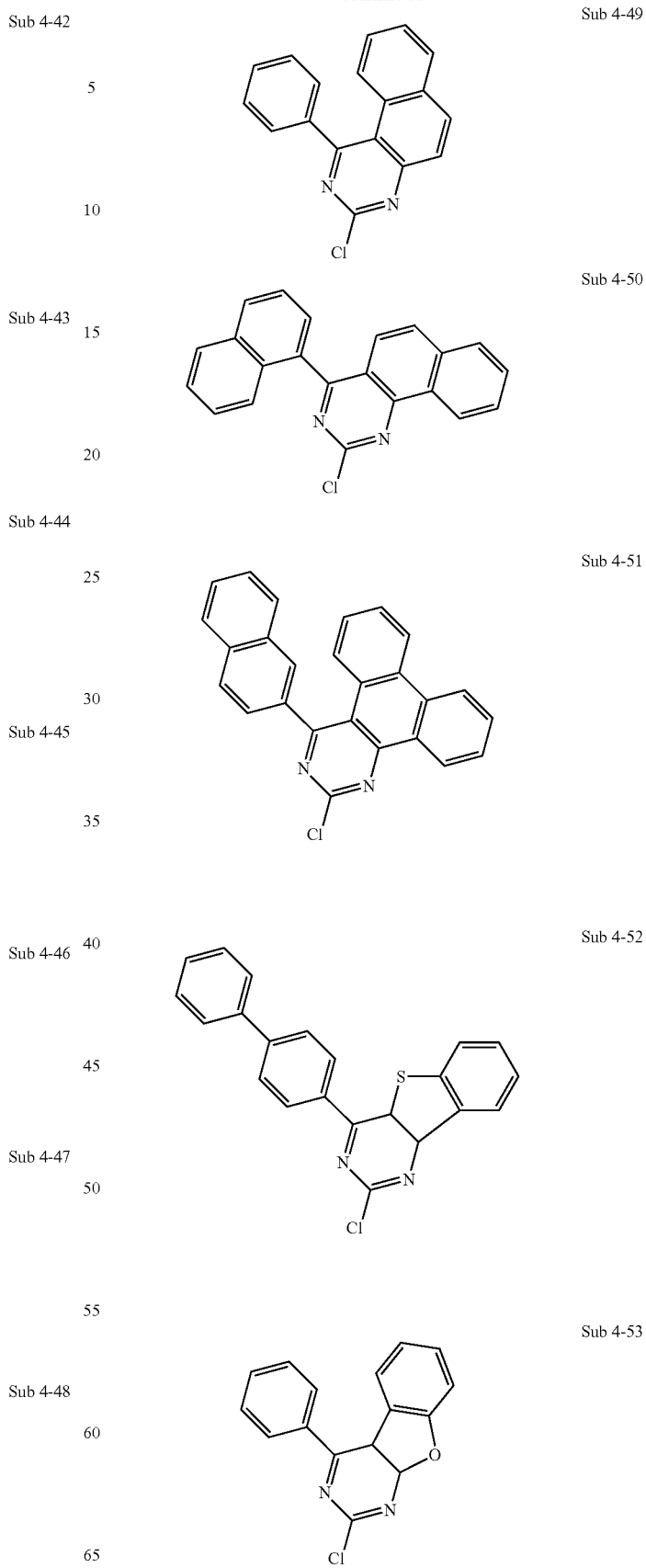
Sub 4-49
Sub 4-50
Sub 4-51
Sub 4-52
Sub 4-53

TABLE 7

| compound | FD-MS | compound | FD-MS |
|---|---|---|---|
| Sub 4-1 | m/z = 155.96($C_6H_5Br$ = 157.01) | Sub 4-2 | m/z = 205.97($C_{10}H_7Br$ = 207.07) |
| Sub 4-3 | m/z = 205.97($C_{10}H_7Br$ = 207.07) | Sub 4-4 | m/z = 231.99($C_{12}H_9Br$ = 233.10) |
| Sub 4-5 | m/z = 309.02($C_{17}H_{12}BrN$ = 310.19) | Sub 4-6 | m/z = 311.01($C_{15}H_{10}BrN_3$ = 312.16) |
| Sub 4-7 | m/z = 310.01($C_{16}H_{11}BrN_2$ = 311.18) | Sub 4-8 | m/z = 310.01($C_{16}H_{11}BrN_2$ = 311.18) |
| Sub 4-9 | m/z = 310.01($C_{16}H_{11}BrN_2$ = 311.18) | Sub 4-10 | m/z = 387.04($C_{21}H_{14}BrN_3$ = 388.26) |
| Sub 4-11 | m/z = 386.04($C_{22}H_{15}BrN_2$ = 387.27) | Sub 4-12 | m/z = 386.04($C_{22}H_{15}BrN_2$ = 387.27) |
| Sub 4-13 | m/z = 348.03($C_{19}H_{13}BrN_2$ = 349.22) | Sub 4-14 | m/z = 271.99($C_{13}H_9BrN_2$ = 273.13) |
| Sub 4-15 | m/z = 283.99($C_{14}H_9BrN_2$ = 285.14) | Sub 4-16 | m/z = 374.01($C_{20}H_{11}BrN_2O$ = 375.22) |
| Sub 4-17 | m/z = 400.06($C_{23}H_{17}BrN_2$ = 401.30) | Sub 4-18 | m/z = 360.03($C_{20}H_{13}BrN_2$ = 361.23) |
| Sub 4-19 | m/z = 476.09($C_{29}H_{21}BrN_2$ = 477.39) | Sub 4-20 | m/z = 284.99($C_{13}H_8BrN_3$ = 286.13) |
| Sub 4-21 | m/z = 289.03($C_{14}H_4D_5BrN_2$ = 290.2) | Sub 4-22 | m/z = 284.99($C_{13}H_8BrN_3$ = 286.13) |
| Sub 4-23 | m/z = 375.00($C_{19}H_{10}BrN_3O$ = 376.2) | Sub 4-24 | m/z = 401.05($C_{22}H_{16}BrN_3$ = 402.29) |
| Sub 4-25 | m/z = 296.02($C_{16}H_9ClN_2S$ = 296.77) | Sub 4-26 | m/z = 322.03($C_{18}H_{11}ClN_2S$ = 322.81) |
| Sub 4-27 | m/z = 322.03($C_{18}H_{11}ClN_2S$ = 322.81) | Sub 4-28 | m/z = 168.98($C_7H_4ClNS$ = 169.63) |
| Sub 4-29 | m/z = 168.98($C_7H_4ClNS$ = 169.63) | Sub 4-30 | m/z = 169.97($C_6H_3ClN_2S$ = 170.62) |
| Sub 4-31 | m/z = 246.00($C_{12}H_7ClN_2S$ = 246.72) | Sub 4-32 | m/z = 322.03($C_{18}H_{11}ClN_2S$ = 322.81) |
| Sub 4-33 | m/z = 322.03($C_{18}H_{11}ClN_2S$ = 322.81) | Sub 4-34 | m/z = 168.98($C_7H_4ClNS$ = 169.63) |
| Sub 4-35 | m/z = 168.98($C_7H_4ClNS$ = 169.63)) | Sub 4-36 | m/z = 169.97($C_6H_3ClN_2S$ = 170.62) |
| Sub 4-37 | m/z = 229.04($C_{12}H_8ClN_3$ = 229.67) | Sub 4-38 | m/z = 279.06($C_{16}H_{10}ClN_3$ = 279.72) |
| Sub 4-39 | m/z = 305.07($C_{18}H_{12}ClN_3$ = 305.76) | Sub 4-40 | m/z = 228.05($C_{13}H_9ClN_2$ = 228.68) |
| Sub 4-41 | m/z = 228.05($C_{13}H_9ClN_2$ = 228.68) | Sub 4-42 | m/z = 229.04($C_{12}H_8ClN_3$ = 229.67) |
| Sub 4-43 | m/z = 229.04($C_{12}H_8ClN_3$ = 229.67) | Sub 4-44 | m/z = 279.06($C_{16}H_{10}ClN_3$ = 279.72) |
| Sub 4-45 | m/z = 305.07($C_{18}H_{12}ClN_3$ = 305.76) | Sub 4-46 | m/z = 228.05($C_{13}H_9ClN_2$ = 228.68) |
| Sub 4-47 | m/z = 228.05($C_{13}H_9ClN_2$ = 228.68) | Sub 4-48 | m/z = 229.04($C_{12}H_8ClN_3$ = 229.67) |
| Sub 4-49 | m/z = 290.06($C_{18}H_{11}ClN_2$ = 290.75) | Sub 4-50 | m/z = 340.08($C_{22}H_{13}ClN_2$ = 340.81) |
| Sub 4-51 | m/z = 390.09($C_{26}H_{15}ClN_2$ = 390.87) | Sub 4-52 | m/z = 374.06($C_{22}H_{15}ClN_2S$ = 374.89) |
| Sub 4-53 | m/z = 282.1($C_{16}H_{11}ClN_2O$ = 282.73) | | |

Synthesis Example of Final Products 2

Synthesis Example of P16-4

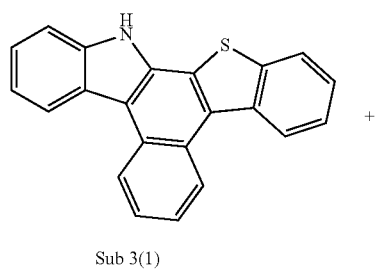

Sub 3(1)

+

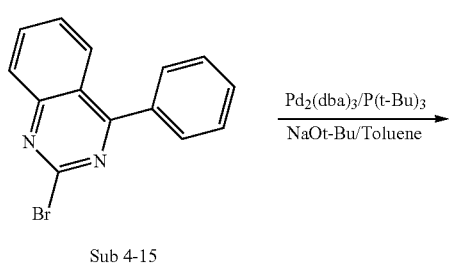

Sub 4-15

$\xrightarrow{Pd_2(dba)_3/P(t\text{-}Bu)_3}{NaOt\text{-}Bu/Toluene}$

-continued

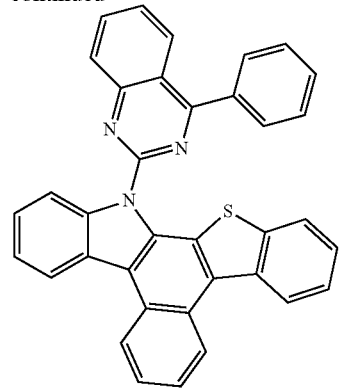

P16-4

Sub 3(1) (15.3 g, 47.3 mmol) was dissolved in toluene (500 ml) in a round bottom flask, and Sub 4-15 (14.8 g, 52.0 mmol), $Pd_2(dba)_3$ (2.2 g, 2.4 mmol), P(t-Bu)$_3$ (1 g, 4.73 mmol), NaOt-Bu (13.6 g, 141.8 mmol) were added and stirred at 100° C. After the reaction was completed, the reaction mixture was extracted with $CH_2Cl_2$ and water. The organic layer was dried over $MgSO_4$ and concentrated. The resulting compound was separated by silicagel column chromatography and recrystallized to obtain 17.0 g of the product. (yield: 68%)

Synthesis Example of P16-25

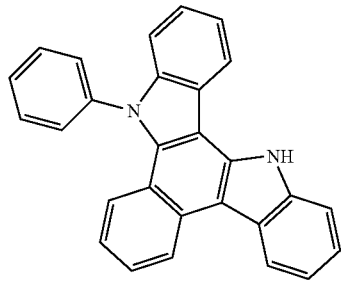

Sub 3(6)

+

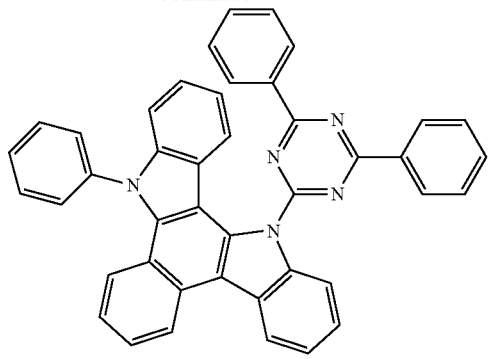

P-16-25

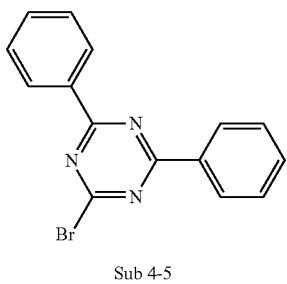

Sub 4-5

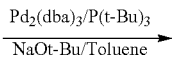

Pd$_2$(dba)$_3$/P(t-Bu)$_3$
NaOt-Bu/Toluene

Sub 3(6) (18.1 g, 47.3 mmol) was dissolved in toluene (500 ml) in a round bottom flask, and Sub 4-5 (16.2 g, 52.0 mmol), Pd$_2$(dba)$_3$ (2.2 g, 2.4 mmol), P(t-Bu)$_3$ (1 g, 4.73 mmol), NaOt-Bu (13.6 g, 141.8 mmol) were added and stirred at 100° C. After the reaction was completed, the reaction mixture was extracted with CH$_2$Cl$_2$ and water. The organic layer was dried over MgSO$_4$ and concentrated. The resulting compound was separated by silicagel column chromatography and recrystallized to obtain 20.3 g of the product. (yield: 70%)

TABLE 8

| compound | FD-MS | compound | FD-MS |
|---|---|---|---|
| P16-1 | m/z = 399.11($C_{28}H_{17}NS$ = 399.51) | P16-2 | m/z = 554.16($C_{37}H_{22}N_4S$ = 554.66) |
| P16-3 | m/z = 553.16($C_{38}H_{23}N_3S$ = 553.67) | P16-4 | m/z = 527.15($C_{36}H_{21}N_3S$ = 527.64) |
| P16-5 | m/z = 577.16($C_{40}H_{23}N_3S$ = 577.71) | P16-6 | m/z = 653.19($C_{46}H_{27}N_3S$ = 653.79) |
| P16-7 | m/z = 720.17($C_{50}H_{28}N_2S_2$ = 720.90) | P16-8 | m/z = 611.20($C_{44}H_{25}N_3O$ = 611.70) |
| P16-9 | m/z = 553.16($C_{38}H_{23}N_3S$ = 553.67) | P16-10 | m/z = 554.16($C_{37}H_{22}N_4S$ = 554.66) |
| P16-11 | m/z = 527.15($C_{36}H_{21}N_3S$ = 527.64) | P16-12 | m/z = 591.18($C_{41}H_{25}N_3S$ = 591.72) |
| P16-13 | m/z = 511.17($C_{36}H_{21}N_3O$ = 511.57) | P16-14 | m/z = 561.18($C_{40}H_{23}N_3O$ = 561.63) |
| P16-15 | m/z = 561.18($C_{40}H_{23}N_3O$ = 561.63) | P16-16 | m/z = 537.18($C_{38}H_{23}N_3O$ = 537.61) |
| P16-17 | m/z = 794.25($C_{56}H_{34}N_4S$ = 794.96) | P16-18 | m/z = 604.17($C_{41}H_{24}N_4S$ = 604.72) |
| P16-19 | m/z = 627.18($C_{44}H_{25}N_3S$ = 627.75) | P16-20 | m/z = 641.19($C_{45}H_{27}N_3S$ = 641.78) |
| P16-21 | m/z = 613.23($C_{43}H_{27}N_5$ = 613.71) | P16-22 | m/z = 612.23($C_{44}H_{28}N_4$ = 612.72) |
| P16-23 | m/z = 583.12($C_{38}H_{21}N_3S_2$ = 583.72) | P16-24 | m/z = 564.23($C_{40}H_{28}N_4$ = 564.68) |
| P16-25 | m/z = 613.23($C_{43}H_{27}N_5$ = 613.71) | P16-26 | m/z = 564.23($C_{40}H_{28}N_4$ = 564.68) |
| P16-27 | m/z = 537.18($C_{38}H_{23}N_3O$ = 537.61) | P16-28 | m/z = 633.13($C_{42}H_{23}N_3S_2$ = 633.78) |
| P16-29 | m/z = 583.12($C_{38}H_{21}N_3S_2$ = 583.73) | P16-30 | m/z = 588.2($C_{38}H_{16}D_5N_3S_2$ = 588.76) |
| P16-31 | m/z = 584.11($C_{37}H_{20}N_4S_2$ = 584.72) | P16-32 | m/z = 659.15($C_{44}H_{25}N_3S_2$ = 659.83) |
| P16-33 | m/z = 643.17($C_{44}H_{25}N_3OS$ = 643.76) | | |

[Example 46] Red Organic Light Emitting Diode (Emitting Auxiliary Layer and Host)

First, on an ITO layer (anode) formed on a glass substrate, $N^1$-(naphthalen-2-yl)-$N^4$,$N^4$-bis(4-(naphthalen-2-yl(phenyl)amino)phenyl)-$N^1$-phenylbenzene-1,4-diamine (hereinafter will be abbreviated as 2-TNATA) was vacuum-deposited to a thickness of 60 nm to form a hole injection layer. Subsequently, NPB was vacuum deposited as hole transport compound on the layer to a thickness of 60 nm to form a hole transport layer. Subsequently, the inventive compound represented by Formula (1) was vacuum-deposited as an emitting auxiliary layer material to a thickness of 60 nm to form an emitting auxiliary layer. The compound represented by Formula (16) was used as a host in the upper of the emitting auxiliary layer, and (piq)$_2$Ir(acac) [bis-(1-phenylisoquinolyl)iridium(III)acetylacetonate] was used as a dopant material, doped at a weight ratio of 95:5, and vacuum deposited at a thickness of 30 nm to form an emitting layer on the emitting auxiliary layer. Subsequently, (1,1'-bisphenyl)-4-olato)bis(2-methyl-8-quinolinolato)aluminum (hereinafter will be abbreviated as BAlq) was vacuum deposited to a thickness of 10 nm to form a hole blocking layer, and tris(8-quinolinol)aluminum (hereinafter will be abbreviated as Alq3) was vacuum deposited to a thickness of 40 nm to form an electron transport layer. Thereafter, an alkali metal halide, LiF was deposited to a thickness of 0.2 nm to form an electron injection layer, and and Al was deposited to a thickness of 150 nm to use a cathode to manufacture an OLED.

To the OLEDs which were manufactured by examples and comparative examples, a forward bias direct current voltage was applied, and electroluminescent (EL) properties were measured using PR-650 of Photoresearch Co., and T95 life was measured using a life measuring apparatus manufactured by McScience Inc. with a reference luminance of 5000 cd/m². In the following table, the manufacture of a device and the results of evaluation are shown.

Comparative Example 13

An organic electroluminescence device was fabricated in the same manner as in Example 2, except that Comparative Compound 2 was used as the emitting auxiliary layer.

TABLE 9

| | Emitting auxiliary layer compound | Phosphorescent host compound | Voltage | Current Density | Brightness (cd/m²) | Efficiency | Lifetime T(95) |
|---|---|---|---|---|---|---|---|
| comparative example (13) | comparative compound 2 | compound (P16-4) | 6.8 | 24.5 | 2500.0 | 10.2 | 102.7 |
| example (46) | compound (P1-1) | compound (P16-4) | 6.1 | 14.8 | 2500.0 | 16.9 | 149.1 |
| example (47) | compound (P1-7) | compound (P16-4) | 6.2 | 15.8 | 2500.0 | 15.8 | 141.8 |
| example (48) | compound (P1-14) | compound (P16-4) | 6.2 | 15.7 | 2500.0 | 15.9 | 136.3 |
| example (49) | compound (P1-20) | compound (P16-4) | 6.1 | 11.6 | 2500.0 | 21.6 | 172.1 |
| example (50) | compound (P1-26) | compound (P16-4) | 6.1 | 11.3 | 2500.0 | 22.2 | 154.8 |
| example (51) | compound (P1-34) | compound (P16-4) | 6.1 | 11.5 | 2500.0 | 21.7 | 139.4 |
| example (52) | compound (P1-59) | compound (P16-4) | 6.1 | 8.5 | 2500.0 | 29.4 | 196.0 |
| example (53) | compound (P1-65) | compound (P16-4) | 6.2 | 9.2 | 2500.0 | 27.0 | 175.6 |
| example (46) | compound (P1-1) | compound (P16-5) | 6.2 | 14.2 | 2500.0 | 17.5 | 144.5 |
| example (47) | compound (P1-7) | compound (P16-5) | 6.2 | 14.2 | 2500.0 | 17.6 | 142.8 |
| example (48) | compound (P1-14) | compound (P16-5) | 6.2 | 14.4 | 2500.0 | 17.4 | 137.1 |
| example (49) | compound (P1-20) | compound (P16-5) | 6.3 | 11.7 | 2500.0 | 21.3 | 174.8 |
| example (50) | compound (P1-26) | compound (P16-5) | 6.1 | 11.6 | 2500.0 | 21.6 | 154.1 |
| example (51) | compound (P1-34) | compound (P16-5) | 6.2 | 12.9 | 2500.0 | 19.4 | 137.8 |
| example (52) | compound (P1-59) | compound (P16-5) | 6.1 | 9.2 | 2500.0 | 27.3 | 197.7 |
| example (53) | compound (P1-65) | compound (P16-5) | 6.0 | 9.1 | 2500.0 | 27.5 | 176.8 |
| example (46) | compound (P1-1) | compound (P16-29) | 6.1 | 14.0 | 2500.0 | 17.8 | 145.1 |
| example (47) | compound (P1-7) | compound (P16-29) | 6.1 | 15.3 | 2500.0 | 16.3 | 143.6 |
| example (48) | compound (P1-14) | compound (P16-29) | 6.1 | 16.2 | 2500.0 | 15.5 | 137.4 |
| example (49) | compound (P1-20) | compound (P16-29) | 6.2 | 12.8 | 2500.0 | 19.5 | 171.6 |
| example (50) | compound (P1-26) | compound (P16-29) | 6.1 | 12.7 | 2500.0 | 19.8 | 153.9 |
| example (51) | compound (P1-34) | compound (P16-29) | 6.3 | 12.4 | 2500.0 | 20.2 | 132.3 |

TABLE 9-continued

| | Emitting auxiliary layer compound | Phosphorescent host compound | Voltage | Current Density | Brightness (cd/m$^2$) | Efficiency | Lifetime T(95) |
|---|---|---|---|---|---|---|---|
| example (52) | compound (P1-59) | compound (P16-29) | 6.3 | 9.1 | 2500.0 | 27.3 | 194.1 |
| example (53) | compound (P1-65) | compound (P16-29) | 6.1 | 9.9 | 2500.0 | 25.3 | 176.8 |

As can be seen from the results of Table 9, when the material for an organic electroluminescence device of the present invention represented by Formula (1) is used as an emitting auxiliary layer and the material for an organic electroluminescence device of the present invention represented by Formula (16) is used as a phosphorescent host, it was confirmed that the driving voltage, the efficiency and the lifetime were remarkably improved as compared to devices that are not That is, Examples 46 to 53 using the compound represented by Formula (1) as the emitting auxiliary layer and the compound represented by Formula (16) as the phosphorescent host showed remarkably excellent results in terms of driving voltage, efficiency and lifetime than Comparative Example 13 using Comparative Compound 2 as an emitting auxiliary.

The inventive compounds represented by Formula (I) have characteristics such as high refractive index, high T1 value and deep HOMO energy level as compared with comparative compound 2, and the inventive compound represented by Formula (16) has not only electron but also hole stability and high T1, compared with conventional host CBP. Therefore, the combination of the two makes it possible to move more holes to the emitting layer quickly and easily, and accordingly, the charge balance in the emitting layer of the hole and the electron is increased, so that light emission is well performed inside the emitting layer rather than at the interface of the hole transport layer, as a result, the deterioration in the ITO and HTL interface is also reduced, thereby maximizing the driving voltage, efficiency, and lifetime of the entire device. That is, it is considered that the combination of Formula (1) and Formula (16) performs electrochemical synergistic action, thereby improving the performance of the entire device.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas comprised within the scope equivalent to the claims belong to the present invention.

What is claimed is:
1. A compound represented by Formula (1) below:

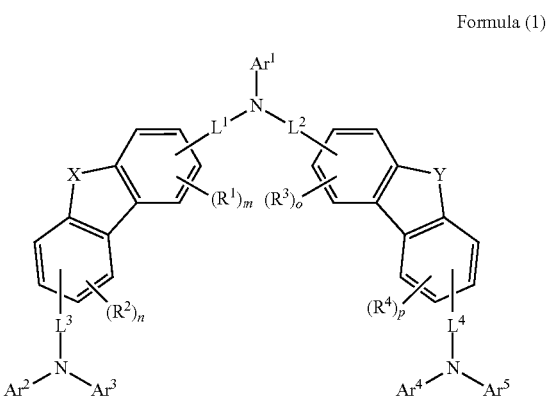

Formula (1)

wherein,
1) X and Y are each independently S or O,
2) $Ar^1$, $Ar^2$, $Ar^3$, $Ar^4$, and $Ar^5$ are each independently selected from the group consisting of a $C_6$-$C_{60}$ aryl group; a $C_2$-$C_{60}$ heterocyclic group including at least one hetero atom of O, N, S, Si or P,
3) $R^1$, $R^2$, $R^3$, and $R^4$ are each independently selected from the group consisting of deuterium; tritium; a halogen; a cyano group; a nitro group; a $C_6$-$C_{60}$ aryl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring, wherein when a plurality of $R^1$ to $R^4$ are present, at least one pair of adjacent $R^1$, $R^2$, $R^3$, and $R^4$ may bond independently to form a ring, and $R^1$ to $R^4$ which do not form a ring are the same as defined above,
4) m, n, o and p are each independently an integer of 0 to 3, and when each of these is an integer of 2 or more, $R^1$ to $R^4$ are the same or different from each other, and a plurality of $R^1$, $R^2$, $R^3$ and $R^4$ are the same or different from each other,
5) $L^1$, $L^2$, $L^3$, and $L^4$ are each independently selected from the group consisting of a single bond, a $C_6$-$C_{60}$ arylene group, and a $C_2$-$C_{60}$ divalent heterocyclic group containing at least one heteroatom selected from O, N, S, Si or P; a divalent fused ring group of a $C_3$-$C_{60}$ aliphatic ring and a $C_6$-$C_{60}$ aromatic ring; and a divalent aliphatic hydrocarbon group, and when they are not a single bond, each may be substituted with one or more substituents selected from the group consisting of deuterium; halogen; a $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; a unsubstituted $C_6$-$C_{20}$ aryl group; $C_6$-$C_{20}$ aryl group substituted with deuterium; $C_2$-$C_{20}$ heterocyclic group; $C_3$-$C_{20}$ cycloalkyl group; $C_7$-$C_{20}$ arylalkyl group, wherein, the aryl group, heterocyclic group, fused ring group, alkyl group, alkenyl group, alkynyl group, alkoxy group, and aryloxy group in any of $Ar^1$ to $Ar^5$, $R^1$ to $R^4$, and $L^1$ to $L^4$ are each unsubstituted or substituted with one or more substituents selected from the group consisting of deuterium; halogen; a silane group substituted or unsubstituted with $C_1$-$C_{20}$ alkyl group or $C_6$-$C_{20}$ aryl group; siloxane group; boron group; germanium group; cyano group; nitro group; a $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; a unsubstituted $C_6$-$C_{20}$ aryl group; $C_6$-$C_{20}$ aryl group substituted with deuterium; a $C_2$-$C_{60}$ heterocyclic group including at least one hetero atom of O, N, S, Si or P; $C_3$-$C_{20}$ cycloalkyl group; and $C_8$-$C_{20}$ arylalkenyl group, with the proviso that $Ar^1$ is not substituted with an amino group, and when these substituents are adjacent to each other, they may be bonded to each other to form a ring.

2. The compound according to claim 1, wherein Formula (1) is represented by any one of following Formula (2) to Formula (11):

Formula (2)

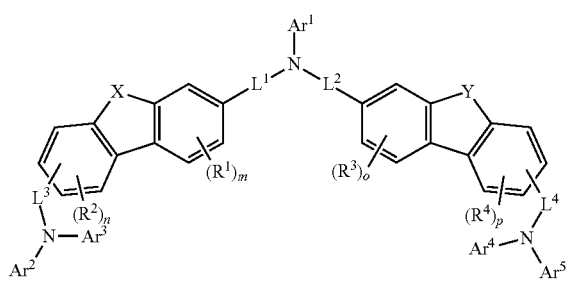

Formula (3)

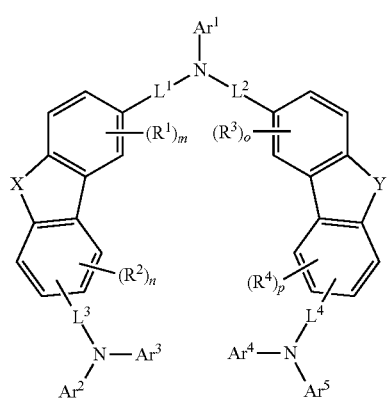

Formula (4)

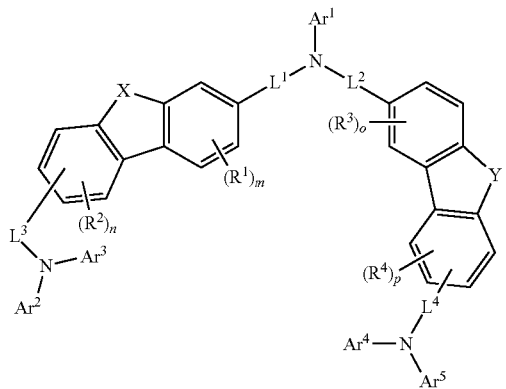

Formula (5)

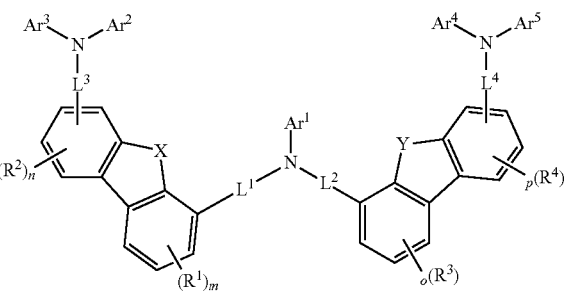

Formula (6)

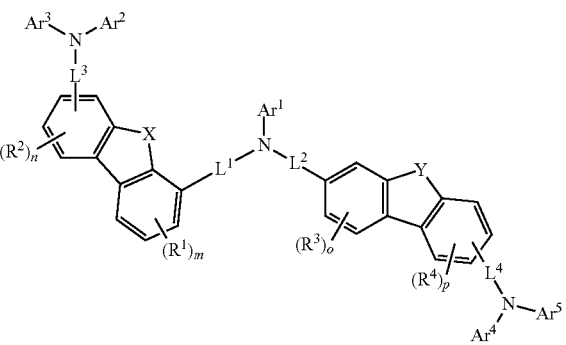

Formula (7)

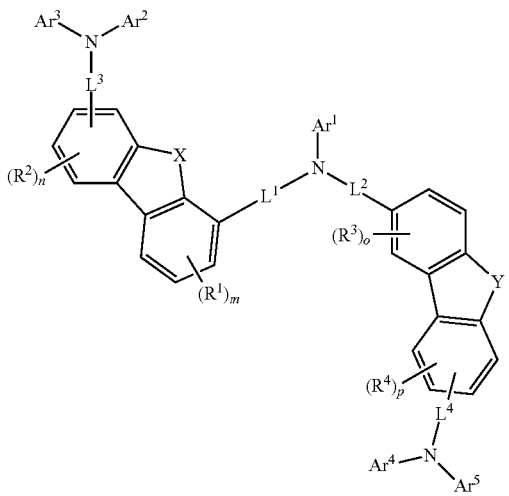

Formula (8)
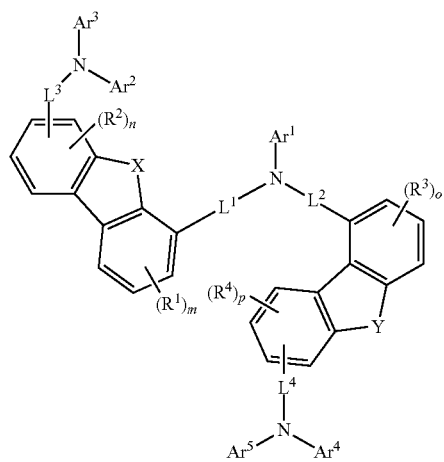
Formula (11)
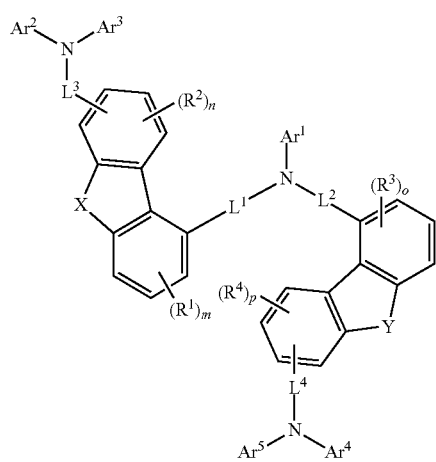
wherein,
X, Y, $Ar^1$, $Ar^2$, $Ar^3$, $Ar^4$, $Ar^5$, $L^1$, $L^2$, $L^3$, $L^4$, $R^1$, $R^2$, $R^3$, $R^4$, m, n, o, and p are the same as defined in claim 1.
3. The compound according to claim 1, wherein Formula (1) is represented by any one of following Formula (12) to Formula (14):
Formula (9)
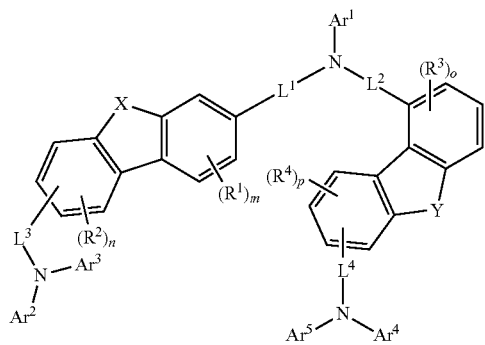
Formula (12)
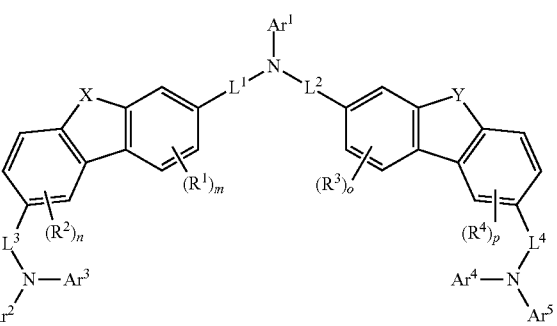
Formula (10)
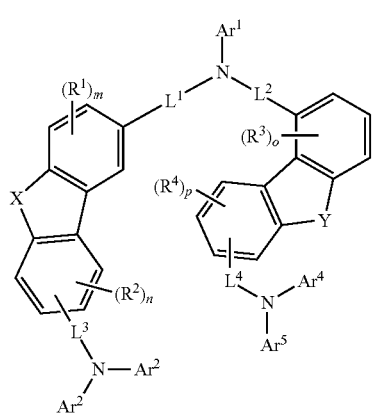
Formula (13)
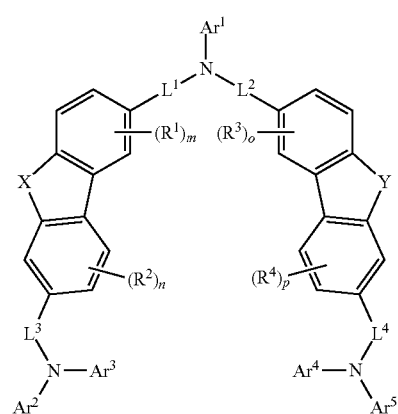

Formula (14)
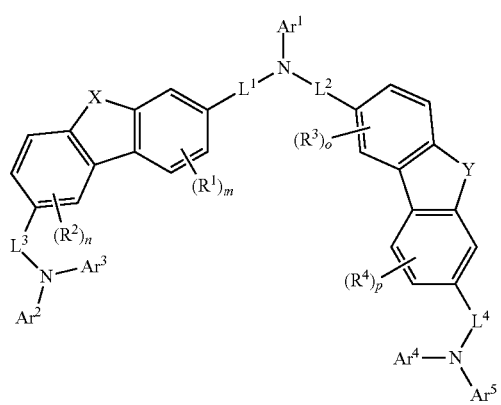
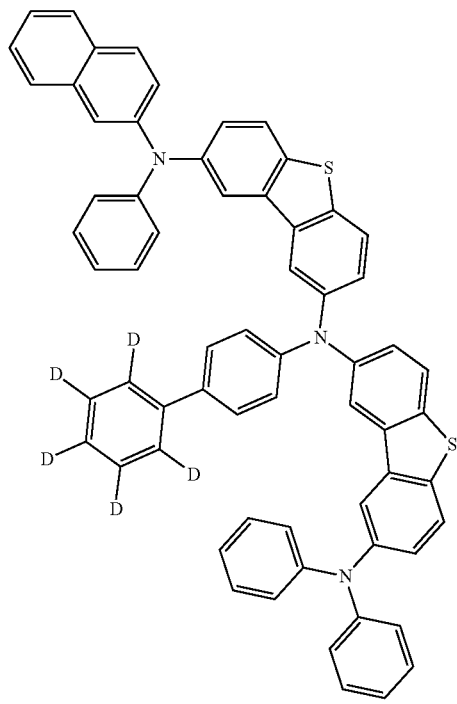
P 1-2
wherein,
X, Y, Ar$^1$, Ar$^2$, Ar$^3$, Ar$^4$, Ar$^5$, L$^1$, L$^2$, L$^3$, L$^4$, R$^1$, R$^2$, R$^3$, R$^4$, m, n, o, and p are the same as defined in claim 1.
4. The compound according to claim 1, wherein the compound of Formula (1) is any one of the following compound P1-1 to P1-112:
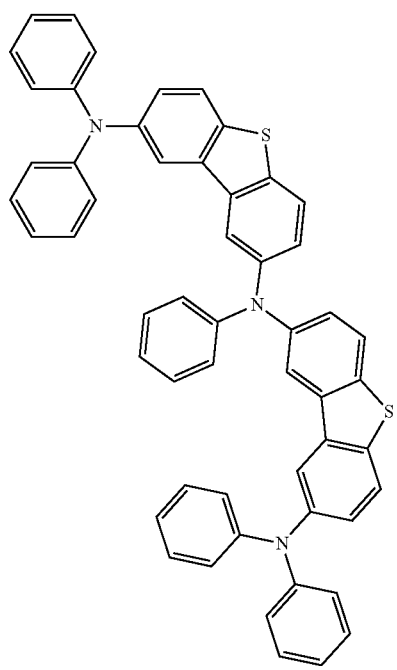
P 1-1
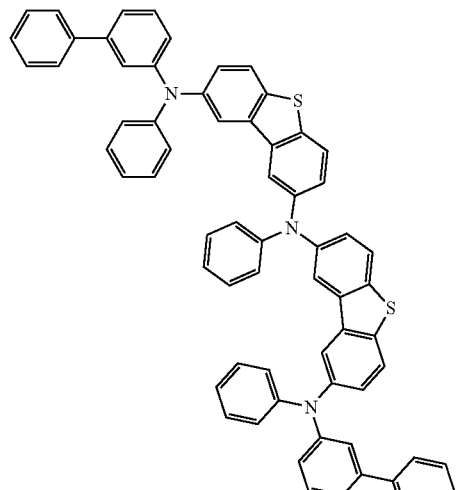
P 1-3

P 1-4
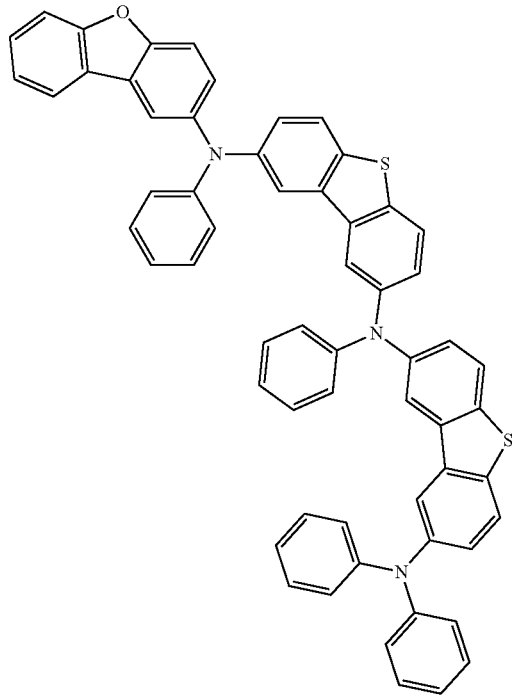
P 1-5
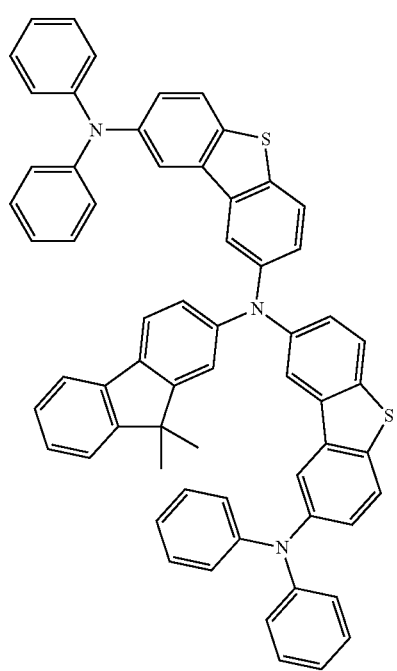
P 1-6
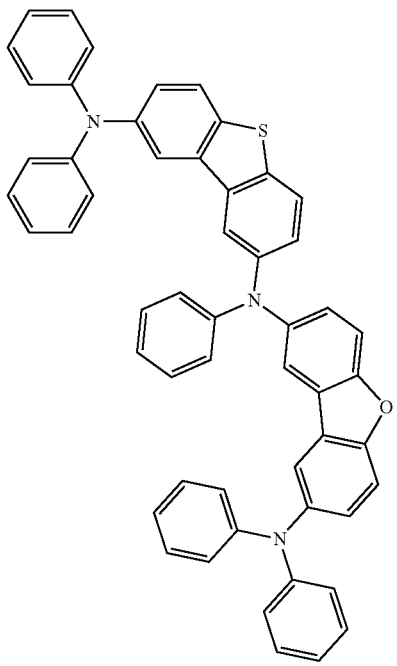
P 1-7
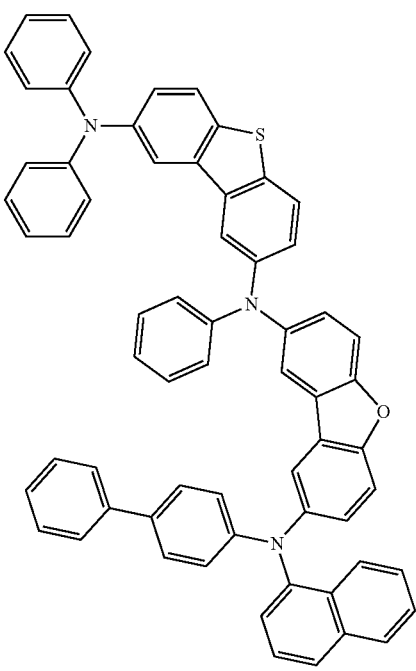

P 1-8
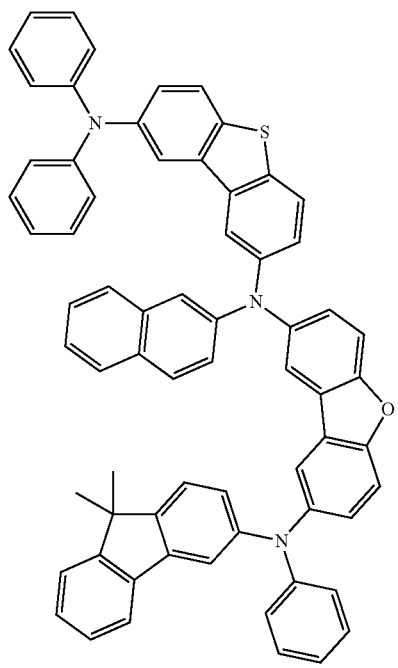
P 1-10
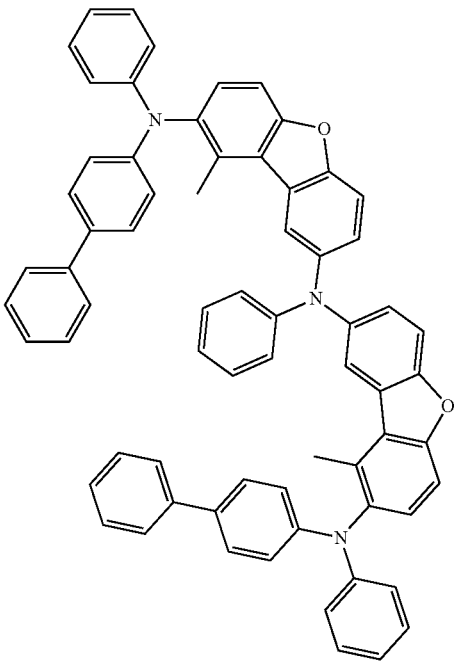
P 1-9
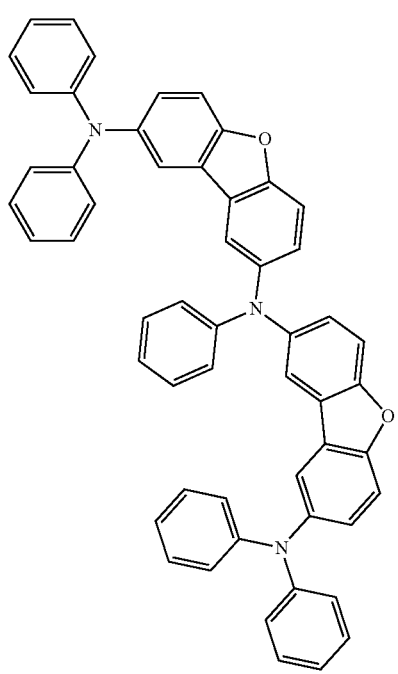
P 1-16
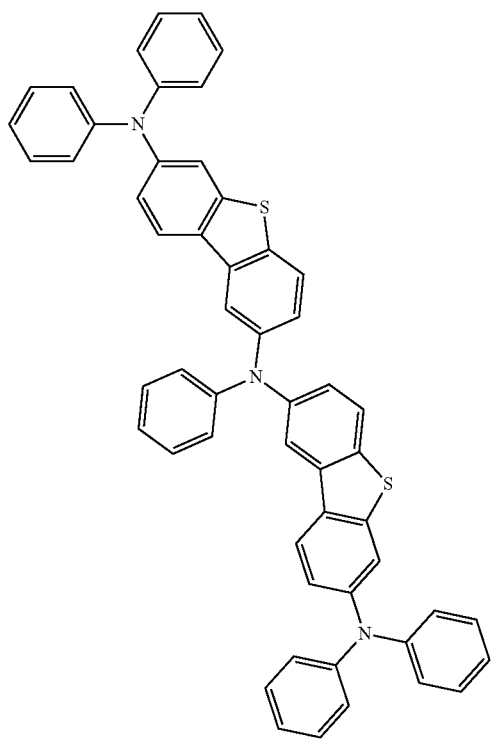

P 1-17
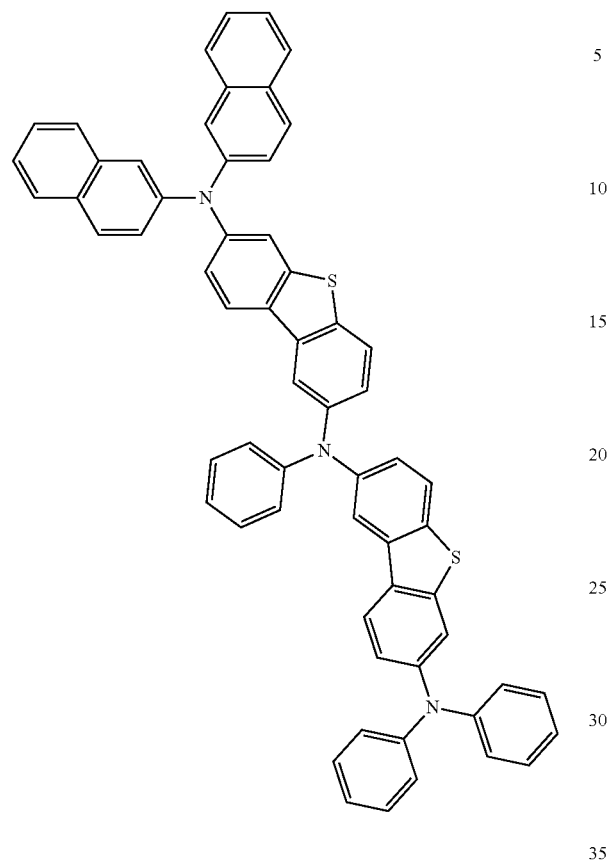
P 1-19
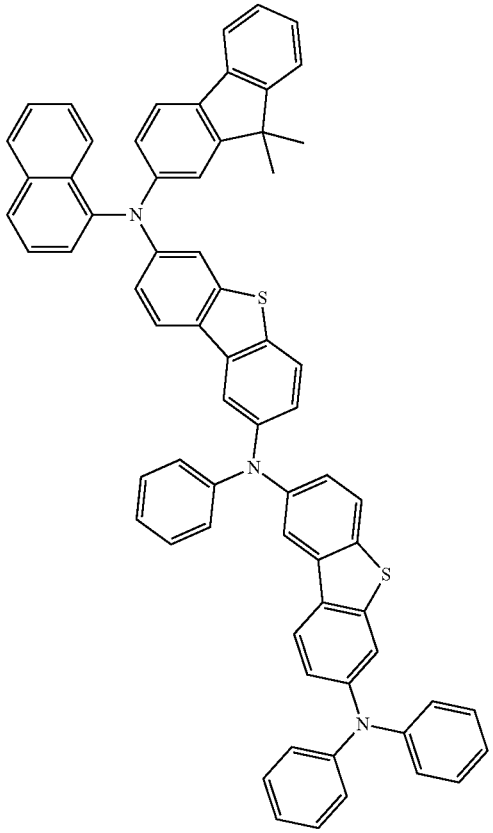
P 1-18
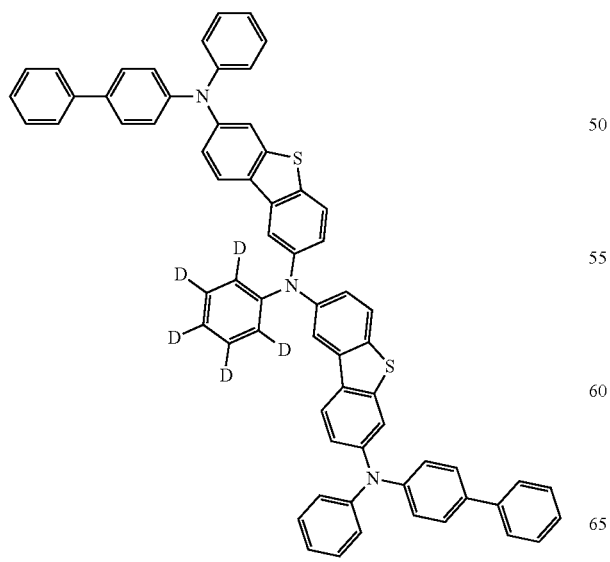
P 1-20
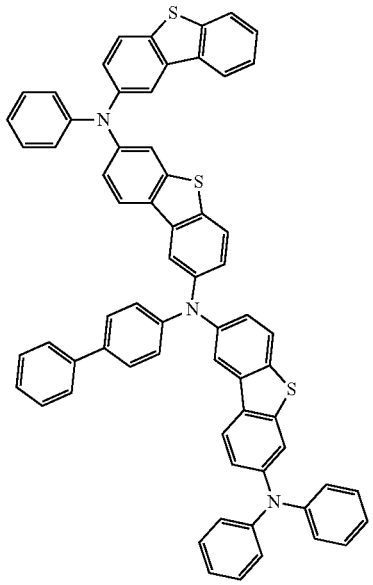

-continued
P 1-21
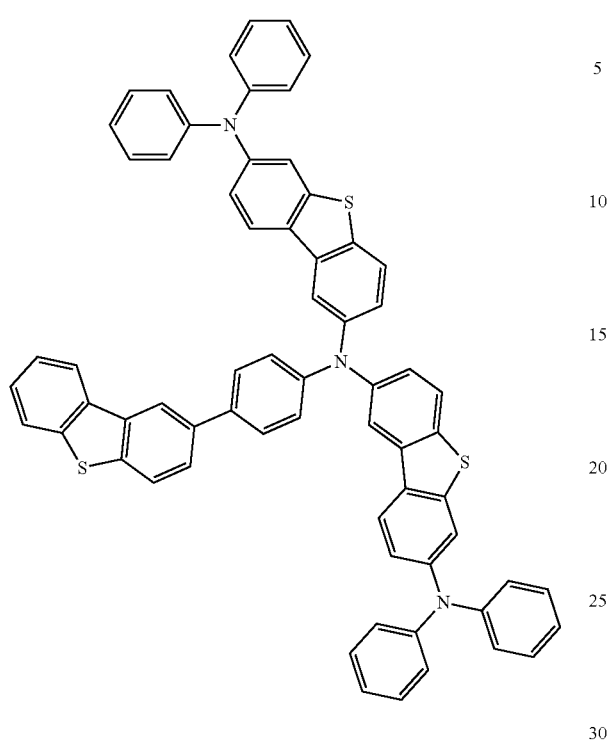
P 1-22
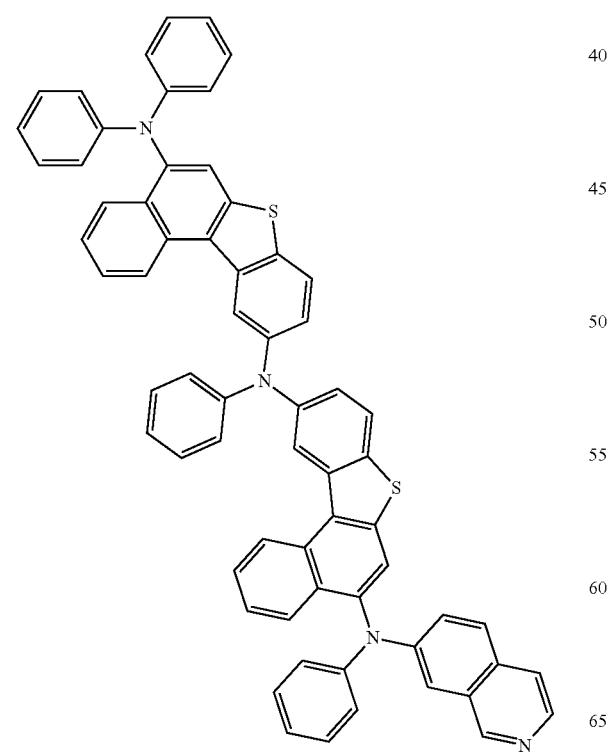
P 1-23
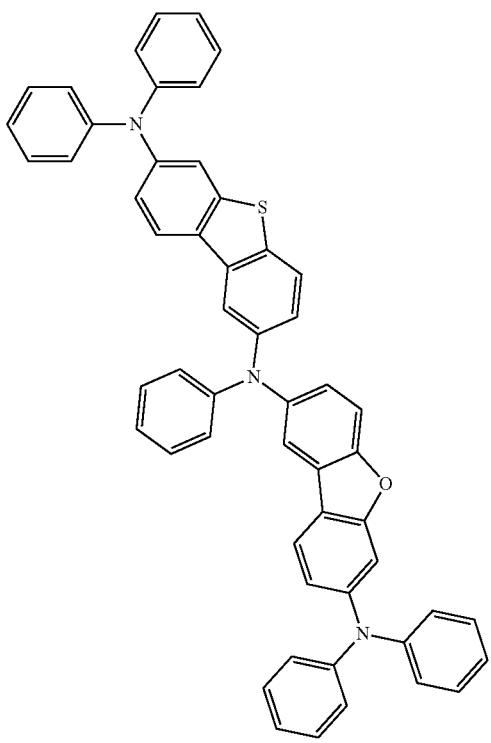
P 1-24
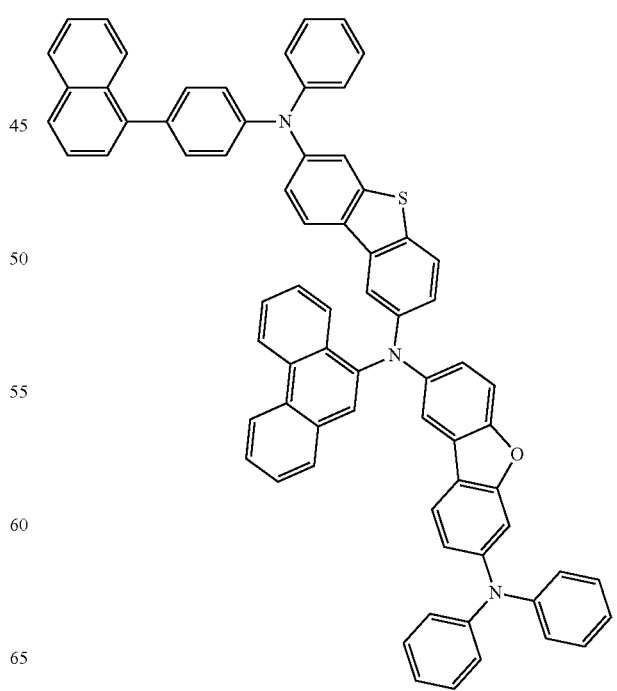

-continued
P 1-25
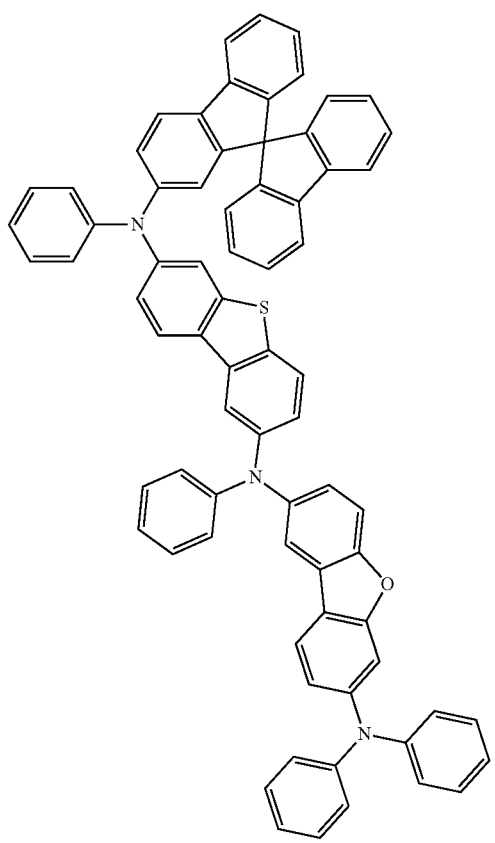
P 1-26
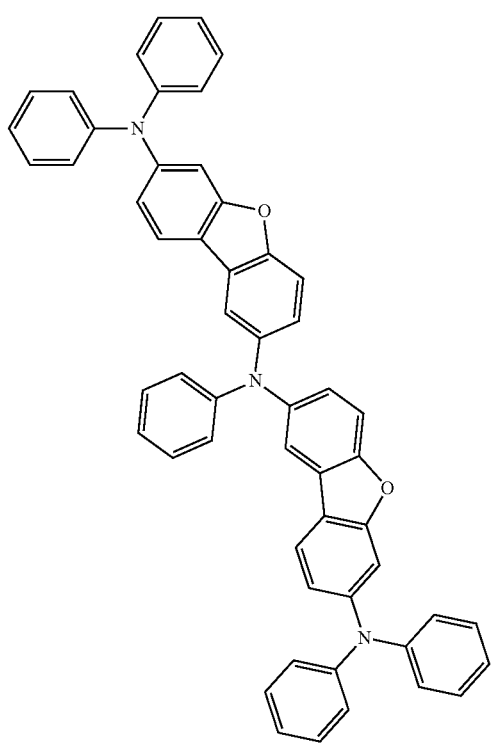
P 1-27
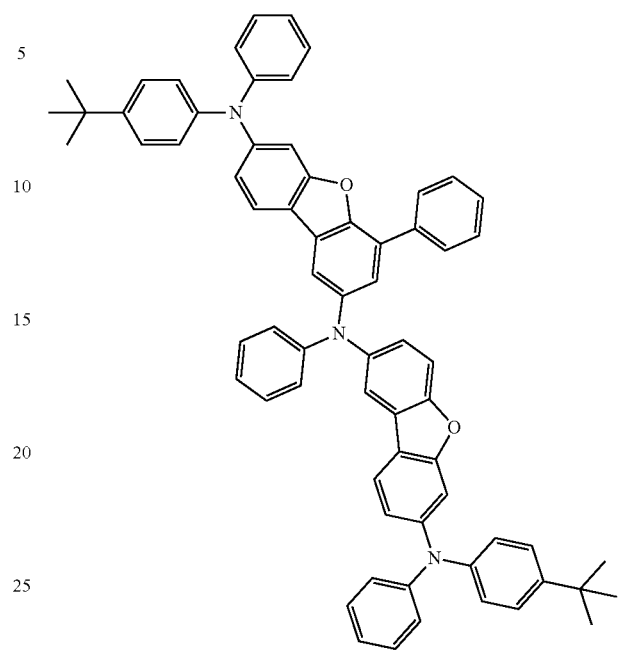
P 1-28
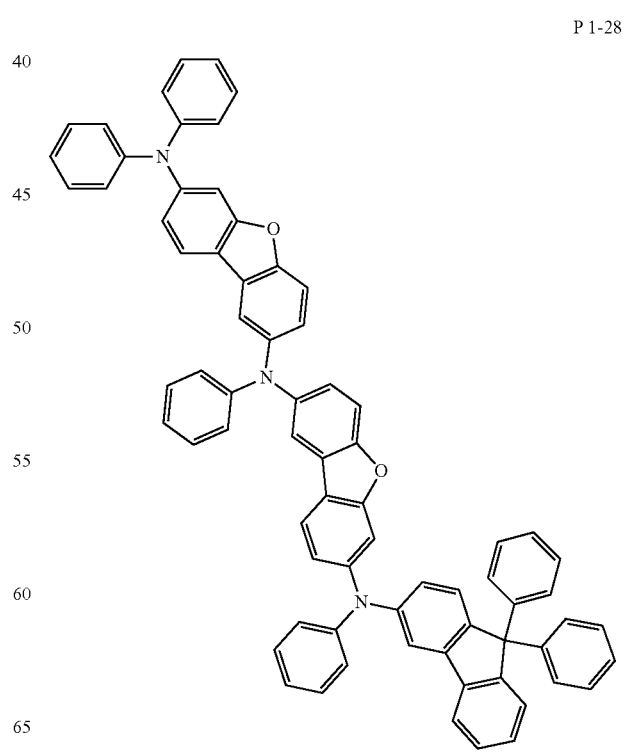

P 1-36
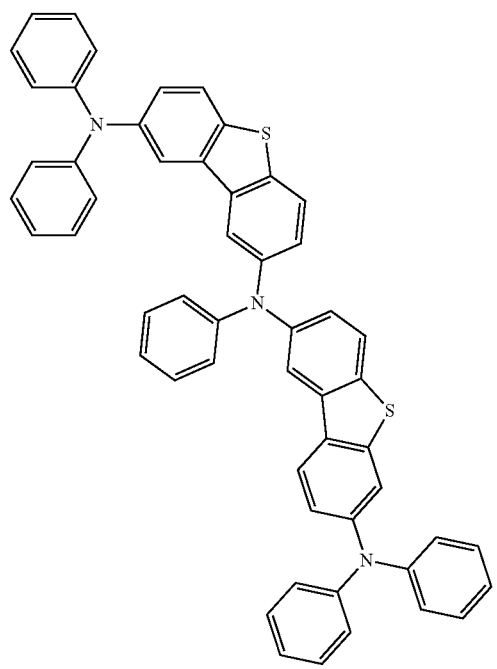
P 1-38
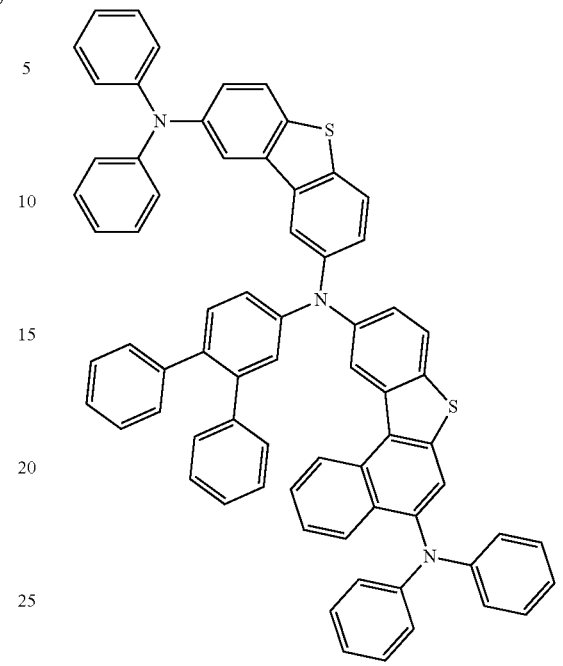
P 1-37
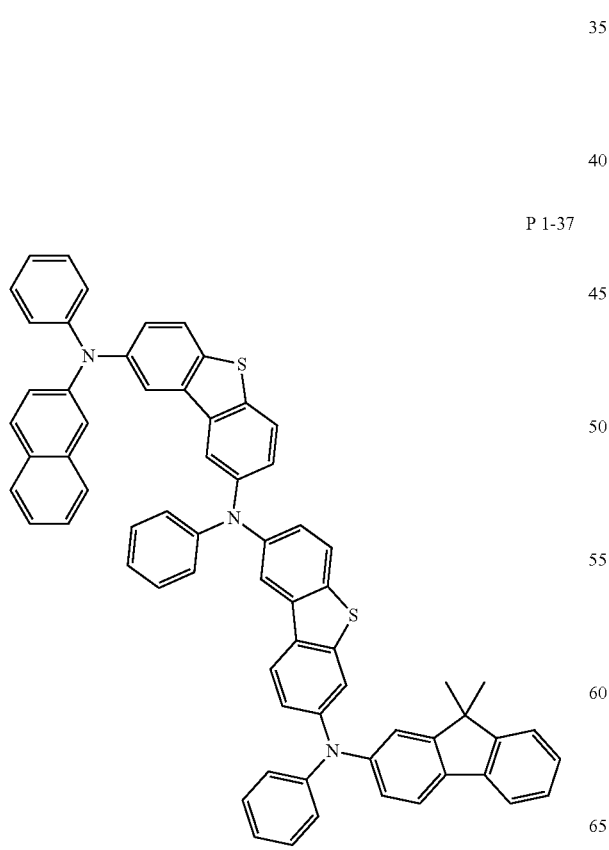
P 1-39
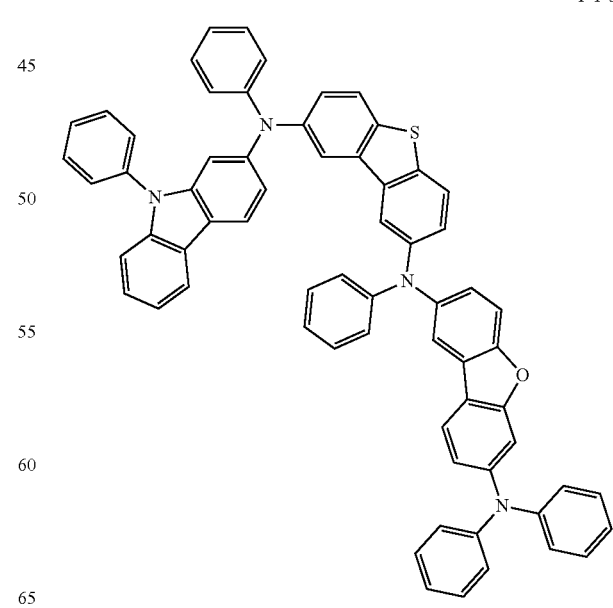

P 1-40
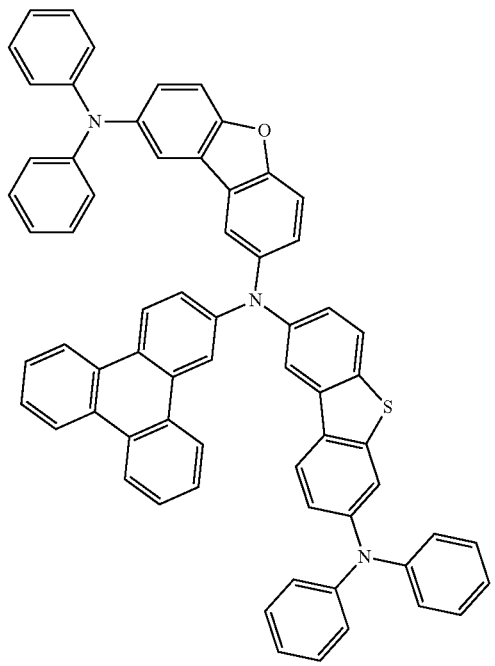
P 1-41
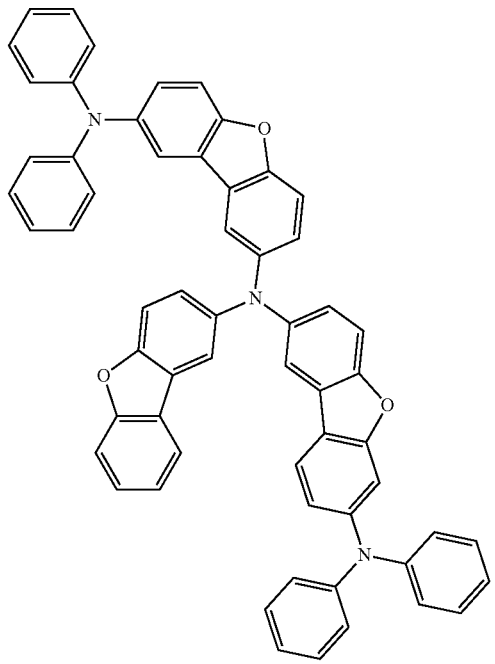
P 1-46
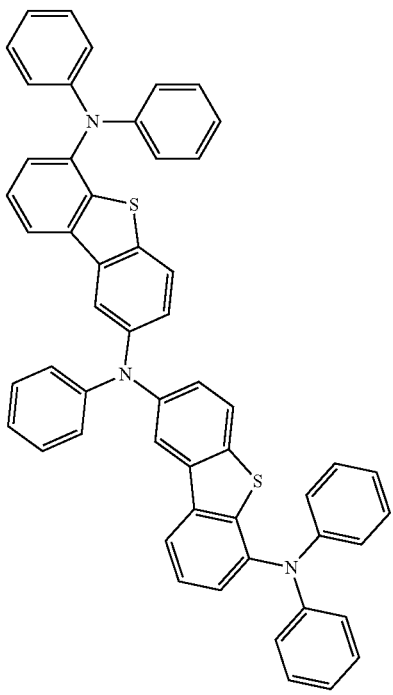
P 1-47
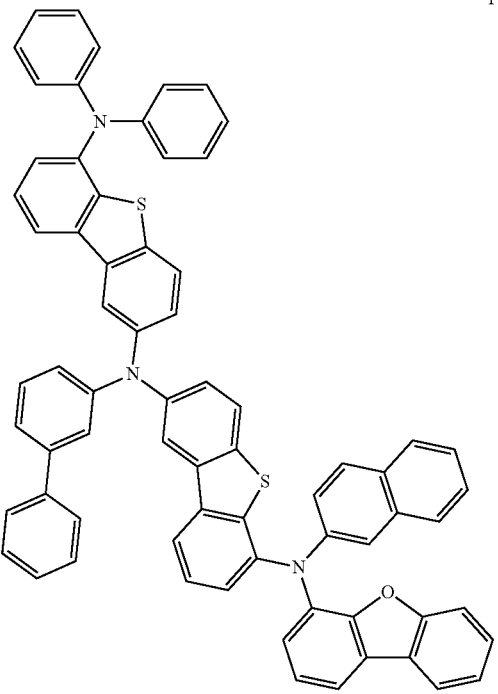

P 1-48
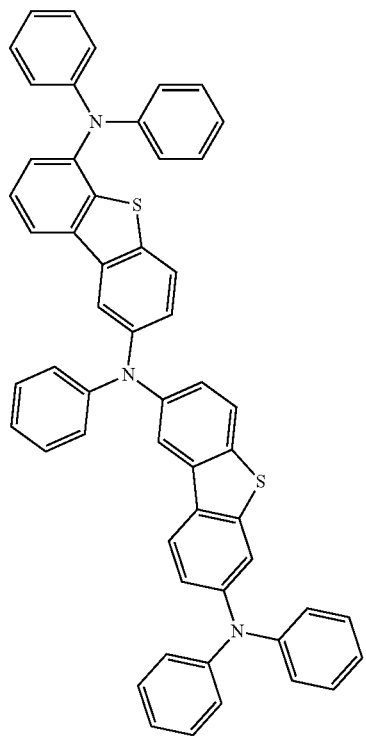
P 1-52
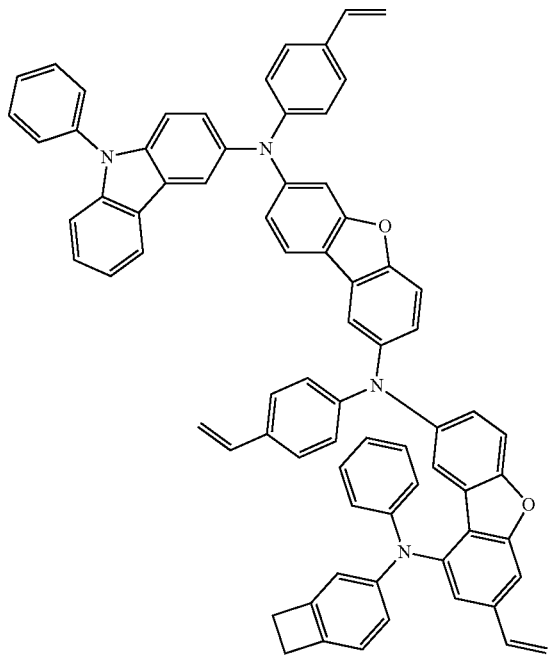
P 1-49
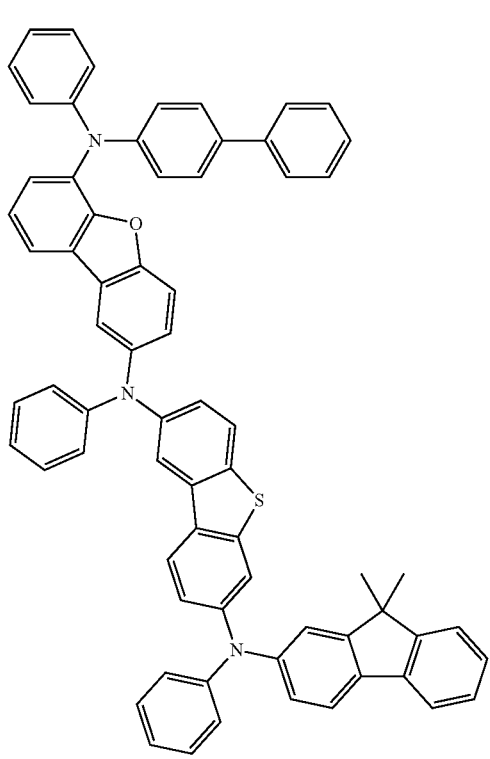
P 1-53
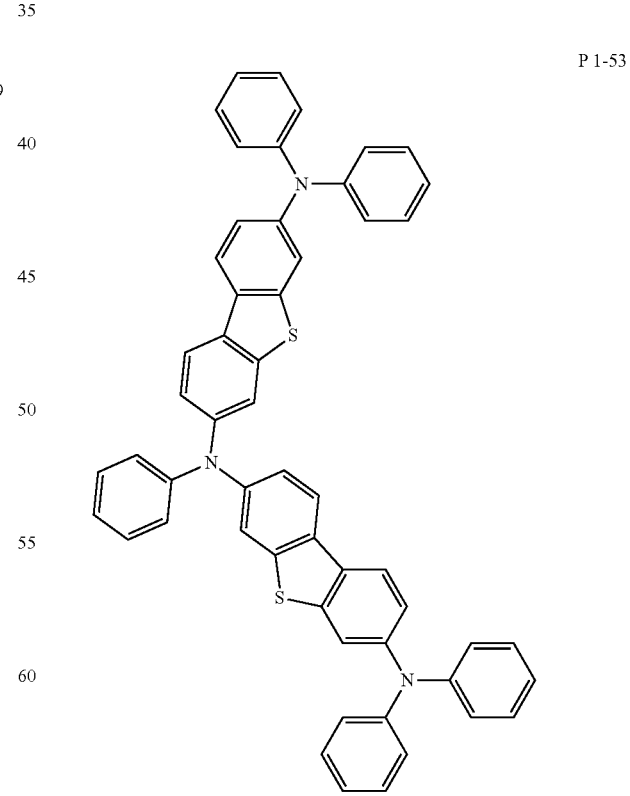

P 1-54
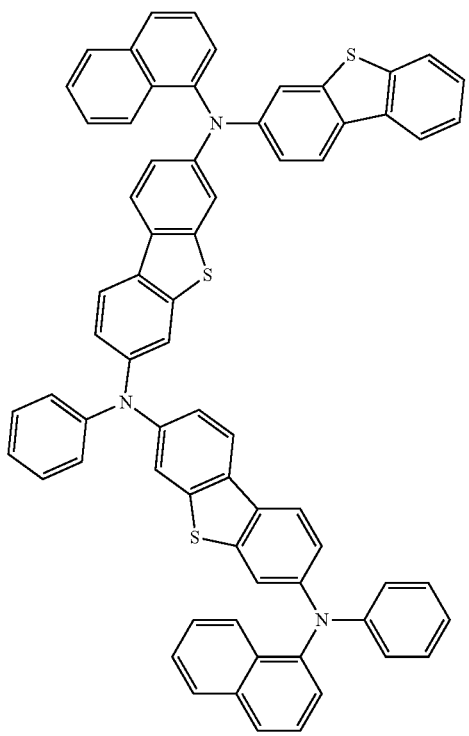
P 1-56
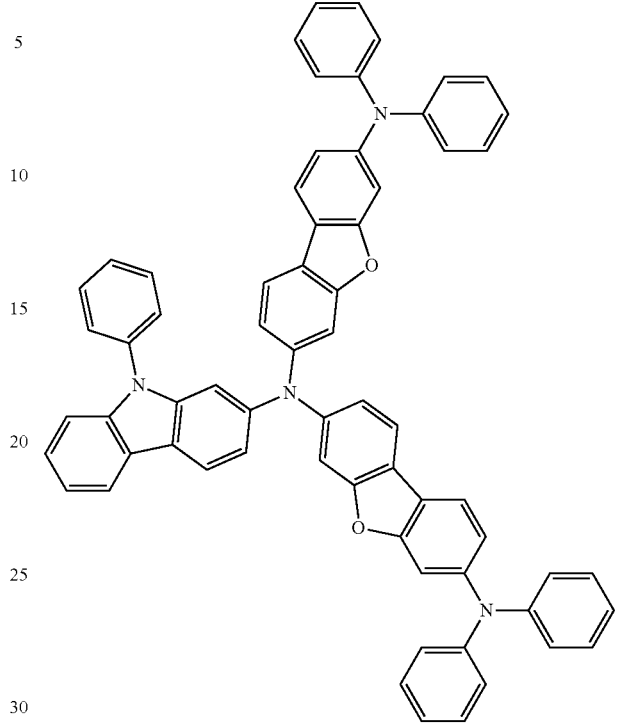
P 1-55
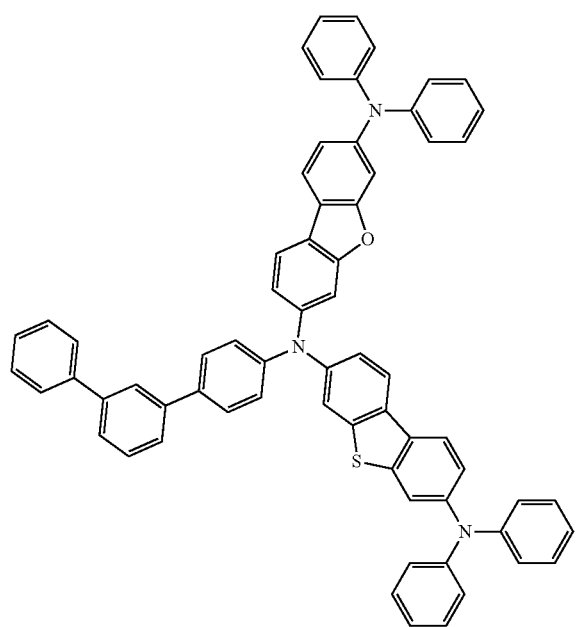
P 1-59
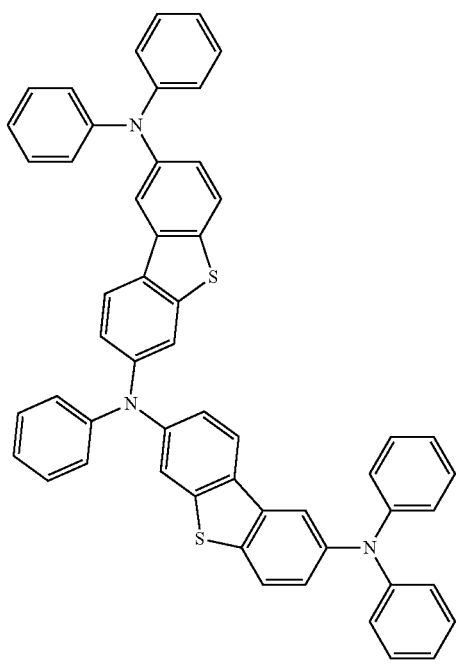

P 1-60
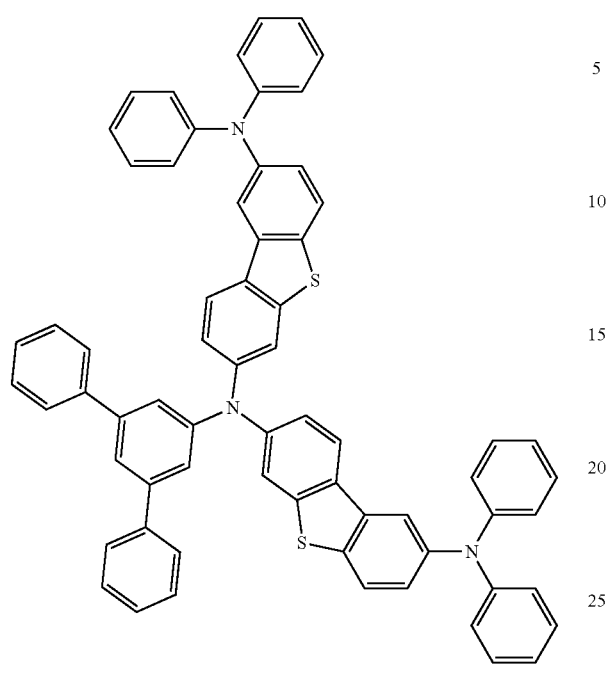
P 1-62
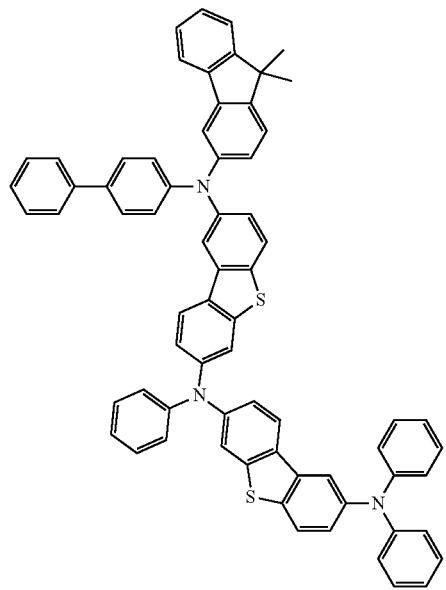
P 1-61
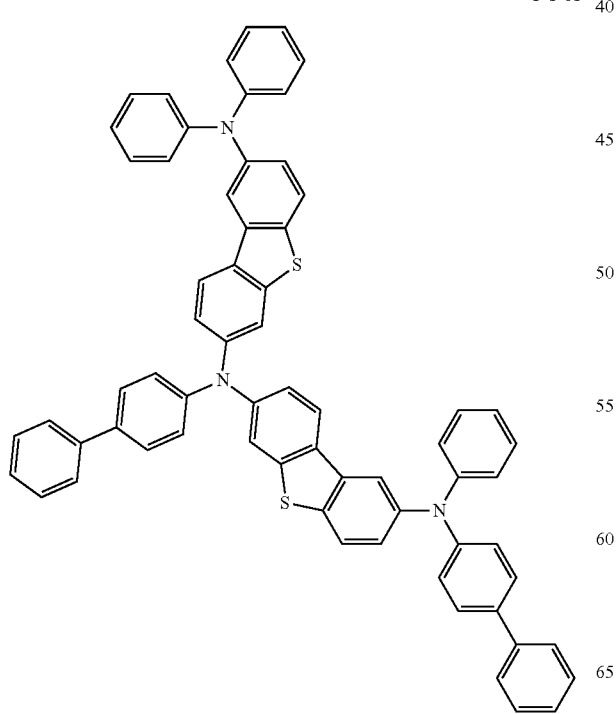
P 1-63
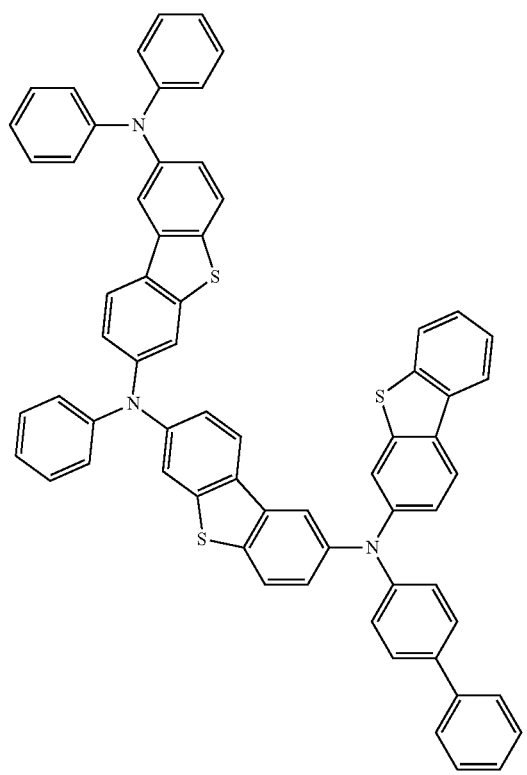

P 1-64
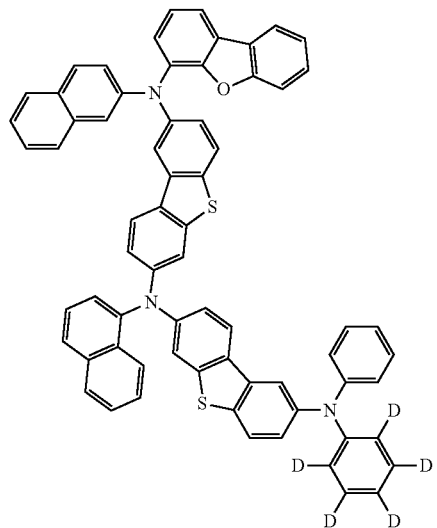
P 1-66
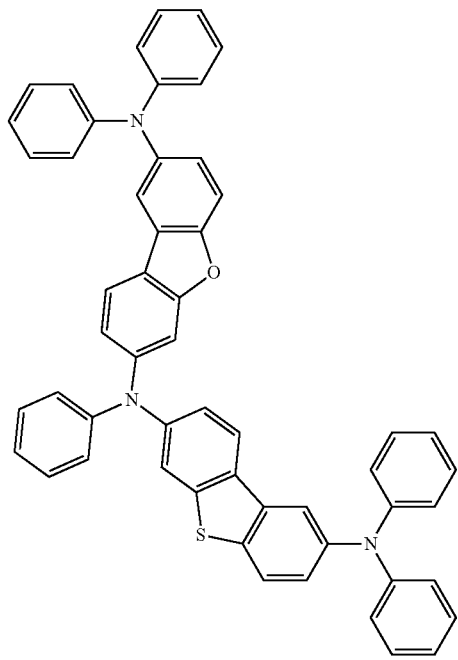
P 1-65
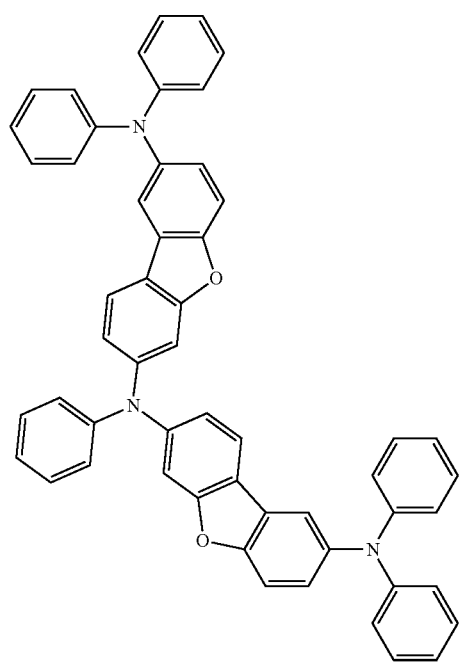
P 1-67
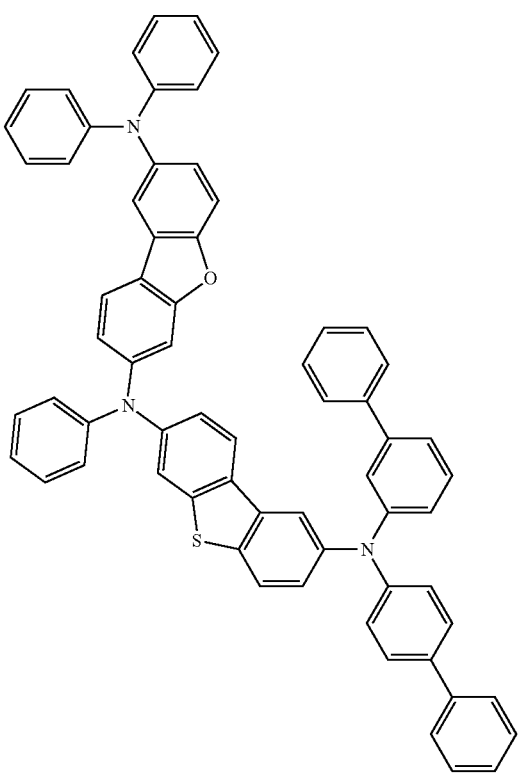

P 1-68
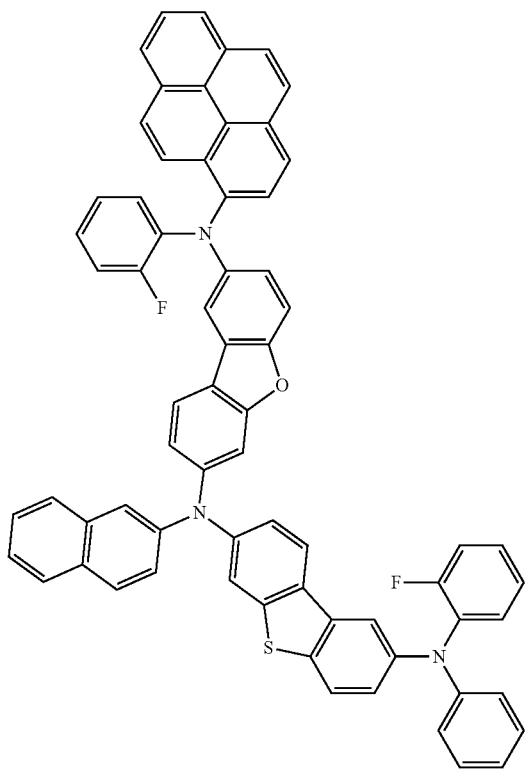
P 1-70
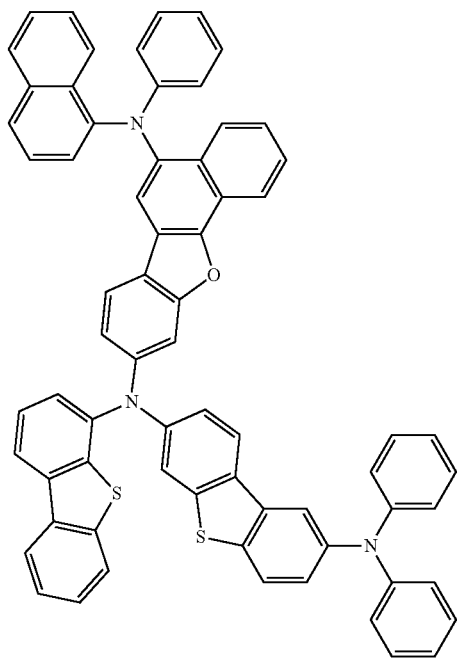
P 1-69
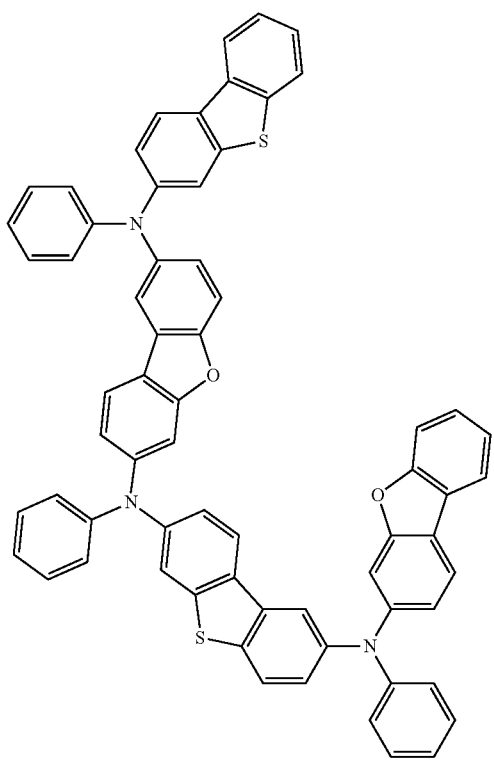
P 1-71
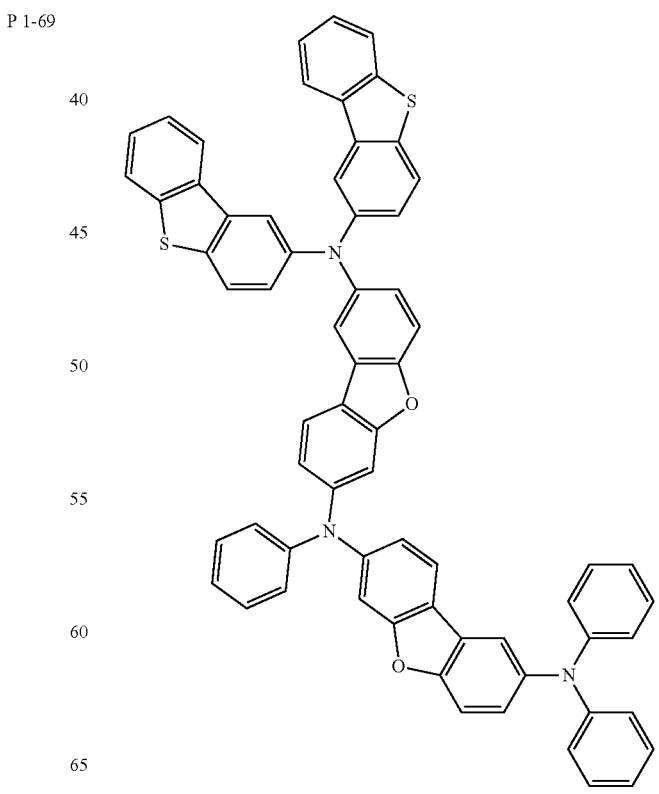

P 1-76
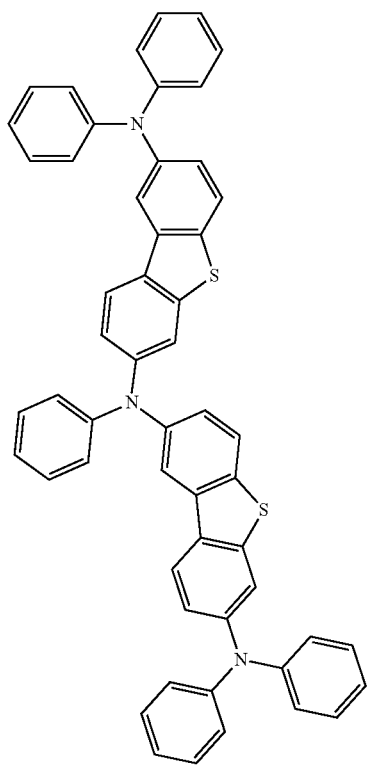
P 1-78
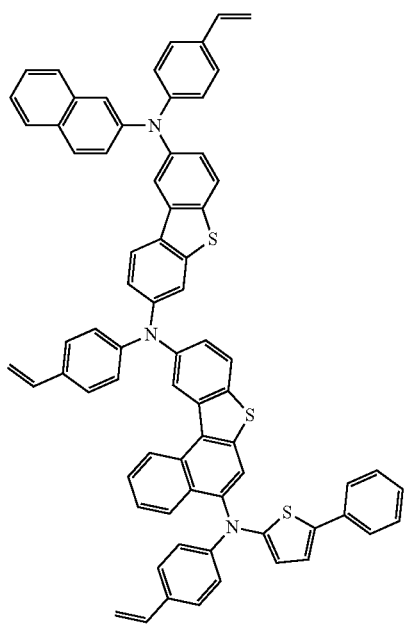
P 1-77
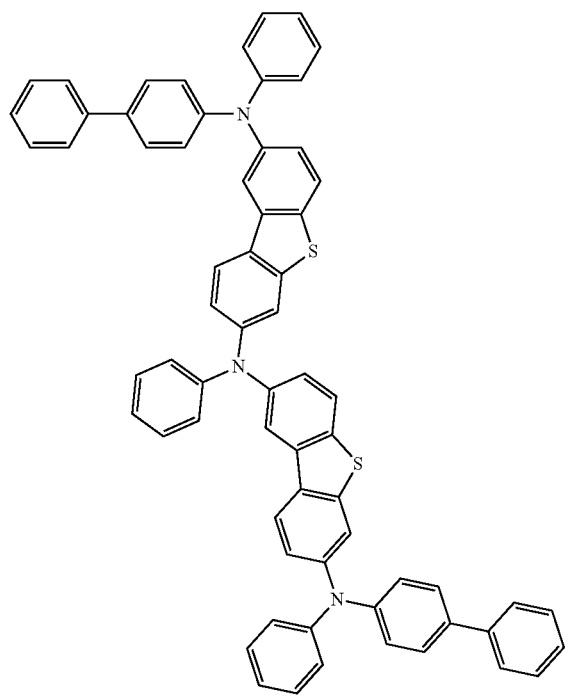
P 1-79
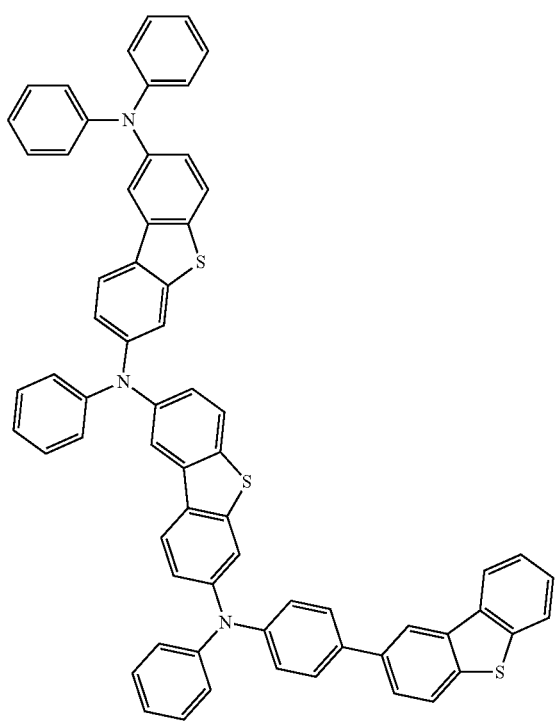

P 1-80
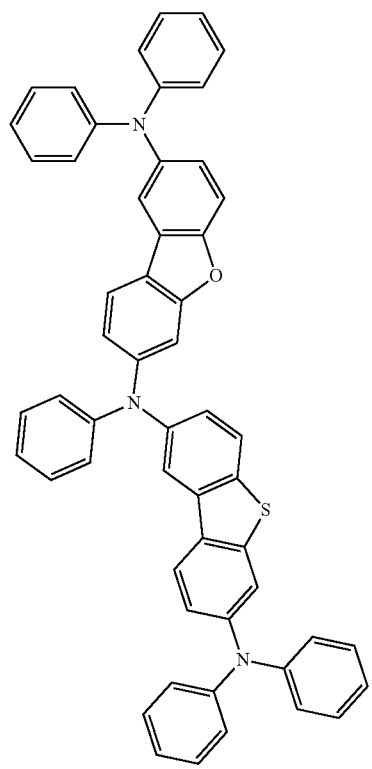
P 1-82
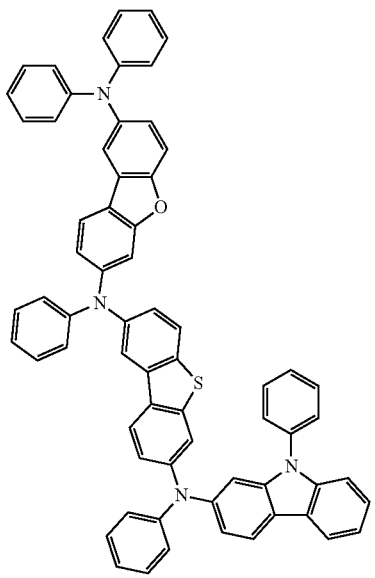
P 1-81
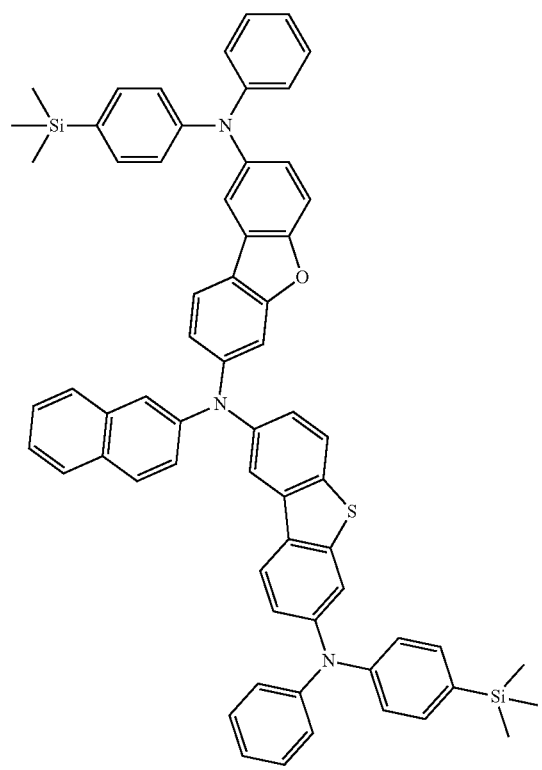
P 1-83
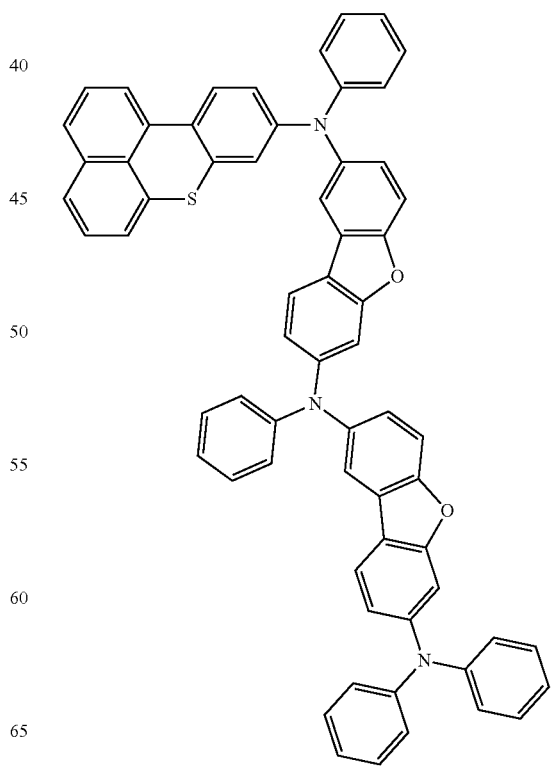

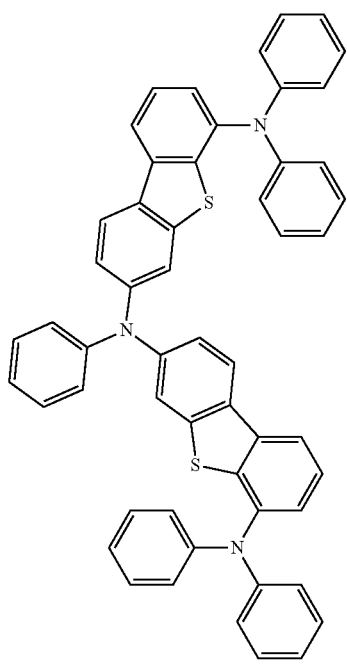
P 1-88
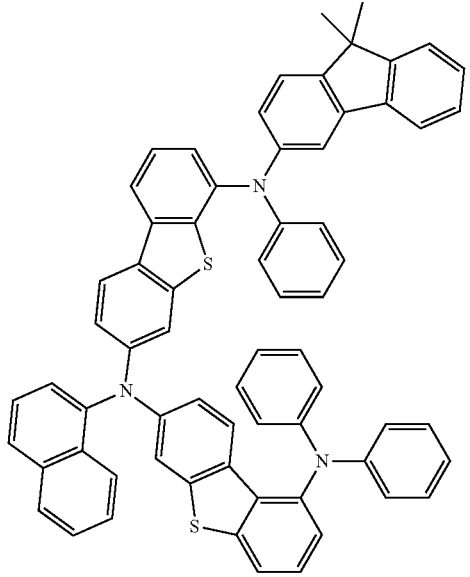
P 1-90
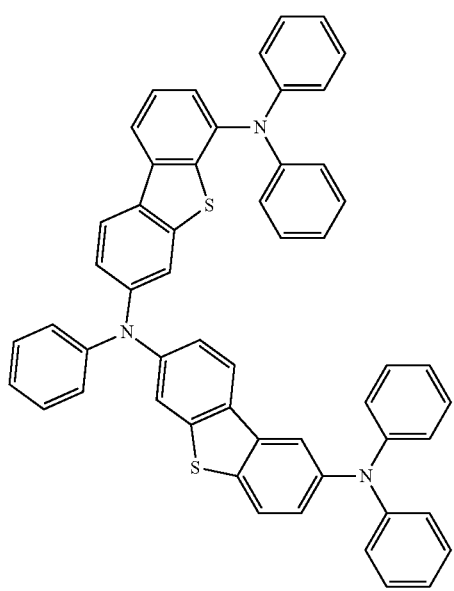
P 1-89
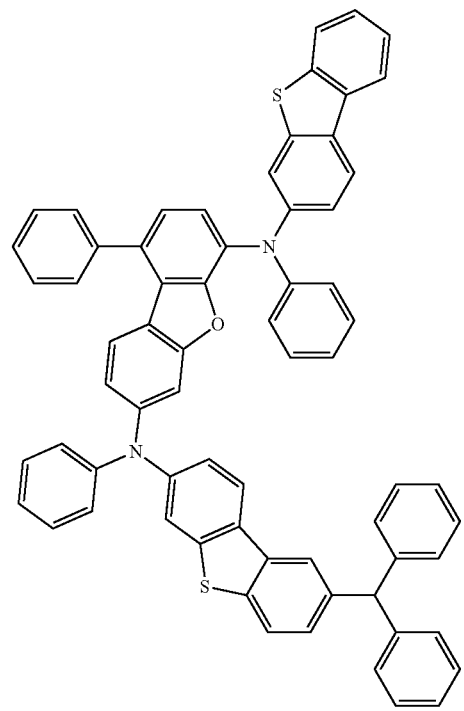
P 1-91

-continued
P 1-93
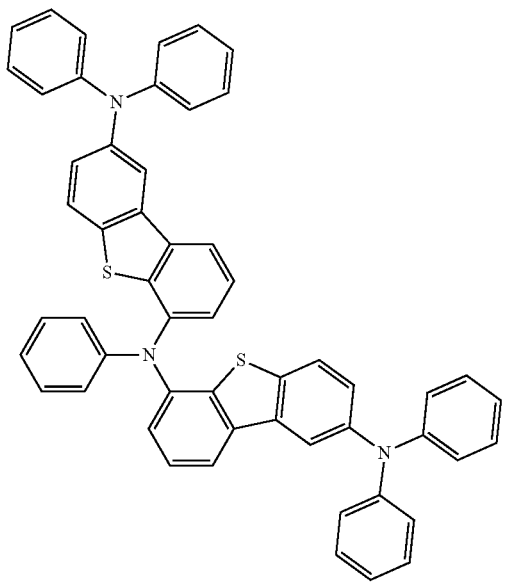
P 1-95
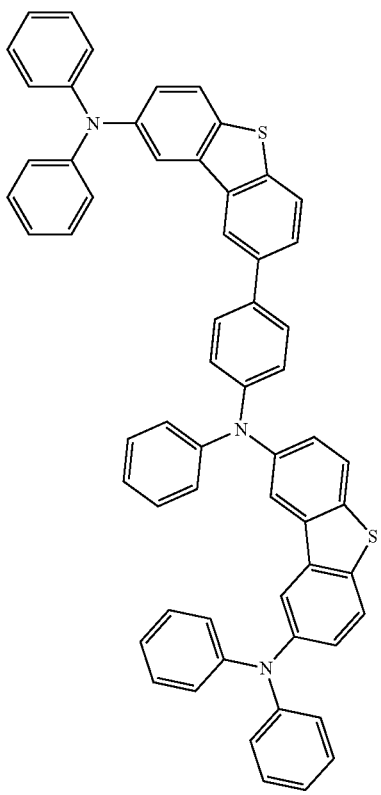
P 1-94
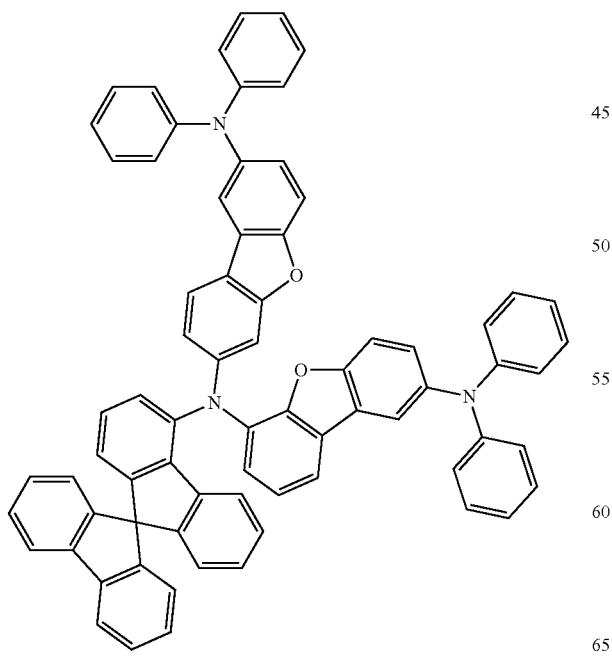
P 1-96
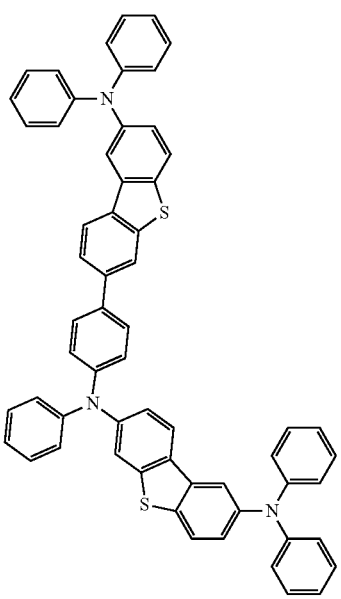

-continued
P 1-97
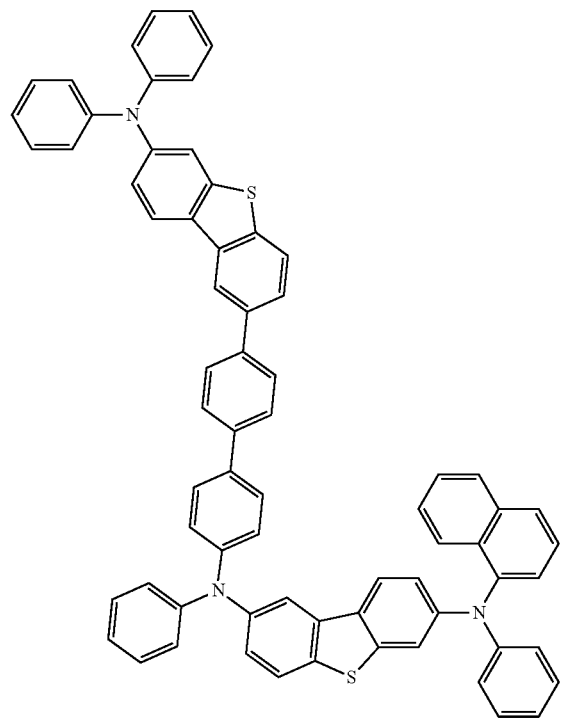
P 1-100
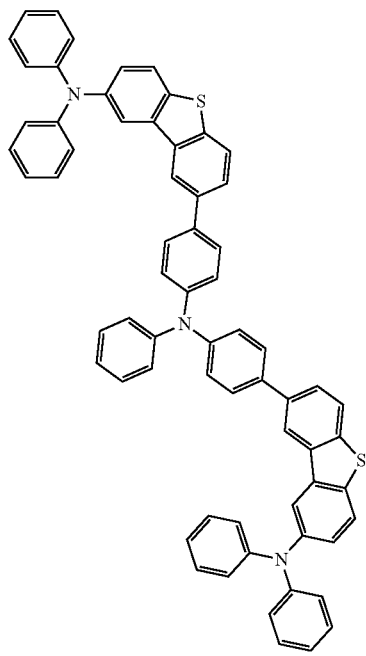
P 1-98
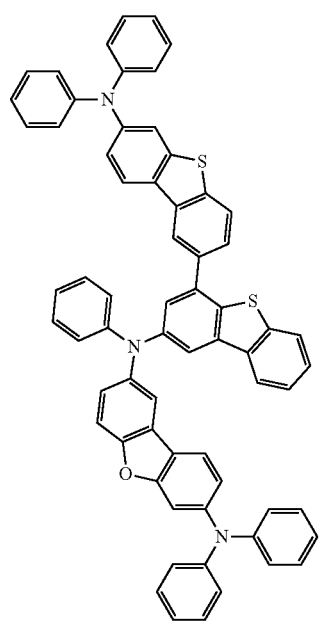
P 1-101
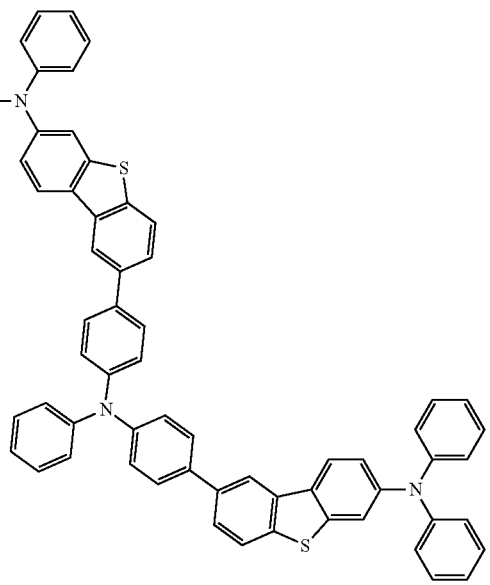

P 1-102
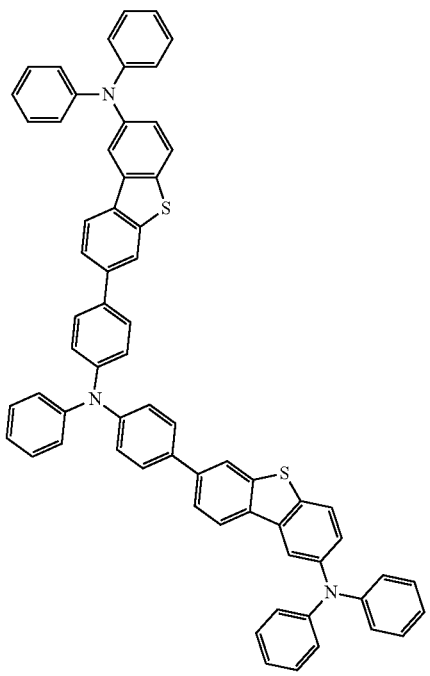
P 1-104
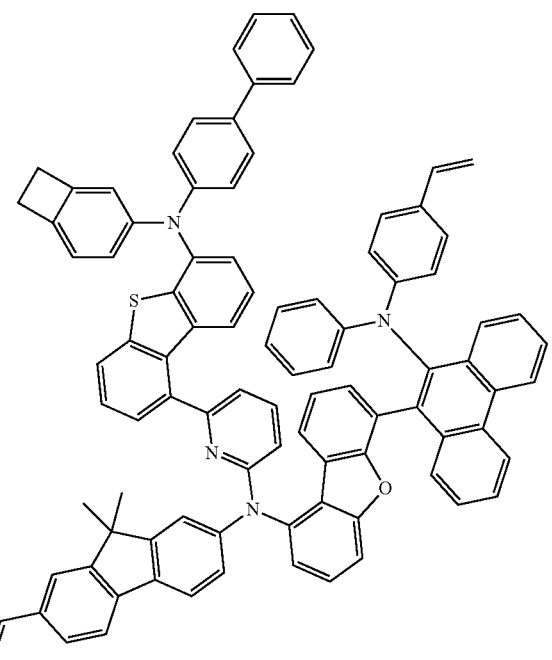
P 1-103
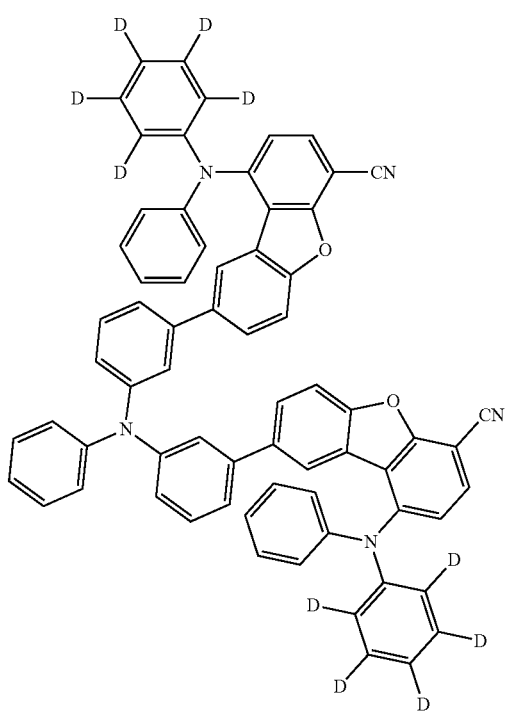
P 1-105
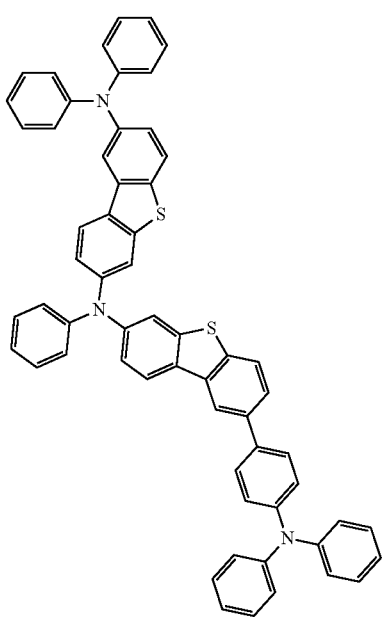

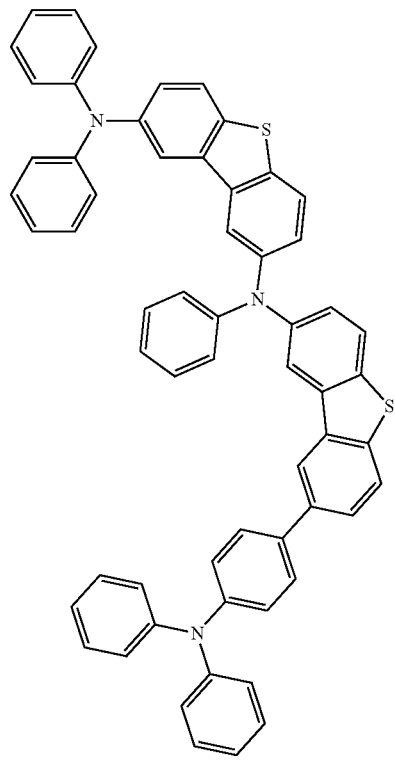
P 1-106
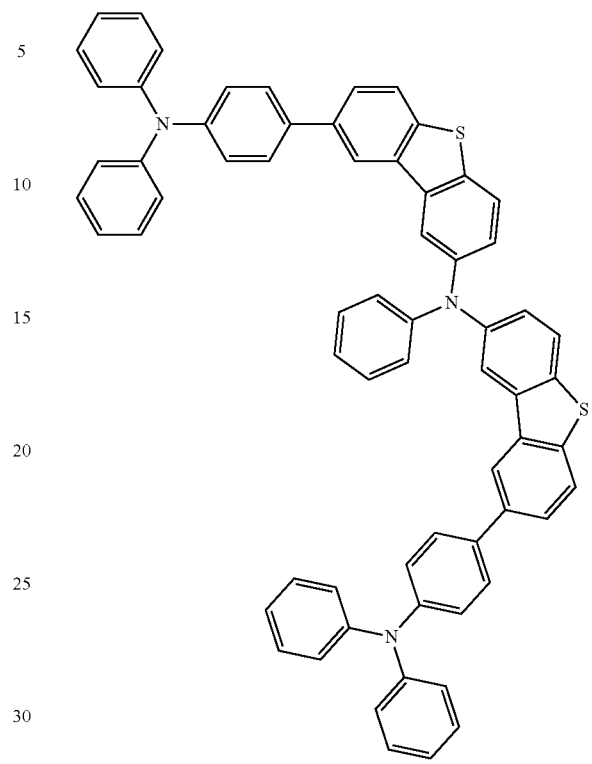
P 1-109
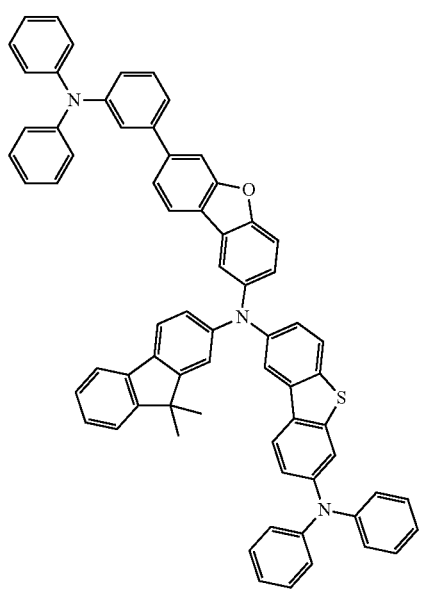
P 1-107
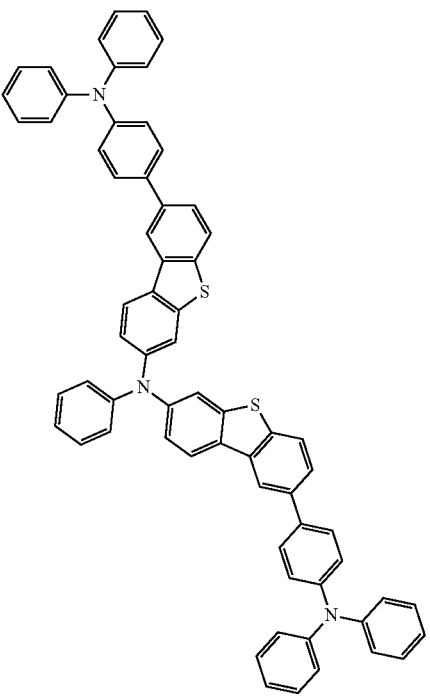
P 1-110

P 1-111

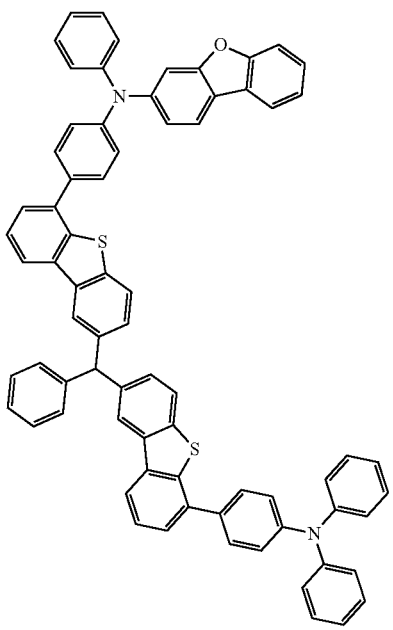

P 1-112

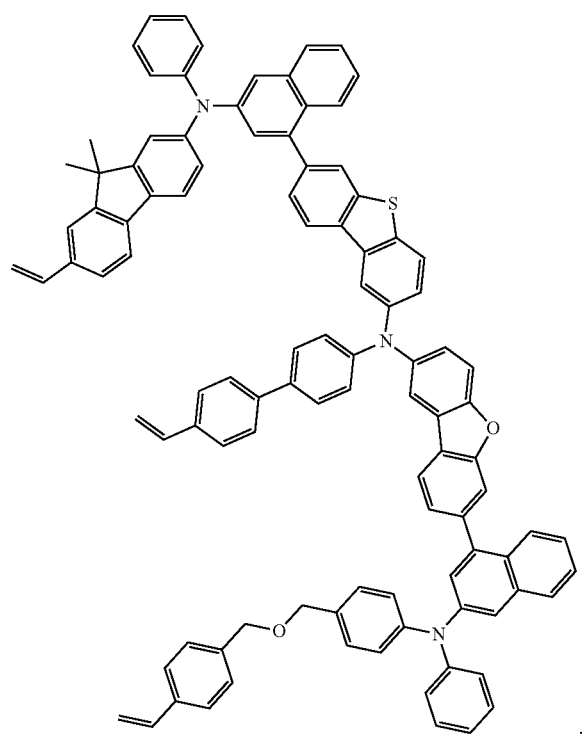

5. An organic electric element comprising: a first electrode; a second electrode; and an organic material layer formed between the first electrode and the second electrode, wherein the organic material layer comprises an hole injection layer, an hole transport layer, an emitting auxiliary layer and an emitting layer, and wherein the organic material layer comprises the compound of claim 1.

6. The organic electric element according to claim 5, wherein the compound comprises a single compound or a mixture of two or more compounds having different structures in at least one of the hole injection layer, the hole transport layer, the emitting auxiliary layer and the emitting layer.

7. The organic electric element according to claim 5, wherein the hole transport layer or the emitting auxiliary layer comprises the compound as a single compound or a mixture of two or more compounds having different structures.

8. The organic electric element according to claim 7, wherein the emitting layer comprises a compound represented by Formula (16):

Formula (16)

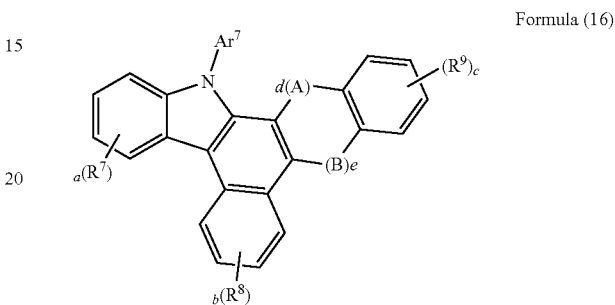

wherein,
1) $Ar^7$ is each independently selected from the group consisting of a $C_6$-$C_{60}$ aryl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; -L'-N($R^a$)($R^b$), where, L' may be selected from the group consisting of a single bond; a $C_6$-$C_{60}$ arylene group; a fused ring group of a $C_3$-$C_{60}$ aliphatic ring and a $C_6$-$C_{60}$ aromatic ring; and a $C_2$-$C_{60}$ heterocyclic group, and the $R^a$ and $R^b$ may be independently selected from the group consisting of a $C_6$-$C_{60}$ aryl group; a fused ring group of a $C_3$-$C_{60}$ aliphatic ring and a $C_6$-$C_{60}$ aromatic ring; and a $C_2$-$C_{60}$ heterocyclic group containing at least one hetero atom of O, N, S, Si, or P,
2) a, b and c are integers of 0 to 4,
3) $R^7$, $R^8$ and $R^9$ are the same or different and are each independently selected from the group consisting of deuterium; a halogen; a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R^a$)($R^b$); and in case a, b and c are 2 or more and are each in plural, being the same or different, or a plurality of $R^7$ or a plurality of $R^8$ or a plurality of $R^9$ may be bonded to each other to form an aromatic or a heteroaromatic ring,
4) A and B are each independently a single bond, S, O, NR', or CR'R",
5) R' and R" are each independently a hydrogen; a $C_6$-$C_{60}$ aryl group; a $C_3$-$C_{60}$ heterocyclic group; or a $C_1$-$C_{50}$ alkyl group; and R' and R" may be bonded to each other to form a Spiro compound,
6) d and e are 0 or 1, provided that d+e is not less than 1.

9. The organic electric element according to claim 8, wherein the compound represented by Formula (16) is represented by the following Formula (17) or (18):

Formula (17)
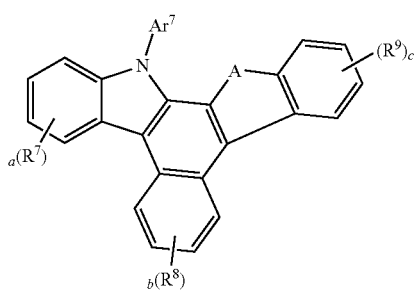
Formula (18)
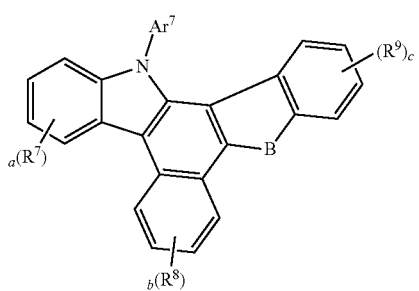
wherein,
R⁷, R⁸, R⁹, A, b, c, Ar⁷, A and B are the same as defined in claim 8.
10. The organic electric element according to claim 8, wherein the compound represented by Formula (16) is represented by any one of the following Formula (19) or (34):
Formula (19)
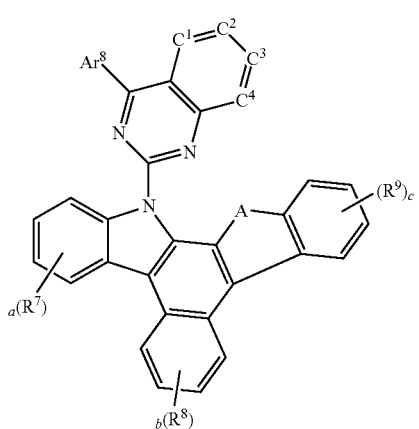
Formula (20)
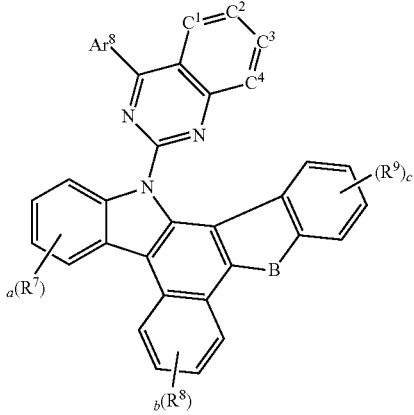
Formula (21)
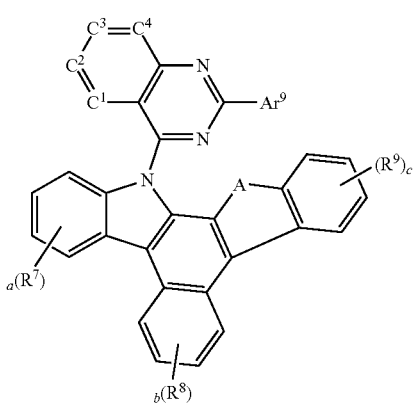
Formula (22)
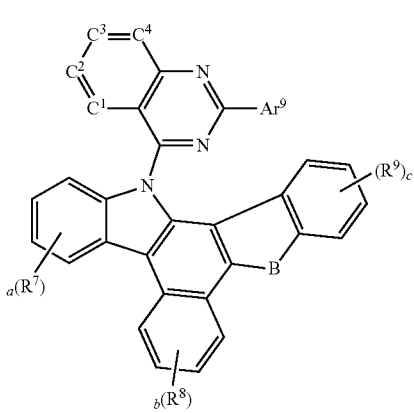

Formula (23)
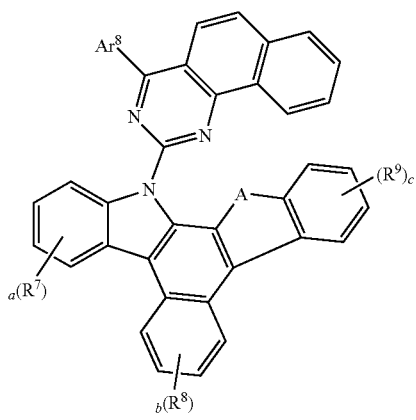
Formula (24)
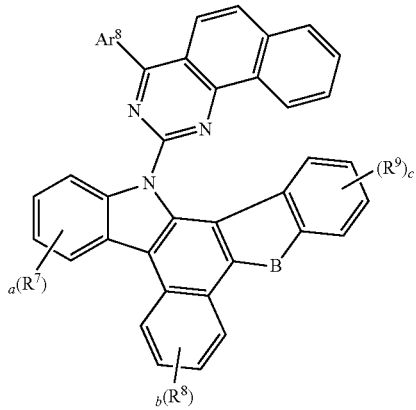
Formula (25)
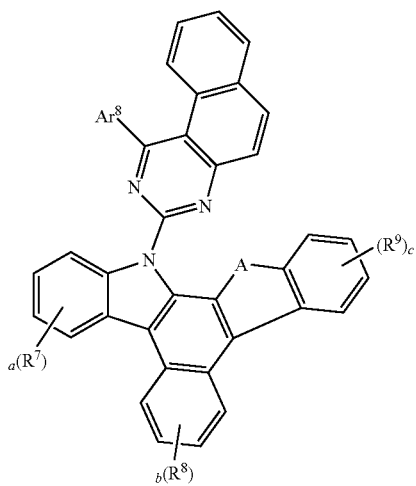
Formula (26)
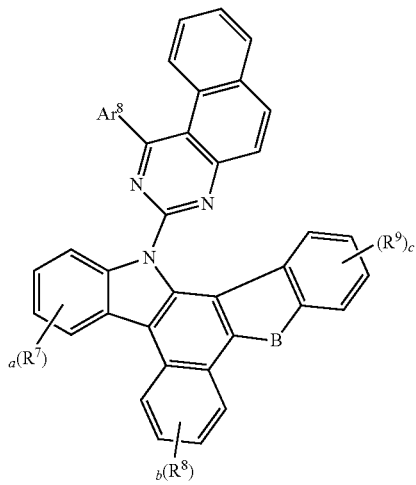
Formula (27)
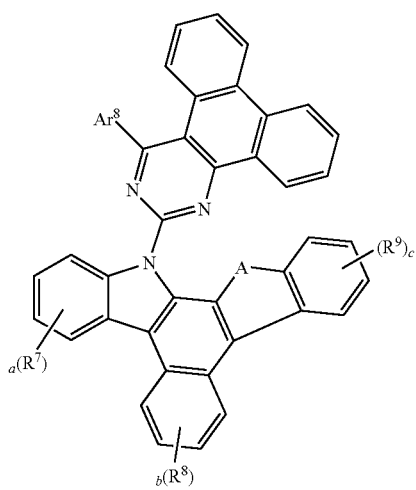
Formula (28)
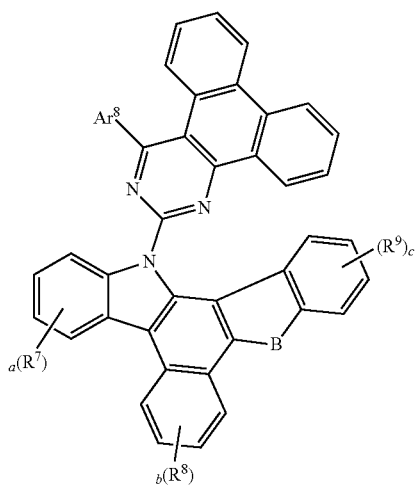

Formula (29)

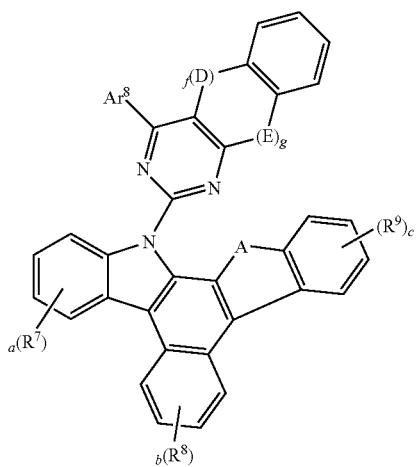

Formula (30)

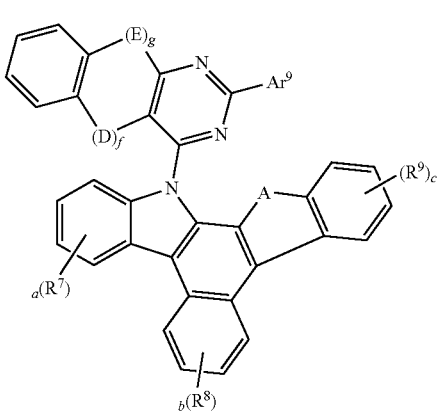

Formula (31)

Formula (32)

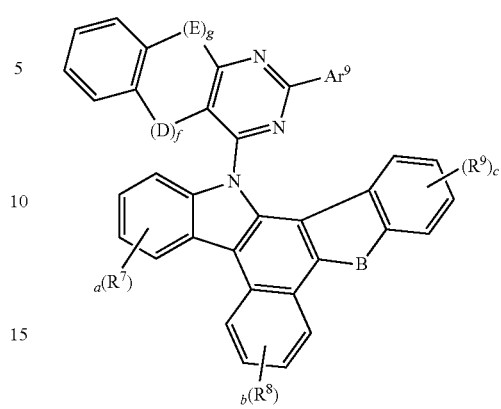

Formula (33)

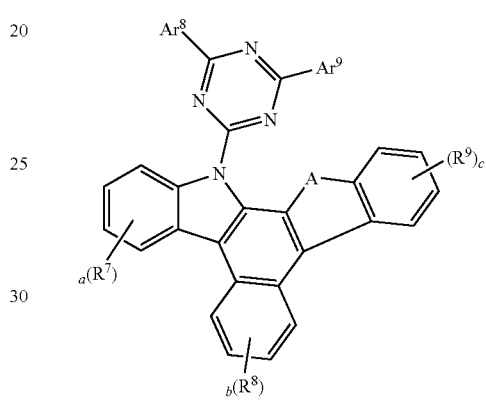

Formula (34)

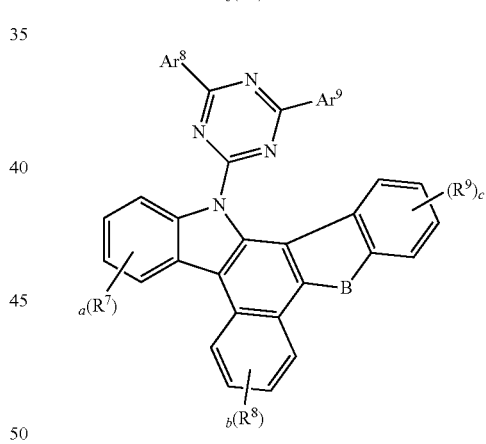

wherein,
1) R⁷, R⁸, R⁹, a, b, c, A and B are the same as defined in claim 8,
2) Ar⁸ and Ar⁹ are each independently selected from the group consisting of a $C_6$-$C_{60}$ aryl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring;
3) C¹, C², C³ and C⁴ are each independently selected from the group consisting of CH and N,
4) D and E are each independently a single bond, S, O, NR', or CR'R", wherein R' and R" are a hydrogen; a $C_6$-$C_{60}$ aryl group; a $C_3$-$C_{60}$ heterocyclic group; or a $C_1$-$C_{50}$ alkyl group;
5) R' and R" may be bonded to each other to form a spiro compound, 6) f and g are 0 or 1, and provided that f+g is not less than 1.
11. The organic electric element according to claim 8, wherein the compound represented by Formula (16) is represented by any one of the following Formula P16-1 to P16-33:
P16-1
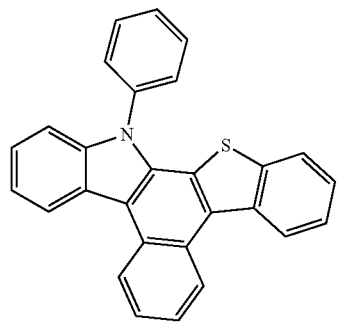
P16-2
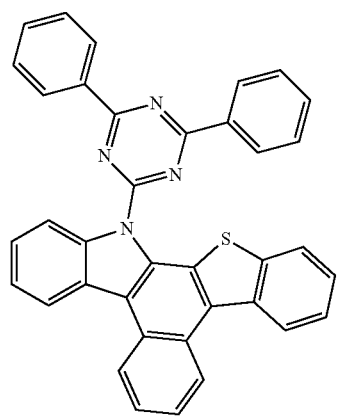
P16-3
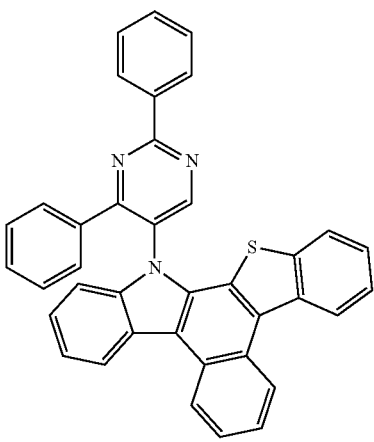
P16-4
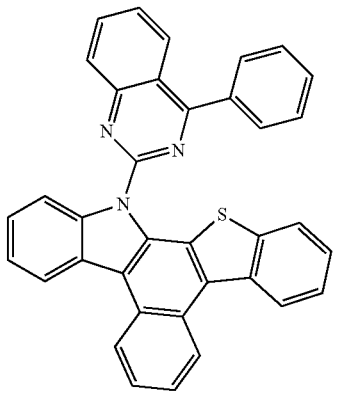
P16-5
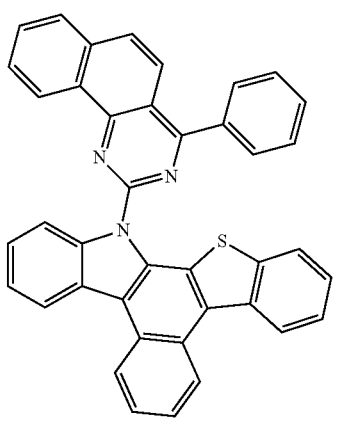
P16-6
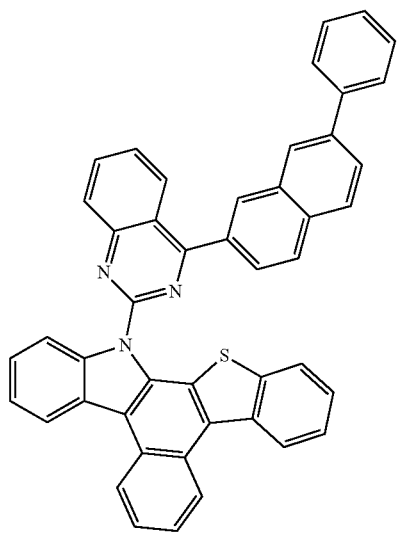

P16-7
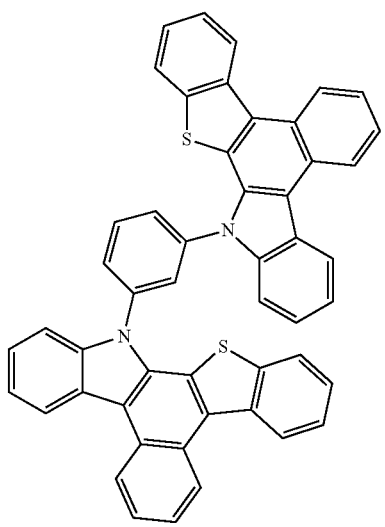
P16-8
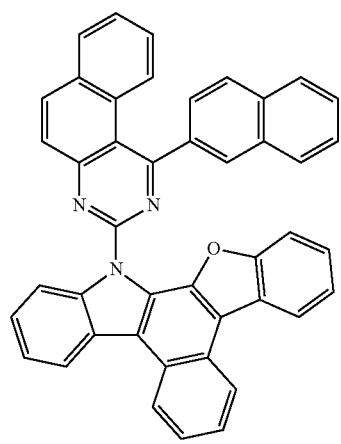
P16-9
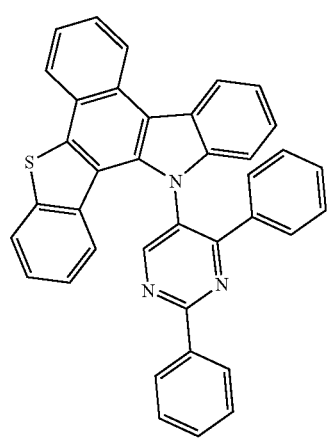
P16-10
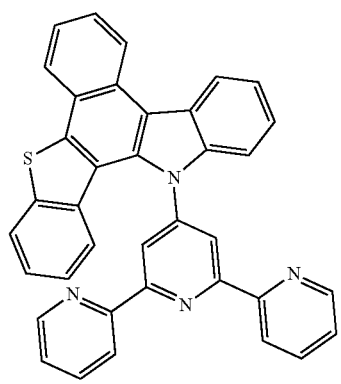
P16-11
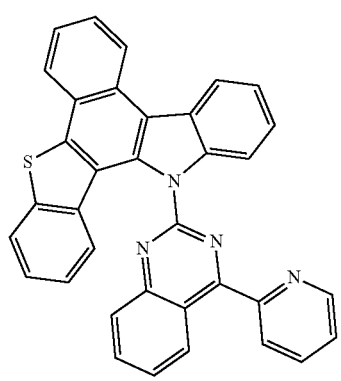
P16-12
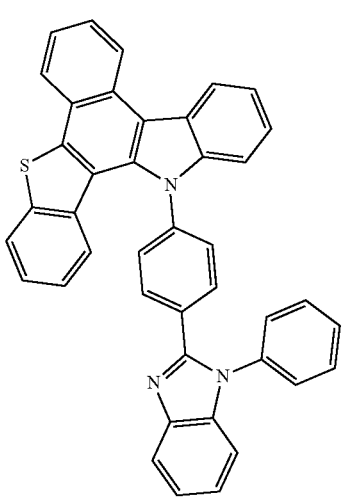
P16-13
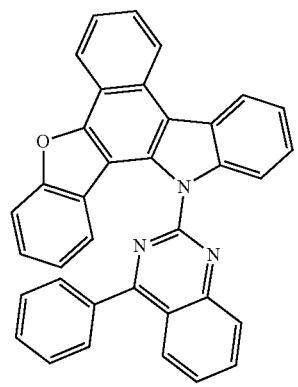

-continued
P16-14
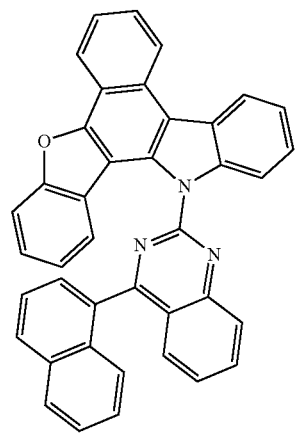
P16-15
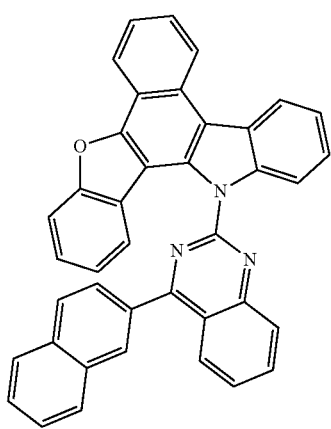
P16-16
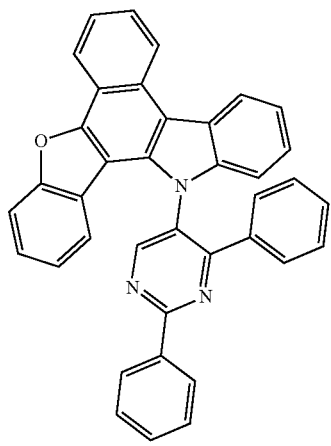
P16-17
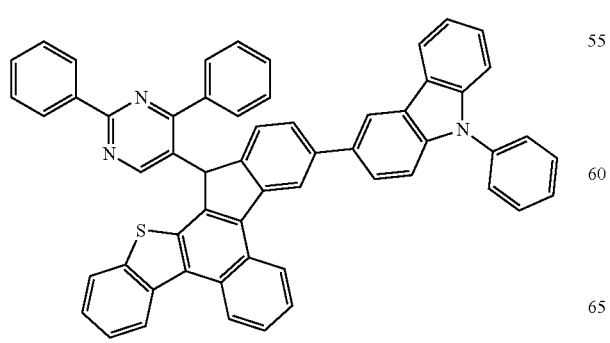
-continued
P16-18
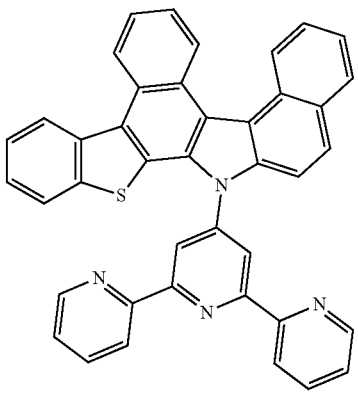
P16-19
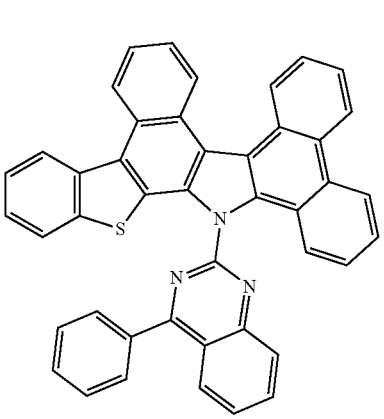
P16-20
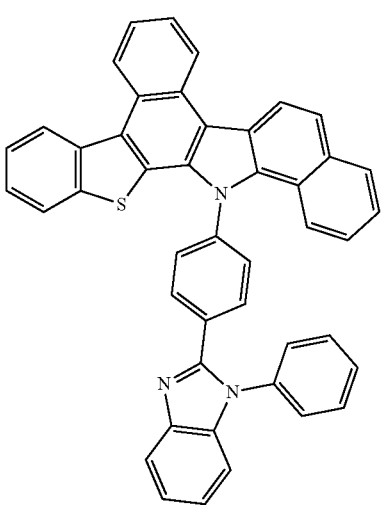

-continued
P16-21
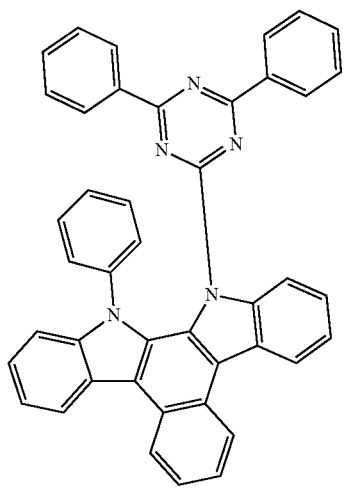
P16-22
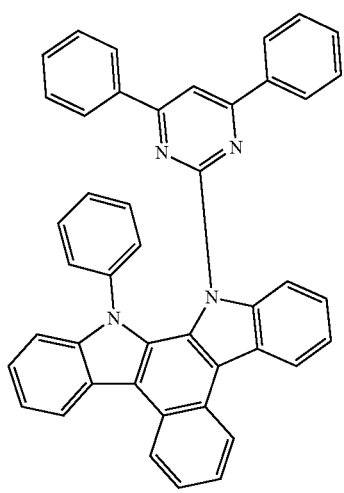
P16-23
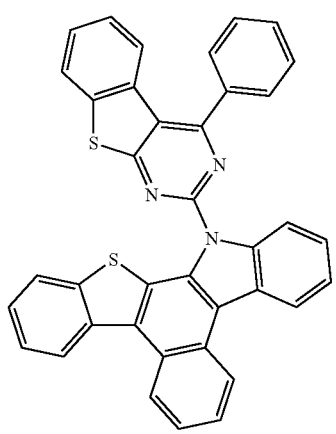
-continued
P16-24
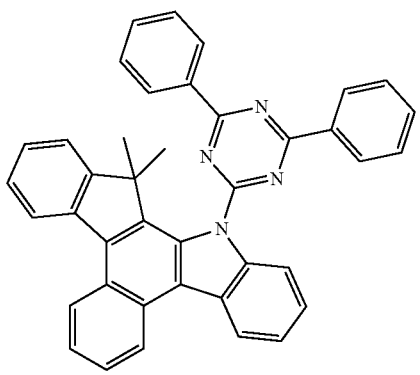
P16-25
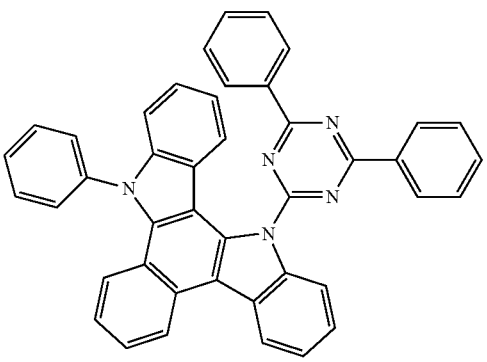
P16-26
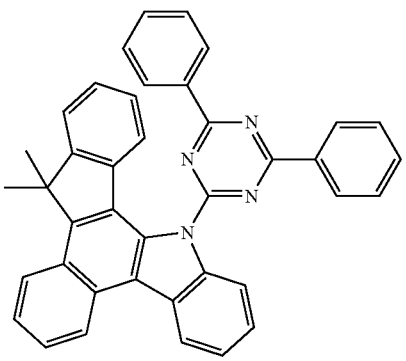
P16-27
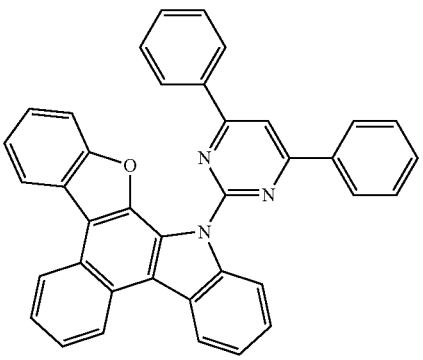

-continued

P16-28

P16-29

P16-30

P16-31

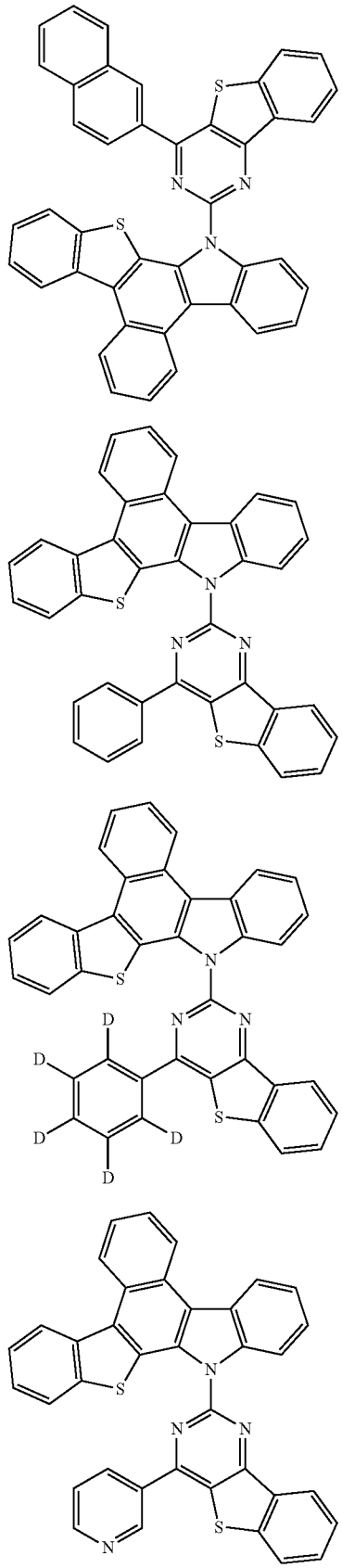

-continued

P16-32

P16-33

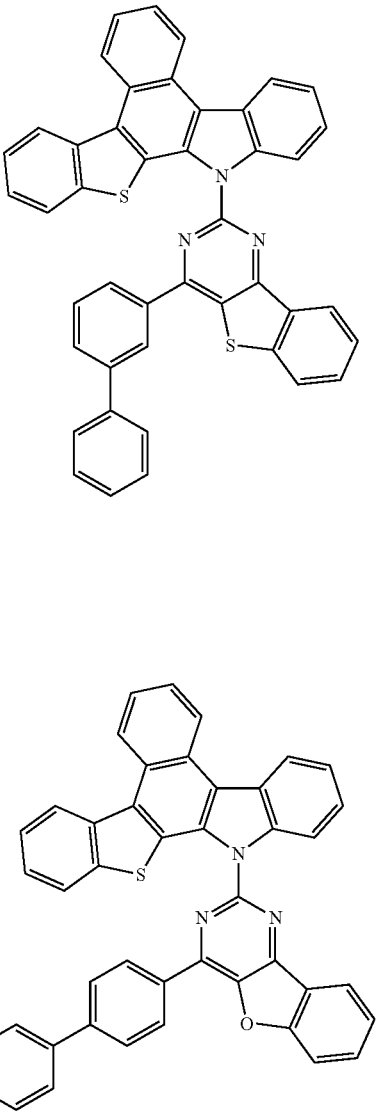

12. The organic electric element according to claim 5, wherein the organic electric element comprises a light efficiency enhancing layer formed on at least one of the opposite sides to the organic material layer of the first electrode and the second electrode.

13. The organic electric element according to claim 5, wherein the organic material layer is formed by one of a spin coating process, a nozzle printing process, an inkjet printing process, a slot coating process, a dip coating process and a roll-to-roll process.

14. An electronic device comprising a display device including the organic electric element according to claim 5; and a control unit for driving the display device.

15. The electronic device according to claim 14, wherein the organic electric element is an OLED, an organic solar cell, an organic photo conductor, an organic transistor and an element for monochromic or white illumination.

* * * * *